(12) United States Patent
Colloca et al.

(10) Patent No.: US 11,214,599 B2
(45) Date of Patent: *Jan. 4, 2022

(54) RECOMBINANT SIMIAN ADENOVIRAL VECTORS ENCODING A HETEROLOGOUS FIBER PROTEIN AND USES THEREOF

(71) Applicant: GLAXOSMITHKLINE BIOLOGICALS SA, Rixensart (BE)

(72) Inventors: Stefano Colloca, Rome (IT); Alfredo Nicosia, Rome (IT); Riccardo Cortese, Rome (IT); Virginia Ammendola, S. Guisepe Vesuviano (IT); Maria Ambrosio, Terzigno (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 116 days.

This patent is subject to a terminal disclaimer.

(21) Appl. No.: 16/710,131

(22) Filed: Dec. 11, 2019

(65) Prior Publication Data

US 2020/0102352 A1 Apr. 2, 2020

Related U.S. Application Data

(60) Continuation of application No. 15/623,723, filed on Jun. 15, 2017, now Pat. No. 10,544,192, which is a division of application No. 13/147,193, filed as application No. PCT/EP2010/000616 on Feb. 2, 2010, now Pat. No. 9,718,863.

(60) Provisional application No. 61/266,342, filed on Dec. 3, 2009, provisional application No. 61/174,852, filed on May 1, 2009, provisional application No. 61/172,624, filed on Apr. 24, 2009.

(30) Foreign Application Priority Data

Feb. 2, 2009 (WO) .................. PCT/EP2009/000672

(51) Int. Cl.

| C07K 14/005 | (2006.01) |
|---|---|
| C12N 7/00 | (2006.01) |
| C12N 15/86 | (2006.01) |
| C12N 15/861 | (2006.01) |
| A61K 39/12 | (2006.01) |
| A61K 39/235 | (2006.01) |
| A61K 48/00 | (2006.01) |
| A61K 39/00 | (2006.01) |

(52) U.S. Cl.
CPC ............ *C07K 14/005* (2013.01); *A61K 39/12* (2013.01); *A61K 39/235* (2013.01); *C12N 7/00* (2013.01); *C12N 15/86* (2013.01); *C12N 15/861* (2013.01); *A61K 39/0011* (2013.01); *A61K 48/00* (2013.01); *A61K 2039/525* (2013.01); *A61K 2039/5256* (2013.01); *A61K 2039/545* (2013.01); *C12N 2710/10321* (2013.01); *C12N 2710/10322* (2013.01); *C12N 2710/10334* (2013.01); *C12N 2710/10343* (2013.01); *C12N 2710/16634* (2013.01); *C12N 2740/16134* (2013.01); *C12N 2770/24234* (2013.01)

(58) Field of Classification Search
None
See application file for complete search history.

(56) References Cited

U.S. PATENT DOCUMENTS

| 5,922,315 A | 7/1999 | Roy |
|---|---|---|
| 8,470,310 B2 | 6/2013 | Roy et al. |
| 2007/0293424 A1 | 12/2007 | Chernysh et al. |

FOREIGN PATENT DOCUMENTS

| RU | 2267496 C2 | 10/2006 |
|---|---|---|
| WO | 1996013597 | 5/1996 |
| WO | 2003000851 | 1/2003 |
| WO | 2003031588 | 4/2003 |
| WO | 2003046124 | 11/2003 |
| WO | 2003102236 | 12/2003 |
| WO | 2005071093 | 8/2005 |
| WO | 2006086284 | 8/2006 |
| WO | 2006133911 | 12/2006 |
| WO | 2009073104 | 6/2009 |
| WO | 2009105084 | 8/2009 |
| WO | 2009146902 | 12/2009 |
| WO | 2009136977 | 3/2010 |

OTHER PUBLICATIONS

DataBase Online GenBank ABU38284.1, dated, Aug. 14, 2007, 1 page.
DataBase Online GenBank ACC27112.1, dated Apr. 14, 2008, 1 page.

(Continued)

*Primary Examiner* — Nicole Kinsey White
(74) *Attorney, Agent, or Firm* — Birch, Stewart, Kolasch & Birch, LLP

(57) ABSTRACT

The present invention relates to novel adenovirus strains with an improved seroprevalence. In one aspect, the present invention relates to isolated polypeptides of adenoviral capsid proteins such as hexon, penton and fiber protein and fragments thereof and polynucleotides encoding the same. Also provided is a vector comprising the isolated polynucleotide according to the invention and adenoviruses comprising the isolated polynucleotides or polypeptides according to the invention and a pharmaceutical composition comprising said vector, adenovirus, polypeptide and/or polynucleotide. The invention also relates to the use of the isolated polynucleotides, the isolated polypeptides, the vector, the adenoviruses and/or the pharmaceutical composition for the therapy or prophylaxis of a disease.

17 Claims, 17 Drawing Sheets
Specification includes a Sequence Listing.

(56) References Cited

OTHER PUBLICATIONS

Russian Office Action and Search Report, dated Apr. 22, 2020, for Russian Application No. 2016143553, with an English translation of the Russian Office Action.
Singer et al., "Genes and Genomes," 1998, p. 63 (2 pages total).
Altschul, et al., J. Mol. Biol.; 1990; pp. 403-410; vol. 215.
Bangari DS and Mittal SK, Vaccine; 2006; pp. 849-862; vol. 24.
Barnes, et al., Sci Transl Med; 2012; vol. 4(115).
Brody, et al., Ann NY Acad Sci.; 1994; pp. 90-101; vol. 716.
Capone, et al., Vaccine; 2010; pp. 256-265; vol. 29(2).
Colloca, et al., Sci Transl Med; 2012; vol. 4(115).
Dambrosio, E., J. Hyg; 1982; pp. 209-219; vol. 89.
Database EMBL Accession No. FJ025899, Jul. 9, 2009.
Database EMBL Accession No. FJ025903, Jul. 9, 2009.
Database EMBL Accession No. FJ025907, Jul. 9, 2009.
Database EMBL Accession No. FJ025926, Jul. 9, 2009.
Davison, Andrew J. et al.; J of Gen Virol.; 2003; pp. 2895-2908; vol. 84.
Deposit Reference 08110601; Virus ChAd83; The European Collection of Cell Cultures; Nov. 6, 2008.
Deposit Reference 08110602; Virus ChAd73; The European Collection of Cell Cultures; Nov. 6, 2008.
Deposit Reference 08110603; Virus ChAd55; The European Collection of Cell Cultures; Nov. 6, 2008.
Deposit Reference 08110604; Virus ChAd147; The European Collection of Cell Cultures; Nov. 6, 2008.
Deposit Reference 08110605; Virus ChAd146; The European Collection of Cell Cultures; Nov. 6, 2008.
Draper, SJ, et al., Nat Med., 2008; pp. 819-821; vol. 14(8).
Draper, et al., J. Immunol., 2010, pp. 7583-7595. vol. 185(12).
Farina, Steven F., et al., "Replication-defective vector based on a chimpanzee adenovirus." Journal of Virology; 2001; pp. 11603-11613; vol. 75(23).
Fattori, Gene Ther.; 2006; pp. 1088-1096; vol. 13(14).
Fisher and Wilson; Biochem J; 1994; pp. 49; vol. 299.
Folgori, A. et al. Nat Med.; 2006; pp. 190-197; vol. 12(2).
Graham & Prevec; In Methods in Molecular Biology: Gene Transfer and Expression Protocols; 1991; pp. 109.
Hierholzer, et al.; J. Infect. Dis.; 1988; pp. 804-813; vol. 158.
Hitt, et al.; Advances in Pharmacology; 1997; pp. 137-206; vol. 40.
Jong, et al.; J Clin Microbiol; 1999; pp. 3940-3945; vol. 37.
Karlin and Altschul; Proc Natl Acad Sci USA; 1993; pp. 5873-5877; vol. 90.
Krieg; J Clin Invest; 2007; pp. 1184-1194; vol. 117(5).
Lauer, Kim P. et al; J Gen Virol;2004; pp. 2615-2625.
Madisch, et al.; J. Virol; 2005; p. 15265-15276; vol. 79(24).
Madisch, et al.; J. Virol; 2007; pp. 8270-8281; vol. 81(15).
Mastrangeli, et al.; Human Gene Therapy; 1996; pp. 79-87; vol. 7.
Mccoy, Kimberly, et al.; J Virol; 2007; pp. 6594-6604; vol. 81(12).
Moore, et al; Science; 2008; pp. 753-755; vol. 320(5877).
NCBI GenBank Locus No. AAS10364 published on Aug. 19, 2004.
NCBI GenBank Locus No. AAS10369 published on Aug. 19, 2004.
NCBI GenBank Locus No. AP.sub.-000330 published on Dec. 8, 2008.
Notice of Preliminary Rejection issued in Korean Application No. 10-2016-7024396 dated Dec. 9, 2016.
O'Hara, et al., J Infect Dis.; 2012; pp. 772-781; vol. 205(5).
Peruzzi, Daniela, et al.; Vaccine; 2009; pp. 1293-1300; vol. 27(9).
Pichla-Gollon, et al.; J. Virol.; 2007; pp. 1680-1689; vol. 81(4).
Plenus Press and Horwitz; Virology; 1990; pp. 1679-1721 eds. B.N. Fields and D.M. Knipe.
Rosario, et al.; Eur J. Immunol; 2010; pp. 1973-1984; vol. 40(7).
Roy, et al., Virology; 2004; pp. 361-372; vol. 324(2).
Russel; J. Gen. Virol.; 2000; pp. 2573-2604; vol. 81.
Rux, et al., J Virol; 2003; pp. 9553-9566; vol. 77(17).
Schnurr and Dondero; Intervirology; 1993; pp. 79-83; vol. 36.
Tauber and Dobner;L Oncogene; 2001; pp. 7847-7854; vol. 20.

FIG. 1A

Adenovirus Hexon Protein

CLUSTAL W (1.83) multiple sequence alignment

```
PanAd1     MATPSMMPQWSYMHISGQDASEYLSPGLVQFARATDSYFSLSNKFRNPTVAPTHDVTTDR
PanAd2     MATPSMMPQWSYMHISGQDASEYLSPGLVQFARATDSYFSLSNKFRNPTVAPTHDVTTDR
PanAd3     MATPSMMPQWSYMHISGQDASEYLSPGLVQFARATDSYFSLSNKFRNPTVAPTHDVTTDR
ChAd55     MATPSMLPQWAYMHIAGQDASEYLSPGLVQFARATDTYFSLGNKFRNPTVAPTHDVTTDR
ChAd73     MATPSMLPQWAYMHIAGQDASEYLSPGLVQFARATDTYFSLGNKFRNPTVAPTHDVTTDR
ChAd83     MATPSMLPQWAYMHIAGQDASEYLSPGLVQFARATDTYFSLGNKFRNPTVAPTHDVTTDR
ChAd146    MATPSMLPQWAYMHIAGQDASEYLSPGLVQFARATDTYFSLGNKFRNPTVAPTHDVTTDR
ChAd147    MATPSMLPQWAYMHIAGQDASEYLSPGLVQFARATDTYFSLGNKFRNPTVAPTHDVTTDR
           ******:***.****:*********************:*****:***************

PanAd1     SQRLTLRFIPVDREDTAYSYKARFTLAVGDNRVLDMASTYFDIRGVLDRGPTFKPYSGTA
PanAd2     SQRLTLRFIPVDREDTAYSYKARFTLAVGDNRVLDMASTYFDIRGVLDRGPTFKPYSGTA
PanAd3     SQRLTLRFIPVDREDTAYSYKARFTLAVGDNRVLDMASTYFDIRGVLDRGPTFKPYSGTA
ChAd55     SQRLTLRFVPVDREDNTYSYKVRYTLAVGDNRVLDMASTYFDIRGVLDRGPSFKPYSGTA
ChAd73     SQRLTLRFVPVDREDNTYSYKVRYTLAVGDNRVLDMASTYFDIRGVLDRGPSFKPYSGTA
ChAd83     SQRLTLRFVPVDREDNTYSYKVRYTLAVGDNRVLDMASTYFDIRGVLDRGPSFKPYSGTA
ChAd146    SQRLTLRFVPVDREDNTYSYKVRYTLAVGDNRVLDMASTYFDIRGVLDRGPSFKPYSGTA
ChAd147    SQRLTLRFVPVDREDNTYSYKVRYTLAVGDNRVLDMASTYFDIRGVLDRGPSFKPYSGTA
           ********:******:*****.*:**************************:*********

<----------------- HVR 1-6 ---------
PanAd1     YNSLAPKGAPNSCEWEQVEP--AEEAAENE-DEEEEEDVVDPQEQEPTTKTHVYAQAPLS
PanAd2     YNSLAPKGAPNPCEWDEAVT--AVDINLDELGEDEDDAEGEAEQQ----KSHVFGQAPYS
PanAd3     YNSLAPKGAPNSCEWEQEETQTAEEAQDEEEEDEAEAEEEMPQEEQAPVKRTHVYAQAPLS
ChAd55     YNSLAPKGAPNTSQWITKDN----------------------------GTDKTYSFGNAPVR
ChAd73     YNALAPKGAPNTSQWITKDN----------------------------GTDKTYSFGNAPVR
ChAd83     YNSLAPKGAPNTSQWITKDN----------------------------GTDKTYSFGNAPVR
ChAd146    YNSLAPKGAPNTSQWITKDN----------------------------GTDKTYSFGNAPVR
ChAd147    YNSLAPKGAPNTSQWVTKDN----------------------------GTDKTYSFGNAPVR
           **:********. .:.:                                  *:: *:.**

---------------------- HVR 1-6 ------------------------
PanAd1     GEKITKDGLQIGTEATAAGGTKDLFADPTFQPEPQVGESQWNEAD--ATAAGGRVLKKTT
PanAd2     GQNITKEGIQISVDTTSQA-QTPLYADKTFQPEPQVGESQWNETE--TNYGAGRVLKKTT
PanAd3     GEKITKDGLQTGTDATATE-QKPIYADPTFQPEPQIGESQWNEAD--ASVAGGRVLKKTT
ChAd55     GLDITEEGLQIGPDESGGE-SKKIFADKTYQPEPQLGDEEWHDTIGAEDKYGGRALKPAT
ChAd73     GLDITEEGLQIRTDESGGE-SKKIFADKTYQPEPQLGDEEWHDTIGAEDKYGGRALKPAT
ChAd83     GLDITEEGLQTGTDESGGE-SKKIFADKTYQPEPQLGDEEWHDTIGAEDKYGGRALKPAT
ChAd146    GLDITEEGLQIGTDESGGK-SKKIFADKTYQPEPQLGDEEWHDTIGAEDKYGGRALKPAT
ChAd147    GLDITEEGLQIGTDDSSTE-SKKIFADKTYQPEPQVGDEEWHDTIGAEDKYGGRALKPAT
           * :*::::.*  . :  :   .:: :** *:******:*::.::     .**.** :*

-------------- HVR 1-6 ----------------------
PanAd1     FNKPCYGSYARPTNANGGQGVLKANAQGVLESQVEMQFFSTSTNATN-RQNNIQFKLVLY
```

FIG. 1B

```
PanAd2   IMKPCYGSYARPTNENGGQGILLEKEGGKPESQVEMQFPSTTQAAAAGNSDNLTPKVVLY
PanAd3   PMKPCYGSYARPTNANGGQGVLVEKDGGKMESQVDMQFFSTSENARN-EANNIQPRLVLY
ChAd55   NMKPCYGSFAKPTNAKGGQAKSRTKDDGTTEPDIDMAFFDDRSQQAS------FSPELVLY
ChAd73   NMKPCYGSFAKPTNAKGGQAKSRTKDDGTTEPDIDMAFFDDRSQQAS------FSPELVLY
ChAd83   NMKPCYGSFAKPTNAKGGQAKSRTKDDGTTEPDIDMAFFDDRSQQAS------FSPELVLY
ChAd146  NMKPCYGSFAKPTNAKGGQAKSRTKDDGTTEPDIDMAFFDDRSQQAS------FSPELVLY
ChAd147  NMKPCYGSFAKPTNAKGGQAKTRTKDDGTTEPDIDMAFFDDRSQQAS------FSPELVLY
         *******.*.***.***.     .    *  *.:::* **.              : *;:***

<---- HVR 1-6 ---------->
PanAd1   SEDVHMETPDTHISYKPTKSDDNSKVMLGQQSMPNRPNYIAFRDNFIGLMYYNSTGNMGV
PanAd2   SEDVHLETPDTHISYMPTSNEAMSRELLGQQAMPNRPNYIAFRDNFIGLMYYNSTGNMGV
PanAd3   SEDVHMETPDTHISYKPAKSDDRSKVMLGQQSMPNRPNYIGFRDNFIGLMYYNSTGNMGV
ChAd55   TENVDLDTPDTHIIYKPGTDETSSSFNLGQQSMPNRPNYIGFRDNFIGLMYYNSTGNMGV
ChAd73   TENVDLDTPDTHIIYKPGTDETSSSFNLGQQSMPNRPNYIGFRDNFIGLMYYNSTGNMGV
ChAd83   TENVDLDTPDTEIIYKPGTDETSSSFNLGQQSMPNRPNYIGFRDNFIGLMYYNSTGNMGV
ChAd146  TENVDLDTPDTHIIYKPGTDETSSSFNXGQQSMPNRPNYIGFRDNFIGLMYYNSTGNMGV
ChAd147  TENVDLETPDTHIIYKPGTDETSSSFNLGQQSMPNRPNYIGFRDNFIGLMYYNSTGNMGV
         :*;*.:;(***** * *  ..: .*      ***;********.****************

PanAd1   LAGQASQLNAVVDLQDRNTELSYQLLLDSMGDRTRYFSMWNQAVDSYDPDVRIIENHGTE
PanAd2   LAGQASQLNAVVDLQDRNTELSYQLLLDSMGDRTRYFSMWNQAVDSYDPDVRIIENHGTE
PanAd3   LAGQASQLNAVVDLQDRNTELSYQLLLDSMGDRTRYFSMWNQAVDSYDPDVRIIENHGTE
ChAd55   LAGQASQLNAVVDLQDRNTELSYQLLLDSLGDRTRYFSMWNQAVDSYDPDVRIIENHGVE
ChAd73   LAGQASQLNAVVDLQDRNTELSYQLLLDSLGDRTRYFSMWNQAVDSYDPDVRIIENHGVE
ChAd83   LAGQASQLNAVVDLQDRNTELSYQLLLDSLGDRTRYFSMWNQAVDSYDPDVRIIENHGVE
ChAd146  LAGQASQLNAVVDLQDRNTELSYQLLLDSLGDRTRYFSMWNQAVDSYDPDVRIIENHGVE
ChAd147  LAGQASQLNAVVDLQDRNTELSYQLLLDSLGDRTRYFSMWNQAVDSYDPDVRIIENHGVE
         ****************************;*****************************;*

<-------- HVR 7 -------->
PanAd1   DELPNYCFPLGGIGITDTYQAIKTNG-NGAGDQATTWQKDSQFADRNEIGVGNNFAMEIN
PanAd2   DELPNYCFPLGSTIRTETLTKVKF-----KTGQDAQWEKDTEFSEKNETRVGNNFAMEIN
PanAd3   DELPNYCFPLGGIGVTDTYQKIKTNG-NGNGGKTTWTKDETFADRNEIGVGNNFAMEIN
ChAd55   DELPNYCFPLNGVGFTDTFQGIKVKTTNNGTANATEWESDTSVNNANEIAKGNPFAMEIN
ChAd73   DELPNYCFPLNGVGFTDTFQGIKVKTTNNGTANATEWESDTSVNNANEIAKGNPFAMEIN
ChAd83   DELPNYCFPLNGVGFTDTFQGIKVKTTNNGTANATEWESDTSVNNANEIAKGNPFAMEIN
ChAd146  DELPNYCFPLNGVGFTDTFQGIKVKTTNNGTANATEWESDTSVNNANEIAKGNPFAMEIN
ChAd147  DELPNYCFPLNGVGFTDTFQGIKVKTTNNGTANATEWESDTSVNNANEIAKGNPFAMEIN
         *********.*;   *;*.     .*     * .*. ;.:*** ** *****

PanAd1   LSANLWRNFLYSNVALYLPDKLKYNPSNVEISDMPNTYDYMNKRVVAPGLVDCYINLGAR
PanAd2   LNANLWRNFLYSNVALYLPDKLKYTPANVQLSSNSMSYDYMNKRVVAPGLVDCYINLGAR
PanAd3   LSANLWRNFLYSNVALYLPDKLKYNPSNVEISDMPNTYDYMNKRVVAPGLVDCYINLGAR
ChAd55   IQANLWRNFLYANVALYLPDSYKYTPANITLPTNTNTYDYMNGRVVAPSLVDAYINIGAR
ChAd73   IQANLWRNFLYANVALYLPDSYKYTPANITLPTNTNTYDYMNGRVVAPSLVDAYINIGAR
ChAd83   IQANLWRNFLYANVALYLPDSYKYTPANITLPTNTNTYDYMNGRVVAPSLVDAYINIGAR
ChAd146  IQANLWRNFLYANVALYLPDSYKYTPANITLPTNTNTYDYMNGRVVAPSLVDAYINIGAR
ChAd147  IQANLWRNFLYANVALYLPDSYKYTPANVTLPTNTNTYEYMNGRVVAPSLVDSYINIGAR
         :.*********;*******.  **; *.  .*; :.  *.::**;*** *****.**:****

PanAd1   WSLDYMDNVNPFNHHRNAGLRYRSMLLGNGRYVPFHIQVPQKFFAIKNLLLLPGSYTYEW
PanAd2   WSLDYMDNVNPFNHHRNAGLRYRSMLLGNGRYVPFHIQVPQKFFAIKNLLLLPGSYTYEW
PanAd3   WSLDYMDNVNPFNHHRNAGLRYRSMLLGNGRYVPFHIQVPQKFFAIKNLLLLPGSYTYEW
```

FIG. 1C

```
ChAd55   WSLDPMDNVRPFNHHRNAGLRYRSMLLGNGRYVPFHIQVPQKFFAIKSLLLLPGSYTYEW
ChAd73   WSLDPMDNVRPFNHHRNAGLRYRSMLLGNGRYVPFHIQVPQKFFAIKSLLLLPGSYTYEW
ChAd83   WSLDPMDNVRPFNHHRNAGLRYRSMLLGNGRYVPFHIQVPQKFFAIKSLLLLPGSYTYEW
ChAd146  WSLDPMDNVRPFNHHRNAGLRYRSMLLGNGRYVPFHIQVPQKFFAIKNLLLLPGSYTYEW
ChAd147  WSLDPMDNVNPFNHHRNAGLRYRSMLLGNXRPVPFHIQVPQKFFAIKSLLLLPGSYTYEW
         ****.***** ****** *********** *.*.**:****************** *****

PanAd1   NFRKDVNMVLQSSLGNDLRVDGASIKFESICLYATFFPMAHNTASTLEAMLRNDTNDQSF
PanAd2   NFRKDVNMVLQSSLGNDLRVDGASIKFESICLYATFFPMAHNTASTLEAMLRNDTNDQSF
PanAd3   NFRKDVNMVLQSSLGNDLRVDGASIKFESICLYATFFPMAHNTASTLEAMLRNDTNDQSF
ChAd55   NFRKDVNMILQSSLGNDLRTDGASIAFTSINLYATFFPMAHNTASTLEAMLRNDTNDQSF
ChAd73   NFRKDVNMILQSSLGNDLRTDGASIAFTSINLYATFFPMAHNTASTLEAMLRNDTNDQSF
ChAd83   NFRKDVNMILQSSLGNDLRTDGASIAFTSINLYATFFPMAHNTASTLEAMLRNDTNDQSF
ChAd146  NFRKDVNMILQSSLGNDLRTDGASIAFTSINLYATFFPMAHNTASTLEAMLRNDTNDQSF
ChAd147  NFRKDVNMILQSSLGNDLRTDGASISFTSINLYATFFPMAHNTASTLEAMLRNDTNDQSF
         *******:*********** ****: *.* ******************************

PanAd1   NDYLSAANMLYPIPANATNVPISIPSRNWAAFRGWAFTRLKTKETPSLGSGFDPYYTYSG
PanAd2   NDYLSAANMLYPIPANATNVPISIPSRNWAAFRGWAFTRLKTKETPSLGSGFDPYYTYSG
PanAd3   NDYLSAANMLYPIPANATNVPISIPSRNWAAFRGWAFTRLKTKETPSLGSGFDPYYTYSG
ChAd55   NDYLSAANMLYPIPANATNVPISIPSRNWAAFRGWSFTRLKTRETPSLGSGFDPYFVYSG
ChAd73   NDYLSAANMLYPIPANATNVPISIPSKNWAAFRGWSFTRLKTRETPSLGSGFDPYFVYSG
ChAd83   NDYLSAANMLYPIPANATNVPISIPSRNWAAFRGWSFTRLKTRETPSLGSGFDPYFVYSG
ChAd146  NDYLSAANMLYPIPANATNVPISIPSRNWAAFRGWSFTRLKTRETPSLGSGFDPYFVYSG
ChAd147  NDYLSAANMLYPIPANATNVPISIPSRNWAAFRGWSFTRLKTKETPSLGSGFDPYFVYSG
         ************************:*********:*******:*************.:***

PanAd1   SIPYLDGTFYLNHTFKKVSVTFDSSVSWPGNDRLLTPNEFEIKRSVDGEGYNVAQCNMTK
PanAd2   SIPYLDGTFYLNRTFKKVSVTFDSSVSWPGNDRLLTPNEFEIKRSVDGEGYNVAQCNMTK
PanAd3   SIPYLDGTFYLNHTFKKVSVTFDSSVSWPGNDRLLTPNEFEIKRSVDGEGYNVAQCNMTK
ChAd55   SIPYLDGTFYLNHTFKKVSITFDSSVSWPGNDRLLTPNEFEIKRTVDGEGYNVAQCNMTK
ChAd73   SIPYLDGTFYLNRTFKKVSITFDSSVSWPGNDRLLTPNEFEIKRTVDGEGYNVAQCNMTK
ChAd83   SIPYLDGTFYLNHTFKKVSITFDSSVSWPGNDRLLTPNEFEIKRTVDGEGYNVAQCNMTK
ChAd146  SIPYLDGTFYLNHTFKKVSITFDSSVSWPGNDRLLTPNEFEIKRTVDGEGYNVAQCNMTK
ChAd147  SIPYLDGTFYLNHTFKKVSITFDSSVSWPGNDRLLTPNEFEIKRTVDGEGYNVAQCNMTK
         ***********:*******:***********************:***************

PanAd1   DWFLIQMLANYNIGYQGFYIPESYKDRMYSFFRNFQPMSRQVVDETKYKDYQQVGIIHQH
PanAd2   DWFLIQMLANYNIGYQGFYIPESYKDRMYSFFRNFQPMSRQVVDETKYKDYQQVGIIHQH
PanAd3   DWFLIQMLANYNIGYQGFYIPESYKDRMYSFFRNFQPMSRQVVDETKYKDYQQVGIIHQH
ChAd55   DWFLVQMLAHYNIGYQGFYVPEGYKDRMYSFFRNFQPMSRQVVDEVNYKDYQAVTLAYQH
ChAd73   DWFLVQMLAHYNIGYQGFYVPEGYKDRMYSFFRNFQPMSRQVVDEVNYKDYQAVTLAYQH
ChAd83   DWFLVQMLAHYNIGYQGFYVPEGYKDRMYSFFRNFQPMSRQVVDEVNYKDYQAVTLAYQH
ChAd146  DWFLVQMLAHYNIGYQGFYVPEGYKDRMYSFFRNFQPMSRQVVDEVNYKDYQAVTLAYQH
ChAd147  DWFLVQMLAHYNIGYQGFYVPEGYKDRMYSFFRNFQPMSRQVVDEVNYKDYQAVTLAYQH
         ****:****:*********:**.************************  *****..:  *:*:

PanAd1   NNSGFVGYLAPTMREGQAYPANPYPLIGKTAVDSITQKKFLCDRTLWRIPFSSNFMSMG
PanAd2   NNSGFVGYLAPTMREGQAYPANPYPLIGKTAVDSVTQKKFLCDRTLWRIPFSSNFMSMG
PanAd3   NNSGFVGYLAPTMREGQAYPANPYPLIGKTAVDSVTQKKFLCDKTLWRIPFSSNFMSMG
ChAd55   NNSGFVGYLAPTMRQGQPYPANYPYPLIGKSAVASVTQKKFLCDRVMWRIPFSSNFMSMG
ChAd73   NNSGFVGYLAPTMRQGQPYPANYPYPLIGKSAVASVTQKKFLCDRVMWRIPFSSNFMSMG
ChAd83   NNSGFVGYLAPTMRQGQPYPANYPYPLIGKSAVASVTQKKFLCDRVMWRIPFSSNFMSMG
ChAd146  NNSGFVGYLAPTMRQGQPYPANYPYPLIGKSAVASVTQKKFLCDRVMWRIPFSSNFMSMG
```

FIG. 1D

```
ChAd147    NRSGFVGYLAPTMRQGQPYPANYPYPLIGKSAVTSVTQKKFLCDRVMKRIPPSSNFMSMG
           ************ .**.**** ;***.***.;** * ;********.;**.******.**

PanAd1     ALTDLGQNLLYANSAHALDMTFEVDPMDEPTLLYVLFEVFDVVRVHQPHRGVIETVYLRT
PanAd2     ALTDLGQNLLYANSAHALDMTFEVDPMDEPTLLYVLFEVFDVVRVHQPHRGVIETVYLRT
PanAd3     ALTDLGQNLLYANSAHALDMTFEVDPMDEPTLLYVLFEVFDVVRVHQPHRGVIETVYLRT
ChAd55     ALTDLGQNMLYANSAHALDMNFEVDPMDESTLLYVVFEVFDVVRVHQPHRGVIEAVYLRT
ChAd73     ALTDLGQNMLYANSAHALDMNFEVDPMDESTLLYVVFEVFDVVRVHQPHRGVIKAVYLRT
ChAd83     ALTDLGQNMLYANSAHALDMNFEVDPMDESTLLYVVFEVFDVVRVHQPHRGVIEAVYLRT
ChAd146    ALTDLGQNMLYANSAHALDMNFEVDPMDESTLLYVVFEVFDVVRVHQPHRGVIEAVYLRT
ChAd147    ALTDLGQNMLYANSAHALDMNFEVDPMDESTLLYVVFEVFDVVRVHQPHRGVIEAVYLRT
           *********.************.************ ************** ;******

PanAd1     PFSAGNATT (SEQ ID NO: 25)
PanAd2     PFSAGNATT (SEQ ID NO: 53)
PanAd3     PFSAGNATT (SEQ ID NO: 54)
ChAd55     PFSAGNATT (SEQ ID NO: 20)
ChAd73     PFSAGNATT (SEQ ID NO: 21)
ChAd83     PFSAGNATT (SEQ ID NO: 22)
ChAd146    PFSAGNATT (SEQ ID NO: 23)
ChAd147    PFSAGNATT (SEQ ID NO: 24)
           *********
```

FIG. 2A

Adenovirus Fiber Protein

CLUSTAL W (1.83) multiple sequence alignment

```
PanAd1    -MKRAKTSDETFNPVYPYDTERGPPSVFFLTPPFVSPDGFQESPPGVLSLRLSEPLVTSN
PanAd2    -NKRAKTSDETFNPVYPYDTENGPPSVFFLTPPFVSPDGFQESPPGVLSLRLSEPLVTSN
PanAd3    -MKRAKTSDETFNPVYPYDTERGPPSVFFLTPPFVSPDGFQESPPGVLSLRLSEPLVTSN
ChAd55    MSKKRVRVDDDFDPVYPYDADN-APTVFFINPPFVSSDGFQEKPLGVLSLRLADPVTTKN
ChAd73    MSKKRVRVDDDFDPVYPYDADN-APTVFFINPPFVSSDGFQEKPLGVLSLRLADPVTTKN
ChAd83    MSKKRVRVDDDFDPVYPYDADN-APTVFFINPPFVSSDGFQEKPLGVLSLRLADPVTTKN
ChAd146   MSKKRVRVDDDFDPVYPYDADN-APTVFFINPPFVSSDGFQEKPLGVLSLRLADPVTTKN
ChAd147   MSKKRARVDDGFDPVYPYDADN-APTVFFINPPFVSSDGFQEKPLGVLSLRLADPVTTKN
            *;   *; *;*****;;* .*;*;**;.*****.*****.* *********;;*;.*;/

PanAd1    GMLALKMGNGLSLDDAGNLTSQDVTTVTPPLKKTKTNLSLQTSAPLTVSSGSLTVAAAAP
PanAd2    GMLALKMGNGLSLDDAGNLTSQDVTTVTPPLKKTKTNLSLQTSAPLTVSSGSLTVAAAAP
PanAd3    GNLALKMGNGLSLDDAGNLTSQDVTTVTPPLKKTKTNLSLQTSAPLTVSSGSLTVAAAAP
ChAd55    GEITLKLGEGVDLDDSGKLISKNAT-----------------------------------
ChAd73    GEITLKLGEGVDLDDSGKLISKNAT-----------------------------------
ChAd83    GEITLKLGEGVDLDSSGKLISNTAT-----------------------------------
ChAd146   GEITLKLGEGVDLDSSGKLISNTAT-----------------------------------
ChAd147   GAVPLKLGEGVDLDDSGKLISKKST-----------------------------------
            * ;.**;;*;*;.**;;*;* *;  *

PanAd1    LAVAGTSLTMQSQAPLTVQDAKLGLATQGPLTVSEGKLTLQTSAPLTAADSSTLTVSATP
PanAd2    LAVAGTSLTMQSQAPLTVQDAKLGLATQGPLTVSEGKLTLQTSAPLTAADSSTLTVSATP
PanAd3    LAVAGTSLTMQSQAPLTVQDAKLGLATQGPLTVSEGKLTLQTSAPLTAADSSTLTVGTTP
ChAd55    -----------------------------------------------------KATA
ChAd73    -----------------------------------------------------KATA
ChAd83    -----------------------------------------------------KAAA
ChAd146   -----------------------------------------------------KAAA
ChAd147   -----------------------------------------------------KANS
                                                                  ..

PanAd1    PLSTSNGGLSIDMQAPIYTTNGKLALNIGAPLHVVD--TLNALTVVTGQGLTINGRALQT
PanAd2    PLSTSNGGLSIDMQAPIYTTNGKLALNIGAPLHVVD--TLNALTVVTGQGLTINGRALQT
PanAd3    PISVSSGSLGLDMEDPMYTHDGKLGIRIGGPLQVVD--SLETLTVVTGNGITVANNALQT
ChAd55    PLSTSNSTISLNMDAPLYNNNGKLGIRIGAPLRVVD--LLNTLAVAYGSGLGLKNNALTV
ChAd73    PLSISNSTISLNMAAPFYNNNGTLSLNVSTPLAVFP--TFNTLGISLGNGLQTSNKLLAV
ChAd83    PLSFSNNTISLNMDHPFYTKDGKLALQVSPPLNILRTSILNTIALGFSSGLGLRGSALAV
ChAd146   PLSFSNNTISLNMDHPFYTKDGKLSLQVSPPLNILRTSILNTIALGFSSGLGLRGSALAV
ChAd147   PLSISNNTISLNMDTPFYTKDGKLTNQVTAPLKLANTAILNTLAMAYGNGLGLNNNALTV
            *;* *;..;;;;;* *;*; ;*.* ;;  ** ;   ;;;* ; *;.*; . * .

PanAd1    RVTGALSYDTEGNIQLQAGGG---------NRIDNNGQLILNVAYPFDAQNNLSLRLGQGP
PanAd2    RVTGALSYDTEGNIQLQAGGG---------NRIDNNGQLILNVAYPFDAQNNLSLRLGQGP
```

FIG. 2B

```
PanAd3    RVAGALGYDSSGNLELRAAGG--------MRINTGGQLILDVAYPFDAQNNLSLRLGQGP
ChAd55    QLVSPLTFDNKGRVKINLGNGPLTVAANRLSVTCKRGLYVTTG-DALESNISWAKG--I
ChAd73    QLTHPLTFSS-NSITVKTD---------------RGLYLHSSGHRGLEANISLKRG--L
ChAd83    QLVSPLTFDTDGNIKLTLD---------------RGLHVTTG--DAIESNISWAKG--L
ChAd146   QLVSPLTFDTDGNIKLTLD---------------RGLHVTTG--DAIESNISWAKG--L
ChAd147   QVTSPLTFDN-SKVKINLGNGPLWVSANKLSIRCLRGLYVAPNN-TGLETNISWANA--M

PanAd1    LIVNSAHNLDLNLNRGLYLFTSGNTKKLEVNIKTAKGLFYDGTAIAINAGDGLQFGSGSD
PanAd2    LIVNSAHNLDLNLNRGLYLFTSGRTKKLEVNIKTAKGLPYDGTAIAINAGDGLQFGSGSD
PanAd3    LYVNTNHNLQLRGNRGLTTTTESNTTKLETKIDS--------------------------
ChAd55    RFEGNAIAANIG--NGLRFGTTSSES---------------------------------
ChAd73    IFDGNAIATYLG--SGLDYGSYDSDGKTRFIITK--------------------------
ChAd83    RFEDGAIATNIG--NGLRFGSSSTET---------------------------------
ChAd146   RFEDGAIATNIG--NGLRFGSSSTET---------------------------------
ChAd147   RFEGNAMAVYIDTNKGLQFGTTSTET---------------------------------

PanAd1    TNPLQTRLGLGLEYDSNKAIITRLGTGLSFDNTGAITVGNKNDDKLTLWTTPDPSPNCRI
PanAd2    TNPLQTRLGLGLEYDSNKAIITRLGTGLSFDNTGAITVGNKNDDKLTLWTTPDPSPNCRI
PanAd3    -----------GLDYNANGAIIAKLGTGLTFDNTGAITVGNTGDDKLTLWTTPDPSPNCRI
ChAd55    -----------DVSNAYPIQVKLGTGLTFDSTGAIVAWNKEDDKLTLWTTADPSPNCHI
ChAd73    ----------IGAGLRFDSNNAMAVKLGTGLSFDSAGALTAGNKEDDKLTLWTTPDPSPNCQL
ChAd83    ----------GVDDAYPIQVKLGSGLSFDSTGAIMAGNKEDDKLTLWTTPDPSPNCQI
ChAd146   ----------GVDDAYPIQVKLGSGLSFDSTGAIMAGNKEDDKLTLWTTPDPSPNCQI
ChAd147   ----------GVTNAYPIQVKLGAGLAFDSTGAIVAWNKENDSLTLWTTPDPSPNCKI

PanAd1    NSEKDAKLTLVLTKCGSQVLASVSVLSVKG--SLAPISGTVTSAQIVLRFDENGVLLSNS
PanAd2    NSEKDAKLTLVLTKCGSQVLASVSVLSVKG--SLAPISGTVTSAQIVLRFDENGVLLSNS
PanAd3    HADKDCKFTLVLTKCGSQILASVAALAVSG--NLSSMTGTVSSVTIFLRFDQNGVLMENS
ChAd55    YSDKDAKLTLCLTKCGSQILGTVSLIAVDT-GSLNEITGQVTTALVSLRFDANGVLQTSS
ChAd73    LSDRDAKFTLCLTKCGSQILGTVAVAAVTVSSALNPINDTVKSAIVFLRFDSDGVLMSNS
ChAd83    LAENDAKLTLCLTKCGSQILATVSVLVVGS-GNLNFITGTVSSAQVFLRFDANGVLLTER
ChAd146   LAENDAKLTLCLTKCGSQILATVSVLVVGS-GNLNFITGTVSSAQVFLRFDANGVLLTER
ChAd147   ASEKDAKLTLCLTKCGSQILGTVSLIAVS--GSLAPITGAVSTALVSLRFNANGALLDKS

PanAd1    SLDPQYWNYRKGDSTEGTAYTNAVGFMPNLTAYPKTQSQTAKSNIVSQVYLNGDKTKPMT
PanAd2    SLDPQYWNYRKGDSTEGTAYTNAVGFMPNLTAYPKTQSQTAKSNIVSQVYLNGDKTKPMT
PanAd3    SLDKEYWNFRNGNSTNATPYTNAVGFMPNLSAYPKTQSQTAKNMIVSEVYLHGDKSKPMI
ChAd55    TLDKEYWNFRKGDVTPAEPYTNAIGFMPNIKAYPEWTNSAAKSHIVGKVYLHGEVSKPLD
ChAd73    SMVGDYWNFREGQTTQSVAYTNAVGFMPNLGAYPKTQSKTPKNSIVSQVYLNGETTMPNT
ChAd83    STLKKYWGYRQGDSIDGTPYVEAVGFMPNLKAYPKSQSSTTKNNIVGQVYNNGDVSKPML
ChAd146   STLKKYWGYRQGDSIDGTPYTNAVGFMPNLKAYPKSQSSTTKNNIVGQVYNNGDVSKPML
ChAd147   TLNKEYWNYRQGSLIFGTPYTHAVGFMPNNKAYFRNTTAASKSHIVGDVYLDGDADRPLS

PanAd1    LTTTLNGTNETG-DATVSTYSMSFSWNWNGS-NYINDTFQTNSFTFSYIAQE (SEQ ID NO: 19)
PanAd2    LFITLNGTRETG-DATVSTYSMSFSWNWNGS-NYINDTFQTNSFTFSYIAQE (SEQ ID NO: 50)
```

FIG. 2C

```
PanAd3     LTITLNGTNESSETSQVSHYSMSFTWSWDSG-KYATETPATNSFTFSYIAEQ (SEQ ID NO: 53)
ChAd55     LIITFNETSNE------PCTYCIRFQNQWGTD-KYKNETLAVSSFTFSYIAQE (SEQ ID NO: 14)
ChAd73     LTITFNGTDEKD-TTPVSTYSMFFTWQWTGDYKDKNITEATNSFTFSYNAQE (SEQ ID NO: 15)
ChAd83     LTITLNGTDDS------NSTYSMSFSYTWTNG-SYVGATFGANSYTFSYIAQE (SEQ ID NO: 16)
ChAd146    LTITLNGTDDS------NSTYSMSFSYTWTNG-SYVGATFGANSYTFSYIAQE (SEQ ID NO: 17)
ChAd147    LIITFNETDDE------PCDYCINFQWKWGAD-QYKDKTLATSSFTFSYIAQE (SEQ ID NO: 18)
```

FIG. 3A

Adenovirus Penton Protein

CLUSTAL W (1.83) multiple sequence alignment

```
PanAd1      -MRRAAMYHEGPPPSYESVVGA--AAASPFASQLEPPYVPPRYLRPTGGRNSIRYSELAP
PanAd2      -MRRAAMYHEGPPPSYESVVGA--AAASPFASQLEPPYVPPRYLRPTGGRNSIRYSELAP
PanAd3      -MRRAAMYHEGPPPSYESVVGA--AAASPFASQLEPPYVPPRYLRPTGGRNSIRYSELAP
ChAd55      MMRR---VYPEGPPPSYESVNQQ--AVAAAMQPPLEAPYVPPRYLAPTEGRNSIRYSELAP
ChAd73      MMRR---VYPEGPPPSYESVNQQ--AVAVAMQPPLEAPYVPPRYLAPTEGRNSIRYSELAP
ChAd83      MMRR---VYPEGPPPSYESVNQQ--AVAAAMQPPLEAPYVPPRYLAPTEGRNSIRYSELAP
ChAd146     MMRR---VYPEGPPPSYESVMQQ--AVAAAMQPPLEAPYVPPRYLAPTEGRNSIRYSELAP
ChAd147     MMRR---AYPEGPPPSYESVMQQANAAAANQPPLEAPYVPPRYLAPTEGRNSIRYSELAP
             ***    * *********;       *.*  .; . ** ********  **  **********

PanAd1      LYDTTRVYLVDNKSADVASLNYQNDHSNFLTTVIQNNDYTPSEASTQTIRLDDRSRWGGD
PanAd2      LYDTTRVYLVDNKSADVASLNYQNDHSNFLTTVIQNNDYTPSEASTQTIRLDDRSHWGGD
PanAd3      LYDTTRVYLVDNKSADVASLNYQRDHSNFLTTVIQNNDYTPSEASTQTINLDDRSRWGGD
ChAd55      LYDTTRLYLVDNKSADIASLNYQNDHSNFLTTVVQNNDFTPTEASTQTINFDERSRWGGQ
ChAd73      LYDTTRLYLVQNKSADIASLNYQNDHSNFLTTVVQNNDFTPTEASTQTINFDERSRWGGQ
ChAd83      LYDTTRLYLVDNKSADIASLNYQNDHSNFLTTVVQNNDFTPTEASTQTINFDERSRWGGQ
ChAd146     LYDTTRLYLVDNKSADIASLNYQNDHSNFLTTVVQNNDFTPTEASTQTINFDERSRWGGQ
ChAd147     LYDTTRLYLVDNKSADIASLNYQNDHSNFLTTVVQNNDFTPTEASTQTINFDERSRWGGQ
             *****;*********;*************;**** (**;********;*;**;*;***;

PanAd1      LKTILRTNMPNVNEFMFTNKFEARVMVSRSHEK--------DDRVELKYEWVEFELPEG
PanAd2      LKTILRTNMPNVNEFMFTNKFKARVMVSRSHTK--------DDRVELKYEWVEFELPEG
PanAd3      LKTILRTNMPNVNEFMFTNKFKARVMVSRSHTK--------DDRVELKYEWVEFELPEG
ChAd55      LKTIMRTNMPNVNEFMYSNKFKARVMVSRKTPNGVAVGDDYDGSQDELTYEWVEFELPEG
ChAd73      LKTIMRTNMPNVNEFMYSNKFEARVMVSRKTPNGVTVGDDYDGSQDELTYEWVEFELPEG
ChAd83      LKTIMRTNMPNVNEFMYSNKFKARVMVSRKTPNGVTVTD---GSQDELTYEWVEFELPEG
ChAd146     LKTIMRTNMPNVNEFLYSNKFKARVMVSRKTPNGVTVTD---GSQDELTYEWVEFELPEG
ChAd147     LKTIMRTNMPNVNEFMYSNKFKARVMVSRKTPNGVTVTEDYDGSQDELKYEWVEFELPEG
             ****;**********;;;***** *****;.  *;          ***;**********

PanAd1      NYSETMTIDLMNNAIVEHYLKVGRQNGVLESDIGVKFDTRNFRLGLDPVTGLVMPGVYTN
PanAd2      NYSETMTIDLMNNAIVEHYLKVGRQNGVLESDIGVKFDTRNFRLGLDPVTGLVMPGVYTN
PanAd3      NYSETMTIDLMNNAIVERYLKVGRQNGVLESDIGVKFDTRNFRLGLDPVTGLVMPGVYTN
ChAd55      NFSVTMTIDLMNNAIIDNYLAVGRQNGVLESDIGVKFDTRNFRLGWDPVTELVMPGVYTN
ChAd73      NFSVTMTIDLMNNAIIDNYLAVGRQNGVLESDIGVKFDTRNFRLGWDPVTELVMPGVYTN
ChAd83      NFSVTMTIDLMNNAIIDNYLAVGRQNGVLESDIGVKFDTRNFRLGWDPVTELVMPGVYTN
ChAd146     NFSVTMTIDLMNNAIIDNYLAVGRQNGVLESDIGVKFDTRNFRLGWDPVTELVMPGVYTN
ChAd147     NFSVTMTIDLMNNAIIDNYLAVGRQNGVLESDIGVKFDTRNFRLGWDPVTELVMPGVYTN
             *;* **********;;;** **********************  ****  *********

PanAd1      EAFHPDIILLPGCGVDFTYSRLSNLLGIRKRQPFQEGFRITYEDLEGGNIPALLDVEAYQ
PanAd2      EAFHPDIILLPGCGVDFTYSRLSMLLGIRKRQPFQEGFRITYEDLEGGNIPALLDVEAYQ
```

FIG. 3B

```
PanAd3    EAFHPDIILLPGCGVDFTYSRLSNLLGIRKRQPFQEGFRITYEDLEGGNIPALLDVEAYQ
ChAd55    EAFHPDIVLLPGCGVDFTESRLSNLLGIRKRQPFQEGFQTLYEDLEGGNIPALLDVEAYE
ChAd73    EAFHPDIVLLPGCGVDFTESRLSNLLGIRKRQPFQEGFQILYEDLEGGNIPALLDVEAYE
ChAd83    EAFHPDIVLLPGCGVDFTESRLSNLLGIRKRQPFQEGFQILYEDLEGGNIPALLDVEAYE
ChAd146   EAFHPDIVLLPGCGVDFTESRLSNLLGIRKRQPFQEGFQIMYEDLEGGNIPALLDVEAYE
ChAd147   EAFHPDIVLLPGCGVDFTESRLSNLLGIRKRQPFQEGFQIMYEDLEGGNIPALLDVDAYE
          ******:*:****** :******:**********:**::******:********:.**:

PanAd1    DSLKEEEAGEGSGGG--AGQEEGGASSEASADPAAAAEAEAADPAMVEEEKDMNDEAVR
PanAd2    NSLKEEEAGEGSGGGG-AGQEEGGASSEASADAAAAEAESAADPAMVEEEKDMNDEAVR
PanAd3    DSLKEEEAGEGSGGGGGAGQEEGGASSEASADAAAAAEAEAADPAMVEEEKDMNDEAVR
ChAd55    KSKEE----------------SAAAATAAVA----------------TASTEVR
ChAd73    KSKEDS----------AAATTAAVATAATTD----------------ADATTTR
ChAd83    KSKED-----------STAVATAATV---------------------ADATVTR
ChAd146   KSKED-----------SAAAATAAVA---------------------TASTEVR
ChAd147   KSKEE-----------SAAAATAAVA---------------------TASTEVR
          .*:*:                :   *.*..                    :*

PanAd1    GDTFATRGEEKKAEAEAAAEEAAAAAA-VEAAAEAEKPPKEPVIKPLTEDSKKRSYNVL
PanAd2    GDTFATRGEEKKAEAEAAAEEAAAAAA-VEAAAEAEKPPKEPVIKPLTEDSKKRSYNVL
PanAd3    GDTFATRGEEKKAEAEAAAEEAAAAAAAVEAAAEAEKPPKEPVIKALTEDSKKRSYNVL
ChAd55    GDNFASAAAVA----EAAETESKIVIQP----------------VEKDSKDRSYNVL
ChAd73    GDTFATQAEEAAALAATDDSESKIVIKP----------------VEKDSKDRSYNVL
ChAd83    GDTFATQAEEAAALAATDDSESKIVIKP----------------VEKDSKDRSYNVL
ChAd146   GDNFASAAAVA----EAAETESKIVIQP----------------VEKDSKDRSYNVL
ChAd147   GDNFASAAAVAA--AEAAETESKIVIQP----------------VEKDSKDRSYNVL
          **.**:: .          *:   :                   :**..**.*****

PanAd1    KDSTNTEYRSWYLAYNYGDPATGVRSWTLLCTPDVTCGSEQVYWSLPDMMQDPVTFRSTR
PanAd2    KDSTNTEYRSWYLAYNYGDPATGVRSWTLLCTPDVTCGSEQVYWSLPDMMQDPVTFRSTR
PanAd3    KDSTNTAYRSWYLAYNYGDPATGVRSWTLLCTPDVTCGSEQVYWSLPDMMQDPVTFRSTR
ChAd55    ADKKNTAYRSWYLAYNYGDPEKGVRSWTLLTTSDVTCGVEQVYWSLPDMMQDPVTFRSTR
ChAd73    ADKKNTAYRSWYLAYNYGDPEKGVRSWTLLTTSDVTCGVEQVYWSLPDMMQDPVTFRSTR
ChAd83    SDGKNTAYRSWYLAYNYGDPEKGVRSWTLLTTSDVTCGVEQVYWSLPDMMQDPVTFRSTR
ChAd146   ADKKNTAYRSWYLAYNYGDPEKGVRSWTLLTTSDVTCGVEQVYWSLPDMMQDPVTFRSTR
ChAd147   PDKINTAYRSWYLAYNYGDPEKGVRSWTLLTTSDVTCGVEQVYWSLPDMMQDPVTFRSTR
           * :**:************ .********.*.****** *********************

PanAd1    QVSNFPVVGAELLPVHSKSFYNDQAVYSQLIRQFTSLTHVFNRFPENQILARPPAPTITT
PanAd2    QVSNFPVVGAELLPVHSKSFYNDQAVYSQLIRQFTSLTHVFNRFPENQILARPPAPTITT
PanAd3    QVSNFPVVGAELLPVHSKSFYNDQAVYSQLIRQFTSLTHVFNRFPENQILARPPAPTITT
ChAd55    QVSNYPVVGAELLPVYSKSFFNEQAVYSQQLRAFTSLTHVFNRFPENQILVRPPAPTITT
ChAd73    QVSNYPVVGAELLPVYSKSFFNEQAVYSQQLRAFTSLTHVFNRFPENQILVRPPAPTITT
ChAd83    QVSNYPVVGAELLPVYSKSFFNEQAVYSQQLRAFTSLTHVFNRFPENQILVRPPAPTITT
ChAd146   QVSNYPVVGAELLPVYSKSFFNEQAVYSQQLRAFTSLTHVFNRFPENQILVRPPAPTITT
ChAd147   QVSNYPVVGAELLPVYSKSFFNEQAVYSQQLRAFTSLTHVFNRFPENQILVRPPAPTITT
          ****:**********:****:*:******  * :******************..********

PanAd1    VSENVPALTDHGTLPLRNSIGGVQRVTVTDARRRTCPYVYKALGIVSPRVLSSRTF (SEQ ID NO:31)
PanAd2    VSENVPALTDHGTLPLRNSIGGVQRVTVTDARRRTCPYVYKALGIVSPRVLSSRTF (SEQ ID NO:52)
PanAd3    VSENVPALTDHGTLPLRNSIGGVQRVTVTDARRRTCPYVYKALGIVSPRVLSSRTF (SEQ ID NO:55)
ChAd55    VSENVPALTDHGTLPLRSSIRGVQRVTVTDARRRTCPYVYKALGVVAPRVLSSRTF (SEQ ID NO:26)
```

FIG. 3C

```
ChAd73    VSENVPALTDHGTLPLRSSIRGVQRVTVTDARRRTCPYVYKALGVVAPRVLSSRTF  (SEQ ID NO: 27)
ChAd83    VSENVPALTDHGTLPLRSSTRGVQRVTVTDARRRTCPYVYKALGVVAPRVLSSRTF  (SEQ ID NO: 28)
ChAd146   VSENVPALTDHGTLPLRSSIRGVQRVTVTDARRRTCPYVYKALGVVAPRVLSSRTF  (SEQ ID NO: 29)
ChAd147   VSENVPALTDHGTLPLRSSIRGVQRVTVTDARRRTCPYVYKALGIVAPRVLSSRTF  (SEQ ID NO: 30)
```

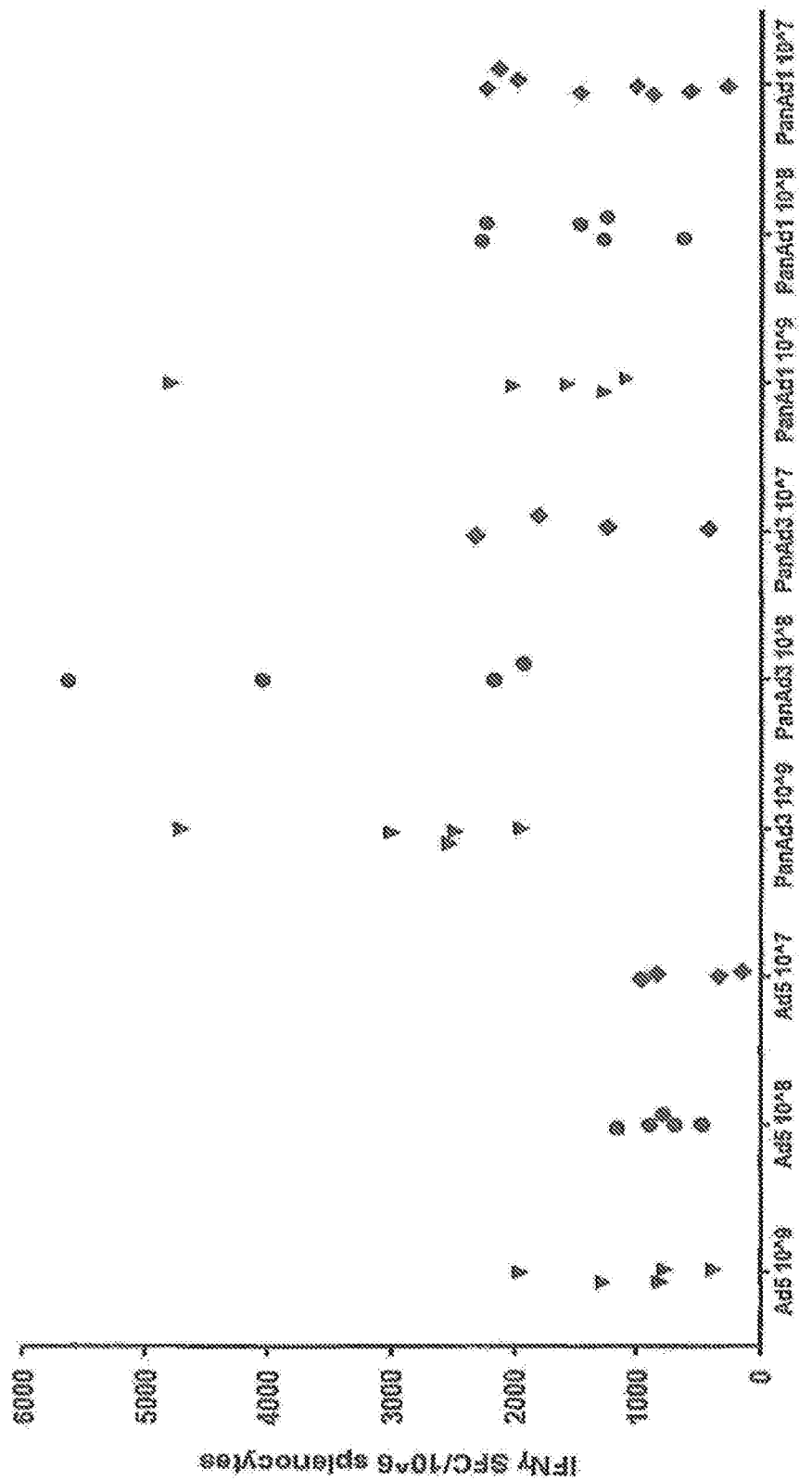

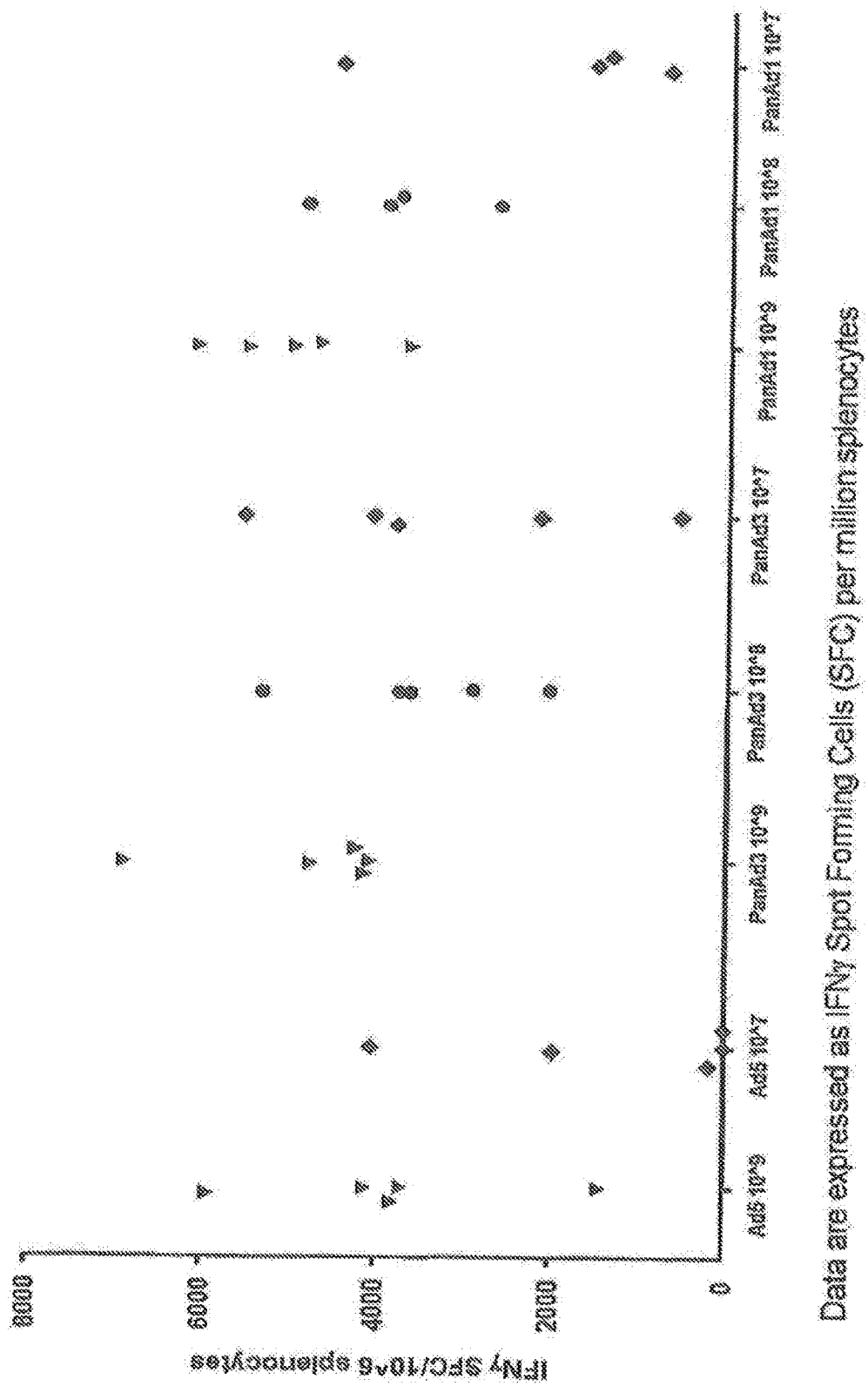

SEQUENCE LISTING

```
<160> NUMBER OF SEQ ID NOS: 65

<210> SEQ ID NO 1
<211> LENGTH: 1503
<212> TYPE: DNA
<213> ORGANISM: Human immunodeficiency virus

<400> SEQUENCE: 1
atgggtgcta gggcttctgt gctgtctggt ggtgagctgg acaagtggga gaagatcagg      60
ctgaggcctg gtggcaagaa gaagtacaag ctaaagcaca ttgtgtgggc ctccagggag     120
```

```
ctggagaggt tgctgtgaa ccctggcctg ctggagacct ctgagggtg caggcagatc    180
ctgggccagc tccagccctc cctgcaaaca ggctctgagg agctgaggtc cctgtacaac    240
acagtggcta ccctgtactg tgtgcaccag aagattgatg tgaaggacac caaggaggcc    300
ctggagaaga ttgaggagga gcagaacaag tccaagaaga aggcccagca ggctgctgct    360
ggcacaggca actccagcca ggtgtcccag aactacccca ttgtgcagaa cctccagggc    420
cagatggtgc accaggccat ctcccccgg accctgaatg cctgggtgaa ggtggtggag    480
gagaaggcct tctcccctga ggtgatcccc atgttctctg ccctgtctga gggtgccacc    540
ccccaggacc tgaacaccat gctgaacaca gtgggggggcc atcaggctgc catgcagatg    600
ctgaaggaga ccatcaatga ggaggctgct gagtgggaca ggctgcatcc tgtgcacgct    660
ggccccattg cccccggcca gatgaggag cccaggggct ctgacattgc tggcaccacc    720
tccaccctcc aggagcagat tggctggatg accaacaacc ccccatccc tgtgggggaa    780
atctacaaga ggtggatcat cctgggcctg aacaagattg tgaggatgta ctcccccacc    840
tccatcctgg acatcaggca gggcccccaag gagcccttca gggactatgt ggacaggttc    900
tacaagaccc tgagggctga gcaggcctcc caggaggtga agaactggat gacagagacc    960
ctgctggtgc agaatgccaa ccctgactgc aagaccatcc tgaaggccct gggccctgct    1020
gccaccctgg aggagatgat gacagcctgc caggggtgg ggggccctgg tcacaaggcc    1080
agggtgctgc tgaggccat gtcccaggtg accaactccg ccaccatcat gatgcagagg    1140
ggcaacttca ggaaccagag gaagacagtg aagtgcttca ctgtggcaa ggtgggccac    1200
attgccaaga ctgtagggc ccccaggaag aagggctgct ggaagtgtgg caaggagggc    1260
caccagatga aggactgcaa tgagaggcag gccaacttcc tgggcaaaat ctggcccctcc    1320
cacaagggca ggcctggcaa cttcctccag tccaggcctg agcccacagc ccctcccgag    1380
gagtccttca ggtttgggga ggagaagacc accccccagcc agaagcagga gcccattgac    1440
aaggagctgt acccccctggc ctccctgagg tccctgtttg gcaacgaccc ctcctcccag    1500
taa                                                                  1503

<210> SEQ ID NO 2
<211> LENGTH: 20
<212> TYPE: DNA
<213> ORGANISM: artificial
<220> FEATURE:
<223> OTHER INFORMATION: TLR9 agonist

<400> SEQUENCE: 2
tccatgacgt tcctgacgtt                                                20

<210> SEQ ID NO 3
<211> LENGTH: 22
<212> TYPE: DNA
<213> ORGANISM: artificial
<220> FEATURE:
<223> OTHER INFORMATION: Primer: HVR7 primer1

<400> SEQUENCE: 3
tgtcctacca rctcttgctt ga                                             22

<210> SEQ ID NO 4
<211> LENGTH: 18
<212> TYPE: DNA
<213> ORGANISM: artificial
<220> FEATURE:
<223> OTHER INFORMATION: primer: HVR7 primer2
```

```
<400> SEQUENCE: 4
gtggaarggc acgtagcg                                              18

<210> SEQ ID NO 5
<211> LENGTH: 20
<212> TYPE: DNA
<213> ORGANISM: artificial
<220> FEATURE:
<223> OTHER INFORMATION: primer: HVR1-6fd

<400> SEQUENCE: 5
caygatgtga ccaccgaccg                                            20

<210> SEQ ID NO 6
<211> LENGTH: 20
<212> TYPE: DNA
<213> ORGANISM: artificial
<220> FEATURE:
<223> OTHER INFORMATION: primer: HVR1-6rev

<400> SEQUENCE: 6
gtgttyctgt cytgcaagtc                                            20

<210> SEQ ID NO 7
<211> LENGTH: 45
<212> TYPE: DNA
<213> ORGANISM: artificial
<220> FEATURE:
<223> OTHER INFORMATION: primer: PanAd1 left end P1

<400> SEQUENCE: 7
atctggaatt cgtttaaacc atcatcaata atataccttta ttttg               45

<210> SEQ ID NO 8
<211> LENGTH: 46
<212> TYPE: DNA
<213> ORGANISM: artificial
<220> FEATURE:
<223> OTHER INFORMATION: primer: PanAd1 left end P2

<400> SEQUENCE: 8
tcaggaacta gttccgtata cctataataa taaaacggag actttg               46

<210> SEQ ID NO 9
<211> LENGTH: 34
<212> TYPE: DNA
<213> ORGANISM: artificial
<220> FEATURE:
<223> OTHER INFORMATION: primer: PanAd1 right end P1

<400> SEQUENCE: 9
tccagcggcg cgccagaccc gagtcttacc agga                            34

<210> SEQ ID NO 10
<211> LENGTH: 51
<212> TYPE: DNA
<213> ORGANISM: artificial
<220> FEATURE:
<223> OTHER INFORMATION: primer: PanAd1 right end P2

<400> SEQUENCE: 10
attcaggatc cgaattcgtt taaaccatca tcaataatat accttatttt g         51

<210> SEQ ID NO 11
```

```
<211> LENGTH: 33
<212> TYPE: DNA
<213> ORGANISM: artificial
<220> FEATURE:
<223> OTHER INFORMATION: primer: pIX P1

<400> SEQUENCE: 11
tattctgcga tcgctgaggt gggtgagtgg gcg                                 33

<210> SEQ ID NO 12
<211> LENGTH: 44
<212> TYPE: DNA
<213> ORGANISM: artificial
<220> FEATURE:
<223> OTHER INFORMATION: primer: pIX P2

<400> SEQUENCE: 12
ttactggcgc gcctgcctcg agtaaacggc atttgcagga gaag                     44

<210> SEQ ID NO 13
<211> LENGTH: 37772
<212> TYPE: DNA
<213> ORGANISM: Adenoviridae - Mastadenovirus

<400> SEQUENCE: 13
catcatcaat aatataccttt attttggatt gaagccaata tgataatgag gtgggcggag     60
cggggcgggg cggggaggag cggcggcgcg gggcgggccg ggaggtgtgg cggaagttga    120
gtttgtaagt gtggcggatg tgacttgcta gcgccggatg tggtaaaagt gacgttttt    180 ggagtgcgac aacgcccacg ggaagtgaca ttttcccgc ggttttacc ggatgtcgta    240 gtgaatttgg gcgttaccaa gtaagatttg gccattttcg cgggaaaact gaatggga    300 agtgaaatct gattaatttc gcgttagtca taccgcgtaa tatttgccga gggccgaggg    360
actttgaccg attacgtgga ggaatcgccc aggtgttttt tgaggtgaat tccgcgttc    420 cgggtcaaag tctccgtttt attattatag tcagctgacg cggagtgtat ttatacccgc    480
tgatctcgtc aagaggccac tcttgagtgc cagcgagtag agttttctcc tctgccgctc    540
cgctctgaca ccgggggaaa aatgagacat ttcacctacg atggcggtgt cctcaccggc    600
cagctggctg cctcggtcct ggacgccctg atcgaggagg tattggccga caattatcct    660
cctccagctc atttgagcc acctactctt cacgaactgt atgatttgga cgtggtggca    720
cctagcgacc cgaacgagca ggcggtttcc agtttttttc ctgactctat gctgttggcc    780
agccaggagg gggtcgagct cgagaccct cctccaatcg ccgtttctcc tgagcctccg    840
accctgacca ggcagcccga tcgccgtgtt ggacctgcga ctatgcccca tctgctgccc    900
gaggtgatcg atctcacctg taacgagtct ggttttccac ccagcgagga tgaggacgaa    960
gagggtgagc agtttgtgtt agattctgtg gaggaacccg gcgcggttg cagatcttgt   1020 caataccatc ggaaaaatac aggagacccc caaattatgt gttccctgtg ttatatgaag   1080
acgacctgta tgtttattta cagtaagttt gtgattggtg gtcggtggg ctgtagtgtg   1140 ggtaggtggt ctgtggtttt ttttttttta atatcagctt gggctaaaaa actgctatgg   1200
taattttttt aaggtccggt gtctgaacct gagcaggaag ctgaaccgga gcctgagagt   1260
cgccccagga gaaggcctgc aattctaact agaccgagtg cacctgtagc gagggacctc   1320
agcagtgcag agaccaccga ttccggtcct tcctcatccc ctccagagat tcatcccgtg   1380
gtgcctttgt gtccctcaa gcccgttgcc gtgagagtta gtgggcggag ggccgccgtg   1440
gagagcattg aggacttgct taatgagaca caggaacctt tggacttgag ctgtaaacgc   1500
```

```
cctaggcaat aaacctgctt acctggactg aatgagttga cgcctatgtt tgcttttgaa    1560
tgacttaatg tgtatataat aaagagtgag ataatgttta attgcatggt gtgtttgatt    1620
ggggcggggt ttgttgggta tataagcttc cctgggctaa acttggttac acttgacctc    1680
atggaggcct gggagtgttt agagagcttt gccgaagtgc gtgccttgct ggaagagagc    1740
tctaataata cctctgggtg gtggaggtat ttttggggct ctccccaggc taagttagtt    1800
tgtagaatca aggaggatta caagtgggaa tttgaacagc ttttgaaatc tgtggtgag    1860 ctcttggatt ctttgaatct gggccaccag gctcttttcc aggacaagat catcaggact    1920
ttggattttt ccacaccggg gcgcattgct gccggggttg cttttctagc ttttttgaag    1980
gataaatgga gcgaagagac ccacttgagt tcgggatacg tcctggattt tctggccata    2040
caactgtgga gagcatggat caggcacaag aacagaatgc aactgttgtc ttccgtccgt    2100
ccgttgctga ttcagccgga ggagcagcag accgggccgg aggaccgggc tcgtctggaa    2160
ccagaagaga gggcaccgga gaggagcgcg tggaacctgg gagccggcct gaacggccat    2220
ccacatcggg agtgaatgtt ggacaggtgg cggatctctt tccagaactg cgacgaatct    2280
taactatcag ggaggatgga caatttgtta aggggcttaa gagggagcgg ggggcttctg    2340
aacataacga ggaggccagt aatttagctt ttagtctgat gaccagacac cgtcccgagt    2400
gcattacttt tcagcagatt aaggataatt gtgccaatga gttagatctg ctgggtcaga    2460
agtacagcat agagcagttg accacttact ggctgcagcc gggtgatgat ctggaggaag    2520
ctattagggt gtatgccaag gtggcccctga ggcccgattg caagtacaag ctcaaggggc    2580
tggtgaatat caggaattgt tgctacattt ctgggaacgg ggcggaggtg gagatagaga    2640
ccgatgacag ggtggccttt aggtgtagca tgatgaatat gtggcctggg gtgctgggca    2700
tggacggggt ggtgattatg aatgtgaggt tcacggggcc caattttaat ggcacggtgt    2760
tcctgggcaa caccaacttg gtgctgcacg gggtgagctt ctatggcttt aacaacacct    2820
gtgtggaggc ctggaccgat gtgaaggtcc gtggctgtgc cttctacgga tgttggaagg    2880
cggtagtgtg tcgccccaag agcaggagtt ccattaaaaa atgcttgttt gagaggtgca    2940
ccctgggggt gctggcggag ggcaactgtc gggtgcgcca caatgtggcc tcagaatgcg    3000
gttgcttcat gctagtcaag agcgtggcgg tcatcaagca taacatggtg tgcggcaaca    3060
gcgaggacaa ggcctcgcag atgctgacct gctcggatgg caactgccac ttactgaaga    3120
ccgtacatat aaccagccac agccgcaagg cctggcccgt gttcgagcac aacgtgttga    3180
cccgctgctc tttgcatctg gcaacagga ggggtgtgtt cctgccctat caatgcaact    3240
tgagccacac caagatcttg ctagagcccg aaagcatgtc caaggtgaac ctgaacgggg    3300
tgtttgacat gaccctgaag atatggaagg tgctgaggta cgacgagacc aggtctcgat    3360
gcaggccctg cgagtgcggg gcaagcata tgaggaacca gcctgtgatg ctggatgtga    3420
ccgaggagct gaggcctgac cacttggttc tggcctgcac cagggccgag tttggttcta    3480
gcgatgaaga cacagactga ggtgggtgag tgggcgtggt ctggggtgg gaagcaatat    3540 ataagttggg ggtcttaggg tctctgtgtc tgttttgcag agggaccgcc ggcgccatga    3600
gcgggagcag tagcagcaac gccttggatg gcagcatcgt gagcccttat ttgacgacgc    3660
gcatgcccca ctgggccggg gtgcgtcaga atgtgatggg ctccagcatc gacggacgac    3720
ccgtgctgcc cgcaaattcc gccacgctga cctacgcgac cgtcgcgggg acccccgttgg    3780 acgccaccgc cgccgccgcc gccaccgccg ccgcctcggc cgtgcgcagc ctggccacgg    3840
```

```
actttgcatt cttgggaccc ttggccaccg gggcggccgc ccgtgccgcc gttcgcgatg    3900
acaagctgac cgccctgctg gcgcagttgg atgcgcttac ccgggaactg ggtgaccttt    3960
cgcagcaggt cgtggccctg cgccagcagg tctccgccct gcaggctagc gggaatgctt    4020
ctcctgcaaa tgccgtttaa gataaataaa accagactct gtttggatta agaaaagta    4080 gcaagtgcat tgctctcttt atttcataat tttccgcgcg cgataggccc gagtccagcg    4140
ttctcggtcg ttgagggtgc ggtgtatctt ctccaggacg tggtagaggt ggctctggac    4200
gttgagatac atgggcatga gcccgtcccg ggggtggagg tagcaccact gcagagcttc    4260
atgctccggg gtggtgttgt agatgatcca gtcgtagcag gagcgctggg catggtgcct    4320
aaaaatgtcc ttaagcagca ggccgatggc caggggagg cccttggtgt aagtgtttac     4380
aaaacggttg agttgggaag ggtgcatgcg gggtgagatg atgtgcatct tagattgtat    4440
ttttagattg gcgatgtttc ctcccagatc ccttctggga ttcatgttgt ggaggaccac    4500
cagcacagta tatccggtgc acttgggaaa tttgtcatgc agcttagagg gaaatgcgtg    4560
gaagaacttg gagacgccct tgtggcctcc cagattctcc atgcattcgt ccatgatgat    4620
ggcaatgggc ccgcgggagg cggcctgggc aaagatgttt ctgggtcac tgacatcgta     4680 gttgtgttcc agggtgagat cgtcatagcc cattttata aagcgcgggc ggagggtgcc     4740
cgactggggg atgatggttc cctcgggccc cggggcgtag ttgccttcgc agatctgcat    4800
ttcccaggcc ttaatctctg agggggaat catatccact gcggggcga tgaagaaaac     4860 ggtttccgga gccggggaga ttaactggga tgagagcagg tttctcagca gctgtgactt    4920
tccacagccg gtgggtccat aaataacacc tataaccggc tgcagctggt agttgagcga    4980
gctgcagctg ccgtcgtccc ggaggagggg ggccacctca ttgagcatgt cccggacgcg    5040
cttgttctcc tcgaccaggt ccgccagaag gcgctcgccg cccagggaca gcagctcttg    5100
caaggaagca aagttttttca gcggtttgag gccgtccgcc gtgggcatgt ttttcagggt    5160
ctggccgagc agctccaggc ggtcccagag ctcggtgacg tgctctacgg catctctatc    5220
cagcatatct cctcgtttcg cgggttgggg cggctttcgc tgtagggcac caggcgatgg    5280
tcgtccagcg cggccagagt catgtccttc catgggcgca gggtcctcgt cagggtggtc    5340
tgggtcacgg tgaaggggtg cgccccgggc tgggcgctgg ccagggtgcg cttgagactg    5400
gtcctgctgg tgctgaagcg ctgccggtct tcgccctgcg cgtcggccag gtagcatttg    5460
accatggtgt cgtagtccag cccctccgcg gcgtgtccct tggcgcgcag cttgcccttg    5520
gaggtggcgc cgcacgcggg gcactgcagg ctcttgagcg cgtagagctt ggggcgagg    5580 aagaccgatt cggggagta ggcgtccgcg ccgcaggccc cgcacacggt ctcgcactcc     5640
accagccagg tgagctcggg gcgctcgggg tcaaaaacca ggtttccccc atgcttttg     5700 atgcgtttct tacctcgggt ctccatgagg cggtgtcccc gttcggtgac gaagaggctg    5760
tccgtgtctc cgtagaccga cttgaggggt ctgtcctcca ggggggtccc tcggtcctct    5820
tcgtagagaa actcggacca ctctgagaca aaggcccgcg tccaggccag gacgaaggag    5880
gccaggtggg aggggtaccg gtcgttgtcc actagggggt ccaccttctc caaggtgtga    5940
agacacatgt cgccctcctc ggcgtccagg aaggtgattg gcttgtaggt gtaggccacg    6000
tgacccgggg ttccggacgg gggggtataa aagggggtgg gggcgcgctc gtcctcactc    6060
tcttccgcat cgctgtctgc gagggccagc tgctggggtg agtattccct ctcgaaggcg    6120
ggcatgacct cagcgctgag gctgtcagtt tctaaaaacg aggaggattt gatgttcacc    6180
tgtcccgagc tgatgccttt gagggtgccc gcgtccatct ggtcagaaaa cacgatcttt    6240
```

```
ttattgtcca gcttggtggc gaacgacccg tagagggcgt tggagagcag cttggcgatg   6300
gagcgcaggg tctgattctt gtcccggtcg gcgcgctcct tggccgcgat gttgagctgc   6360
acgtactcgc gcgcgacgca gcgccactcg gggaagacgg tggtgcgctc gtcgggcacc   6420
aggcgcacgc gccagccgcg gttgtgcagg gtgacgaggt ccacgctggt ggcgacctcg   6480
ccgcgcaggc gctcgttggt ccagcagagg cgcccgccct tgcgcgagca aaggggggc   6540 aggggggtcga gttgggtttc gtccgggggg tccgcgtcca ccgtgaagac cccggggcgc   6600
aggcgcgcgt cgaagtagtc gatcttgcat ccttgcaagt ccagcgcccg ctgccagtcg   6660
cgggcggcga gcgcgcgctc gtaggggttg agcggcgggc cccagggcat ggggtgggtg   6720
agcgcggagg cgtacatgcc gcagatgtca tagacgtaga ggggctcccg gaggatgccc   6780
aggtaggtgg ggtagcagcg gccgccgcg atgctggcgc gcacgtagtc gtagagctcg    6840
tgcgaggggg cgaggaggtc ggggcccagg ttggtgcggg cggggcgctc cgcgcggaag   6900
acgatctgcc tgaagatggc atgcgagttg aagagatgg tggggcgctg gaagacgttg    6960
aagctggcgt cctgcaggcc gacggcgtcg cgcacgaagg aggcgtagga ctcgcgcagc   7020
ttgtgcacca gctcggcggt gacctgcacg tcgagcgcgc agtagtcgag ggtctcgcgg   7080
atgatgtcat acttagcctg ccccttcttt ttccacagct cgcggttgag gacgaactct   7140
tcgcggtctt tccagtactc ttggatcggg aaaccgtccg gctccgaacg gtaagagccc   7200
agcatgtaga actggttgac ggcctggtag gcgcagcagc ccttctccac gggcagggcg   7260
taggcctgcg cggccttgcg gagcgaggtg tgggtcaggg cgaaggtgtc cctgaccatg   7320
accttgaggt actggtgttt gaagtcggag tcgtcgcagc cgccccgctc ccagagcgag   7380
aagtcggtgc gcttttttgga gcgggggttg ggcagcgcga aggtgacatc gttgtagagg   7440
atcttgcccg cgcgaggcat gaagttgcgg gtgatgcgga agggccccgg cacttccgag   7500
cggttgttga tgacctgggc ggcgagcacg atctcgtcga agccgttgat gttgtggccc   7560
acgatgtaga gttccaggaa gcggggccgg cccttgacgc tgggcagctt ctttagctct   7620
tcgtaggtga gctcctcggg cgaggcgagg ccgtgctcgg ccagggccca gtccgccagg   7680
tgcgggttgt ccgcgaggaa ggaccgccag aggtcgcggg ccaggagggt ctgcaggcgg   7740
tccctgaagg tcctgaactg gcggcctacg gccatctttt cggggggtgac gcagtagaag   7800 gtgaggggt cttgctgcca ggggtcccag tcgagctcca gggcgaggtc gcgcgcggcg    7860
gcgaccaggc gctcgtcgcc cccgaatttc atgaccagca tgaagggcac gagctgcttt   7920
ccgaaggcgc ccatccaagt gtaggtctct acatcgtagg tgacaaagag acgttccgtg   7980
cgaggatgcg agccgatcgg gaagaactgg atctcccgcc accagttgga ggagtggctg   8040
ttgatgtggt gaaagtagaa gtcccgtcgg cgggccgagc actcgtgctg gcttttgtaa   8100
aagcgagcgc agtactggca gcgctgcacg ggctgtacct cttgcacgag atgcacctgc   8160
cgaccgcgga cgaggaagct gagtgggaat ctgagccccc gcatggctc gcggcctggc    8220 tggtgctctt ctactttgga tgcgtggccg tcaccgtctg gctcctcgag gggtgttacg   8280
gtggagcgga tcaccacgcc gcgcgagccg caggtccaga tatcggcgcg cggcggtcgg   8340
agtttgatga cgacatcgcg cagctgggag ctgtccatgg tctggagctc ccgcggcggc   8400
ggcaggtcag ccgggagttc ttgcaggttt acctcgcaga cacgggccag ggcgcgggc    8460 aggtccaggt ggtacttgaa ttcgagaggc gtgttggtgg cggcgtcgat ggcttgcagt   8520
atgccgcagc cccggggcgc gacgacggtg ccccgcgggg cggtgaagct cccgccgccg   8580
```

```
ctcctgctgt cgccgccggt ggcggggctt agaagcggtg ccgcggtcgg gcccccggag    8640 gtagggggg ctccggtccc gcgggcaggg gcggcagcgg cacgtcggcg ccgcgcgcg     8700 gcaggagctg gtgctgcgcc cggaggttgc tggcgaaggc gacgacgcgg cggttgatct   8760
cctggatctg gcgcctctgc gtgaagacga cgggtccggt gagcttgaac ctgaaagaga  8820
gttcgacaga atcaatctcg gtgtcattga ccgcgacctg gcgcaggatc tcctgcacgt  8880
cgcccgagtt gtcttggtag gcgatctcgg ccatgaactg ttcaatctct tcctcctgga  8940
ggtctccgcg tccggcgcgc tccacggtgg ccgccaggtc gttggagatg cgcgccatga  9000
gctgcgagaa ggcgttgagt ccgccctcgt tccacactcg gctgtagacc acgccgccct  9060
ggtcgtcgcg ggcgcgcatg accacctgcg cgaggttgag ttccacgtgg cgcgcaaaga  9120
cggcgtagtt gcgcaggcgc tggaagaggt agttgagggt ggtggcggtg tgctcggcca  9180
caaagaagta catgacccag cggcgcaacg tggattcgtt gatgtccccc aaggcctcca  9240
gtcgctccat ggcctcgtag aagtccacgg cgaagttgaa aaactgggag ttgcgcgccg  9300
acacggtcaa ctcctcctcc agaagacgga tgagctcggc gacggtgtcg cgcacctcgc  9360
gctcgaaggc tatgggaatc tcttcctccg ccagcatcac cacctcttcc tcttcttcct  9420
cctctggcac ttccatgatg gcttcctcct cttcgggggg tggcggcggg ggaggggcg   9480 ctcggcgccg gcggcggcgc accgggaggc ggtccacgaa gcgctcgatc atctccccgc  9540
ggcggcgacg catggtctcg gtgacggcgc ggccgttctc tcggggacgc agctggaaga  9600
cgccgccggt catctggtgc tgggcgggt ggccgtgggg cagcgagacc gcgctgacga  9660
tgcatcttaa caattgctgc gtaggtacgc cgccgaggga cctgagggag tccagatcca  9720
ccggatccga aacctttcg aggaaggcat ctaaccagtc gcagtcgcaa ggtaggctga   9780
gcaccgtggc gggcggcggg gggtgggggg agtgtctggc ggaggtgctg ctgatgatgt  9840
aattgaagta ggcggtcttg acacggcgga tggtcgacag gagcaccata tctttgggcc  9900
cggcctgctg gatgcggagg cggtcggcca tgccccaggc ttcgttctgg catctgcgca  9960
ggtctttgta gtagtcttgc atgagccttt ccaccggcac ctcttctcct tcttcttctg  10020
acatctctgc tgcatctgcg gccctggggc gacggcgcgc gccctgccc ccatgcgcg    10080 tcaccccgaa cccctgagc ggctggagca gggccaggtc ggcgacgacg cgctcggcca   10140
ggatggcctg ctggacctgc gtgagggtgg tttggaagtc atccaagtcc acgaagcggt  10200
ggtaggcgcc cgtgttgatg gtgtaggtgc agttggccat gacggaccag ttgacggtct  10260
ggtggcccgg ttgcgtcatc tcggtgtacc tgaggcgcga gtaggcgcgc gagtcgaaga  10320
tgtagtcgtt gcaagtccgc accaggtact ggtagcccac caggaagtgc ggcggcggct  10380
ggcggtagag gggccagcgg agggtggcgg gggctccggg ggccaggtct tccagcatga  10440
ggcggtggta ttcgtagatg tacctggaca tccaggtgat gcccgcggcg gtggtggagg  10500
cgcgcgggaa gtcgcgcacc cggttccaga tgttgcgcag cggcagaaag tgctccatgg  10560
taggcgtgct ctggccggtc aggcgcgcgc agtcgttgat actctagacc agggaaaacg  10620
aaagccggtc agcgggcact cttccgtggt ctggtggata aattcgcaag ggtatcatgg  10680
cggagggcct cggttcgagc cccgggcccg ggccggacgg tccgccatga tccacgcggt  10740
taccgcccgc gtgtcgaacc caggtggcga cgtcagacaa cggtggagtg ttccttttgg  10800
gttttttttc caattttttc tggcggggcg ccgacgccgc cgcgtaagag actagagtgc  10860
aaaagcgaaa gcagtaagtg gctcgctccc tgtagcccgg aggatccttg ctaagggttg  10920
cgttgcggcg aacccggtt cgagtctggc tctcgcgggc cgctcgggtc ggccggaacc   10980
```

```
gcggctaagg cgggattggc ctccccctca ttaaagaccc cgcttgcgga ttcctccgga   11040
cacaggggac gagccccttt ttacttttgc ttttctcaga tgcatccggt gctgcggcag   11100
atgcgccccc cgcccagca gcagcagcaa catcagcaag agcggcacca gcagcagcgg   11160
gagtcatgca gggccccctc gcccacgctc ggcggtccgg cgacctcggc gtccgcggcc   11220
gtgtctggag ccggcggcgg ggggctggcg gacgacccgg aggagccccc gcggcgcagg   11280
gccagacagt acctggacct ggaggagggc gagggcctgg cgcgactggg ggcgccgtcc   11340
cccgagcgcc acccgcgggt gcagctgaag cgcgactcgc gcgaggcgta cgtgcctcgg   11400
cagaacctgt tcagagaccg cgcgggcgag gagcccgagg agatgcggga ccgcaggttc   11460
gccgcggggc gggagctgcg gcaggggctg aaccgggagc ggctgctgcg cgaggaggac   11520
tttgagcccg acgcgcggac ggggatcagc cccgcgcgcg cgcacgtggc ggccgccgac   11580
ctggtgacgg catacgagca gacggtgaac caggagatca acttccaaaa aagcttcaac   11640
aaccacgtgc gcacgctggt ggcgcgcgag gaggtgacca tcggcctgat gcacctgtgg   11700
gactttgtga gcgcgctgga gcagaacccc aacagcaagc ctctgacggc gcagctgttc   11760
ctgatagtgc agcacagcag ggacaacgag gcgttcaggg acgcgctgct gaacatcacc   11820
gagcccgagg gtcggtggct cctggacctg attaacatct tgcagagcat agtggtgcag   11880
gagcgcagcc tgagcctggc cgacaaggtg gcggccatca attactcgat gctcagtctg   11940
ggcaagtttt acgcgcgcaa aatctaccag acgccgtacg tgcccataga caaggaggtg   12000
aagatcgacg gcttctacat gcgcatggcg ctgaaggtgc tgaccctgag cgacgacctg   12060
ggcgtgtacc gcaacgagcg catccacaag gccgtgagcg tgagccggcg gcgcgagctg   12120
agcgaccgcg agctgatgca cagcctgcag cgggcgctgg cggggggcgg cagcggcgac   12180
agggaggccg agtcctactt cgaggcgggg gcggacctgc gctgggtgcc cagccggagg   12240
gccctggagg ccgcggggc ccgccgcgag gactatgcag acgaggagga ggaggatgac   12300
gaggagtacg agctagagga gggcgagtac ctggactaaa ccgcaggtgg tgttttggt   12360 agatgcaaga cccgaacgtg gtggacccgg cgctgcgggc ggctctgcag agccagccgt   12420
ccggccttaa ctctacagac gactggcgac aggtcatgga ccgcatcatg tcgctgacgg   12480
cgcgcaatcc ggacgcgttc cggcagcagc cgcaggccaa caggctctcc gccatcttgg   12540
aggcggtggt gcctgcgcgc gcgaaccca cgcacgagaa ggtgctggcc atagtgaacg   12600
cgctggccga gaacagggcc atccgcccgg acgaggccgg gctggtgtac gacgcgctgc   12660
tgcagcgcgt ggcccgctac aacagcgca acgtgcagac caacctggac cggctggtgg   12720
gggacgtgcg cgaggcggtg gcgcagcggg agcgcgcgga gcggcagggc aacctgggct   12780
ccatggtggc gctgaacgcc ttcctgagca cgcagccggc caacgtgccg cggggggcagg   12840 aggactacac caactttgta agcgcgctgc ggctgatggt gaccgagacc cccagagcg   12900 aggtgtacca gtcggggccg gactacttct tccagaccag cagacagggc ctgcagacgg   12960
tgaacctgag ccaggctttc aagaacctgc gggggctgtg gggggtgaag cgcccaccg   13020 gggaccgggc gacggtgtcc agcctgctga cgcccaactc gcgcctgctg ctgctgctga   13080
tcgcgccgtt cacggacagc ggcagcgtgt cccgggagac ctacctcggg cacctgctga   13140
cgctgtaccg cgaggccatc gggcagaccc aggtggacga gcacaccttc caggagatca   13200
ccagcgtgag ccgcgcgctg gggcaggagg acacggcag cctggaggcg accctgaact   13260
acctgctgac caaccggcgg cagaagatcc cctcgctgca tagtttgacc accgaggagg   13320
```

```
agcgcatcct gcgctacgtg cagcagagcg tgagcctgaa cctgatgcgc gacggggtga   13380
cgcccagcgt ggcgctggac atgaccgcgc gcaacatgga accgggcatg tacgccgcgc   13440
accggcctta catcaaccgc ctgatggact acttgcatcg cgcggcggcc gtgaaccccg   13500
agtacttcac caacgccatc ctgaaccgc actggctccc gccgcccggg ttctacagcg   13560
ggggcttcga ggtccccgag gccaacgacg gcttcctgtg ggacgacatg gacgacagcg   13620
tgttctcccc gcggccgcag gcgctggcgg aggcgtcgct gctccgcctc cccaagaagg   13680
aagagagccg ccggcccagc agcgcggcgg cctctctgtc cgagctgggg gcggcggccg   13740
cgcggcccgg gtccctgggg ggcagcccct ttcccagcct ggtggggtct ctgcagagcg   13800
ggcgcaccac ccggccccgg ctgctgggcg aggacgagta cctgaacaac tccctgatgc   13860
agccggtgcg ggagaaaaac ctgccccccg ccttccccaa caacgggata gagagcctgg   13920
tagacaagat gagcagatgg aagacctatg cgcaggagca cagggactcg cccgtgctcc   13980
gtccgcccac gcggcgccag cgccacgacc ggcagcgggg gctggtgtgg gatgacgagg   14040
actccgcgga cgatagcagc gtgctggacc tgggggggag cggcggcaac ccgttcgcgc   14100
acctgcgccc ccgcctgggg aggatgtttc aataaaaaaa aaaaaaaatc aagcatgatg   14160
caaggttttt taagcggata aataaaaaac tcaccaaggc catggcgacc gagcgttgtt   14220
ggtttcttgt tgtgttccct tagtatgcgg cgcgcggcga tgtaccacga gggacctcct   14280
ccctcttatg agagcgtggt gggcgcggcg gcggcctctc cctttgcgtc gcagctggag   14340
ccgccgtacg tgcctccgcg gtacctgcgg cctacggggg gaagaaacag catccgttac   14400
tcggagctgg cgcccctgta cgacaccacc cgggtgtacc tggtggacaa caagtcggcg   14460
gacgtggcct ccctgaacta ccagaacgac cacagcaatt ttttgaccac ggtcatccag   14520
aacaatgact acacccccgag cgaggccagc acccagacca tcaatctgga tgaccggtcg   14580
cactggggcg gcgacctgaa aaccatcctg cacaccaaca tgcccaacgt gaacgagttc   14640
atgttcacca ataagttcaa ggcgcgggtg atggtgtcgc gctcgcacac caaggacgac   14700
cgggtggagc tgaagtacga gtgggtagag ttcgagctgc ccgagggcaa ctactcggag   14760
accatgacca tagacctgat gaacaacgcg atcgtggagc actatctgaa agtgggcagg   14820
cagaacgggg tcctggagag cgacatcggg gtcaagttcg acaccaggaa cttccgcctg   14880
gggctggacc cggtcaccgg gctggttatg cccggggtct acaccaacga ggccttccac   14940
cccgacatca tcctgctgcc cggctgcggg gtggacttca cctacagccg cctgagcaac   15000
ctgctgggca tccgcaagcg gcagcccttc caggagggct tcaggatcac ctacgaggac   15060
ctggaggggg gcaacatccc cgcgctcctg gatgtggagg cctaccagga tagcttgaag   15120
gaagaagagg cgggagaggg cagcggcggt ggcgccggtc aggaggaggg cggggcctcc   15180
tctgaggcct ctgcggaccc agccgctgcc gccgaggcgg aggcggccga ccccgcgatg   15240
gtggtagagg aagagaagga tatgaacgac gaggcggtgc gcggcgacac ctttgccact   15300
cggggggagg agaagaaagc ggaggccgag gccgcggcag aggaggcggc agcagcggcg   15360
gcggcagtag aggcggcggc cgaggcggag aagccccca aggagcccgt gattaagccc   15420
ctgaccgaag atagcaagaa gcgcagttac aacgtgctca aggacagcac caacaccgag   15480
taccgcagct ggtacctggc ctacaactac ggcgacccgg cgacggggt gcgctcctgg   15540 accctgctgt gtacgccgga cgtgacctgc ggctcggagc aggtgtactg gtcgctgccc   15600
gacatgatgc aagaccccgt gaccttccgc tccacgcggc aggtcagcaa cttcccggtg   15660
gtgggcgccg agctgctgcc cgtgcactcc aagagcttct acaacgacca ggccgtctac   15720
```

```
tcccagctca tccgccagtt cacctctctg acccacgtgt tcaatcgctt tcctgagaac   15780
cagattctgg cgcgcccgcc cgcccccacc atcaccaccg tcagtgaaaa cgttcctgct   15840
ctcacagatc acgggacgct accgctgcgc aacagcatcg gaggagtcca gcgagtgacc   15900
gtaactgacg ccagacgccg cacctgcccc tacgtttaca aggccctggg catagtctcg   15960
ccgcgcgtcc tttccagccg cacttttttaa gcatgtccat cctcatctcg cccagcaata   16020
acaccggctg gggcctgctg cgcgcgccca gcaagatgtt cggaggggcg aggaagcgct   16080
ccgaccagca ccccgtgcgc gtgcgcgggc actaccgcgc tccctggggc gcgcacaaac   16140
gcgggcgcac cggcaccgcg gggcgcacca ccgtggacga agccatcgac tcggtggtgg   16200
agcaggcgcg caactacacg cccgcggtct ccaccgtgga cgcggctatc gagagcgtgg   16260
tgcgaggcgc gcggcggtac gccaaggcga agagccgccg gaggcgcgtg gcccgccgcc   16320
accgccgccg acccgggagc gccgccaagc gcgccgccgc cgccttgctc cgtcgggcca   16380
gacgcacggg ccgccgtgcc gccatgaggg ccgcgcgccg cctggccgcc ggcatcacca   16440
ccgtggcccc ccgcgccaga agacgcgcgg ccgccgccgc cgccgcggcc atcagcgacc   16500
tggccaccag gcgccggggc aacgtgtact gggtgcgcga ctcggtgagc ggcacgcgcg   16560
tgcccgtgcg cttccgcccc ccgcggactt gagaggagag gacaggaaaa agcaacaaca   16620
tcaacaacac caccactgag tctcctgctg ttgtgtgtat cccagcggcg cgcgcgcaca   16680
cggcgacatg tccaagcgca aaatcaaaga agagatgctc caggtcgtcg cgccggagat   16740
ctatgggccc ccgaagaagg aagagcagga tttcaagccc cgcaagataa agcgggtcaa   16800
aaagaaaaag aaagatgacg atgatggcga ggtggagttt ctgcgcgcca cggcgcccag   16860
gcgcccgctg cagtggaagg gtcggcgcgt aaagcgcgtt ctgcgccccg gcaccgcggt   16920
ggtcttcacg cccggcgagc gctccaccag cactttcaag cgcgtctatg acgaggtgta   16980
cggcgacgaa gacctgctgg agcaggccaa cgatcgctcc ggagagtttg cttacgggaa   17040
gcggcaccgg gcgatggaga aggacgaggt gctggcgctg ccgctggacc ggggcaaccc   17100 caccccagc ctgaagcccg tgaccctgca gcaggtgcta ccggccagcg cgccctccga   17160
gatgaagcgg ggcctgaagc gcgagggcgg cgacctggcg cccaccgtgc agctaatggt   17220
gcccaagcgg cagaggctgg aggacgtgct ggagaaaatg aaagtagacc ccggcctgca   17280 gccgacatc agggtccgcc ccatcaagca ggtggcgccg ggcctcggcg tgcagaccgt   17340
ggacgtggtc atccccaccg gcgcctcctc ttccagcgcc gccgccgccg ccactagcac   17400
cgcggacatg gagacgcaga ctagccccgc cgccacctcc tcggcggagg tacagacgga   17460
cccctggttg ccgccgccgg cgaccgcccc ctcgcgcgca cgccgcgggc gcaggaagta   17520
cggcgccgcc agcgcgctca tgcccgagta cgccttgcat ccttccatcg cgcccacccc   17580
cggctaccga ggctacagtt accgcccgcg aagagccaag ggctccaccc gccgcagccg   17640
ccgcgccgcc acctctaccc gccgccgcag tcgccgccgc cgccggcagc ccgcgctggc   17700
tccgatctcc gtgaaaagag tggcgcgcaa cgggaacacc ttggtgctgc caggggcgcg   17760
ctaccacccc agcatcgttt aaaaagcctg ttgtggttct tgcagatatg gccctcactt   17820
gccgcctccg tttcccggtg ccgggatacc gaggaagatc gcgccgcagg aggggtatgg   17880
ccggacgcgg cctgagcgga ggcagtcgcc gtgcgcaccg gcggcgacgc gccaccagcc   17940
gacgcatgcg cggcggagtg ctgcctctgc tgatcccccct gatcgccgcg gcgatcggcg   18000
ccgtgcccgg gatcgcctcc gtggccttgc aggcgtccca gaggcgttga cacagacttc   18060
```

```
ttgcaagctt gcaaaaatat ggaaaaatcc ccccaataaa aaagtctaga ctctcacgct   18120
cgcttggtcc tgtgactatt ttgtagaaaa aagatggaag acatcaactt tgcgtcgctg   18180
gccccgcgtc acggctcgcg cccgttcctg ggacactgga acgatatcgg caccagcaac   18240
atgagcggtg gcgccttcag ttggggctct ctgtggagcg gcattaaaaa tatcggttct   18300
gccgttaaga attacggcac caaggcctgg aacagcagca cgggccagat gttgagagac   18360
aagttgaaag agcagaactt ccagcagaag gtggtggagg gtctggcctc cggcatcaac   18420
ggggtggtgg acctggccaa tcaggccgtg caaaataaga tcaacagcag actggacccc   18480
cggccgccgg tggaggagct gccgccggcg ctggagacgg tgtccccga tgggcggggc    18540
gaaaagcgcc cgcggcccga cagggaagag accactctgg tcacgcacac cgatgagccg   18600
cccccctacg aggaagccct gaagcaaggc ttgcccacca ctcggcccat cgcgcccatg   18660
gccaccgggg tggtgggccg ccacacccccc gccacgctgg acctgcctcc tcctcctgtt   18720
tcttcttcgg ccgccgatgc gcagcagcag aaggcggcgc tgcccggtcc gcccgcggcc   18780
gccccccgtc ccaccgccag tcgagcgccc ctgcgtcgcg cggccagcgg cccccgcggg   18840
gtcgcgaggc acagcagcgg caactggcag aacacgctga acagcatcgt gggtctgggg   18900
gtgcagtccg tgaagcgccg ccgatgctac tgaatagctt agctaacggt gttgtatgtg   18960
tgtatgcgtc ctatgtcacc gccagaggag ctgctgagtc gccgccgttc gcgcgcccac   19020
cgccactacc accgccggta ccactccagc gcccctcaag atggcgaccc catcgatgat   19080
gccgcagtgg tcgtacatgc acatctcggg ccaggacgcc tcggagtacc tgagccccgg   19140
gctggtgcag ttcgcccgcg ccaccgacag ctacttcagc ctgagtaaca agtttaggaa   19200
ccccacggtg gcgcccacgc acgatgtgac caccgaccgg tcccagcgcc tgacgctgcg   19260
gttcatcccc gtgaccgcg aggacaccgc gtactcttac aaggcgcggt tcaccctggc    19320
cgtgggcgac aaccgcgtgc tggacatggc ctccacctac tttgacatcc gcggcgtgct   19380
ggacagggc cccaccttca gccctactc cggcaccgcc tacaactccc tggccccaa     19440
gggcgccccc aactcctgcg agtgggagca agtggagcca gctgaagagg cagcagaaaa   19500
tgaagatgaa gaagaagaag aggatgttgt tgatcctcag gaacaggagc ccactactaa   19560
aacacatgta tatgctcaag ctccccttc tggcgagaaa attaccaaag atggtctgca    19620
aataggaact gaggctacgg cagcaggagg cactaaagac ttatttgcag acctacatt    19680
ccagccagaa ccccaagttg gcgaatctca gtggaatgag gcggatgcta cagcagctgg   19740
aggtagagtg ctcaaaaaga ccactcccat gaaaccttgc tatggctcat atgcccgccc   19800
cacaaatgcc aatgggggcc aaggtgtgct aaaggcaaat gcccagggag tgctcgagtc   19860
tcaggttgag atgcagttct tttccacttc tacaaatgcc acaaacgagc aaaacaacat   19920
ccagcccaaa ttggtgctgt acagcgagga tgtgcatatg gagaccccag acacacacat   19980
ctcctacaag cctacaaaaa gcgatgataa ttcaaaagtc atgctgggtc agcagtccat   20040
gcccaacagg ccaaattaca tcgccttcag agacaacttt atcgggctca tgtattataa   20100
cagcactggc aacatggggg tgctggcagg tcaggcctca cagttgaatg cagtggtgga   20160
cctgcaagac agaaacacag aactgtccta ccagctcttg cttgattcca tgggagacag   20220
aaccagatac tttccatgt ggaatcaggc cgtggacagt tatgacccag atgtcagaat     20280
tattgaaaat catggaaccg aagatgagct gcccaactat tgtttccctc tgggaggcat   20340
agggatacct gacacttacc aggccattaa gactaatggc aatggggcag agatcaagc    20400
caccacgtgg cagaaagact cacaatttgc agaccgcaac gaaataggg tgggaaacaa     20460
```

```
cttcgccatg gagatcaacc tcagtgccaa cctgtggagg aacttcctct actccaacgt    20520
ggccctgtac ctgccagaca agcttaagta caacccctcc aacgtggaaa tctctgacaa    20580
ccccaacacc tacgactaca tgaacaagcg agtggtggcc ccggggctgg tggactgcta    20640
catcaacctg ggcgcgcgct ggtccctgga ctacatggac aacgtcaacc ccttcaacca    20700
ccaccgcaat gcgggcctgc gctaccgctc catgcttctg ggcaacgggc gctacgtgcc    20760
cttccacatc caggtgcccc agaagttctt tgccatcaag aacctcctcc tcctgccggg    20820
ctcctacacc tacgagtgga acttcaggaa ggatgtcaac atggtcctgc agagctctct    20880
gggcaacgac ctcagggtcg acggggccag catcaagttc gagagcatct gcctctacgc    20940
caccttcttc cccatggccc acaacacggc ctccacgctc gaggccatgc tcaggaacga    21000
caccaacgac cagtccttca cgactacctc tccgccgcc aacatgctct accccatccc    21060
cgccaacgcc accaacgtcc ccatctccat cccctcgcgc aactgggcgg ccttccgcgg    21120
ctgggccttc acccgcctta agaccaagga gaccccctcc ctgggctcgg gtttcgaccc    21180
ctactacacc tactcgggct ccataccta cctggacgga accttctacc tcaaccacac    21240
tttcaagaag gtctcggtca ccttcgactc ctcggtcagc tggccgggca acgaccgcct    21300
gctcaccccc aacgagttcg agatcaagcg ctcggtcgac ggggagggct acaacgtagc    21360
ccagtgcaac atgaccaagg actggttcct catccagatg ctggccaact acaacatcgg    21420
ctatcagggc ttctacatcc cagagagcta caaggacagg atgtactcct tctttaggaa    21480
cttccagccc atgagccggc aggtggtgga cgaaaccaag tacaaggact accagcaggt    21540
gggcatcatc caccagcaca caactcgggg cttcgtgggc tacctcgccc ccaccatgcg    21600
cgagggacag gcctacccg ccaacttccc ctacccgctc attggcaaga ccgcggtcga    21660
cagcatcacc cagaaaaagt tcctctgcga ccgcaccctc tggcgcatcc ccttctccag    21720
caacttcatg tccatgggtg cgctcacgga cctgggccag aacctgctct atgccaactc    21780
cgcccacgcg ctcgacatga ccttcgaggt cgaccccatg gacgagccca cccttctcta    21840
tgttctgttc gaagtctttg acgtggttcg ggtccaccag ccgcaccgcg gcgtcatcga    21900
gaccgtgtac ctgcgcacgc ccttctcggc cggcaacgcc accacctaaa gaagcaagcc    21960
gccaccgcca ccacctgcat gtcgtcgggt tccaccgagc aggagctcaa ggccatcgtc    22020
agagacctgg gatgcgggcc ctattttttg ggcaccttcg acaaacgctt cccgggcttc    22080
gtcgccccgc acaagctggc ctgcgccatc gtcaacacgg ccggccgcga gaccggggc    22140 gtgcactggc tggccttcgc ctggaacccg cgctccaaaa catgctacct cttttgacccc    22200 ttcggattct cggaccagcg gctcaagcag atctaccagt tcgagtacga gggcctgctg    22260
cgccgcagcg ccatcgcctc ctcgcccgac cgctgcgtca ccctcgagaa gtccacccag    22320
accgtgcagg ggcccgactc ggccgcctgc ggtctcttct gctgcatgtt cctgcatgcc    22380
tttgtgcact ggccccagag tcccatggac cgcaaccca ccatgaactt gctgacgggg    22440
atccccaact ccatgctcca gagcccccag gccgcgccca cctgcgccg caaccaggag    22500 cggctctaca gcttcctgga gcgccactcg ccctacttcc gccgcacag cgcgcagatc    22560 agggggggcca cctctttctg ccgcatgcaa gagatgcaag ggaaaatgca atgatgtaca    22620
cagacacttt ctttttctca ataaatggca actttattta tacatgctct ctctcgggta    22680
ttcatttccc caccacccac cacccgccgc cgtaaccatc tgctgctggc ttttaaaaa    22740 tcgaaagggt tctgccggga atcgccgtgc gccacgggca gggacacgtt gcggaactgg    22800
```

-continued

```
tagcgggtgc cccacttgaa ctcgggcacc accatgcggg gcaagtcggg gaagttgtcg   22860
gcccacaggc cgcgggtcag caccagcgcg ttcatcaggt cgggcgccga gatcttgaag   22920
tcgcagttgg ggccgccgcc ctgcgcgcgc gagttgcggt acaccgggtt gcaacactgg   22980
aacaccagca gcgccggata attcacgctg gccagcacgc tccggtcgga gatcagctcg   23040
gcgtccaggt cctccgcgtt gctcagcgcg aacggggtca gcttgggcac ctgccgcccc   23100
aggaagggag cgtgccccgg cttcgagttg cagtcgcagc gcagcgggat cagcaggtgc   23160
ccgcggccgg actcggcgtt ggggtacagc gcgcgcatga aggcctccat ctggcggaag   23220
gccatctggg ccttggcgcc ctccgagaag aacatgccgc aggacttgcc cgagaactgg   23280
ttcgcggggc agctagcgtc gtgcaggcag cagcgcgcgt cggtgttggc aatctgcacc   23340
acgttgcgcc cccaccggtt cttcacgatc ttggccttgg aagcctgctc cttcagcgcg   23400
cgctgcccgt tctcgctggt cacatccatc tcgatcacgt gctccttgtt caccatgctg   23460
ctgccgtgca gacacttcag ctcgccctcc acctcggtgc agcggtgctg ccacagcgcg   23520
cagcccgtgg gctcgaaatg cttgtaggtc acctccgcgt aggactgcag gtaggcctgc   23580
aggaagcgcc ccatcatggt cacgaaggtc ttgttgctgc tgaaggtcag ctgcagcccg   23640
cggtgctcct cgttcagcca ggccttgcac acggccgcca gcgcctccac ctggtcgggc   23700
agcatcttga agttcagctt cagctcattc tccacatggt acttgtccat cagcgcgcgc   23760
gcagcctcca tgcccttctc ccaggccgac accagcggca ggctcaaggg gttcaccacc   23820
gtcgcagtcg ccgccgcgct ttcgctttcc gctccgctgt tctcttcttc ctcctcctct   23880
tcttcctcgc cgcccgcgcg cagccccgc accacgggg cgtcttcctg caggcgccgc    23940
accgagcgct tgccgctcct gccctgcttg atgcgcacgg gcgggttgct gaagcctacc   24000
atcaccagcg cggcctcttc ttgctcgtcc tcgctgtcca ctatgacctc ggggagggc    24060 gacctcagaa ccgtggcgcg ctgcctcttc tttttcctgg gggcgtttgc aagctccgcg   24120
gccgcggccg ccgccgaggt cgaaggccga gggctgggcg tgcgcggcac cagcgcgtcc   24180
tgcgagccgt cctcgtcctc ggactcgagg cggcagcgag cccgcttctt tgggggcgcg   24240
cggggcggcg gcgcggggg cggcggcgac ggagacgggg acgagacatc gtccagggtg    24300
ggaggacggc gggccgcgcc gcgtccgcgc tcggggtgg tttcgcgctg gtcctcttcc     24360
cgactggcca tctcccactg ctccttctcc tataggcaga aagagatcat ggagtctctc   24420
atgcaagtcg agaaggagga ggacagccta accaccgccc cctctgagcc ctccgccgcc   24480
accgccgcgg acgacgcgcc taccaccgcc gccaccacca ccaccattac cacccctaccc  24540 ggcgacgcag ccccgatcga gaaggaagtg ttgatcgagc aggacccggg ttttgtgagc   24600
gaagaggagg atgaggagga tgaaaaggag aaggataccg ccgcctcagt gccaaaagag   24660
gataaaaagc aagaccagga cgacgcagag acagatgagg cagcaatcgg gcgggggggac  24720 gagaggcatg atgatgatga tgatgacggc tacctagacg tgggagacga cgtgctgctt   24780
aagcacctgc accgccagtg cgtcatcgtc tgcgacgcgc tgcaggagcg ctgcgaagtg   24840
cccctggacg tggcggaggt cagccgcgcc tacgagcggc acctcttcgc gccacacgtg   24900 cccccccaagc gccgggagaa cggcacctgc gagcccaacc cgcgcctcaa cttctacccg   24960
gtcttcgcgg tacccgaggt gctggccacc taccacatct tcttccaaaa ctgcaagatc   25020
cccctctcct gccgcgccaa ccgcaccgcg ccgacaagg cgctggccct gcggcagggc    25080
gcccacatac ctgatatcgc ctctctggag gaggtgccca agatcttcga gggtctcggt   25140
cgcgacgaga acgggcggc gaacgctctg caaggagaca gcgaaaacga gagtcactcg   25200
```

```
ggggtgctgg tggagctcga gggcgacaac gcgcgcctgg ccgtgctcaa gcgcagcatc   25260
gaagtcaccc acttcgccta cccggcgctc aacctgcccc ccaaggtcat gagtgtggtc   25320
atgagcgagc tcatcatgcg ccgcgcccag cccctggacg cggatgcaaa cttgcaagag   25380
ccctccgagg aaggcctgcc cgcggtcagc gacgagcagc tggcgcgctg gctggagacc   25440
cgcgaccccg cccagctgga ggagcggcgc aagctcatga tggccgcggt gctcgtcacc   25500
gtggagctcg agtgtctgca gcgcttcttc ggggaccccg agatgcagcg caagctcgag   25560
gagaccctgc actacacctt ccgccagggc tacgtgcgcc aggcctgcaa gatctccaac   25620
gtggagctct gcaacctggt ctcctacctg ggcatcctgc acgagaaccg cctcgggcag   25680
aacgtcctgc actccaccct caaaggggag gcgcgccgcg actacgtccg cgactgcgtc   25740
tacctcttcc tctgctacac gtggcagaca gccatggggg tctggcagca gtgcctggag   25800
gagcgcaacc tcaaggagct ggagaagctc ctcaggcgcg ccctcaggga cctctggagg   25860
ggcttcaacg agcgctcggt ggccgccgcg ctggcggaca tcatcttccc cgagcgcctg   25920
ctcaaaaccc tgcagcaggg cctgcccgac ttcaccagcc agagcatgct gcagaacttc   25980
aggaccttca tcctggagcg ctcgggcatc ctgccggcca cctgctgcgc gctgcccagc   26040
gacttcgtgc ccatcaggta cagggagtgc ccgccgccgc tctggggcca ctgctacctc   26100
ttccagctgg ccaactacct cgcctaccac tcggatctca tggaagacgt gagcggcgag   26160
ggcctgctcg agtgccactg ccgctgcaac ctgtgcacgc cccaccgctc tctagtctgc   26220
aacccgcagc tgctcagcga gagtcagatt atcggtacct tcgagctgca gggtccctcg   26280
cccgacgaaa agtccgcggc tccggggttg aaactcactc cggggctgtg gacttccgcc   26340
tacctacgca aatttgtacc tgaagactac cacgcccacg agatcaggtt ttacgaagac   26400
caatcccgcc cgcccaaggc ggagctcacc gcctgcgtca ttacccaggg ccacatcctg   26460
ggccaattgc aagccatcaa caaagcccgc caagagttct tgctgaaaaa gggtcggggg   26520
gtgtacctgg accccagtc cggcgaggag ctaaacccgc tacccccgcc gccgcccag    26580
cagcgggacc ttgcttccca ggatggcacc cagaaagaag cagccgccgc cgccgccagc   26640
atacatgctt ctggaggaag aggaggactg ggacagtcag gcagaggagg tttcggacga   26700
ggacgaggag gaggagatga tggaagactg ggaggaggac agcctagacg aggaagcttc   26760
agaggccgaa gaggtggcag acgcaacacc atcaccctcg gccgcagccc cctcgccggc   26820
gccccgaaa tcctccgacc ccagcagcag cgctataacc tccgctcctc cggcgccggc   26880
gcccaccgc agcagaccca accgtagatg ggacactaca ggaaccgggg tcggtaagtc   26940
caagtgcccc ccagcgccgc ccccgcaaca ggagcaacag cagcagcagc ggcgacaggg   27000
ctaccgctcg tggcgcggac acaagaacgc catagtcgcc tgcttgcaag actgcggggg   27060
caacatctcc ttcgcccgcc gcttcctgct cttccaccac ggggtggctt ttccccgcaa   27120
tgtcctgcat tactaccgtc atctctacag cccctactgc ggcggcagcg gcgacccaga   27180
gggagcggcg gcagcagcag cgccagccac agcggcgacc acctaggaag acctccgcgg   27240
gcaagacggc gggagccggg agacccgcgg cggcggcggt agcggcggcg gcgggcgcac   27300
tgcgcctctc gcccaacgaa cccctctcga cccgggagct cagacacagg atcttcccca   27360
ctctgtatgc tatcttccag cagagcagag gccaggaaca ggagctgaaa ataaaaaaca   27420
gatctctgcg ctccctcacc cgcagctgtc tgtatcacaa aagcgaagat cagcttcggc   27480
gcacgctgga ggacgcggag gcactcttca gcaaatactg cgcgctgact cttaaggact   27540
```

```
agccgcgcgc ccttctcgaa tttaggcggg agaaagacta cgtcatcgcc gaccgccgcc    27600
cagcccaccc agccgacatg agcaaagaga ttcccacgcc ctacatgtgg agctaccagc    27660
cgcagatggg actcgcggcg ggagcggccc aagactactc cacccgcatg aactacatga    27720
gcgcggggcc ccacatgatc tcacgggtta atgggatccg cgcccagcga aaccaaatac    27780
tgctggaaca ggcggccata accgccacac cccgtcatga cctcaatccc cgaaattggc    27840
ccgccgccct cgtgtaccag gaaacccect ctgccaccac cgtggtactt ccgcgtgaca    27900
cccaggccga agtccagatg actaactcag gggcgcagct cgcgggcggc tttcgtcacg    27960
gggtgcggcc gcaccggccg ggtatattac acctggcgat cagaggccga ggtattcagc    28020
tcaacgacga gtcggtgagc tcttcgctcg gtctccgtcc ggacggaacc ttccagatcg    28080
ccggatcagg tcgctcctca ttcacgcctc gccaggcgta cctgactctg cagacctcct    28140
cctcggagcc tcgctccggc ggcatcggca ccctccagtt cgtggaggag ttcgtgccct    28200
cggtctactt caaccccttc tcgggacctc ccggacgcta ccccgaccag ttcatcccga    28260
actttgacgc ggtgaaggac tcggcggacg gctacgactg aatgtcaagt gctgaggcag    28320
agagcgttcg cctgaaacac ctccagcact gccgccgctt cgcctgcttt gcccgcagct    28380
ccggtgagtt ctgctacttt cagctgcccg aggagcatac cgaggggccg cgcacggcg    28440 tccgcctaac cacccagggc gaggttacct gtaccttat ccgggagttt accctccgtc    28500
ccctgctagt ggagcgggag cggggttctt gtgtcataac tatcgcctgc aactgcccta    28560
accctggatt acatcaagat ctttgttgtc acctgtgcgc tgagtataat aaacgctgag    28620
atcagactct actggggctc ctgtcgccat cctgtgaacg ccaccgtctt cacccacccc    28680
gagcagcccc aggcgaacct cacctgcggc ctgcgtcgga gggccaagaa gtacctcacc    28740
tggtacttca acggcacccc ctttgtggtt tacaacagct cgaccagga cggagttgcc    28800 ttgagagacg acctttccgg tctcagctac tccattcaca gaacaccac cctccacctc    28860 ttccctccct acctgccggg aacctacgag tgcgtcaccg gccgctgcac ccacctcctc    28920
cgcctgatcg taaaccagac cttccgggga acacacctct tccccagaac aggaggtgag    28980
ctcaggaaac cccctggggc ccagggcgga gacttacctt cgacccttgt ggggttagga    29040
ttttttatcg ccgggttgct ggctctcctg atcaaagctt ccttgagatt tgttctctcc    29100
ctttactttt atgaacagct caacttctaa taacgctacc tttctcagg aatcgggtag    29160 taacttctct tctgaaatcg ggctgggtgt gctgcttact ctgttgattt ttttccttat    29220
catacttagc cttctgtgcc tcaggctcgc cgcctgctgc gcacatatct acatctacag    29280
ccggttgctt aactgctggg gtcgccatcc aagatgaacg gggctcaggt gctatgtctg    29340
ctggccctgg tggcctgcag tgccgccgtc aattttgagg aacccgcttg caatgtgact    29400
ttcaagcctg aaggcgcaca ttgcaccact ctggttaaat gtgtgacctc tcatgagaaa    29460
ctgctcatcg cctacaaaaa caaaacaggc gagttcgcgg tctatagcgt gtggcaaccc    29520
ggagaccata ataactactc agtcaccgtc ttcgagggtg cggagtctaa gaaattcgat    29580
tacacctttc ccttcgagga gatgtgtgaa gcggtcatgt acctgtccaa acagtacaag    29640
ctgtggcccc ccaccccga ggcgtgtgtg gaaaacactg gtctttctg ctgtctctct    29700 ctgacaatca ctgtgcttgc tctaatctgc acgctgctgt acatgaaatt caggcagagg    29760
cgaatcttta tcgatgagaa aaaaatgcct tgatcgctaa caccggcttt ctgtctgcag    29820
aatgaaagca atcacctccc tactaatcag caccaccctc cttgcgattg cccatggggtt    29880 gacacgaatc gaagtgccag tggggtccaa tgtcaccatg gtgggccccg ccggcaattc    29940
```

```
ctccctgatg tgggaaaaat atgtccgtaa tcaatgggat cattactgct ctaatcgaat    30000
ctgtatcaag cccagagcca tctgcgacgg gcaaaatcta actttgattg atgtgcaaat    30060
gacggatgct gggtactatt acgggcagcg gggagaaatg attaattact ggcgacccca    30120
caaggactac atgctgcatg tagtcaaggc agtccccact actaccaccc ccaccactac    30180
cactcccacc actcccacta ctaccacccc caccactact actagcactg ctactaccgc    30240
tgcccgcaaa gctattaccc gcaaaagcac catgcttagc accaagcccc attctcactc    30300
ccacgccggc gggcccaccg gtgcggcctc agaaaccacc gagctttgct tctgccaatg    30360
cactaacgcc agcgcccacg aactgttcga cctggagaat gaggatgatg accagctgag    30420
ctccgcttgc ccggtcccgc tgcccgcaga gccggtcgcc ctgaagcagc tcggtgatcc    30480
atttaatgac tctcctgttt atccctctcc cgaatacccg cccgactcta ccttccacat    30540
cacgggcacc aacgacccca acctctcctt ctacctgatg ctgctgcttt gtatctctgt    30600
ggtatcttcc gcgctcatgt tactgggcat gttctgctgc ctcatctgcc gcagaaagag    30660
aaagtctcgc tctcagggcc aaccactgat gcccttcccc taccccccag attttgcaga    30720
taacaagata tgagcacgct gctgacacta accgctttac tcgcctgcgc tctaaccctt    30780
gtcgcttgcg aatccagata ccacaatgtc acagttgtga caggagaaaa tgttacattc    30840
aactccacgg ccgacaccca gtggtcgtgg agcggccacg gtagctatgt atacatctgc    30900
aatagctcca cctcccctag catgtcctct cccaagtacc actgcaatgc cagcctgttc    30960
accctcatca acgcctccac ctcggacaat ggactctatg taggctatgt gacacccggt    31020
gggcggggaa agacccacgc ctacaacctg caagttcgcc acccctccac caccgccacc    31080
acctctgccg cccctacccg cagcagcagc agcatcagca gcagcagcag cagcagcaga    31140
ttcctgactt taatcctagc cagctcaaca accaccgcca ccgctgagac cacccacagc    31200
tccgcgcccg aaaccaccca cacccaccac ccagagacga ccgcggcctc cagtgaccag    31260
atgtcggcca acatcaccgc ctcgggtctt gaacttgctt caaccccac cccaaaacca    31320 gtggatgcag ccgacgtctc cgccctcgtc aatgactggg cggggctggg aatgtggtgg    31380
ttcgccatag gcatgatggc gctctgcctg cttctgctct ggctcatctg ctgcctcaac    31440
cgcaggcggg ccagacccat ctatagaccc atcattgttc tcaacccgc tgatgatggg    31500 atccatagat tggatggtct gaaaaaccta cttttctctt ttacagtatg ataaattgag    31560
acatgcctcg cattttcatg tacttgacac ttctcccact ttttctgggg tgttctacgc    31620
tggccgccgt ctctcacctc gaggtagact gcctcacacc cttcactgtc tacctgattt    31680
acggattggt caccctcact ctcatctgca gcctaatcac agtagtcatc gccttcatcc    31740
agtgcattga ctacatctgt gtgcgcctcg catacctgag acaccacccg cagtaccgag    31800
acaggaacat tgcccaactc ctaagactgc tctaatcatg cataagactg tgatctgcct    31860
cctcatcctc ctctccctgc ccgctctcgt ctcatgccag cccgccacaa aacctccacg    31920
aaaaagacat gcctcctgtc gcttgagcca actgtggaat attcccaaat gctacaatga    31980
aaagagcgag ctttccgaag cctggctata tgcggtcatg tgtgtccttg tcttctgcag    32040
cacaatcttt gccctcatga tctaccccca ctttgatttg ggatggaatg cggtcgatgc    32100
catgaattac cctaccttc ccgcgcccga tatgattcca ctccgacagg ttgtggtgcc    32160
cgtcgccctc aatcaacgcc ccccatcccc tacacccact gaggtcagct actttaatct    32220
aacaggcgga gatgactgac actctagatc tagaaatgga cggcatcggc accgagcagc    32280
```

```
gtctcctaca gaggcgcaag caggcggctg aacaagagcg cctcaatcag gagctccgag    32340
atctcattaa cctgcaccag tgcaaaaaag gcatcttttg cctggtcaag caggccgatg    32400
tcacctacga gaaaaccggt aacagccacc gcctcagcta caagctgccc acccaacgcc    32460
agaagttggt gctcatggtg ggtcagaatc ccatcaccgt cacccagcac tcggtggaga    32520
ccgaggggtg tctgcactcc ccctgtcagg gtccggaaga cctctgcacc ctggtaaaga    32580
ccctgtgtgg tcttagagat ttaatcccct ttaactaatc aaacactgga atcaataaaa    32640
agaatcactt actttaaatc agtcagcagg tctctgtcca ctttattcag cagcacctcc    32700
ttcccctcct cccaactctg gtactccaaa cgcctcctgg cggcaaactt cctccacacc    32760
ctgaagggaa tgtcagattc ttgctcctgt ccctccgcac ccactatctt catgttgttg    32820
cagatgaagc gcgccaaaac gtctgacgag accttcaacc ccgtgtaccc ctatgacacg    32880
gaaaacgggc ctccctccgt ccctttcctc accctccct tcgtgtcccc cgacggattt    32940
caagaaagcc ccccaggggt cctgtctctg cgcctgtcag agcccctggt cacttcccac    33000
ggcatgcttg ccctgaaaat gggaaatggc ctctccctgg atgacgccgg caacctcacc    33060
tctcaagatg tcaccaccgt caccccctccc ctcaaaaaaa ccaagaccaa cctcagcctc    33120
cagacctcag ccccccctgac cgttagctct gggtccctca ccgtcgcggc cgccgctcca    33180
ctggcggtgg ccggcacctc tctcaccatg caatctcagg cccccttgac agtgcaagat    33240
gcaaaactcg gcctggccac ccagggaccc ctgaccgtgt ctgaaggcaa actcaccttg    33300
cagacatcgg ctccactgac ggccgctgac agcagcactc tcactgttag tgccacacct    33360
cccctcagca caagcaatgg tagtttgagc attgacatgc aggccccgat ttataccacc    33420
aatggaaaac tggcacttaa cattggtgct ccctgcatg tggtagacac cctaaatgca    33480
ctaactgtag taactggcca gggtcttacc ataaatggaa gagccctgca aactagagtc    33540
acgggtgccc tcagttatga cacagaaggc aacatccaac tgcaagccgg aggggtatg    33600 cgcattgaca ataatggcca acttatcctt aatgtagctt atccatttga tgctcaaaac    33660
aacctcagcc ttagacttgg ccaaggtccc ctaattgtta actctgccca caacttggat    33720
cttaacctta acagaggcct ttacttattt acatctggaa acacgaaaaa actggaagtt    33780
aacataaaaa cagccaaagg tctattttta c gatggcaccg ctatagcaat caatgcaggt    33840
gacgggctac agtttgggtc tggttcagat acaaatccat gcaaactaa acttggattg    33900 gggctggaat atgactccaa caaagctata atcactaaac ttggaactgg cctaagcttt    33960
gacaacacag gtgccatcac agtaggcaac aaaaatgatg acaagcttac cttgtggacc    34020
acaccagacc cctcccccaaa ctgcagaatt aattcagaaa aagatgctaa actcacacta    34080
gttttgacta aatgcggcag ccaggtgtta gccagcgttt ctgttttatc tgtaaaaggc    34140
agccttgccc ccatcagcgg cacagtaact agcgcccaga ttgttttaag atttgatgaa    34200
aacggagttt tattgagcaa ttcttctctt gaccccaat actggaacta tagaaaaggc    34260
gattctacag aaggcactgc atatactaat gctgtgggat ttatgcccaa cctcacagca    34320
taccctaaaa cacagagcca gactgctaaa agcaacattg taagtcaagt ttacttgaat    34380
ggggacaaaa caaacccat gaccctaacc atcaccctca atggaactaa tgaaacaggg    34440
gatgctacag taagcacata ctccatgtca ttttcatgga actggaatgg aagtaattac    34500
attaatgaca ccttccaaac caactccttt accttctcct acatcgccca agaataaaaa    34560
agcatgacgc tttgttctct gattcagtgt gtttctttta ttttttttca attacaacag    34620
aatcattcaa gtcattctcc atttagctta atagacccag tagtgcaaag ccccatacta    34680
```

```
gcttatttca gacagtataa attaaaccat accttttgat ttcaatatta aaaaaatcat   34740
cacaggatcc tagtcgtcag gccgccccct ccctgccaag acacagaata cacaatcctc   34800 tcccccggc tggctttaaa caacaccatc tggttggtga cagacaggtt cttcggggtt    34860
atattccaca cggtctcctg gcgggccagg cgctcgtcgg tgatgctgat aaactctccc   34920
ggcagctcgc tcaagttcac gtcgctgtcc agcggctgaa cctcatgctg acgcggtaac   34980
tgcgcgaccg gctgctgaac aaacggaggc gcgcctaca aggggtaga gtcataatcc     35040 tccgtcagga tagggcggtt atgcagcagc agcgagcgaa tcatctgctg ccgccgccgc   35100
tccgtccggc aggaaaacaa catcccggtg gtctcctccg ctataatccg caccgcccgc   35160
agcataagcc tcctcgttct ccgcgcgcag caccgcaccc tgatctcact caggttggcg   35220
cagtaggtac agcacatcac cacgatgtta ttcatgatcc cacagtgcaa ggcgctgtat   35280
ccaaagctca tgcccgggac caccgccccc acgtgaccgt cgtaccagaa gcgcaggtaa   35340
atcaagtgcc gaccctcat gaacgtgctg gacataaaca tcacctcctt gggcatgttg     35400
taattcacca cctcccggta ccagatgaat ctctgattga acacggcccc ttccaccacc   35460
atcctgaacc aagaggctag gacctgccca ccggctatgc actgcaggga acccgggtta   35520
gaacaatgac aatgcagact ccagggctcg taaccgtgga tcatccggct gctgaagaca   35580
tcgatgttgg cgcaacacag acacgtgc atacacttcc tcatgattag cagctcctcc     35640
ctcgtcagga tcatatccca agggataacc cattcttgaa tcaacgtaaa gcccacagag   35700
cagggaaggc ctcgcacata actcacgttg tgcatggtta gcgtgttgca ttccggaaac   35760
agcggatgat cctccagtat cgaggcgcgg gtctcgttct cacagggagg taaggggcc    35820 ctgctgtacg gactgtggcg ggacgaccga gatcgtgttg agcgtaacgt catggaaaag   35880
ggaacgccgg acgtggtcat acttcttgaa gcagaaccag gctcgcgcgt gacagacctc   35940
cttgcgtcta cggtctcgcc gcttagctcg ctccgtgtga tagttgtagt acagccactc   36000
tctcaaagcg tcgaggcgac acctggcgtc aggatgtatg tagactccgt cttgcaccgc   36060
ggccctgata atatccacca ccgtagaata agccacacca agccaagcaa tacactcgct   36120
ttgcgagcgg cagacaggag gagcggggag agacggaagg accatcataa aattttaaag   36180
aatattttcc aatacttcga aatcaagatc taccaaatgg caacgctccc ctccactggc   36240
gcggtcaaac tctacggcca aagaacagat aacggcattt ttaagatgtt cccggacggc   36300
gtctaaaaga caaccgctc tcaagtcgac ataaattata agccaaaagc catcgggatc    36360
catatccact atggacgcgc cggcggcgtc caccaaaccc aaataatttt cttctctcca   36420
gcgcagcaaa atcccagtaa gcaactccct gatattaaga tgaaccatgc caaaaatctg   36480
ttcaagagcg ccctccacct tcattctcaa gcagcgcatc atgattgcaa aaattcaggt   36540
tcctcagaca cctgtatgag attcaaaacg ggaatattaa caaaaattcc tctgtcgcgc   36600
agatcccttc gcagggcaag ctgaacataa tcagacaggt ctgaacgaac cagcgaggcc   36660
aaatccccgc caggaaccag atccagagac cctatgctga ttatgacgcg catactcggg   36720
gctatgctaa ccagcgtagc gccgatgtag gcgtgctgca tgggcggcga aataaaatgc   36780
aaggtgctgg ttaaaaaatc aggcaaagcc tcgcgcaaaa aagctaagac atcataatca   36840
tgctcatgca ggtagttgca ggtaagctca ggaaccaaaa cggaataaca cacgattttc   36900
ctctcaaaca tgacttccag gtgactgcat aagaaaaaaa ttataaataa taaatattaa   36960
ttaaataaat taaacattgg aagcctgtct cacaacagga aaaaccactc tgatcaacat   37020
```

-continued

```
aagacgggcc acgggcatgc ccgcgtgacc ataaaaaaat cggtctccgt gattacaaag    37080
caccacagat agctccccgg tcatgtcggg ggtcatcatg tgagactgtg tatacacgtc    37140
cgggctgttg acatcggtca agaaagaaa tcgagctaca tagcccggag gaatcaacac     37200
ccgcacgcgg aggtacagca aaacggtccc cataggagga atcacaaaat tagtaggaga    37260
aaaaaaaaca taaacaccag aaaaaccctc ttgccgaggc aaaacagcgc cctcccgttc    37320
caaaacaaca taaagcgctt ccacaggagc agccatgaca aagacccgag tcttaccagg    37380
aaaattttaa aaaagattcc tcaacgcagc accagcacca acacctgtca gtgtaaaatg    37440
ccaagcgccg agcgagtata tataggaata aaaagtgacg taaacggtta aagtccagaa    37500
aacgcccaga aaaaccgcac gcgaacctac gccccgaaac gaaagccaaa aaacagtgaa    37560
cacgcccttt cggcgtcaac ttccgctttc ccacggtacg tcacttccgc atatagtaaa    37620
actacgctac ccaacatgca agaagccacg ccccaaaaca cgtcacacct cccggcccgc    37680
cccgcgccgc cgctcctccc cgccccgccc cgctccgccc acctcattat catattggct    37740
tcaatccaaa ataaggtata ttattgatga tg                                 37772
```

<210> SEQ ID NO 14
<211> LENGTH: 440
<212> TYPE: PRT
<213> ORGANISM: Adenoviridae - Mastadenovirus

<400> SEQUENCE: 14

```
Met Ser Lys Lys Arg Val Arg Val Asp Asp Asp Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
        50                  55                  60

Lys Leu Gly Glu Gly Val Asp Leu Asp Asp Ser Gly Lys Leu Ile Ser
65                  70                  75                  80

Lys Asn Ala Thr Lys Ala Thr Ala Pro Leu Ser Ile Ser Asn Ser Thr
                85                  90                  95

Ile Ser Leu Asn Met Asp Ala Pro Leu Tyr Asn Asn Asn Gly Lys Leu
                100                 105                 110

Gly Ile Arg Ile Gly Ala Pro Leu Lys Val Val Asp Leu Leu Asn Thr
            115                 120                 125

Leu Ala Val Ala Tyr Gly Ser Gly Leu Gly Leu Lys Asn Asn Ala Leu
        130                 135                 140

Thr Val Gln Leu Val Ser Pro Leu Thr Phe Asp Asn Lys Gly Asn Val
145                 150                 155                 160

Lys Ile Asn Leu Gly Asn Gly Pro Leu Thr Val Ala Ala Asn Arg Leu
                165                 170                 175

Ser Val Thr Cys Lys Arg Gly Leu Tyr Val Thr Thr Thr Gly Asp Ala
                180                 185                 190

Leu Glu Ser Asn Ile Ser Trp Ala Lys Gly Ile Arg Phe Glu Gly Asn
            195                 200                 205

Ala Ile Ala Ala Asn Ile Gly Lys Gly Leu Glu Phe Gly Thr Thr Ser
        210                 215                 220

Ser Glu Ser Asp Val Ser Asn Ala Tyr Pro Ile Gln Val Lys Leu Gly
225                 230                 235                 240
```

-continued

```
Thr Gly Leu Thr Phe Asp Ser Thr Gly Ala Ile Val Ala Trp Asn Lys
                245                 250                 255

Glu Asp Asp Lys Leu Thr Leu Trp Thr Thr Ala Asp Pro Ser Pro Asn
            260                 265                 270

Cys His Ile Tyr Ser Asp Lys Asp Ala Lys Leu Thr Leu Cys Leu Thr
        275                 280                 285

Lys Cys Gly Ser Gln Ile Leu Gly Thr Val Ser Leu Ile Ala Val Asp
    290                 295                 300

Thr Gly Ser Leu Asn Pro Ile Thr Gly Gln Val Thr Thr Ala Leu Val
305                 310                 315                 320

Ser Leu Lys Phe Asp Ala Asn Gly Val Leu Gln Thr Ser Ser Thr Leu
                325                 330                 335

Asp Lys Glu Tyr Trp Asn Phe Arg Lys Gly Asp Val Thr Pro Ala Glu
            340                 345                 350

Pro Tyr Thr Asn Ala Ile Gly Phe Met Pro Asn Ile Lys Ala Tyr Pro
        355                 360                 365

Lys Asn Thr Asn Ser Ala Ala Lys Ser His Ile Val Gly Lys Val Tyr
    370                 375                 380

Leu His Gly Glu Val Ser Lys Pro Leu Asp Leu Ile Ile Thr Phe Asn
385                 390                 395                 400

Glu Thr Ser Asn Glu Thr Cys Thr Tyr Cys Ile Asn Phe Gln Trp Gln
                405                 410                 415

Trp Gly Thr Asp Lys Tyr Lys Asn Glu Thr Leu Ala Val Ser Ser Phe
            420                 425                 430

Thr Phe Ser Tyr Ile Ala Gln Glu
        435                 440

<210> SEQ ID NO 15
<211> LENGTH: 443
<212> TYPE: PRT
<213> ORGANISM: Adenoviridae - Mastadenovirus

<400> SEQUENCE: 15

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Glu Ile Thr Leu
    50                  55                  60

Lys Leu Gly Glu Gly Val Asp Leu Asp Asp Ser Gly Lys Leu Ile Ser
65                  70                  75                  80

Lys Asn Ala Thr Lys Ala Thr Ala Pro Leu Ser Ile Ser Asn Ser Thr
                85                  90                  95

Ile Ser Leu Asn Met Ala Ala Pro Phe Tyr Asn Asn Gly Thr Leu
            100                 105                 110

Ser Leu Asn Val Ser Thr Pro Leu Ala Val Phe Pro Thr Phe Asn Thr
        115                 120                 125

Leu Gly Ile Ser Leu Gly Asn Gly Leu Gln Thr Ser Asn Lys Leu Leu
    130                 135                 140

Ala Val Gln Leu Thr His Pro Leu Thr Phe Ser Ser Asn Ser Ile Thr
145                 150                 155                 160

Val Lys Thr Asp Lys Gly Leu Tyr Ile Asn Ser Ser Gly Asn Arg Gly
                165                 170                 175
```

```
Leu Glu Ala Asn Ile Ser Leu Lys Arg Gly Leu Ile Phe Asp Gly Asn
            180                 185                 190

Ala Ile Ala Thr Tyr Leu Gly Ser Gly Leu Asp Tyr Gly Ser Tyr Asp
            195                 200                 205

Ser Asp Gly Lys Thr Arg Pro Ile Ile Thr Lys Ile Gly Ala Gly Leu
210                 215                 220

Asn Phe Asp Ser Asn Asn Ala Met Ala Val Lys Leu Gly Thr Gly Leu
225                 230                 235                 240

Ser Phe Asp Ser Ala Gly Ala Leu Thr Ala Gly Asn Lys Glu Asp Asp
            245                 250                 255

Lys Leu Thr Leu Trp Thr Thr Pro Asp Pro Ser Pro Asn Cys Gln Leu
            260                 265                 270

Leu Ser Asp Arg Asp Ala Lys Phe Thr Leu Cys Leu Thr Lys Cys Gly
            275                 280                 285

Ser Gln Ile Leu Gly Thr Val Ala Val Ala Ala Val Thr Val Ser Ser
            290                 295                 300

Ala Leu Asn Pro Ile Asn Asp Thr Val Lys Ser Ala Ile Val Phe Leu
305                 310                 315                 320

Arg Phe Asp Ser Asp Gly Val Leu Met Ser Asn Ser Ser Met Val Gly
            325                 330                 335

Asp Tyr Trp Asn Phe Arg Glu Gly Gln Thr Thr Gln Ser Val Ala Tyr
            340                 345                 350

Thr Asn Ala Val Gly Phe Met Pro Asn Leu Gly Ala Tyr Pro Lys Thr
            355                 360                 365

Gln Ser Lys Thr Pro Lys Asn Ser Ile Val Ser Gln Val Tyr Leu Asn
            370                 375                 380

Gly Glu Thr Thr Met Pro Met Thr Leu Thr Ile Thr Phe Asn Gly Thr
385                 390                 395                 400

Asp Glu Lys Asp Thr Thr Pro Val Ser Thr Tyr Ser Met Thr Phe Thr
            405                 410                 415

Trp Gln Trp Thr Gly Asp Tyr Lys Asp Lys Asn Ile Thr Phe Ala Thr
            420                 425                 430

Asn Ser Phe Thr Phe Ser Tyr Met Ala Gln Glu
            435                 440

<210> SEQ ID NO 16
<211> LENGTH: 425
<212> TYPE: PRT
<213> ORGANISM: Adenoviridae - Mastadenovirus

<400> SEQUENCE: 16

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
            35                  40                  45

Leu Arg Leu Ala Asp Pro Val Thr Thr Lys Asn Gly Glu Ile Thr Leu
            50                  55                  60

Lys Leu Gly Glu Gly Val Asp Leu Asp Ser Ser Gly Lys Leu Ile Ser
65                  70                  75                  80

Asn Thr Ala Thr Lys Ala Ala Ala Pro Leu Ser Phe Ser Asn Asn Thr
            85                  90                  95

Ile Ser Leu Asn Met Asp His Pro Phe Tyr Thr Lys Asp Gly Lys Leu
```

```
            100                 105                 110
Ala Leu Gln Val Ser Pro Pro Leu Asn Ile Leu Arg Thr Ser Ile Leu
        115                 120                 125

Asn Thr Leu Ala Leu Gly Phe Gly Ser Gly Leu Gly Leu Arg Gly Ser
    130                 135                 140

Ala Leu Ala Val Gln Leu Val Ser Pro Leu Thr Phe Asp Thr Asp Gly
145                 150                 155                 160

Asn Ile Lys Leu Thr Leu Asp Arg Gly Leu His Val Thr Thr Gly Asp
                165                 170                 175

Ala Ile Glu Ser Asn Ile Ser Trp Ala Lys Gly Leu Lys Phe Glu Asp
            180                 185                 190

Gly Ala Ile Ala Thr Asn Ile Gly Asn Gly Leu Glu Phe Gly Ser Ser
        195                 200                 205

Ser Thr Glu Thr Gly Val Asp Asp Ala Tyr Pro Ile Gln Val Lys Leu
    210                 215                 220

Gly Ser Gly Leu Ser Phe Asp Ser Thr Gly Ala Ile Met Ala Gly Asn
225                 230                 235                 240

Lys Glu Asp Asp Lys Leu Thr Leu Trp Thr Thr Pro Asp Pro Ser Pro
                245                 250                 255

Asn Cys Gln Ile Leu Ala Glu Asn Asp Ala Lys Leu Thr Leu Cys Leu
            260                 265                 270

Thr Lys Cys Gly Ser Gln Ile Leu Ala Thr Val Ser Val Leu Val Val
        275                 280                 285

Gly Ser Gly Asn Leu Asn Pro Ile Thr Gly Thr Val Ser Ser Ala Gln
290                 295                 300

Val Phe Leu Arg Phe Asp Ala Asn Gly Val Leu Leu Thr Glu His Ser
305                 310                 315                 320

Thr Leu Lys Lys Tyr Trp Gly Tyr Arg Gln Gly Asp Ser Ile Asp Gly
                325                 330                 335

Thr Pro Tyr Val Asn Ala Val Gly Phe Met Pro Asn Leu Lys Ala Tyr
            340                 345                 350

Pro Lys Ser Gln Ser Ser Thr Thr Lys Asn Asn Ile Val Gly Gln Val
        355                 360                 365

Tyr Met Asn Gly Asp Val Ser Lys Pro Met Leu Leu Thr Ile Thr Leu
    370                 375                 380

Asn Gly Thr Asp Asp Ser Asn Ser Thr Tyr Ser Met Ser Phe Ser Tyr
385                 390                 395                 400

Thr Trp Thr Asn Gly Ser Tyr Val Gly Ala Thr Phe Gly Ala Asn Ser
                405                 410                 415

Tyr Thr Phe Ser Tyr Ile Ala Gln Glu
            420                 425

<210> SEQ ID NO 17
<211> LENGTH: 425
<212> TYPE: PRT
<213> ORGANISM: Adenoviridae - Mastadenovirus

<400> SEQUENCE: 17

Met Ser Lys Lys Arg Val Arg Val Asp Asp Phe Asp Pro Val Tyr
1               5                   10                  15

Pro Tyr Asp Ala Asp Asn Ala Pro Thr Val Pro Phe Ile Asn Pro Pro
                20                  25                  30

Phe Val Ser Ser Asp Gly Phe Gln Glu Lys Pro Leu Gly Val Leu Ser
            35                  40                  45
```

```
Leu Arg Leu Ala Asp Pro Val Thr Thr Lys Asn Gly Glu Ile Thr Leu
 50                  55                  60
Lys Leu Gly Glu Gly Leu Asp Leu Asp Ser Ser Gly Lys Leu Ile Ser
 65                  70                  75                  80
Asn Thr Ala Thr Lys Ala Ala Pro Leu Ser Phe Ser Asn Asn Thr
                 85                  90                  95
Ile Ser Leu Asn Met Asp His Pro Phe Tyr Thr Lys Asp Gly Lys Leu
                100                 105                 110
Ser Leu Gln Val Ser Pro Pro Leu Asn Ile Leu Arg Thr Ser Ile Leu
                115                 120                 125
Asn Thr Leu Ala Leu Gly Phe Gly Ser Gly Leu Gly Leu Arg Gly Ser
130                 135                 140
Ala Leu Ala Val Gln Leu Val Ser Pro Leu Thr Phe Asp Thr Asp Gly
145                 150                 155                 160
Asn Ile Lys Leu Thr Leu Asp Arg Gly Leu His Val Thr Thr Gly Asp
                165                 170                 175
Ala Ile Glu Ser Asn Ile Ser Trp Ala Lys Gly Leu Lys Phe Glu Asp
                180                 185                 190
Gly Ala Ile Ala Thr Asn Ile Gly Asn Gly Leu Glu Phe Gly Ser Ser
                195                 200                 205
Ser Thr Glu Thr Gly Val Asp Asp Ala Tyr Pro Ile Gln Val Lys Leu
210                 215                 220
Gly Ser Gly Leu Ser Phe Asp Ser Thr Gly Ala Ile Met Ala Gly Asn
225                 230                 235                 240
Lys Glu Asp Asp Lys Leu Thr Leu Trp Thr Thr Pro Asp Pro Ser Pro
                245                 250                 255
Asn Cys Gln Ile Leu Ala Glu Asn Asp Ala Lys Leu Thr Leu Cys Leu
                260                 265                 270
Thr Lys Cys Gly Ser Gln Ile Leu Ala Thr Val Ser Val Leu Val Val
                275                 280                 285
Gly Ser Gly Asn Leu Asn Pro Ile Thr Gly Thr Val Ser Ser Ala Gln
                290                 295                 300
Val Phe Leu Arg Phe Asp Ala Asn Gly Val Leu Leu Thr Glu His Ser
305                 310                 315                 320
Thr Leu Lys Lys Tyr Trp Gly Tyr Arg Gln Gly Asp Ser Ile Asp Gly
                325                 330                 335
Thr Pro Tyr Thr Asn Ala Val Gly Phe Met Pro Asn Leu Lys Ala Tyr
                340                 345                 350
Pro Lys Ser Gln Ser Ser Thr Thr Lys Asn Asn Ile Val Gly Gln Val
                355                 360                 365
Tyr Met Asn Gly Asp Val Ser Lys Pro Met Leu Leu Thr Ile Thr Leu
                370                 375                 380
Asn Gly Thr Asp Asp Ser Asn Ser Thr Tyr Ser Met Ser Phe Ser Tyr
385                 390                 395                 400
Thr Trp Thr Asn Gly Ser Tyr Val Gly Ala Thr Phe Gly Ala Asn Ser
                405                 410                 415
Tyr Thr Phe Ser Tyr Ile Ala Gln Glu
                420                 425

<210> SEQ ID NO 18
<211> LENGTH: 442
<212> TYPE: PRT
<213> ORGANISM: Adenoviridae - Mastadenovirus

<400> SEQUENCE: 18
```

```
Met Ser Lys Lys Arg Ala Arg Val Asp Asp Gly Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Ala Val Pro Leu
50                  55                      60

Lys Leu Gly Glu Gly Val Asp Leu Asp Asp Ser Gly Lys Leu Ile Ser
65                  70                  75                  80

Lys Lys Ser Thr Lys Ala Asn Ser Pro Leu Ser Ile Ser Asn Asn Thr
                85                  90                  95

Ile Ser Leu Asn Met Asp Thr Pro Phe Tyr Thr Lys Asp Gly Lys Leu
                100                 105                 110

Thr Met Gln Val Thr Ala Pro Leu Lys Leu Ala Asn Thr Ala Ile Leu
            115                 120                 125

Asn Thr Leu Ala Met Ala Tyr Gly Asn Gly Leu Gly Leu Asn Asn Asn
        130                 135                 140

Ala Leu Thr Val Gln Val Thr Ser Pro Leu Thr Phe Asp Asn Ser Lys
145                 150                 155                 160

Val Lys Ile Asn Leu Gly Asn Gly Pro Leu Met Val Ser Ala Asn Lys
                165                 170                 175

Leu Ser Ile Asn Cys Leu Arg Gly Leu Tyr Val Ala Pro Asn Asn Thr
                180                 185                 190

Gly Leu Glu Thr Asn Ile Ser Trp Ala Asn Ala Met Arg Phe Glu Gly
            195                 200                 205

Asn Ala Met Ala Val Tyr Ile Asp Thr Asn Lys Gly Leu Gln Phe Gly
        210                 215                 220

Thr Thr Ser Thr Glu Thr Gly Val Thr Asn Ala Tyr Pro Ile Gln Val
225                 230                 235                 240

Lys Leu Gly Ala Gly Leu Ala Phe Asp Ser Thr Gly Ala Ile Val Ala
                245                 250                 255

Trp Asn Lys Glu Asn Asp Ser Leu Thr Leu Trp Thr Thr Pro Asp Pro
                260                 265                 270

Ser Pro Asn Cys Lys Ile Ala Ser Glu Lys Asp Ala Lys Leu Thr Leu
            275                 280                 285

Cys Leu Thr Lys Cys Gly Ser Gln Ile Leu Gly Thr Val Ser Leu Leu
        290                 295                 300

Ala Val Ser Gly Ser Leu Ala Pro Ile Thr Gly Ala Val Ser Thr Ala
305                 310                 315                 320

Leu Val Ser Leu Lys Phe Asn Ala Asn Gly Ala Leu Leu Asp Lys Ser
                325                 330                 335

Thr Leu Asn Lys Glu Tyr Trp Asn Tyr Arg Gln Gly Asp Leu Ile Pro
            340                 345                 350

Gly Thr Pro Tyr Thr His Ala Val Gly Phe Met Pro Asn Lys Lys Ala
        355                 360                 365

Tyr Pro Lys Asn Thr Thr Ala Ala Ser Lys Ser His Ile Val Gly Asp
370                 375                 380

Val Tyr Leu Asp Gly Asp Ala Asp Lys Pro Leu Ser Leu Ile Ile Thr
385                 390                 395                 400

Phe Asn Glu Thr Asp Asp Glu Thr Cys Asp Tyr Cys Ile Asn Phe Gln
                405                 410                 415
```

```
Trp Lys Trp Gly Ala Asp Gln Tyr Lys Asp Lys Thr Leu Ala Thr Ser
            420                 425                 430

Ser Phe Thr Phe Ser Tyr Ile Ala Gln Glu
        435                 440

<210> SEQ ID NO 19
<211> LENGTH: 577
<212> TYPE: PRT
<213> ORGANISM: Adenoviridae - Mastadenovirus

<400> SEQUENCE: 19

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
        195                 200                 205

Ala Pro Leu His Val Val Asp Thr Leu Asn Ala Leu Thr Val Val Thr
210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
            260                 265                 270

Tyr Pro Phe Asp Ala Gln Asn Asn Leu Ser Leu Arg Leu Gly Gln Gly
        275                 280                 285

Pro Leu Ile Val Asn Ser Ala His Asn Leu Asp Leu Asn Leu Asn Arg
290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350
```

```
Leu Gln Thr Lys Leu Gly Leu Gly Leu Glu Tyr Asp Ser Asn Lys Ala
            355                 360                 365

Ile Ile Thr Lys Leu Gly Thr Gly Leu Ser Phe Asp Asn Thr Gly Ala
            370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
            405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
            435                 440                 445

Thr Ser Ala Gln Ile Val Leu Arg Phe Asp Glu Asn Gly Val Leu Leu
            450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
            485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
            515                 520                 525

Thr Ile Thr Leu Asn Gly Thr Asn Glu Thr Gly Asp Ala Thr Val Ser
            530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
            565                 570                 575

Glu

<210> SEQ ID NO 20
<211> LENGTH: 937
<212> TYPE: PRT
<213> ORGANISM: Adenoviridae - Mastadenovirus

<400> SEQUENCE: 20

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
            50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
            85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
            115                 120                 125

Ala Pro Asn Thr Ser Gln Trp Ile Thr Lys Asp Asn Gly Thr Asp Lys
            130                 135                 140
```

```
Thr Tyr Ser Phe Gly Asn Ala Pro Val Arg Gly Leu Asp Ile Thr Glu
145                 150                 155                 160

Glu Gly Leu Gln Ile Gly Pro Asp Glu Ser Gly Gly Glu Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
        195                 200                 205

Leu Lys Pro Ala Thr Asn Met Lys Pro Cys Tyr Gly Ser Phe Ala Lys
    210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
        275                 280                 285

Glu Thr Ser Ser Ser Phe Asn Leu Gly Gln Gln Ser Met Pro Asn Arg
290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
    370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
    450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
        515                 520                 525

Arg Tyr Arg Ser Met Leu Leu Gly Asn Gly Arg Tyr Val Pro Phe His
    530                 535                 540

Ile Gln Val Pro Gln Lys Phe Phe Ala Ile Lys Ser Leu Leu Leu Leu
545                 550                 555                 560
```

Pro Gly Ser Tyr Thr Tyr Glu Trp Asn Phe Arg Lys Asp Val Asn Met
            565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
            595                 600                 605

His Asn Thr Ala Ser Thr Leu Glu Ala Met Leu Arg Asn Asp Thr Asn
            610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
            645                 650                 655

Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
            675                 680                 685

Ser Ile Pro Tyr Leu Asp Gly Thr Phe Tyr Leu Asn His Thr Phe Lys
            690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
            725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
            755                 760                 765

Pro Glu Gly Tyr Lys Asp Arg Met Tyr Ser Phe Phe Arg Asn Phe Gln
            770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
            805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Ala Ser Val Thr Gln Lys Lys
            835                 840                 845

Phe Leu Cys Asp Arg Val Met Trp Arg Ile Pro Phe Ser Ser Asn Phe
            850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
            885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
            915                 920                 925

Pro Phe Ser Ala Gly Asn Ala Thr Thr
            930                 935

<210> SEQ ID NO 21
<211> LENGTH: 937
<212> TYPE: PRT
<213> ORGANISM: Adenoviridae - Mastadenovirus

<400> SEQUENCE: 21

-continued

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
            35                  40                  45

Thr Val Ala Pro Thr His Asp Val Thr Thr Asp Arg Ser Gln Arg Leu
50                  55                  60

Thr Leu Arg Phe Val Pro Val Asp Gly Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ala Leu Ala Pro Lys Gly
            115                 120                 125

Ala Pro Asn Thr Ser Gln Trp Ile Thr Lys Asp Asn Gly Thr Asp Lys
130                 135                 140

Thr Tyr Ser Phe Gly Asn Ala Pro Val Arg Gly Leu Asp Ile Thr Glu
145                 150                 155                 160

Glu Gly Leu Gln Ile Arg Thr Asp Glu Ser Gly Gly Glu Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
            195                 200                 205

Leu Lys Pro Ala Thr Asn Met Lys Pro Cys Tyr Gly Ser Phe Ala Lys
210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
            275                 280                 285

Glu Thr Ser Ser Ser Phe Asn Leu Gly Gln Gln Ser Met Pro Asn Arg
290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
            355                 360                 365

Asn Gln Ala Val Asp Ser Tyr Asp Pro Asp Val Arg Ile Ile Glu Asn
370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415
```

-continued

```
Asn Gly Thr Ala Asn Ala Thr Glu Trp Ser Asp Thr Ser Val Asn
            420                 425                 430
Asn Ala Asn Glu Ile Ala Lys Gly Asn Pro Phe Ala Met Glu Ile Asn
        435                 440                 445
Ile Gln Ala Asn Leu Trp Arg Asn Phe Leu Tyr Ala Asn Val Ala Leu
    450                 455                 460
Tyr Leu Pro Asp Ser Tyr Lys Tyr Thr Pro Ala Asn Ile Thr Leu Pro
465                 470                 475                 480
Thr Asn Thr Asn Thr Tyr Asp Tyr Met Asn Gly Arg Val Val Ala Pro
                485                 490                 495
Ser Leu Val Asp Ala Tyr Ile Asn Ile Gly Ala Arg Trp Ser Leu Asp
            500                 505                 510
Pro Met Asp Asn Val Asn Pro Phe Asn His His Arg Asn Ala Gly Leu
        515                 520                 525
Arg Tyr Arg Ser Met Leu Leu Gly Asn Gly Arg Tyr Val Pro Phe His
    530                 535                 540
Ile Gln Val Pro Gln Lys Phe Ala Ile Lys Ser Leu Leu Leu Leu
545                 550                 555                 560
Pro Gly Ser Tyr Thr Tyr Glu Trp Asn Phe Arg Lys Asp Val Asn Met
                565                 570                 575
Ile Leu Gln Ser Ser Leu Gly Asn Asp Leu Arg Thr Asp Gly Ala Ser
            580                 585                 590
Ile Ala Phe Thr Ser Ile Asn Leu Tyr Ala Thr Phe Phe Pro Met Ala
        595                 600                 605
His Asn Thr Ala Ser Thr Leu Glu Ala Met Leu Arg Asn Asp Thr Asn
    610                 615                 620
Asp Gln Ser Phe Asn Asp Tyr Leu Ser Ala Ala Asn Met Leu Tyr Pro
625                 630                 635                 640
Ile Pro Ala Asn Ala Thr Asn Val Pro Ile Ser Ile Pro Ser Arg Asn
                645                 650                 655
Trp Ala Ala Phe Arg Gly Trp Ser Phe Thr Arg Leu Lys Thr Arg Glu
            660                 665                 670
Thr Pro Ser Leu Gly Ser Gly Phe Asp Pro Tyr Phe Val Tyr Ser Gly
        675                 680                 685
Ser Ile Pro Tyr Leu Asp Gly Thr Phe Tyr Leu Asn His Thr Phe Lys
    690                 695                 700
Lys Val Ser Ile Thr Phe Asp Ser Ser Val Ser Trp Pro Gly Asn Asp
705                 710                 715                 720
Arg Leu Leu Thr Pro Asn Glu Phe Glu Ile Lys Arg Thr Val Asp Gly
                725                 730                 735
Glu Gly Tyr Asn Val Ala Gln Cys Asn Met Thr Lys Asp Trp Phe Leu
            740                 745                 750
Val Gln Met Leu Ala His Tyr Asn Ile Gly Tyr Gln Gly Phe Tyr Val
        755                 760                 765
Pro Glu Gly Tyr Lys Asp Arg Met Tyr Ser Phe Phe Arg Asn Phe Gln
    770                 775                 780
Pro Met Ser Arg Gln Val Val Asp Glu Val Asn Tyr Lys Asp Tyr Gln
785                 790                 795                 800
Ala Val Thr Leu Ala Tyr Gln His Asn Asn Ser Gly Phe Val Gly Tyr
                805                 810                 815
Leu Ala Pro Thr Met Arg Gln Gly Gln Pro Tyr Pro Ala Asn Tyr Pro
            820                 825                 830
Tyr Pro Leu Ile Gly Lys Ser Ala Val Ala Ser Val Thr Gln Lys Lys
```

```
                    835                 840                 845
    Phe Leu Cys Asp Arg Val Met Trp Arg Ile Pro Phe Ser Ser Asn Phe
        850                 855                 860

Met Ser Met Gly Ala Leu Thr Asp Leu Gly Gln Asn Met Leu Tyr Ala
    865                 870                 875                 880

Asn Ser Ala His Ala Leu Asp Met Asn Phe Glu Val Asp Pro Met Asp
                    885                 890                 895

Glu Ser Thr Leu Leu Tyr Val Val Phe Glu Val Phe Asp Val Val Arg
                900                 905                 910

Val His Gln Pro His Arg Gly Val Ile Lys Ala Val Tyr Leu Arg Thr
                915                 920                 925

Pro Phe Ser Ala Gly Asn Ala Thr Thr
        930                 935

<210> SEQ ID NO 22
<211> LENGTH: 937
<212> TYPE: PRT
<213> ORGANISM: Adenoviridae - Mastadenovirus

<400> SEQUENCE: 22

Met Ala Thr Pro Ser Met Leu Pro Gln Trp Ala Tyr Met His Ile Ala
    1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Ser Leu Gly Asn Lys Phe Arg Asn Pro
                35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
    65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
                100                 105                 110

Phe Lys Pro Tyr Ser Gly Thr Ala Tyr Asn Ser Leu Ala Pro Lys Gly
                115                 120                 125

Ala Pro Asn Thr Ser Gln Trp Ile Thr Lys Asp Asn Gly Thr Asp Lys
    130                 135                 140

Thr Tyr Ser Phe Gly Asn Ala Pro Val Arg Gly Leu Asp Ile Thr Glu
    145                 150                 155                 160

Glu Gly Leu Gln Ile Gly Thr Asp Glu Ser Gly Gly Glu Ser Lys Lys
                    165                 170                 175

Ile Phe Ala Asp Lys Thr Tyr Gln Pro Glu Pro Gln Leu Gly Asp Glu
                180                 185                 190

Glu Trp His Asp Thr Ile Gly Ala Glu Asp Lys Tyr Gly Gly Arg Ala
                195                 200                 205

Leu Lys Pro Ala Thr Asn Met Lys Pro Cys Tyr Gly Ser Phe Ala Lys
                210                 215                 220

Pro Thr Asn Ala Lys Gly Gly Gln Ala Lys Ser Arg Thr Lys Asp Asp
    225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
                260                 265                 270
```

```
Asp Leu Asp Thr Pro Asp Thr His Ile Ile Tyr Lys Pro Gly Thr Asp
            275                 280                 285

Glu Thr Ser Ser Ser Phe Asn Leu Gly Gln Gln Ser Met Pro Asn Arg
290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
            355                 360                 365

Asn Gln Ala Val Asp Ser Tyr Asp Pro Asp Val Arg Ile Ile Glu Asn
370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
435                 440                 445

Ile Gln Ala Asn Leu Trp Arg Asn Phe Leu Tyr Ala Asn Val Ala Leu
            450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
            515                 520                 525

Arg Tyr Arg Ser Met Leu Leu Gly Asn Gly Arg Tyr Val Pro Phe His
530                 535                 540

Ile Gln Val Pro Gln Lys Phe Phe Ala Ile Lys Ser Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ala Phe Thr Ser Ile Asn Leu Tyr Ala Thr Phe Phe Pro Met Ala
            595                 600                 605

His Asn Thr Ala Ser Thr Leu Glu Ala Met Leu Arg Asn Asp Thr Asn
610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Arg Glu
            660                 665                 670

Thr Pro Ser Leu Gly Ser Gly Phe Asp Pro Tyr Phe Val Tyr Ser Gly
            675                 680                 685

Ser Ile Pro Tyr Leu Asp Gly Thr Phe Tyr Leu Asn His Thr Phe Lys
```

```
                    690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                    725                 730                 735

Glu Gly Tyr Asn Val Ala Gln Cys Asn Met Thr Lys Asp Trp Phe Leu
                740                 745                 750

Val Gln Met Leu Ala His Tyr Asn Ile Gly Tyr Gln Gly Phe Tyr Val
            755                 760                 765

Pro Glu Gly Tyr Lys Asp Arg Met Tyr Ser Phe Phe Arg Asn Phe Gln
        770                 775                 780

Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
                    805                 810                 815

Leu Ala Pro Thr Met Arg Gln Gly Gln Pro Tyr Pro Ala Asn Tyr Pro
                820                 825                 830

Tyr Pro Leu Ile Gly Lys Ser Ala Val Ala Ser Val Thr Gln Lys Lys
            835                 840                 845

Phe Leu Cys Asp Arg Val Met Trp Arg Ile Pro Phe Ser Ser Asn Phe
        850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
                    885                 890                 895

Glu Ser Thr Leu Leu Tyr Val Val Phe Glu Val Phe Asp Val Val Arg
                900                 905                 910

Val His Gln Pro His Arg Gly Val Ile Glu Ala Val Tyr Leu Arg Thr
            915                 920                 925

Pro Phe Ser Ala Gly Asn Ala Thr Thr
        930                 935

<210> SEQ ID NO 23
<211> LENGTH: 937
<212> TYPE: PRT
<213> ORGANISM: Adenoviridae - Mastadenovirus
<220> FEATURE:
<221> NAME/KEY: misc_feature
<222> LOCATION: (296)..(296)
<223> OTHER INFORMATION: Xaa can be any naturally occurring amino acid

<400> SEQUENCE: 23

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110
```

```
Phe Lys Pro Tyr Ser Gly Thr Ala Tyr Asn Ser Leu Ala Pro Lys Gly
        115                 120                 125

Ala Pro Asn Thr Ser Gln Trp Ile Thr Lys Asp Asn Gly Thr Asp Lys
130                 135                 140

Thr Tyr Ser Phe Gly Asn Ala Pro Val Arg Gly Leu Asp Ile Thr Glu
145                 150                 155                 160

Glu Gly Leu Gln Ile Gly Thr Asp Glu Ser Gly Gly Lys Ser Lys Lys
                165                 170                 175

Ile Phe Ala Asp Lys Thr Tyr Gln Pro Glu Pro Gln Leu Gly Asp Glu
            180                 185                 190

Glu Trp His Asp Thr Ile Gly Ala Glu Asp Lys Tyr Gly Gly Arg Ala
        195                 200                 205

Leu Lys Pro Ala Thr Asn Met Lys Pro Cys Tyr Gly Ser Phe Ala Lys
    210                 215                 220

Pro Thr Asn Ala Lys Gly Gly Gln Ala Lys Ser Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Asp Thr Pro Asp Thr His Ile Ile Tyr Lys Pro Gly Thr Asp
        275                 280                 285

Glu Thr Ser Ser Ser Phe Asn Xaa Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
    370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
    450                 455                 460

Tyr Leu Pro Asp Ser Tyr Lys Tyr Thr Pro Ala Asn Ile Thr Leu Pro
465                 470                 475                 480

Thr Asn Thr Asn Thr Tyr Asp Tyr Met Asn Gly Arg Val Val Ala Pro
                485                 490                 495

Ser Leu Val Asp Ala Tyr Ile Asn Ile Gly Ala Arg Trp Ser Leu Asp
            500                 505                 510

Pro Met Asp Asn Val Asn Pro Phe Asn His His Arg Asn Ala Gly Leu
        515                 520                 525
```

-continued

```
Arg Tyr Arg Ser Met Leu Leu Gly Asn Gly Arg Tyr Val Pro Phe His
    530                 535                 540
Ile Gln Val Pro Gln Lys Phe Ala Ile Lys Asn Leu Leu Leu Leu
545                 550                 555                 560
Pro Gly Ser Tyr Thr Tyr Glu Trp Asn Phe Arg Lys Asp Val Asn Met
                565                 570                 575
Ile Leu Gln Ser Ser Leu Gly Asn Asp Leu Arg Thr Asp Gly Ala Ser
                580                 585                 590
Ile Ala Phe Thr Ser Ile Asn Leu Tyr Ala Thr Phe Phe Pro Met Ala
                595                 600                 605
His Asn Thr Ala Ser Thr Leu Glu Ala Met Leu Arg Asn Asp Thr Asn
    610                 615                 620
Asp Gln Ser Phe Asn Asp Tyr Leu Ser Ala Ala Asn Met Leu Tyr Pro
625                 630                 635                 640
Ile Pro Ala Asn Ala Thr Asn Val Pro Ile Ser Ile Pro Ser Arg Asn
                645                 650                 655
Trp Ala Ala Phe Arg Gly Trp Ser Phe Thr Arg Leu Lys Thr Arg Glu
                660                 665                 670
Thr Pro Ser Leu Gly Ser Gly Phe Asp Pro Tyr Phe Val Tyr Ser Gly
                675                 680                 685
Ser Ile Pro Tyr Leu Asp Gly Thr Phe Tyr Leu Asn His Thr Phe Lys
                690                 695                 700
Lys Val Ser Ile Thr Phe Asp Ser Ser Val Ser Trp Pro Gly Asn Asp
705                 710                 715                 720
Arg Leu Leu Thr Pro Asn Glu Phe Glu Ile Lys Arg Thr Val Asp Gly
                725                 730                 735
Glu Gly Tyr Asn Val Ala Gln Cys Asn Met Thr Lys Asp Trp Phe Leu
                740                 745                 750
Val Gln Met Leu Ala His Tyr Asn Ile Gly Tyr Gln Gly Phe Tyr Val
                755                 760                 765
Pro Glu Gly Tyr Lys Asp Arg Met Tyr Ser Phe Arg Asn Phe Gln
                770                 775                 780
Pro Met Ser Arg Gln Val Val Asp Glu Val Asn Tyr Lys Asp Tyr Gln
785                 790                 795                 800
Ala Val Thr Leu Ala Tyr Gln His Asn Asn Ser Gly Phe Val Gly Tyr
                805                 810                 815
Leu Ala Pro Thr Met Arg Gln Gly Gln Pro Tyr Pro Ala Asn Tyr Pro
                820                 825                 830
Tyr Pro Leu Ile Gly Lys Ser Ala Val Ala Ser Val Thr Gln Lys Lys
                835                 840                 845
Phe Leu Cys Asp Arg Val Met Trp Arg Ile Pro Phe Ser Ser Asn Phe
850                 855                 860
Met Ser Met Gly Ala Leu Thr Asp Leu Gly Gln Asn Met Leu Tyr Ala
865                 870                 875                 880
Asn Ser Ala His Ala Leu Asp Met Asn Phe Glu Val Asp Pro Met Asp
                885                 890                 895
Glu Ser Thr Leu Leu Tyr Val Val Phe Glu Val Phe Asp Val Val Arg
                900                 905                 910
Val His Gln Pro His Arg Gly Val Ile Glu Ala Val Tyr Leu Arg Thr
                915                 920                 925
Pro Phe Ser Ala Gly Asn Ala Thr Thr
930                 935
```

-continued

```
<210> SEQ ID NO 24
<211> LENGTH: 937
<212> TYPE: PRT
<213> ORGANISM: Adenoviridae - Mastadenovirus
<220> FEATURE:
<221> NAME/KEY: misc_feature
<222> LOCATION: (538)..(538)
<223> OTHER INFORMATION: Xaa can be any naturally occurring amino acid

<400> SEQUENCE: 24

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Val Thr Lys Asp Asn Gly Thr Asp Lys
    130                 135                 140

Thr Tyr Ser Phe Gly Asn Ala Pro Val Arg Gly Leu Asp Ile Thr Glu
145                 150                 155                 160

Glu Gly Leu Gln Ile Gly Thr Asp Asp Ser Ser Thr Glu Ser Lys Lys
                165                 170                 175

Ile Phe Ala Asp Lys Thr Tyr Gln Pro Glu Pro Gln Val Gly Asp Glu
            180                 185                 190

Glu Trp His Asp Thr Ile Gly Ala Glu Asp Lys Tyr Gly Gly Arg Ala
        195                 200                 205

Leu Lys Pro Ala Thr Asn Met Lys Pro Cys Tyr Gly Ser Phe Ala Lys
    210                 215                 220

Pro Thr Asn Ala Lys Gly Gly Gln Ala Lys Thr Arg Thr Lys Asp Asp
225                 230                 235                 240

Gly Thr Thr Glu Pro Asp Ile Asp Met Ala Phe Phe Asp Asp Arg Ser
                245                 250                 255

Gln Gln Ala Ser Phe Ser Pro Glu Leu Val Leu Tyr Thr Glu Asn Val
            260                 265                 270

Asp Leu Glu Thr Pro Asp Thr His Ile Ile Tyr Lys Pro Gly Thr Asp
        275                 280                 285

Glu Thr Ser Ser Ser Phe Asn Leu Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365
```

```
Asn Gln Ala Val Asp Ser Tyr Asp Pro Asp Val Arg Ile Ile Glu Asn
        370                 375                 380

His Gly Val Glu Asp Glu Leu Pro Asn Tyr Cys Phe Pro Leu Asn Gly
385                 390                 395                 400

Val Gly Phe Thr Asp Thr Phe Gln Gly Ile Lys Val Lys Thr Thr Asn
                405                 410                 415

Asn Gly Thr Ala Asn Ala Thr Glu Trp Glu Ser Asp Thr Ser Val Asn
            420                 425                 430

Asn Ala Asn Glu Ile Ala Lys Gly Asn Pro Phe Ala Met Glu Ile Asn
        435                 440                 445

Ile Gln Ala Asn Leu Trp Arg Asn Phe Leu Tyr Ala Asn Val Ala Leu
450                 455                 460

Tyr Leu Pro Asp Ser Tyr Lys Tyr Thr Pro Ala Asn Val Thr Leu Pro
465                 470                 475                 480

Thr Asn Thr Asn Thr Tyr Glu Tyr Met Asn Gly Arg Val Val Ala Pro
                485                 490                 495

Ser Leu Val Asp Ser Tyr Ile Asn Ile Gly Ala Arg Trp Ser Leu Asp
                500                 505                 510

Pro Met Asp Asn Val Asn Pro Phe Asn His His Arg Asn Ala Gly Leu
        515                 520                 525

Arg Tyr Arg Ser Met Leu Leu Gly Asn Xaa Arg Phe Val Pro Phe His
        530                 535                 540

Ile Gln Val Pro Gln Lys Phe Phe Ala Ile Lys Ser Leu Leu Leu Leu
545                 550                 555                 560

Pro Gly Ser Tyr Thr Tyr Glu Trp Asn Phe Arg Lys Asp Val Asn Met
                565                 570                 575

Ile Leu Gln Ser Ser Leu Gly Asn Asp Leu Arg Thr Asp Gly Ala Ser
            580                 585                 590

Ile Ser Phe Thr Ser Ile Asn Leu Tyr Ala Thr Phe Phe Pro Met Ala
        595                 600                 605

His Asn Thr Ala Ser Thr Leu Glu Ala Met Leu Arg Asn Asp Thr Asn
        610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Thr Lys Glu
                660                 665                 670

Thr Pro Ser Leu Gly Ser Gly Phe Asp Pro Tyr Phe Val Tyr Ser Gly
            675                 680                 685

Ser Ile Pro Tyr Leu Asp Gly Thr Phe Tyr Leu Asn His Thr Phe Lys
        690                 695                 700

Lys Val Ser Ile Thr Phe Asp Ser Ser Val Ser Trp Pro Gly Asn Asp
705                 710                 715                 720

Arg Leu Leu Thr Pro Asn Glu Phe Glu Ile Lys Arg Thr Val Asp Gly
                725                 730                 735

Glu Gly Tyr Asn Val Ala Gln Cys Asn Met Thr Lys Asp Trp Phe Leu
            740                 745                 750

Val Gln Met Leu Ala His Tyr Asn Ile Gly Tyr Gln Gly Phe Tyr Val
        755                 760                 765

Pro Glu Gly Tyr Lys Asp Arg Met Tyr Ser Phe Phe Arg Asn Phe Gln
770                 775                 780
```

```
Pro Met Ser Arg Gln Val Val Asp Glu Val Asn Tyr Lys Asp Tyr Gln
785                 790                 795                 800

Ala Val Thr Leu Ala Tyr Gln His Asn Asn Ser Gly Phe Val Gly Tyr
            805                 810                 815

Leu Ala Pro Thr Met Arg Gln Gly Gln Pro Tyr Pro Ala Asn Tyr Pro
            820                 825                 830

Tyr Pro Leu Ile Gly Lys Ser Ala Val Thr Ser Val Thr Gln Lys Lys
            835                 840                 845

Phe Leu Cys Asp Arg Val Met Trp Arg Ile Pro Phe Ser Ser Asn Phe
            850                 855                 860

Met Ser Met Gly Ala Leu Thr Asp Leu Gly Gln Asn Met Leu Tyr Ala
865                 870                 875                 880

Asn Ser Ala His Ala Leu Asp Met Asn Phe Glu Val Asp Pro Met Asp
            885                 890                 895

Glu Ser Thr Leu Leu Tyr Val Val Phe Glu Val Phe Asp Val Val Arg
            900                 905                 910

Val His Gln Pro His Arg Gly Val Ile Glu Ala Val Tyr Leu Arg Thr
            915                 920                 925

Pro Phe Ser Ala Gly Asn Ala Thr Thr
            930                 935

<210> SEQ ID NO 25
<211> LENGTH: 962
<212> TYPE: PRT
<213> ORGANISM: Adenoviridae - Mastadenovirus

<400> SEQUENCE: 25

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
            115                 120                 125

Ala Pro Asn Ser Cys Glu Trp Glu Gln Val Glu Pro Ala Glu Glu Ala
130                 135                 140

Ala Glu Asn Glu Asp Glu Glu Glu Glu Asp Val Val Asp Pro Gln
145                 150                 155                 160

Glu Gln Glu Pro Thr Thr Lys Thr His Val Tyr Ala Gln Ala Pro Leu
                165                 170                 175

Ser Gly Glu Lys Ile Thr Lys Asp Gly Leu Gln Ile Gly Thr Glu Ala
            180                 185                 190

Thr Ala Ala Gly Gly Thr Lys Asp Leu Phe Ala Asp Pro Thr Phe Gln
            195                 200                 205

Pro Glu Pro Gln Val Gly Glu Ser Gln Trp Asn Glu Ala Asp Ala Thr
        210                 215                 220
```

```
Ala Ala Gly Gly Arg Val Leu Lys Lys Thr Thr Pro Met Lys Pro Cys
225                 230                 235                 240

Tyr Gly Ser Tyr Ala Arg Pro Thr Asn Ala Asn Gly Gly Gln Gly Val
            245                 250                 255

Leu Lys Ala Asn Ala Gln Gly Val Leu Glu Ser Gln Val Glu Met Gln
        260                 265                 270

Phe Phe Ser Thr Ser Thr Asn Ala Thr Asn Glu Gln Asn Asn Ile Gln
    275                 280                 285

Pro Lys Leu Val Leu Tyr Ser Glu Asp Val His Met Glu Thr Pro Asp
290                 295                 300

Thr His Ile Ser Tyr Lys Pro Thr Lys Ser Asp Asp Asn Ser Lys Val
305                 310                 315                 320

Met Leu Gly Gln Gln Ser Met Pro Asn Arg Pro Asn Tyr Ile Ala Phe
            325                 330                 335

Arg Asp Asn Phe Ile Gly Leu Met Tyr Tyr Asn Ser Thr Gly Asn Met
        340                 345                 350

Gly Val Leu Ala Gly Gln Ala Ser Gln Leu Asn Ala Val Val Asp Leu
    355                 360                 365

Gln Asp Arg Asn Thr Glu Leu Ser Tyr Gln Leu Leu Leu Asp Ser Met
370                 375                 380

Gly Asp Arg Thr Arg Tyr Phe Ser Met Trp Asn Gln Ala Val Asp Ser
385                 390                 395                 400

Tyr Asp Pro Asp Val Arg Ile Ile Glu Asn His Gly Thr Glu Asp Glu
            405                 410                 415

Leu Pro Asn Tyr Cys Phe Pro Leu Gly Gly Ile Gly Ile Thr Asp Thr
        420                 425                 430

Tyr Gln Ala Ile Lys Thr Asn Gly Asn Gly Ala Gly Asp Gln Ala Thr
    435                 440                 445

Thr Trp Gln Lys Asp Ser Gln Phe Ala Asp Arg Asn Glu Ile Gly Val
450                 455                 460

Gly Asn Asn Phe Ala Met Glu Ile Asn Leu Ser Ala Asn Leu Trp Arg
465                 470                 475                 480

Asn Phe Leu Tyr Ser Asn Val Ala Leu Tyr Leu Pro Asp Lys Leu Lys
            485                 490                 495

Tyr Asn Pro Ser Asn Val Glu Ile Ser Asp Asn Pro Asn Thr Tyr Asp
        500                 505                 510

Tyr Met Asn Lys Arg Val Val Ala Pro Gly Leu Val Asp Cys Tyr Ile
    515                 520                 525

Asn Leu Gly Ala Arg Trp Ser Leu Asp Tyr Met Asp Asn Val Asn Pro
530                 535                 540

Phe Asn His His Arg Asn Ala Gly Leu Arg Tyr Arg Ser Met Leu Leu
545                 550                 555                 560

Gly Asn Gly Arg Tyr Val Pro Phe His Ile Gln Val Pro Gln Lys Phe
            565                 570                 575

Phe Ala Ile Lys Asn Leu Leu Leu Pro Gly Ser Tyr Thr Tyr Glu
        580                 585                 590

Trp Asn Phe Arg Lys Asp Val Asn Met Val Leu Gln Ser Ser Leu Gly
    595                 600                 605

Asn Asp Leu Arg Val Asp Gly Ala Ser Ile Lys Phe Glu Ser Ile Cys
610                 615                 620

Leu Tyr Ala Thr Phe Phe Pro Met Ala His Asn Thr Ala Ser Thr Leu
625                 630                 635                 640
```

```
Glu Ala Met Leu Arg Asn Asp Thr Asn Asp Gln Ser Phe Asn Asp Tyr
                645                 650                 655

Leu Ser Ala Ala Asn Met Leu Tyr Pro Ile Pro Ala Asn Ala Thr Asn
            660                 665                 670

Val Pro Ile Ser Ile Pro Ser Arg Asn Trp Ala Ala Phe Arg Gly Trp
        675                 680                 685

Ala Phe Thr Arg Leu Lys Thr Lys Glu Thr Pro Ser Leu Gly Ser Gly
690                 695                 700

Phe Asp Pro Tyr Tyr Thr Tyr Ser Gly Ser Ile Pro Tyr Leu Asp Gly
705                 710                 715                 720

Thr Phe Tyr Leu Asn His Thr Phe Lys Lys Val Ser Val Thr Phe Asp
                725                 730                 735

Ser Ser Val Ser Trp Pro Gly Asn Asp Arg Leu Leu Thr Pro Asn Glu
            740                 745                 750

Phe Glu Ile Lys Arg Ser Val Asp Gly Glu Gly Tyr Asn Val Ala Gln
        755                 760                 765

Cys Asn Met Thr Lys Asp Trp Phe Leu Ile Gln Met Leu Ala Asn Tyr
770                 775                 780

Asn Ile Gly Tyr Gln Gly Phe Tyr Ile Pro Glu Ser Tyr Lys Asp Arg
785                 790                 795                 800

Met Tyr Ser Phe Phe Arg Asn Phe Gln Pro Met Ser Arg Gln Val Val
                805                 810                 815

Asp Glu Thr Lys Tyr Lys Asp Tyr Gln Gln Val Gly Ile Ile His Gln
            820                 825                 830

His Asn Asn Ser Gly Phe Val Gly Tyr Leu Ala Pro Thr Met Arg Glu
        835                 840                 845

Gly Gln Ala Tyr Pro Ala Asn Phe Pro Tyr Pro Leu Ile Gly Lys Thr
850                 855                 860

Ala Val Asp Ser Ile Thr Gln Lys Lys Phe Leu Cys Asp Arg Thr Leu
865                 870                 875                 880

Trp Arg Ile Pro Phe Ser Ser Asn Phe Met Ser Met Gly Ala Leu Thr
                885                 890                 895

Asp Leu Gly Gln Asn Leu Leu Tyr Ala Asn Ser Ala His Ala Leu Asp
            900                 905                 910

Met Thr Phe Glu Val Asp Pro Met Asp Glu Pro Thr Leu Leu Tyr Val
        915                 920                 925

Leu Phe Glu Val Phe Asp Val Val Arg Val His Gln Pro His Arg Gly
930                 935                 940

Val Ile Glu Thr Val Tyr Leu Arg Thr Pro Phe Ser Ala Gly Asn Ala
945                 950                 955                 960

Thr Thr

<210> SEQ ID NO 26
<211> LENGTH: 531
<212> TYPE: PRT
<213> ORGANISM: Adenoviridae - Mastadenovirus

<400> SEQUENCE: 26

Met Met Arg Arg Val Tyr Pro Glu Gly Pro Pro Ser Tyr Glu Ser
1               5                   10                  15

Val Met Gln Gln Ala Val Ala Ala Met Gln Pro Leu Glu Ala
                20                  25                  30

Pro Tyr Val Pro Pro Arg Tyr Leu Ala Pro Thr Glu Gly Arg Asn Ser
            35                  40                  45
```

```
Ile Arg Tyr Ser Glu Leu Ala Pro Leu Tyr Asp Thr Thr Arg Leu Tyr
 50                  55                  60

Leu Val Asp Asn Lys Ser Ala Asp Ile Ala Ser Leu Asn Tyr Gln Asn
 65                  70                  75                  80

Asp His Ser Asn Phe Leu Thr Thr Val Val Gln Asn Asn Asp Phe Thr
                 85                  90                  95

Pro Thr Glu Ala Ser Thr Gln Thr Ile Asn Phe Asp Glu Arg Ser Arg
                100                 105                 110

Trp Gly Gly Gln Leu Lys Thr Ile Met His Thr Asn Met Pro Asn Val
                115                 120                 125

Asn Glu Phe Met Tyr Ser Asn Lys Phe Lys Ala Arg Val Met Val Ser
                130                 135                 140

Arg Lys Thr Pro Asn Gly Val Ala Val Gly Asp Asp Tyr Asp Gly Gly
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
                180                 185                 190

Asp Asn Tyr Leu Ala Val Gly Arg Gln Asn Gly Val Leu Glu Ser Asp
                195                 200                 205

Ile Gly Val Lys Phe Asp Thr Arg Asn Phe Arg Leu Gly Trp Asp Pro
                210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
                260                 265                 270

Gly Phe Gln Ile Leu Tyr Glu Asp Leu Glu Gly Gly Asn Ile Pro Ala
                275                 280                 285

Leu Leu Asp Val Glu Ala Tyr Glu Lys Ser Lys Glu Glu Ser Ala Ala
                290                 295                 300

Ala Ala Thr Ala Ala Val Ala Thr Ala Ser Thr Glu Val Arg Gly Asp
305                 310                 315                 320

Asn Phe Ala Ser Ala Ala Val Ala Glu Ala Ala Glu Thr Glu Ser
                325                 330                 335

Lys Ile Val Ile Gln Pro Val Glu Lys Asp Ser Lys Asp Arg Ser Tyr
                340                 345                 350

Asn Val Leu Ala Asp Lys Lys Asn Thr Ala Tyr Arg Ser Trp Tyr Leu
                355                 360                 365

Ala Tyr Asn Tyr Gly Asp Pro Glu Lys Gly Val Arg Ser Trp Thr Leu
                370                 375                 380

Leu Thr Thr Ser Asp Val Thr Cys Gly Val Glu Gln Val Tyr Trp Ser
385                 390                 395                 400

Leu Pro Asp Met Met Gln Asp Pro Val Thr Phe Arg Ser Thr Arg Gln
                405                 410                 415

Val Ser Asn Tyr Pro Val Val Gly Ala Glu Leu Leu Pro Val Tyr Ser
                420                 425                 430

Lys Ser Phe Phe Asn Glu Gln Ala Val Tyr Ser Gln Leu Arg Ala
                435                 440                 445

Phe Thr Ser Leu Thr His Val Phe Asn Arg Phe Pro Glu Asn Gln Ile
450                 455                 460

Leu Val Arg Pro Pro Ala Pro Thr Ile Thr Thr Val Ser Glu Asn Val
```

```
                465                 470                 475                 480
            Pro Ala Leu Thr Asp His Gly Thr Leu Pro Leu Arg Ser Ser Ile Arg
                            485                 490                 495
            Gly Val Gln Arg Val Thr Val Thr Asp Ala Arg Arg Thr Cys Pro
                            500                 505                 510
            Tyr Val Tyr Lys Ala Leu Gly Val Ala Pro Arg Val Leu Ser Ser
                            515                 520                 525
            Arg Thr Phe
                    530

<210> SEQ ID NO 27
<211> LENGTH: 541
<212> TYPE: PRT
<213> ORGANISM: Adenoviridae - Mastadenovirus

<400> SEQUENCE: 27

Met Met Arg Arg Val Tyr Pro Glu Gly Pro Pro Ser Tyr Glu Ser
1               5                   10                  15

Val Met Gln Gln Ala Val Ala Val Met Gln Pro Pro Leu Glu Ala
                20                  25                  30

Pro Tyr Val Pro Pro Arg Tyr Leu Ala Pro Thr Glu Gly Arg Asn Ser
                35                  40                  45

Ile Arg Tyr Ser Glu Leu Ala Pro Leu Tyr Asp Thr Thr Arg Leu Tyr
50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
                100                 105                 110

Trp Gly Gly Gln Leu Lys Thr Ile Met His Thr Asn Met Pro Asn Val
                115                 120                 125

Asn Glu Phe Met Tyr Ser Asn Lys Phe Lys Ala Arg Val Met Val Ser
130                 135                 140

Arg Lys Thr Pro Asn Gly Val Thr Val Gly Asp Asp Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
                180                 185                 190

Asp Asn Tyr Leu Ala Val Gly Arg Gln Asn Gly Val Leu Glu Ser Asp
                195                 200                 205

Ile Gly Val Lys Phe Asp Thr Arg Asn Phe Arg Leu Gly Trp Asp Pro
210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
                260                 265                 270

Gly Phe Gln Ile Leu Tyr Glu Asp Leu Glu Gly Gly Asn Ile Pro Ala
                275                 280                 285

Leu Leu Asp Val Glu Ala Tyr Glu Lys Ser Lys Glu Asp Ser Ala Ala
                290                 295                 300
```

```
Ala Thr Thr Ala Ala Val Ala Thr Ala Thr Asp Ala Asp Ala
305                 310                 315                 320

Thr Thr Thr Arg Gly Asp Thr Phe Ala Thr Gln Ala Glu Ala Ala
                325                 330                 335

Ala Leu Ala Ala Thr Asp Asp Ser Glu Ser Lys Ile Val Ile Lys Pro
            340                 345                 350

Val Glu Lys Asp Ser Lys Asp Arg Ser Tyr Asn Val Leu Ala Asp Lys
        355                 360                 365

Lys Asn Thr Ala Tyr Arg Ser Trp Tyr Leu Ala Tyr Asn Tyr Gly Asp
    370                 375                 380

Pro Glu Lys Gly Val Arg Ser Trp Thr Leu Leu Thr Thr Ser Asp Val
385                 390                 395                 400

Thr Cys Gly Val Glu Gln Val Tyr Trp Ser Leu Pro Asp Met Met Gln
                405                 410                 415

Asp Pro Val Thr Phe Arg Ser Thr Arg Gln Val Ser Asn Tyr Pro Val
                420                 425                 430

Val Gly Ala Glu Leu Leu Pro Val Tyr Ser Lys Ser Phe Phe Asn Glu
            435                 440                 445

Gln Ala Val Tyr Ser Gln Gln Leu Arg Ala Phe Thr Ser Leu Thr His
        450                 455                 460

Val Phe Asn Arg Phe Pro Glu Asn Gln Ile Leu Val Arg Pro Pro Ala
465                 470                 475                 480

Pro Thr Ile Thr Thr Val Ser Glu Asn Val Pro Ala Leu Thr Asp His
                485                 490                 495

Gly Thr Leu Pro Leu Arg Ser Ser Ile Arg Gly Val Gln Arg Val Thr
            500                 505                 510

Val Thr Asp Ala Arg Arg Arg Thr Cys Pro Tyr Val Tyr Lys Ala Leu
        515                 520                 525

Gly Val Val Ala Pro Arg Val Leu Ser Ser Arg Thr Phe
    530                 535                 540

<210> SEQ ID NO 28
<211> LENGTH: 532
<212> TYPE: PRT
<213> ORGANISM: Adenoviridae - Mastadenovirus

<400> SEQUENCE: 28

Met Met Arg Arg Val Tyr Pro Glu Gly Pro Pro Ser Tyr Glu Ser
1               5                   10                  15

Val Met Gln Gln Ala Val Ala Ala Met Gln Pro Leu Glu Ala
        20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
        50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Gly Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
130                 135                 140
```

```
Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
            165                 170                 175

Val Thr Met Thr Ile Asp Leu Met Asn Asn Ala Ile Ile Asp Asn Tyr
        180                 185                 190

Leu Ala Val Gly Arg Gln Asn Gly Val Leu Glu Ser Asp Ile Gly Val
    195                 200                 205

Lys Phe Asp Thr Arg Asn Phe Arg Leu Gly Trp Asp Pro Val Thr Glu
210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
            260                 265                 270

Ile Leu Tyr Glu Asp Leu Glu Gly Gly Asn Ile Pro Ala Leu Leu Asp
        275                 280                 285

Val Glu Ala Tyr Glu Lys Ser Lys Glu Asp Ser Thr Ala Val Ala Thr
    290                 295                 300

Ala Ala Thr Val Ala Asp Ala Thr Val Thr Arg Gly Asp Thr Phe Ala
305                 310                 315                 320

Thr Gln Ala Glu Glu Ala Ala Leu Ala Ala Thr Asp Asp Ser Glu
                325                 330                 335

Ser Lys Ile Val Ile Lys Pro Val Glu Lys Asp Ser Lys Asp Arg Ser
            340                 345                 350

Tyr Asn Val Leu Ser Asp Gly Lys Asn Thr Ala Tyr Arg Ser Trp Tyr
        355                 360                 365

Leu Ala Tyr Asn Tyr Gly Asp Pro Glu Lys Gly Val Arg Ser Trp Thr
    370                 375                 380

Leu Leu Thr Thr Ser Asp Val Thr Cys Gly Val Glu Gln Val Tyr Trp
385                 390                 395                 400

Ser Leu Pro Asp Met Met Gln Asp Pro Val Thr Phe Arg Ser Thr Arg
                405                 410                 415

Gln Val Ser Asn Tyr Pro Val Val Gly Ala Glu Leu Leu Pro Val Tyr
            420                 425                 430

Ser Lys Ser Phe Phe Asn Glu Gln Ala Val Tyr Ser Gln Gln Leu Arg
        435                 440                 445

Ala Phe Thr Ser Leu Thr His Val Phe Asn Arg Phe Pro Glu Asn Gln
    450                 455                 460

Ile Leu Val Arg Pro Pro Ala Pro Thr Ile Thr Thr Val Ser Glu Asn
465                 470                 475                 480

Val Pro Ala Leu Thr Asp His Gly Thr Leu Pro Leu Arg Ser Ser Ile
                485                 490                 495

Arg Gly Val Gln Arg Val Thr Val Thr Asp Ala Arg Arg Thr Cys
            500                 505                 510

Pro Tyr Val Tyr Lys Ala Leu Gly Val Val Ala Pro Arg Val Leu Ser
        515                 520                 525

Ser Arg Thr Phe
    530
```

<210> SEQ ID NO 29
<211> LENGTH: 528

<212> TYPE: PRT
<213> ORGANISM: Adenoviridae - Mastadenovirus

<400> SEQUENCE: 29

```
Met Met Arg Arg Val Tyr Pro Glu Gly Pro Pro Ser Tyr Glu Ser
1               5                   10                  15

Val Met Gln Gln Ala Val Ala Ala Met Gln Pro Pro Leu Glu Ala
                20                  25                  30

Pro Tyr Val Pro Pro Arg Tyr Leu Ala Pro Thr Glu Gly Arg Asn Ser
            35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
            115                 120                 125

Asn Glu Phe Leu Tyr Ser Asn Lys Phe Lys Ala Arg Val Met Val Ser
130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
            180                 185                 190

Leu Ala Val Gly Arg Gln Asn Gly Val Leu Glu Ser Asp Ile Gly Val
            195                 200                 205

Lys Phe Asp Thr Arg Asn Phe Arg Leu Gly Trp Asp Pro Val Thr Glu
210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
            260                 265                 270

Ile Met Tyr Glu Asp Leu Glu Gly Gly Asn Ile Pro Ala Leu Leu Asp
            275                 280                 285

Val Glu Ala Tyr Glu Lys Ser Lys Glu Asp Ser Ala Ala Ala Ala Thr
290                 295                 300

Ala Ala Val Ala Thr Ala Ser Thr Glu Val Arg Gly Asp Asn Phe Ala
305                 310                 315                 320

Ser Ala Ala Ala Val Ala Glu Ala Ala Glu Thr Glu Ser Lys Ile Val
                325                 330                 335

Ile Gln Pro Val Glu Lys Asp Ser Lys Asp Arg Ser Tyr Asn Val Leu
            340                 345                 350

Ala Asp Lys Lys Asn Thr Ala Tyr Arg Ser Trp Tyr Leu Ala Tyr Asn
            355                 360                 365

Tyr Gly Asp Pro Glu Lys Gly Val Arg Ser Trp Thr Leu Leu Thr Thr
            370                 375                 380

Ser Asp Val Thr Cys Gly Val Glu Gln Val Tyr Trp Ser Leu Pro Asp
385                 390                 395                 400
```

```
Met Met Gln Asp Pro Val Thr Phe Arg Ser Thr Arg Gln Val Ser Asn
                405                 410                 415

Tyr Pro Val Val Gly Ala Glu Leu Leu Pro Val Tyr Ser Lys Ser Phe
            420                 425                 430

Phe Asn Glu Gln Ala Val Tyr Ser Gln Gln Leu Arg Ala Phe Thr Ser
        435                 440                 445

Leu Thr His Val Phe Asn Arg Phe Pro Glu Asn Gln Ile Leu Val Arg
    450                 455                 460

Pro Pro Ala Pro Thr Ile Thr Thr Val Ser Glu Asn Val Pro Ala Leu
465                 470                 475                 480

Thr Asp His Gly Thr Leu Pro Leu Arg Ser Ser Ile Arg Gly Val Gln
            485                 490                 495

Arg Val Thr Val Thr Asp Ala Arg Arg Arg Thr Cys Pro Tyr Val Tyr
            500                 505                 510

Lys Ala Leu Gly Val Val Ala Pro Arg Val Leu Ser Ser Arg Thr Phe
            515                 520                 525

<210> SEQ ID NO 30
<211> LENGTH: 535
<212> TYPE: PRT
<213> ORGANISM: Adenoviridae - Mastadenovirus

<400> SEQUENCE: 30

Met Met Arg Arg Ala Tyr Pro Glu Gly Pro Pro Ser Tyr Glu Ser
1               5                   10                  15

Val Met Gln Gln Ala Met Ala Ala Ala Ala Met Gln Pro Pro Leu
            20                  25                  30

Glu Ala Pro Tyr Val Pro Pro Arg Tyr Leu Ala Pro Thr Glu Gly Arg
            35                  40                  45

Asn Ser Ile Arg Tyr Ser Glu Leu Ala Pro Leu Tyr Asp Thr Thr Arg
    50                  55                  60

Leu Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Ser Thr Gln Thr Ile Asn Phe Asp Glu Arg
            100                 105                 110

Ser Arg Trp Gly Gly Gln Leu Lys Thr Ile Met His Thr Asn Met Pro
        115                 120                 125

Asn Val Asn Glu Phe Met Tyr Ser Asn Lys Phe Lys Ala Arg Val Met
    130                 135                 140

Val Ser Arg Lys Thr Pro Asn Gly Val Thr Val Thr Glu Asp Tyr Asp
145                 150                 155                 160

Gly Ser Gln Asp Glu Leu Lys Tyr Glu Trp Val Glu Phe Glu Leu Pro
                165                 170                 175

Glu Gly Asn Phe Ser Val Thr Met Thr Ile Asp Leu Met Asn Asn Ala
            180                 185                 190

Ile Ile Asp Asn Tyr Leu Ala Val Gly Arg Gln Asn Gly Val Leu Glu
        195                 200                 205

Ser Asp Ile Gly Val Lys Phe Asp Thr Arg Asn Phe Arg Leu Gly Trp
    210                 215                 220

Asp Pro Val Thr Glu Leu Val Met Pro Gly Val Tyr Thr Asn Glu Ala
225                 230                 235                 240

Phe His Pro Asp Ile Val Leu Leu Pro Gly Cys Gly Val Asp Phe Thr
```

```
            245                 250                 255
Glu Ser Arg Leu Ser Asn Leu Leu Gly Ile Arg Lys Arg Gln Pro Phe
        260                 265                 270

Gln Glu Gly Phe Gln Ile Met Tyr Glu Asp Leu Glu Gly Gly Asn Ile
    275                 280                 285

Pro Ala Leu Leu Asp Val Asp Ala Tyr Glu Lys Ser Lys Glu Glu Ser
290                 295                 300

Ala Ala Ala Ala Thr Ala Ala Val Ala Thr Ala Ser Thr Glu Val Arg
305                 310                 315                 320

Gly Asp Asn Phe Ala Ser Ala Ala Val Ala Ala Ala Glu Ala Ala
            325                 330                 335

Glu Thr Glu Ser Lys Ile Val Ile Gln Pro Val Glu Lys Asp Ser Lys
            340                 345                 350

Asp Arg Ser Tyr Asn Val Leu Pro Asp Lys Ile Asn Thr Ala Tyr Arg
            355                 360                 365

Ser Trp Tyr Leu Ala Tyr Asn Tyr Gly Asp Pro Glu Lys Gly Val Arg
    370                 375                 380

Ser Trp Thr Leu Leu Thr Thr Ser Asp Val Thr Cys Gly Val Glu Gln
385                 390                 395                 400

Val Tyr Trp Ser Leu Pro Asp Met Met Gln Asp Pro Val Thr Phe Arg
                405                 410                 415

Ser Thr Arg Gln Val Ser Asn Tyr Pro Val Val Gly Ala Glu Leu Leu
            420                 425                 430

Pro Val Tyr Ser Lys Ser Phe Phe Asn Glu Gln Ala Val Tyr Ser Gln
        435                 440                 445

Gln Leu Arg Ala Phe Thr Ser Leu Thr His Val Phe Asn Arg Phe Pro
450                 455                 460

Glu Asn Gln Ile Leu Val Arg Pro Pro Ala Pro Thr Ile Thr Thr Val
465                 470                 475                 480

Ser Glu Asn Val Pro Ala Leu Thr Asp His Gly Thr Leu Pro Leu Arg
                485                 490                 495

Ser Ser Ile Arg Gly Val Gln Arg Val Thr Val Thr Asp Ala Arg Arg
            500                 505                 510

Arg Thr Cys Pro Tyr Val Tyr Lys Ala Leu Gly Ile Val Ala Pro Arg
        515                 520                 525

Val Leu Ser Ser Arg Thr Phe
        530                 535

<210> SEQ ID NO 31
<211> LENGTH: 581
<212> TYPE: PRT
<213> ORGANISM: Adenoviridae - Mastadenovirus

<400> SEQUENCE: 31

Met Arg Arg Ala Ala Met Tyr His Glu Gly Pro Pro Pro Ser Tyr Glu
1               5                   10                  15

Ser Val Val Gly Ala Ala Ala Ala Ser Pro Phe Ala Ser Gln Leu Glu
            20                  25                  30

Pro Pro Tyr Val Pro Pro Arg Tyr Leu Arg Pro Thr Gly Gly Arg Asn
        35                  40                  45

Ser Ile Arg Tyr Ser Glu Leu Ala Pro Leu Tyr Asp Thr Thr Arg Val
    50                  55                  60

Tyr Leu Val Asp Asn Lys Ser Ala Asp Val Ala Ser Leu Asn Tyr Gln
65                  70                  75                  80
```

```
Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
            100                 105                 110

His Trp Gly Gly Asp Leu Lys Thr Ile Leu His Thr Asn Met Pro Asn
            115                 120                 125

Val Asn Glu Phe Met Phe Thr Asn Lys Phe Lys Ala Arg Val Met Val
        130                 135                 140

Ser Arg Ser His Thr Lys Asp Asp Arg Val Glu Leu Lys Tyr Glu Trp
145                 150                 155                 160

Val Glu Phe Glu Leu Pro Glu Gly Asn Tyr Ser Glu Thr Met Thr Ile
                165                 170                 175

Asp Leu Met Asn Asn Ala Ile Val Glu His Tyr Leu Lys Val Gly Arg
            180                 185                 190

Gln Asn Gly Val Leu Glu Ser Asp Ile Gly Val Lys Phe Asp Thr Arg
        195                 200                 205

Asn Phe Arg Leu Gly Leu Asp Pro Val Thr Gly Leu Val Met Pro Gly
    210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
            260                 265                 270

Leu Glu Gly Gly Asn Ile Pro Ala Leu Leu Asp Val Glu Ala Tyr Gln
        275                 280                 285

Asp Ser Leu Lys Glu Glu Ala Gly Glu Gly Ser Gly Gly Gly Gly Ala
    290                 295                 300

Gly Gln Glu Glu Gly Gly Ala Ser Ser Glu Ala Ser Ala Asp Pro Ala
305                 310                 315                 320

Ala Ala Ala Glu Ala Glu Ala Ala Asp Pro Ala Met Val Val Glu Glu
                325                 330                 335

Glu Lys Asp Met Asn Asp Glu Ala Val Arg Gly Asp Thr Phe Ala Thr
            340                 345                 350

Arg Gly Glu Glu Lys Lys Ala Glu Ala Glu Ala Ala Glu Glu Ala
        355                 360                 365

Ala Ala Ala Ala Ala Val Glu Ala Ala Glu Ala Glu Lys Pro
    370                 375                 380

Pro Lys Glu Pro Val Ile Lys Pro Leu Thr Glu Asp Ser Lys Lys Arg
385                 390                 395                 400

Ser Tyr Asn Val Leu Lys Asp Ser Thr Asn Thr Glu Tyr Arg Ser Trp
                405                 410                 415

Tyr Leu Ala Tyr Asn Tyr Gly Asp Pro Ala Thr Gly Val Arg Ser Trp
            420                 425                 430

Thr Leu Leu Cys Thr Pro Asp Val Thr Cys Gly Ser Glu Gln Val Tyr
        435                 440                 445

Trp Ser Leu Pro Asp Met Met Gln Asp Pro Val Thr Phe Arg Ser Thr
    450                 455                 460

Arg Gln Val Ser Asn Phe Pro Val Val Gly Ala Glu Leu Leu Pro Val
465                 470                 475                 480

His Ser Lys Ser Phe Tyr Asn Asp Gln Ala Val Tyr Ser Gln Leu Ile
                485                 490                 495

Arg Gln Phe Thr Ser Leu Thr His Val Phe Asn Arg Phe Pro Glu Asn
```

| | 500 | | | 505 | | | | 510 | | | |
|---|---|---|---|---|---|---|---|---|---|---|---|
| Gln | Ile | Leu | Ala | Arg | Pro | Pro | Ala | Pro | Thr | Ile | Thr | Thr | Val | Ser | Glu |
| | | | 515 | | | | 520 | | | | 525 | | | | |

Asn Val Pro Ala Leu Thr Asp His Gly Thr Leu Pro Leu Arg Asn Ser
        530                 535                 540

Ile Gly Gly Val Gln Arg Val Thr Val Thr Asp Ala Arg Arg Thr
545             550                 555                 560

Cys Pro Tyr Val Tyr Lys Ala Leu Gly Ile Val Ser Pro Arg Val Leu
                565             570                 575

Ser Ser Arg Thr Phe
            580

<210> SEQ ID NO 32
<211> LENGTH: 1323
<212> TYPE: DNA
<213> ORGANISM: Adenoviridae - Mastadenovirus

<400> SEQUENCE: 32

```
atgtccaaaa agcgcgtccg ggtggatgat gacttcgacc ccgtctaccc ctacgatgca      60
gacaacgcac cgaccgtgcc cttcatcaac cctcccttcg tctcttcaga tggattccaa     120
gaaaagcccc tggggggtgtt gtccctgcga ctggctgacc ccgtcaccac caagaacggg     180
gaaatcaccc tcaagctggg agaggggggtg gacctcgacg actcgggaaa actcatctcc     240
aaaaatgcca ccaaggccac tgcccctctc agtatttcca acagcaccat ttcccttaac     300
atggatgccc ctctttacaa caacaatgga agttaggca taagaatagg agcacctcta     360
aaggtagtag acttactaaa cactttagct gtagcctatg gatcgggtct aggtctcaag     420
aataatgccc ttacagttca gttagttttct ccactcactt ttgataacaa aggcaatgta     480
aaaattaact tagggaatgg cccattaaca gttgcggcaa accgactgag tgttacctgc     540
aaaagaggtt tatatgtcac tactacagga gatgcactcg aaagcaacat aagctgggct     600
aaaggtataa gatttgaagg aaatgcaata gcagcaaata ttggcaaagg cttgaatttt     660
ggtactacta gttcagagtc agatgtcagc aatgcttatc ctatccaagt aaaactaggt     720
actggtctca cctttgacag cacaggtgca attgtcgctt ggaacaaaga agatgacaaa     780
cttacactgt ggaccacagc cgatccatct ccaaactgtc acatatattc tgacaaggat     840
gctaagctta cactctgctt gacaaagtgt ggcagtcaga tactgggcac tgtttctctc     900
atagctgttg atactggtag cttaaatcca ataacaggac aagtaaccac tgctcttgtt     960
tcacttaaat tcgatgccaa tggagttttg caaaccagtt caacattgga caaagaatat    1020
tggaatttta gaaaaggaga tgtgacacct gctgagccat atactaatgc tataggtttt    1080
atgcccaata taaggcata tccgaaaaac acaaattcag ctgcaaaaag tcacattgtg    1140
ggaaaagtat acctacatgg ggaagtaagc aagccactag acttgataat tacatttaat    1200
gaaaccagta tgaaacctg taccttattgc attaacttttc agtggcagtg gggaactgac    1260
aaatataaaa atgaaacgct tgctgtcagt tcattcacct tttcctacat tgcccaagaa    1320
taa                                                                   1323
```

<210> SEQ ID NO 33
<211> LENGTH: 1332
<212> TYPE: DNA
<213> ORGANISM: Adenoviridae - Mastadenovirus

<400> SEQUENCE: 33

```
atgtccaaaa agcgcgtccg ggtggatgat gacttcgacc ccgtctaccc ctacgatgca     60
gacaacgcac cgaccgtgcc cttcatcaac ccccccttcg tctcttcaga tggattccaa    120
gagaagcccc tgggggtgtt gtccctgcga ctggccgacc ccgtcaccac caagaacggg    180
gaaatcaccc tcaagctggg agaggggtg gacctcgacg actcgggaaa actcatctcc     240
aaaaatgcca ccaaggccac tgcccctctc agtatttcca acagcaccat ttcccttaac    300
atggctgccc cttttacaa caacaatgga acgttaagtc tcaatgtttc tacaccatta     360
gcagtatttc ccacttttaa cactttaggt atcagtcttg caacggtct tcaaacttct     420 aataagttgc tggctgtaca gttaactcat cctcttacat tcagctcaaa tagcatcaca    480
gtaaaaacag acaaaggact ctatattaat tctagtggaa acagagggct tgaggctaac    540
ataagcctaa aaagaggact gattttttgat ggtaatgcta ttgcaacata ccttggaagt    600
ggtttagact atggatccta tgatagcgat ggaaaaacaa gacccatcat caccaaaatt    660
ggagcaggct tgaattttga ttctaataat gccatggctg tgaagctagg cacaggttta    720
agttttgact ctgccggtgc cttaacagct ggaaacaaag aggatgacaa gctaacactt    780
tggactacac ctgaccccag ccctaattgt caattacttt cagacagaga tgccaaattt    840
accctatgtc ttacaaaatg cggtagtcaa atactaggca ctgttgcagt agctgctgtt    900
actgtaagtt cagcactaaa tccaattaat gacacagtaa aaagcgccat agtattcctt    960
agatttgact ctgacggtgt gctcatgtca aactcatcaa tggtaggtga ttactggaac   1020
tttagggaag acagaccac ccaaagtgtg gcctatacaa atgctgtggg attcatgccc    1080
aatctaggtg catatcctaa aacccaaagc aaaacaccaa aaatagtat agtaagccag    1140 gtatatttaa atggagaaac tactatgcca atgacactga caataacttt caatggcact   1200
gatgaaaaag acacaacacc tgtcagcact tactctatga cttttacatg gcagtggact    1260
ggagactata aggacaagaa tattacctttt gctaccaact cctttactttt ctcctacatg    1320 gcccaagaat aa                                                        1332

<210> SEQ ID NO 34
<211> LENGTH: 1278
<212> TYPE: DNA
<213> ORGANISM: Adenoviridae - Mastadenovirus

<400> SEQUENCE: 34
atgtccaaaa agcgcgtccg ggtggatgat gacttcgacc ccgtctaccc ctacgatgca     60
gacaacgcac cgaccgtgcc cttcatcaac ccccccttcg tctcttcaga tggattccaa    120
gagaagcccc tgggggtgtt gtccctgcga ctggccgacc ccgtcaccac caagaacggg    180
gaaatcaccc tcaagctggg agaggggtg gacctcgact cctcgggaaa actcatctcc     240
aacacggcca ccaaggccgc tgcccctctc agttttttcca acaacaccat ttcccttaac    300
atggatcacc ccttttacac taaagatgga aaattagcct acaagtttc tccaccatta     360 aatatactga gaacaagcat tctaaacaca ctagctttag gttttggatc aggtttagga    420
ctccgtggct ctgccttggc agtacagtta gtctctccac ttacatttga tactgatgga    480
aacataaagc ttaccttaga cagaggtttg catgttacaa caggagatgc aattgaaagc    540
aacataagct gggctaaagg ttttaaaattt gaagatggag ccatagcaac caacattgga    600
aatgggttag agtttggaag cagtagtaca gaaacaggtg tcgatgatgc ttacccaatc    660
caagttaaac ttggatctgg ccttagcttt gacagtacag gagccataat ggctggtaac    720
aaagaagacg ataaactcac tttgtggaca acacctgatc catcaccaaa ctgtcaaata    780
```

```
ctcgcagaaa atgatgcaaa actaacactt tgcttgacta aatgtggtag tcaaatactg    840
gccactgtgt cagtcttagt tgtaggaagt ggaaacctaa accccattac tggcaccgta    900
agcagtgctc aggtgtttct acgttttgat gcaaacggtg ttcttttaac agaacattct    960
acactaaaaa aatactgggg gtataggcag ggagatagca tagatggcac tccatatgtc   1020
aatgctgtag gattcatgcc caatttaaaa gcttatccaa agtcacaaag ttctactact   1080
aaaaataata tagtagggca agtatacatg aatggagatg tttcaaaacc tatgcttctc   1140
actataaccc tcaatggtac tgatgacagc aacagtacat attcaatgtc attttcatac   1200
acctggacta atggaagcta tgttggagca acatttggag ctaactctta taccttctcc   1260
tacatcgccc aagaatga                                                 1278
```

<210> SEQ ID NO 35
<211> LENGTH: 1278
<212> TYPE: DNA
<213> ORGANISM: Adenoviridae - Mastadenovirus

<400> SEQUENCE: 35

```
atgtccaaaa agcgcgtccg ggtggatgat gacttcgacc ccgtctaccc ctacgatgca     60
gacaacgcac cgaccgtgcc cttcatcaac cccccccttcg tctcttcaga tggattccaa    120
gagaagcccc tggggtgct gtccctgcga ctggccgacc ccgtcaccac caagaacggg      180
gaaatcaccc tcaagctggg agaggggctg gacctcgact cctcgggaaa actcatctcc    240
aacacggcca ccaaggccgc cgcccctctc agttttttcca acaacaccat tcccttaac    300 atggatcacc ccttttacac taaagatgga aaattatcct tacaagtttc tccaccatta   360
aatatactga gaacaagcat tctaaacaca ctagctttag gttttggatc aggtttagga   420
ctccgtggct ctgccttggc agtacagtta gtctctccac ttacatttga tactgatgga   480
aacataaagc ttaccttaga cagaggtttg catgttacaa caggagatgc aattgaaagc   540
aacataagct gggctaaagg tttaaaattt gaagatggag ccatagcaac caacattgga   600
aatgggttag agtttggaag cagtagtaca gaaacaggtg ttgatgatgc ttacccaatc   660
caagttaaac ttggatctgg ccttagcttt gacagtacag gagccataat ggctggtaac   720
aaagaagacg ataaacttac tttgtgggac acacctgatc catcaccaaa ctgtcaaata   780
ctcgcagaaa atgatgcaaa actaacactt tgcttgacta aatgtggtag tcaaatactg   840
gccactgtgt cagtcttagt tgtaggaagt ggaaacctaa accccattac tggcaccgta   900
agcagtgctc aggtgtttct acgttttgat gcaaacggtg ttcttttaac agaacattct   960
acactaaaaa aatactgggg gtataggcag ggagatagca tagatggcac tccatatacc  1020
aatgctgtag gattcatgcc caatttaaaa gcttatccaa agtcacaaag ttctactact  1080
aaaaataata tagtagggca agtatacatg aatggagatg tttcaaaacc tatgcttctc  1140
actataaccc tcaatggtac tgatgacagc aacagtacat attcaatgtc attttcatac  1200
acctggacta atggaagcta tgttggagcg acatttgggg ctaactctta taccttctca  1260
tacatcgccc aagaatga                                                 1278
```

<210> SEQ ID NO 36
<211> LENGTH: 1329
<212> TYPE: DNA
<213> ORGANISM: Adenoviridae - Mastadenovirus

<400> SEQUENCE: 36

| | |
|---|---:|
| atgtccaaaa agcgcgcgcg ggtggatgat ggcttcgacc ccgtgtaccc ctacgatgca | 60 |
| gacaacgcac cgactgtgcc cttcatcaac cctcccttcg tctcttcaga tggattccaa | 120 |
| gaaaagcccc tgggggtgtt gtccctgcgt ctggccgacc ccgtcaccac caagaatggg | 180 |
| gctgtccccc tcaagctcgg ggaggggtg gacctcgacg actcgggaaa actcatctcc | 240 |
| aaaaaatcca ccaaggccaa ttcccctctc agtatttcca caacaccat ttcccttaac | 300 |
| atggataccc cttttatac caaagatgga aaattaacca tgcaggtaac tgcaccatta | 360 |
| aagttagcaa acacggccat actaaacaca ctagctatgg cctatggaaa tggtttaggt | 420 |
| ctaaacaaca atgctctcac tgttcaggta acatctccac tcacatttga taatagcaaa | 480 |
| gtcaagatta acctagggaa tggaccacta atggtatctg ctaacaagct ttcaatcaac | 540 |
| tgcttacggg gtctatatgt tgcccctaat aataccggac tagaaaccaa cataagctgg | 600 |
| gcaaacgcaa tgcgctttga gggtaatgca atggctgttt atatagacac aaataaaggc | 660 |
| ctacaatttg gcactactag cacagaaaca ggtgtcacca atgcttaccc catacaagtc | 720 |
| aaacttggcg caggccttgc atttgatagc acaggagcta ttgttgcttg aacaaagaa | 780 |
| aatgacagcc tcactttgtg gactacacca gatccctctc caaattgtaa aatagcatct | 840 |
| gaaaaggatg caaaactcac actttgcttg acaaagtgtg gtagtcaaat cctaggcact | 900 |
| gtctccctat tagcagtcag tggcagcttg gctcctatca caggggctgt tagtactgca | 960 |
| cttgtatcac tcaaattcaa tgctaatgga gccctttgg acaaatcaac tctgaacaaa | 1020 |
| gaatactgga actacagaca aggagatcta attccaggta caccatatac acatgctgtg | 1080 |
| ggtttcatgc ctaacaaaaa agcctaccct aaaaacacaa ctgcagcttc caagagccac | 1140 |
| attgtgggtg atgtgtattt agatggagat gcagataagc ctttatctct tatcatcact | 1200 |
| ttcaatgaaa ctgatgatga aacctgtgat tactgcatca actttcaatg gaatggggga | 1260 |
| gctgatcaat ataaggataa gacactcgca accagttcat tcaccttctc atacatcgcc | 1320 |
| caagaataa | 1329 |

<210> SEQ ID NO 37
<211> LENGTH: 1731
<212> TYPE: DNA
<213> ORGANISM: Adenoviridae - Mastadenovirus

<400> SEQUENCE: 37

| | |
|---|---:|
| atgaagcgcg ccaaaacgtc tgacgagacc ttcaaccccg tgtaccccta tgacacggaa | 60 |
| aacgggcctc cctccgtccc tttcctcacc cctcccttcg tgtccccga cggatttcaa | 120 |
| gaaagcccc cagggggtcct gtctctgcgc ctgtcagagc ccctggtcac ttcccacggc | 180 |
| atgcttgccc tgaaaatggg aaatggcctc tccctggatg acgccggcaa cctcacctct | 240 |
| caagatgtca ccaccgtcac ccctcccctc aaaaaaacca agaccaacct cagcctccag | 300 |
| acctcagccc ccctgaccgt tagctctggg tccctcaccg tcgcggccgc cgctccactg | 360 |
| gcggtggccg gcacctctct caccatgcaa tctcaggccc ccttgacagt gcaagatgca | 420 |
| aaactcggcc tggccacccca gggacccctg accgtgtctg aaggcaaact caccttgcag | 480 |
| acatcggctc cactgacggc cgctgacagc agcactctca ctgttagtgc cacacctccc | 540 |
| ctcagcacaa gcaatggtag tttgagcatt gacatgcagg ccccgattta taccaccaat | 600 |
| ggaaaactgg cacttaacat tggtgctccc ctgcatgtgg tagacaccct aaatgcacta | 660 |
| actgtagtaa ctggccaggg tcttaccata aatggaagag ccctgcaaac tagagtcacg | 720 |
| ggtgccctca gttatgacac agaaggcaac atccaactgc aagccggagg gggtatgcgc | 780 |

```
attgacaata atggccaact tatccttaat gtagcttatc catttgatgc tcaaaacaac      840
ctcagcctta gacttggcca aggtcccta attgttaact ctgcccacaa cttggatctt      900
aaccttaaca gaggcctta cttatttaca tctggaaaca cgaaaaaact ggaagttaac      960
ataaaaacag ccaaaggtct attttacgat ggcaccgcta tagcaatcaa tgcaggtgac     1020
gggctacagt ttgggtctgg ttcagataca aatccattgc aaactaaact tggattgggg     1080
ctggaatatg actccaacaa agctataatc actaaacttg gaactggcct aagctttgac     1140
aacacaggtg ccatcacagt aggcaacaaa aatgatgaca gcttaccctt gtggaccaca     1200
ccagacccct ccccaaactg cagaattaat tcagaaaaag atgctaaaact cacactagtt    1260 ttgactaaat gcggcagcca ggtgttagcc agcgtttctg ttttatctgt aaaaggcagc     1320 cttgcccca tcagcggcac agtaactagc gcccagattg ttttaagatt tgatgaaaac      1380
ggagttttat tgagcaattc ttctcttgac ccccaatact ggaactatag aaaaggcgat     1440
tctacagaag gcactgcata tactaatgct gtgggattta tgcccaacct cacagcatac     1500
cctaaaacac agagccagac tgctaaaagc aacattgtaa gtcaagttta cttgaatggg     1560
gacaaaacaa aacccatgac cctaaccatc accctcaatg aactaatga acagggat       1620 gctacagtaa gcacatactc catgtcattt tcatggaact ggaatggaag taattacatt     1680
aatgacacct tccaaaccaa ctcctttacc ttctcctaca tcgcccaaga a              1731

<210> SEQ ID NO 38
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t

<400> SEQUENCE: 38
atggccaccc catcgatgct gccccagtgg gcgtacatgc acatcgccgg acaggacgct       60
tcggagtacc tgagtccggg tctggtgcag ttcgcccgcg ccacagacac ctacttcagt      120
ctggggaaca agtttaggaa ccccacggtg gcgcccacgc acgatgtgac caccgaccgc      180
agccagcggc tgacgctgcg cttcgtgccc gtggaccgcg aggacaacac ctactcgtac      240
aaagtgcgct acacgctggc cgtgggcgac aaccgcgtgc tggacatggc cagcacctac      300
tttgacatcc gcggcgtgct ggatcggggc cccagcttca accntactc cggcaccgcn      360 tacaacagcc tggctcccaa gggagcgccc aacacctcac agtggataac caaagacaat      420
ggaactgata agacatacag ttttggaaat gctccagtca gaggattgga cattacagaa      480
gagggtctcc aaataggacc cgatgagtca ggggtgaaa gcaagaaaat ttttgcagac      540
aaaacctatc agcctgaacc tcagcttgga gatgaggaat ggcatgatac tattggagct      600
gaagacaagt atggaggcag agcgcttaaa cctgccacca acatgaaacc ctgctatggg     660
tctttcgcca agccaactaa tgctaaggga ggtcaggcta aaagcagaac caaggacgat      720
ggcactactg agcctgatat tgacatggcc ttctttgacg atcgcagtca gcaagctagt     780
ttcagtccag aacttgtttt gtatactgag aatgtcgatc tggacacccc ggatacccac      840
attatttaca aacctggcac tgatgaaaca agttcttctt tcaacttggg tcagcagtcc     900
```

| | |
|---|---|
| atgcccaaca gacccaacta catcggcttc agagacaact ttatcggtct catgtactac | 960 |
| aacagtactg gcaatatggg tgtactagct ggacaggcct cccagctgaa tgctgtggtg | 1020 |
| gacttgcagg acagaaacac tgaactgtcc taccagctct tgcttgactc tctgggtgac | 1080 |
| agaaccaggt atttcagtat gtggaaccag gcggtggaca gctacgaccc cgatgtgcgc | 1140 |
| attattgaaa tcacggtgt ggaggatgaa ctacccaact attgcttccc tttgaatggt | 1200 |
| gtgggcttta cagatacatt ccagggaatt aaggttaaaa ctaccaataa cggaacagca | 1260 |
| aatgctacag agtgggaatc tgatacctct gtcaataatg ctaatgagat tgccaagggc | 1320 |
| aatcctttcg ccatggagat caacatccag gccaacctgt ggcggaactt cctctacgcg | 1380 |
| aacgtggcgc tgtacctgcc cgactcctac aagtacacgc cggccaacat cacgctgccc | 1440 |
| accaacacca acacctacga ttacatgaac ggccgcgtgg tagcgccctc gctggtggac | 1500 |
| gcctacatca acatcggggc cgcgctggtcg ctggaccccca tggacaacgt caacccctttc | 1560 |
| aaccaccacc gcaacgcggg cctgcgctac cgctccatgc tcctgggcaa cgggcgctac | 1620 |
| gtgcccttcc acatccaggt gccccaaaag ttttttcgcca tcaagagcct cctgctcctg | 1680 |
| cccgggtcct acacctacga gtggaacttc cgcaaggacg tcaacatgat cctgcagagc | 1740 |
| tccctcggca cgacctgcg cacggacggg gcctccatcg ccttcaccag catcaacctc | 1800 |
| tacgccacct tcttccccat ggcgcacaac accgcctcca cgctcgaggc catgctgcgc | 1860 |
| aacgacacca cgaccagtc cttcaacgac tacctctcgg cggccaacat gctctacccc | 1920 |
| atcccggcca acgccaccaa cgtgcccatc tccatcccct cgcgcaactg gccgcttc | 1980 |
| cgcggctggt ccttcacgcg cctcaagacc cgcgagacgc cctcgctggg ctccgggttc | 2040 |
| gaccccctact tcgtctactc gggctccatc ccctacctcg acggcaccttt ctacctcaac | 2100 |
| cacacccttca agaaggtctc catcaccttc gactcctccg tcagctggcc cggcaacgac | 2160 |
| cgcctcctga cgcccaacga gttcgaaatc aagcgcaccg tcgacggaga ggggtacaac | 2220 |
| gtggcccagt gcaacatgac caaggactgg ttcctggttc agatgctggc ccactacaac | 2280 |
| atcggctacc agggcttcta cgtgcccgag ggctacaagg accgcatgta ctccttcttc | 2340 |
| cgcaacttcc agcccatgag ccgccaggtc gtggacgagt caactacaa ggactaccag | 2400 |
| gccgtcaccc tggcctacca gcacaacaac tcgggcttcg tcggctacct cgcgcccacc | 2460 |
| atgcgccagg acagcccta ccccgccaac taccccctacc cgctcatcgg caagagcgcc | 2520 |
| gtcgccagcg tcacccagaa aaagttcctc tgcgaccggg tcatgtggcg catcccctttc | 2580 |
| tccagcaact tcatgtccat gggcgcgctc accgacctcg ccagaacat gctctacgcc | 2640 |
| aactccgccc acgcgctaga catgaatttc gaagtcgacc ccatggatga gtccacccttt | 2700 |
| ctctatgttg tcttcgaagt cttcgacgtc gtccgagtgc accagcccca ccgcggcgtc | 2760 |
| atcgaggccg tctacctgcg cacgcccttc tcggccggta acgccaccac ctaa | 2814 |

<210> SEQ ID NO 39
<211> LENGTH: 2814
<212> TYPE: DNA
<213> ORGANISM: Adenoviridae - Mastadenovirus

<400> SEQUENCE: 39

| | |
|---|---|
| atggccaccc catcgatgct gccccagtgg gcgtacatgc acatcgccgg acaggacgct | 60 |
| tcggagtacc tgagtccggg tctggtgcag tttgcccgcg ccacagacac ctacttcagt | 120 |
| ctggggaaca agtttaggaa ccccacggtg gcgcccacgc acgatgtgac caccgaccgc | 180 |
| agccagcggc tgacgctgcg cttcgtgccc gtggacggcg aggacaacac ctactcgtac | 240 |

```
aaagtgcgct acacgctggc cgtgggcgac aaccgcgtgc tggacatggc cagcacctac    300
tttgacatcc gcggcgtgct ggatcggggc cccagcttca aaccctactc cggcaccgcc    360
tacaacgctc tggctcccaa gggagcgccc aacacctcac agtggataac caaagacaat    420
ggaactgata agacatacag ttttggaaat gctccagtca gaggattgga cattacagaa    480
gagggtctcc aaataagaac cgatgagtca ggggtgaaa gcaagaaaat ttttgcagac    540
aaaacctatc agcctgaacc tcagcttgga gatgaggaat ggcatgatac tattggagct    600
gaagacaagt atggaggcag agcgcttaaa cctgccacca acatgaaacc ctgctatggg    660
tctttcgcca agccaactaa tgctaaggga ggtcaggcta aaagcagaac caaggacgat    720
ggcactactg agcctgatat tgacatggcc ttctttgacg atcgcagtca gcaagctagt    780
ttcagtccag aacttgtttt gtatactgag aatgtcgatc tggacacccc ggatacccac    840
attatttaca aacctggcac tgatgaaaca agttcttctt tcaacttggg tcagcagtcc    900
atgcccaaca gacccaacta cattgggttc agagacaact ttatcgggct catgtactac    960
aacagcactg gcaatatggg tgtactggct ggtcaggcct cccagctgaa tgctgtggtg   1020
gacttgcagg acagaaacac cgaactgtcc taccagctct tgcttgactc tctgggtgac   1080
agaaccaggt atttcagtat gtggaatcag gcggtggaca gttatgaccc cgatgtgcgc   1140
attattgaaa atcacggtgt ggaggatgaa ctccccaact attgcttccc tttgaatggt   1200 gtgggctta cagatacatt ccagggaatt aaggttaaaa ctaccaataa cggaacagca   1260
aatgctacag agtgggaatc tgatacctct gtcaataatg ctaatgagat tgccaagggc   1320
aatcctttcg ccatggagat caacatccag gccaacctgt ggcggaactt cctctacgcg   1380
aacgtggcgc tgtacctgcc cgactcctac aagtacacgc cggccaacat cacgctgccg   1440
accaacacca cacctacga ttacatgaac ggccgcgtgg tggcgccctc gctggtggac   1500
gcctacatca acatcggggc gcgctggtcg ctggaccca tggacaacgt caacccttc   1560 aaccaccacc gaaacgcggg cctgcgatac cgctccatgc tcctgggcaa cgggcgctac   1620 gtgccttcc acatccaggt gccccaaaag ttttttcgcca tcaagagcct cctgctcctg   1680
cccgggtcct acacctacga gtggaacttc cgcaaggacg tcaacatgat cctgcagagc   1740
tccctcggca acgacctgcg cacggacggg gcttccatcg ccttcaccag catcaacctc   1800
tacgccacct tcttccccat ggcgcacaac accgcctcca cgctcgaggc catgctgcgc   1860
aacgacacca cgaccagtc cttcaacgac tacctctcgg cggccaacat gctctacccc   1920
atcccggcca acgccaccaa cgtgcccatc tccatcccct cgcgcaactg gccgccttc   1980 cgcggmtggt ccttcacgcg cctcaagacc cgcgagacgc cctcgctagg ctccgggttc   2040 gaccctact tcgtctactc gggctccatc ccctaccttg acggcacctt ctacctcaac   2100 cacccttca agaaggtctc catcaccttc gactcctccg tcagctggcc cggcaacgac   2160
cgcctcctga cgcccaacga gttcgaaatc aagcgcaccg tcgacggaga ggggtacaac   2220
gtggcccagt gcaacatgac caaggactgg ttcctggtcc agatgctggc ccactacaac   2280
atcggctacc agggcttcta cgtgcccgag ggctacaagg accgcatgta ctccttcttc   2340
cgcaacttcc agcccatgag ccgccaggtc gtggacgagt caactacaa ggactaccag   2400 gccgtcaccc tggcctacca gcacaacaac tcgggcttcg tcggctacct cgcgcccacc   2460
atgcgccagg acagcccta ccccgccaac taccccctacc cgctcatcgg caagagcgcc   2520
gtcgccagcg tcacccagaa aaagttcctc tgcgaccggg tcatgtggcg catcccttc   2580
```

```
tccagcaact tcatgtccat gggcgcgctc accgacctcg gccaaaacat gctttacgcc    2640
aactccgccc acgcgctaga catgaatttc gaagtcgacc ccatggatga gtccacccttt   2700 ctctatgttg tcttcgaagt cttcgacgtc gtccgagtgc accagcccca ccgcggcgtc    2760
atcaaggccg tctacctgcg caccccccttc tcggccggta acgccaccac ctaa          2814
```

<210> SEQ ID NO 40
<211> LENGTH: 2814
<212> TYPE: DNA
<213> ORGANISM: Adenoviridae - Mastadenovirus

<400> SEQUENCE: 40

```
atggccaccc catcgatgct gccccagtgg gcgtacatgc acatcgccgg acaggacgct     60
tcggagtacc tgagtccggg tctggtgcag ttcgcccgcg ccacagacac ctacttcagt    120
ctggggaaca gtttaggaa ccccacgtg gcacccacg acgatgtgac caccgaccgc      180
agccagcggc tgacgctgcg cttcgtgccc gtgaccgcg aggacaacac ctactcgtac     240
aaagtgcgct cacgctggc cgtgggcgac aaccgcgtgc tggacatggc cagcacctac    300
tttgacatcc gcggcgtgct ggatcggggc cccagcttca accctactc cggcaccgcc    360 tacaacagcc tggctcccaa gggagcgccc aacacctcac agtggataac caagacaat    420 ggaactgata agacatacag ttttggaaat gctccagtca gaggattgga cattacagaa    480
gagggtctcc aaataggaac cgatgagtca ggggtgaaa gcaagaaaat ttttgcagac    540
aaaacctatc agcctgaacc tcagcttgga gatgaggaat ggcatgatac tattggagct    600
gaagacaagt atgaggcag agcgcttaaa cctgccacca catgaaacc ctgctatggg    660 tctttcgcca gccaactaa tgctaaggga ggtcaggcta aaagcagaac caaggacgat    720
ggcactactg agcctgatat tgacatggcc ttctttgacg atcgcagtca gcaagctagt    780
ttcagtccag aacttgtttt gtatactgag aatgtcgatc tggacacccc ggatacccac    840
attatttaca aacctggcac tgatgaaaca agttcttctt tcaacttggg tcagcagtcc    900
atgcccaaca gacccaacta cattggcttc agagacaact ttatcgggct catgtactac    960
aacagcactg gcaatatggg tgtactggcc ggtcaggccc cccagctgaa tgctgtggtg   1020
gacttgcagg acagaaacac tgaactgtcc taccagctct tgcttgactc tctgggtgac   1080
agaaccaggt atttcagtat gtggaatcag gcggtggaca gctatgaccc cgatgtgcgc   1140
attattgaaa atcacggtgt ggaggatgaa ctccccaact attgcttccc tttgaatggt   1200 gtgggctta cagatacatt ccagggaatt aaggttaaaa ctacaaataa cggaacagca   1260
aatgctacag agtgggaatc tgatacctct gtcaataatg ctaatgagat tgccaagggc   1320
aatcctttcg ccatggagat caacatccag gccaacctgt ggcggaactt cctctacgcg   1380
aacgtggcgc tgtacctgcc cgactcctac aagtacacgc cggccaacat cacgctgccc   1440
accaacacca cacctacga ttacatgaac ggccgcgtgg tggcgccctc gctggtggac   1500
gcctacatca catcgggggc gcgctggtcg ctggacccca tggacaacgt caaccccttc   1560
aaccaccacc gcaacgcggg cctgcgctac cgctccatgc tcctgggcaa cgggcgctac   1620
gtgcccttcc acatccaggt gccccaaaag ttttttcgcca tcaagagcct cctgctcctg   1680
cccgggtcct acacctacga gtggaacttc cgcaaggacg tcaacatgat cctgcagagc   1740
tccctcggca cgaccctgcg cacggacggg gcctccatcg ccttccaccag catcaacctc   1800 tacgccacct tcttccccat ggcgcacaac accgcctcca cgctcgaggc catgctgcgc   1860
aacgacacca cgaccagtc cttcaacgac tacctctcgg cggccaacat gctctacccc   1920
```

```
atcccggcca acgccaccaa cgtgcccatc tccatcccct cgcgcaactg ggccgccttc    1980
cgcggatggt ccttcacgcg cctcaagacc cgcgagacgc cctcgctcgg ctccgggttc    2040
gaccccatct tcgtctactc gggctccatc ccctacctcg acggcacctt ctacctcaac    2100
cacaccttca agaaggtctc catcaccttc gactcctccg tcagctggcc cggcaacgac    2160
cgcctcctga cgcccaacga gttcgaaatc aagcgcaccg tcgacggaga ggggtacaac    2220
gtggcccagt gcaacatgac caaggactgg ttcctggtcc agatgctggc ccactacaac    2280
atcggctacc agggcttcta cgtgcccgag ggctacaagg accgcatgta ctccttcttc    2340
cgcaacttcc agcccatgag ccgccaggtc gtggacgagg tcaactacaa ggactaccag    2400
gccgtcaccc tggcctacca gcacaacaac tcgggcttcg tcggctacct cgcgcccacc    2460
atgcgccagg ccagcccta ccccgccaac taccccctacc cgctcatcgg caagagcgcc    2520
gtcgccagcg tcacccagaa aaagttcctc tgcgaccggg tcatgtggcg catcccctc    2580 tccagcaact tcatgtccat gggcgcgctc accgacctcg ccagaacat gctctacgcc    2640 aactccgccc acgcgctaga catgaatttc gaagtcgacc ccatggatga gtccaccctt    2700
ctctatgttg tcttcgaagt cttcgacgtc gtccgagtgc accagcccca ccgcggcgtc    2760
atcgaggccg tctacctgcg cacgcccttc tcggccggca acgccaccac ctaa         2814
```

<210> SEQ ID NO 41
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (887)..(887)
<223> OTHER INFORMATION: n is a, c, g, or t

<400> SEQUENCE: 41

```
atggccaccc catcgatgct gccccagtgg gcgtacatgc acatcgccgg acaggacgct      60
tcggagtacc tgagtccggg tctggtgcag ttcgcccgcg ccacagacac ctacttcagt     120
ctggggaaca agtttaggaa ccccacggtg gcgcccacgc acgatgtgac caccgaccgc     180
agccagcggc tgacgctgcg cttcgtgccc gtggaccgcg aggacaacac ctactcgtac     240
aaagtgcgct acacgctggc cgtgggcgac aaccgcgtgc tggacatggc cagcacntac    300
tttgacatcc gcgcgtgct ggatcggggc cccagcttca acccctactc cggcaccgcn    360
tacaacagcc tggctcccaa gggagcgccc aacacctcac agtggataac caaagacaat    420
ggaactgata agacatacag ttttggaaat gctccagtca gaggattgga cattacagaa    480
gagggtctcc aaataggaac cgatgagtca gggggtaaaa gcaagaaaat ttttgcagac    540
aaaacctatc agcctgaacc tcagcttgga gatgaggaat ggcatgatac tattggagct    600
gaagacaagt atggaggcag agcgcttaaa cctgccacca catgaaacc ctgctatggg    660 tcttttcgcca agccaactaa tgctaaggga ggtcaggcta aaagcagaac caaggacgat    720
ggcactactg agcctgatat tgacatggcc ttttttgacg atcgcagtca gcaagctagt    780
ttcagtccag aacttgtttt gtatactgag aatgtcgatc tggacacccc ggataccac    840
```

```
attatttaca aacctggcac tgatgaaaca agttcttctt tcaactnggg tcagcagtcc     900
atgcccaaca gacccaatta cattggcttc agagacaact ttatcggact catgtactac     960
aacagcactg gcaatatggg tgtactggct ggacaggcct cccagctgaa tgctgtggtg    1020
gacttgcagg acagaaacac cgaactgtcc taccagctct tgcttgactc tctgggcgac    1080
agaaccaggt atttcagtat gtggaatcag gcggtggaca gctatgaccc cgatgtgcgc    1140
attattgaaa tcacggtgt ggaggatgaa cttcccaact attgcttccc tttgaatggt     1200
gtgggcttta cagatacatt ccagggaatt aaggttaaaa ctaccaataa cggaacagca    1260
aacgctacag agtgggaatc tgatacctct gtcaataatg ctaatgagat tgccaagggc    1320
aatcctttcg ccatggagat caacatccag gccaacctgt ggcggaactt cctctacgcg    1380
aacgtggcgc tgtacctgcc cgactcctac aagtacacgc cggccaacat cacgctgccc    1440
accaacacca cacctacga ttacatgaac ggccgcgtgg tggcgccctc gctggtggac     1500
gcctacatca acatcggggc gcgctggtcg ctggacccca tggacaacgt caacccttc     1560 aaccaccacc gcaacgcggg cctgcgatac cgctccatgc tcctgggcaa cgggcgctac    1620
gtgcccttcc acatccaggt gccccaaaag ttttcgcca tcaagaacct cctgctcctg      1680
cccgggtcct acacctacga gtggaacttc cgcaaggacg tcaacatgat cctgcagagc    1740
tccctcggca cgacctgcg cacggacggg gcctccatcg ccttcaccag catcaacctc      1800
tacgccacct tcttccccat ggcgcacaac accgcctcca cgctcgaggc catgctgcgc    1860
aacgacacca cgaccagtc cttcaacgac tacctctcgg cggccaacat gctctacccc     1920
atcccggcca acgccaccaa cgtgcccatc tccatcccct cgcgcaactg gccgccttc     1980 cgcggatggt ccttcacgcg cctcaagacc cgcgagacgc cctcgctcgg ctccgggttt    2040 gaccctact tcgtctactc gggctccatc ccctacctcg acggcacctt ctacctcaac     2100
cacaccttca agaaggtctc catcaccttc gactcctccg tcagctggcc cggcaacgac    2160
cgcctcctga cgcccaacga gttcgaaatc aagcgcaccg tcgacggaga ggggtacaac    2220
gtggcccagt gcaacatgac caaggactgg ttcctggtcc agatgctggc ccactacaac    2280
atcggctacc agggcttcta cgtgcccgag ggctacaagg accgcatgta ctccttcttc    2340
cgcaacttcc agcccatgag ccgccaggtc gtggacgagg tcaactacaa ggactaccag    2400
gccgtcaccc tggcctacca gcacaacaac tcgggcttcg tcggctacct cgcgcccacc    2460
atgcgccagg ccagcccta ccccgccaac taccctacc cgctcatcgg caagagcgcc     2520
gttgccagcg tcacccagaa aaagttcctc tgcgaccggg tcatgtggcg catccccttc    2580
tccagcaact tcatgtccat gggcgcgctc accgacctcg gcagaacat gctctacgcc     2640 aactccgccc acgcgctaga catgaatttc gaagtcgacc ccatggatga gtccacccctt   2700 ctctatgttg tcttcgaagt cttcgacgtc gtccgagtgc accagcccca ccgcggcgtc    2760
atcgaggccg tctacctgcg cacgcccttc tcggccggca acgccaccac ctaa          2814
```

<210> SEQ ID NO 42
<211> LENGTH: 2814
<212> TYPE: DNA
<213> ORGANISM: Adenoviridae - Mastadenovirus
<220> FEATURE:
<221> NAME/KEY: misc_feature
<222> LOCATION: (1612)..(1612)
<223> OTHER INFORMATION: n is a, c, g, or t

<400> SEQUENCE: 42

```
atggccaccc catcgatgct gccccagtgg gcgtacatgc acatcgccgg acaggacgct      60
```

```
tcggagtacc tgagtccggg tctggtgcag ttcgcccgcg ccacagacac ctacttcagt   120
ctggggaaca agtttaggaa ccccacggtg gcgcccacgc acgatgtgac caccgaccgc   180
agccagcgac tgacgctgcg cttcgtgccc gtggaccgcg aggacaacac ctactcgtac   240
aaagtgcgct acacgctggc cgtgggcgac aaccgcgtgc tggacatggc cagcacctac   300
tttgacatcc gcggcgtgct ggaccggggc cctagcttca aaccctactc cggcaccgcc   360
tacaacagcc tggcccccaa gggagcaccc aacacctcac agtgggtgac caaagacaat   420
gggactgata aacatacag ctttggtaat gctcctgtca gaggcttgga cattacagaa   480
gagggtctcc aaataggaac cgatgactct caaccgaaa gcaagaaaat ttttgcagac   540
aaaacatatc agcctgaacc tcaggttgga gatgaggaat ggcatgacac cattggggct   600
gaagacaaat atggaggcag agctcttaaa cctgccacca catgaaacc ctgttatggt   660 tcttttgcca agccaactaa tgctaaggga ggtcaggcta aaaccagaac caaagacgat   720
ggaactaccg agcctgatat tgacatggcc ttctttgacg atcgcagtca gcaggctagt   780
ttcagcccag aacttgtttt gtatactgag aatgtggatt tggagacccc agatacccac   840
attatttaca aacccggtac tgatgaaaca agttcttctt tcaacttggg tcagcaatcc   900
atgcccaaca gacccaacta cattggtttc agagacaact ttattggctt gatgtactac   960
aacagcactg gcaacatggg tgtgctggct ggtcaggctt ctcagctgaa tgccgtggtt  1020
gacttgcaag acagaaacac cgagctgtcc taccagctct tgcttgactc tctgggcgac  1080
agaacccggt atttcagtat gtggaatcag gcggtggaca gctatgatcc tgatgtgcgc  1140
attattgaaa accatggtgt ggaagatgaa ctgccaaact attgcttccc tttaaatggt  1200
gtgggcttta cagacacatt ccagggaatt aaggttaaaa ctaccaacaa cggtactgct  1260
aatgctacag agtgggaatc tgatacttct gtcaataatg ccaatgagat tgccaagggt  1320
aatccattcg ccatggaaat caacatccaa gccaacctgt ggaggaactt cctctatgcc  1380
aacgtggccc tgtacttgcc cgattcttac aagtacacgc cggccaacgt caccctgccc  1440
accaacacca cacctacga gtacatgaac ggccgggtgg tggcgccctc gctggtggac  1500
tcctacatca acatcggggc gcgctggtcg ctggacccca tggacaacgt caatcccttc  1560
aaccaccacc gcaatgcggg gctgcgctac cgctccatgc tcctgggcaa cnggcgcttc  1620
gtgcccttcc acatccaggt gccccagaaa tttttcgcca tcaagagcct cctgctcctg  1680
cccgggtcct acacctacga gtggaacttc cgcaaggacg tcaacatgat cctgcagagc  1740
tccctcggca acgacctgcg cacggacggg gcctccatct ccttcaccag catcaacctc  1800
tacgccacct tcttccccat ggcgcacaac acggcctcca ctctcgaggc catgctgcgc  1860
aacgacacca cgaccagtc cttcaacgac tacctctcgg cggccaacat gctctacccc  1920
atcccggcca acgccaccaa cgtgcccatc tccatccct cgcgcaactg gccgcctc    1980 cgcggctggt ccttcacgcg cctcaagacc aaggagacgc cctcgctggg ctccgggttc  2040 gaccccact tcgtctactc gggctccatc ccctacctcg acggcacctt ctacctcaac  2100
cacaccttca gaaggtctc catcaccttc gactcctccg tcagctggcc cggcaacgac  2160
cggctcctga cgcccaacga gttcgaaatc aagcgcaccg tcgacggcga gggatacaac  2220
gtggcccagt gcaacatgac caaggactgg ttcctggtcc agatgctggc ccactacaac  2280
atcggctacc agggcttcta cgtgcccgag ggctacaagg accgcatgta ctccttcttc  2340
cgcaacttcc agcccatgag ccgccaggtg gtggacgagg tcaactacaa ggactaccag  2400
```

| | |
|---|---|
| gccgtcaccc tggcctacca gcacaacaac tcgggcttcg tcggctacct cgcgcccacc | 2460 |
| atgcgtcagg gccagcccta ccccgccaac taccccctacc cgctcatcgg caagagcgcc | 2520 |
| gtcaccagcg tcacccagaa aaagttcctc tgcgaccgcg tcatgtggcg catcccttc | 2580 |
| tccagcaact tcatgtccat gggcgcgctc accgacctcg gccagaacat gctctatgcc | 2640 |
| aactccgccc acgcgctaga catgaatttc gaagtcgacc ccatggatga gtccacccctt | 2700 |
| ctctatgttg tcttcgaagt cttcgacgtc gtccgagtgc accagcccca ccgcggcgtc | 2760 |
| atcgaggccg tctacctgcg cacccccttc tcggccggta acgccaccac ctaa | 2814 |

<210> SEQ ID NO 43
<211> LENGTH: 2886
<212> TYPE: DNA
<213> ORGANISM: Adenoviridae - Mastadenovirus

<400> SEQUENCE: 43

| | |
|---|---|
| atggcgaccc catcgatgat gccgcagtgg tcgtacatgc acatctcggg ccaggacgcc | 60 |
| tcggagtacc tgagccccgg gctggtgcag ttcgcccgcg ccaccgacag ctacttcagc | 120 |
| ctgagtaaca agtttaggaa ccccacggtg gcgcccacgc acgatgtgac caccgaccgg | 180 |
| tcccagcgcc tgacgctgcg gttcatcccc gtggaccgcg aggacaccgc gtactcttac | 240 |
| aaggcgcggt tcaccctggc cgtgggcgac aaccgcgtgc tggacatggc ctccacctac | 300 |
| tttgacatcc gcgcgtgct ggacaggggc cccaccttca gccctactc cggcaccgcc | 360 |
| tacaactccc tggcccccaa gggcgccccc aactcctgcg agtgggagca agtggagcca | 420 |
| gctgaagagg cagcagaaaa tgaagatgaa gaagaagaag aggatgttgt tgatcctcag | 480 |
| gaacaggagc ccactactaa aacacatgta tatgctcaag ctccccttc tggcgagaaa | 540 |
| attaccaaag atggtctgca ataggaact gaggctacgg cagcaggagg cactaaagac | 600 |
| ttatttgcag accctacatt ccagccagaa ccccaagttg gcgaatctca gtggaatgag | 660 |
| gcggatgcta cagcagctgg aggtagagtg ctcaaaaaga ccactcccat gaaaccttgc | 720 |
| tatggctcat atgcccgccc cacaaatgcc aatgggggcc aaggtgtgct aaaggcaaat | 780 |
| gcccaggag tgctcgagtc tcaggttgag atgcagttct tttccacttc tacaaatgcc | 840 |
| acaaacgagc aaaacaacat ccagcccaaa ttggtgctgt acagcgagga tgtgcatatg | 900 |
| gagaccccag acacacacat ctcctacaag cctacaaaaaa gcgatgataa ttcaaaagtc | 960 |
| atgctgggtc agcagtccat gcccaacagg ccaaattaca tcgccttcag agacaacttt | 1020 |
| atcgggctca tgtattataa cagcactggc aacatggggg tgctggcagg tcaggcctca | 1080 |
| cagttgaatg cagtggtgga cctgcaagac agaaacacag aactgtccta ccagctcttg | 1140 |
| cttgattcca tgggagacag aaccagatac tttcccatgt ggaatcaggc cgtggacagt | 1200 |
| tatgacccag atgtcagaat tattgaaaat catggaaccg aagatgagct gcccaactat | 1260 |
| tgtttccctc tgggaggcat agggataact gacacttacc aggccattaa gactaatggc | 1320 |
| aatgggggcag gagatcaagc caccacgtgg cagaaagact cacaatttgc agaccgcaac | 1380 |
| gaaataggg tggaaacaa cttcgccatg gagatcaacc tcagtgccaa cctgtggagg | 1440 |
| aacttcctct actccaacgt ggccctgtac ctgccagaca gcttaagta caacccctcc | 1500 |
| aacgtggaaa tctctgacaa ccccaacacc tacgactaca tgaacaagcg agtggtggcc | 1560 |
| ccggggctgg tggactgcta catcaacctg ggcgcgcgct ggtccctgga ctacatggac | 1620 |
| aacgtcaacc cttcaacca ccaccgcaat gcgggcctgc gctaccgctc catgcttctg | 1680 |
| ggcaacgggc gctacgtgcc cttccacatc caggtgccc agaagttctt tgccatcaag | 1740 |

```
aacctcctcc tcctgccggg ctcctacacc tacgagtgga acttcaggaa ggatgtcaac   1800
atggtcctgc agagctctct gggcaacgac ctcaggtcg acggggccag catcaagttc   1860
gagagcatct gcctctacgc caccttcttc cccatggccc acaacacggc ctccacgctc   1920
gaggccatgc tcaggaacga caccaacgac cagtccttca cgactacct ctccgccgcc   1980
aacatgctct accccatccc cgccaacgcc accaacgtcc ccatctccat cccctcgcgc   2040
aactgggcgg ccttccgcgg ctgggccttc acccgcctta agaccaagga gaccccctcc   2100
ctgggctcgg gtttcgaccc ctactacacc tactcgggct ccatacccta cctggacgga   2160
accttctacc tcaaccacac tttcaagaag gtctcggtca ccttcgactc ctcggtcagc   2220
tggccgggca acgaccgcct gctcaccccc aacgagttcg agatcaagcg ctcggtcgac   2280
ggggagggct acaacgtagc ccagtgcaac atgaccaagg actggttcct catccagatg   2340
ctggccaact acaacatcgg ctatcagggc ttctacatcc agagagcta caaggacagg   2400
atgtactcct tctttaggaa cttccagccc atgagccggc aggtggtgga cgaaaccaag   2460
tacaaggact accagcaggt gggcatcatc caccagcaca caactcggg cttcgtgggc   2520
tacctcgccc ccaccatgcg cgagggacag gcctaccccg ccaacttccc ctacccgctc   2580
attggcaaga ccgcggtcga cagcatcacc cagaaaaagt tcctctgcga ccgcaccctc   2640
tggcgcatcc ccttctccag caacttcatg tccatgggtg cgctcacgga cctgggccag   2700
aacctgctct atgccaactc cgcccacgcg ctcgacatga ccttcgaggt cgaccccatg   2760
gacgagccca cccttctcta tgttctgttc gaagtctttg acgtggttcg ggtccaccag   2820
ccgcaccgcg cgtcatcga gaccgtgtac ctgcgcacgc ccttctcggc cggcaacgcc   2880
accacc                                                               2886
```

<210> SEQ ID NO 44
<211> LENGTH: 1596
<212> TYPE: DNA
<213> ORGANISM: Adenoviridae - Mastadenovirus

<400> SEQUENCE: 44

```
atgatgaggc gcgtgtaccc ggagggtcct cctccctcgt acgagagcgt gatgcagcag     60
gcggtggcgg cggcgatgca gccccgctg gaggcgcctt acgtgccccc gcggtacctg    120
gcgcctacgg aggggcggaa cagcattcgt tactcggagc tggcaccctt gtacgatacc    180
acccggttgt acctggtgga caacaagtcg gcggacatcg cctcgctgaa ctaccagaac    240
gaccacagca acttcctgac caccgtggtg cagaacaacg atttcacccc cacggaggcc    300
agcaccccaga ccatcaactt tgacgagcgc tcgcggtggg gcggccagct gaaaaccatc    360
atgcacacca acatgcccaa cgtgaacgag ttcatgtaca gcaacaagtt caggcgcgg    420
gtgatggtct cgcgcaagac ccccaacggg gtcgcggtag gggatgatta tgatggtggt    480
caggacgagc tgacctacga gtgggtggag tttgagctgc cgagggcaa cttctcggtg    540
accatgacca tcgatctgat gaacaacgcc atcatcgaca actacttggc ggtggggcgg    600
cagaacgggg tgctggagag cgacatcggc gtgaagttcg acacgcgcaa cttccggctg    660
ggctgggacc ccgtgaccga gctggtgatg ccggcgtgt acaccaacga ggccttccac    720
ccgacattg tcctgctgcc cggctgcggc gtggacttca ccgagagccg cctcagcaac    780
ctgctggca tccgcaagcg gcagcccttc caggagggct tccagatcct gtacgaggac    840
ctggaggggg gcaacatccc cgcgctcttg gatgtcgaag cctacgagaa aagcaaggag    900
```

```
gagagcgccg ccgcggcgac cgcagccgta gccaccgcct ctaccgaggt gcggggcgat      960
aattttgcta gcgccgcagc agtggccgag gcggctgaaa ccgaaagtaa gatagtgatc     1020
cagccggtgg agaaggacag caaggacagg agctacaacg tgctcgcgga caagaaaaac     1080
accgcctacc gcagctggta cctggcctac aactacggcg accccgagaa gggcgtgcgc     1140
tcctggacgc tgctcaccac ctcggacgtc acctgcggcg tggagcaagt ctactggtcg     1200
ctgcccgaca tgatgcaaga cccggtcacc ttccgctcca cgcgtcaagt tagcaactac     1260
ccggtggtgg gcgccgagct cctgcccgtc tactccaaga gcttcttcaa cgagcaggcc     1320
gtctactcgc agcagctgcg cgccttcacc tcgctcacgc acgtcttcaa ccgcttcccc     1380
gagaaccaga tcctcgtccg cccgcccgcg cccaccatta ccaccgtcag tgaaaacgtt     1440
cctgctctca cagatcacgg gaccctgccg ctgcgcagca gtatccgggg agtccagcgc     1500
gtgaccgtca ctgacgccag acgccgcacc tgcccctacg tctacaaggc cctgggcgta     1560
gtcgcgccgc gcgtcctctc gagccgcacc ttctaa                              1596

<210> SEQ ID NO 45
<211> LENGTH: 1626
<212> TYPE: DNA
<213> ORGANISM: Adenoviridae - Mastadenovirus

<400> SEQUENCE: 45
atgatgaggc gcgtgtaccc ggagggtcct cctccctcgt acgagagcgt gatgcagcag       60
gcggtggcgg tggcgatgca gccccgctg gaggcgcctt acgtgccccc gcggtacctg      120
gcgcctacga aggggcggaa cagcattcgt tactcggagc tggcaccctt gtacgatacc      180
acccggttgt acctggtgga caacaagtcg gcggacatcg cctcgctgaa ctaccagaac      240
gaccacagca acttcctgac caccgtggtg cagaacaacg atttcacccc cacgcgaggcc     300 agcacccaga ccatcaactt tgacgagcgc tcgcggtggg gcggccagct gaaaaccatc      360
atgcacacca acatgcccaa cgtgaacgag ttcatgtaca gcaacaagtt caaggcgcgg      420
gtgatggtct cgcgcaagac ccccaacggg gtgacggtag gggatgatta tgatggtagt      480
caggacgagc tgacctacga gtgggtggag tttgagctgc ctgagggcaa cttctcggtg      540
accatgacca tcgatctgat gaacaacgcc atcatcgaca actacttggc ggtggggcgg      600
cagaacgggg tgctggaaag cgacatcggc gtgaagttcg acacgcgcaa cttccggctg      660
ggctgggacc ccgtgaccga gctggtgatg ccggcgtgt acaccaacga ggccttccac      720
cccgacatcg tcctgctgcc cggctgcggc gtggacttca ccgagagccg cctcagcaac      780
ctgctgggca tccgcaagcg gcagcccttc caggagggct ccagatcct gtacgaggac      840 ctggaggggg gcaacatccc cgcgctcttg gatgtcgaag cctatgagaa aagcaaggag      900
gatagcgccg cagcgacgac cgcagccgtg gctactgccg cgaccaccga tgcagatgca      960
actactacca ggggcgatac atttgccacc caggcggagg aagcagccgc cctagcggcg     1020
accgatgata gtgaaagtaa gatagtcatc aagccggtgg agaaggacag caaggacagg     1080
agctacaacg tgctcgcgga caagaaaaac accgcctacc gcagctggta cctggcctac     1140
aactacggcg accccgagaa gggcgtgcgc tcctggacgc tgctcaccac ctcggacgtc     1200
acctgcggcg tggagcaagt ctactggtcg ctgcccgaca tgatgcaaga cccggtcacc     1260
ttccgctcca cgcgtcaagt tagcaactac ccggtggtgg gcgccgagct cctgcccgtc     1320
tactccaaga gcttcttcaa cgagcaggcc gtctactcgc agcagctgcg cgccttcacc     1380
tcgctcacgc acgtcttcaa ccgcttcccc gagaaccaga tcctcgttcg cccgcccgcg     1440
```

```
cccaccatta ccaccgtcag tgaaaacgtt cctgctctca cagatcacgg gaccctgccg    1500
ctgcgcagca gtatccgggg agtccagcgc gtgaccgtca ctgacgccag acgccgcacc    1560 tgccctacg tctacaaggc cctgggcgta gtcgcgccgc gcgtcctctc gagccgcacc    1620
ttctaa                                                               1626

<210> SEQ ID NO 46
<211> LENGTH: 1599
<212> TYPE: DNA
<213> ORGANISM: Adenoviridae - Mastadenovirus

<400> SEQUENCE: 46
atgatgaggc gcgtgtaccc ggagggtcct cctccctcgt acgagagcgt gatgcagcag      60
gcggtggcgg cggcgatgca gccccgctg gaggcgcctt acgtgccccc gcggtacctg    120
gcgcctacgg aggggcggaa cagcattcgt tactcggagc tggcacccct gtacgatacc    180
acccggttgt acctggtgga caacaagtcg gcggacatcg cctcgctgaa ctaccagaac    240
gaccacagca acttcctgac caccgtggtg cagaacaacg atttcacccc cacggaggcc    300
agcacccaga ccatcaactt tgacgagcgc tcgcggtggg gcggccagct gaaaaccatc    360
atgcacacca acatgcccaa cgtgaacgag ttcatgtaca gcaacaagtt caaggcgcgg    420
gtgatggtct cgcgcaagac ccccaacggg gtcacagtaa cagatggtag tcaggacgag    480
ctgacctacg agtgggtgga gtttgagctg cccgagggca acttctcggt gaccatgacc    540
atcgatctga tgaacaacgc catcatcgac aactacttgg cggtggggcg gcagaacggg    600
gtgctggaga gcgacatcgg cgtgaagttc gacacgcgca acttccggct gggctgggac    660
cccgtgaccg agctggtgat gccgggcgtg tacaccaacg aggccttcca ccccgacatc    720
gtcctgctgc ccggctgcgg cgtggacttc accgagagcc gcctcagcaa cctgctgggc    780
atccgcaagc ggcagccctt ccaggagggc ttccagatcc tgtacgagga cctgaggggg    840
ggcaacatcc ccgcgctctt ggatgtcgaa gcctacgaga aagcaagga ggatagcacc    900 gccgtggcta ccgccgcgac tgtgcagat gccactgtca ccaggggcga tacattcgcc    960
acccaggcgg aggaagcagc cgccctagcg gcgaccgatg atagtgaaag taagatagtt   1020
atcaagccgg tggagaagga cagcaaggac aggagctaca acgttctatc ggatggaaag   1080
aacaccgcct accgcagctg gtacctggcc tacaactacg cgaccccga agggcgtg     1140 cgctcctgga cgctgctcac caccctcgga ctcacctgcg gcgtggagca agtctactgg   1200
tcgctgcccg acatgatgca agacccggtc accttccgct ccacgcgtca agttagcaac   1260
tacccggtgg tgggcgccga gctcctgccc gtctactcca agagcttctt caacgagcag   1320
gccgtctact cgcagcagct gcgcgccttc acctcgctca cgcacgtctt caaccgcttc   1380
cccgagaacc agatcctcgt ccgcccgccc gcgcccacca ttaccaccgt cagtgaaaac   1440
gttcctgctc tcagatcaca cgggaccctg ccgctgcgca gcagtatccg gggagtccag   1500
cgcgtgaccg tcactgacgc cagacgccgc acctgcccct acgtctacaa ggccctgggc   1560
gtagtcgcgc gcgcgtcct ctcgagccgc accttctaa                            1599

<210> SEQ ID NO 47
<211> LENGTH: 1587
<212> TYPE: DNA
<213> ORGANISM: Adenoviridae - Mastadenovirus

<400> SEQUENCE: 47
```

-continued

| | |
|---|---|
| atgatgaggc gcgtgtaccc ggagggtcct cctccctcgt acgagagcgt gatgcagcag | 60 |
| gcggtggcgg cggcgatgca gccccgctg gaggcgcctt acgtgccccc gcggtacctg | 120 |
| gcgcctacgg aggggcggaa cagcattcgt tactcggagc tggcacccct tgtacgatacc | 180 |
| acccggttgt acctggtgga caacaagtcg gcggacatcg cctcgctgaa ctaccagaac | 240 |
| gaccacagca acttcctgac caccgtggtg cagaacaacg atttcacccc cacggaggcc | 300 |
| agcacccaga ccatcaactt tgacgagcgc tcgcggtggg gcggccagct gaaaaccatc | 360 |
| atgcacacca acatgcccaa cgtgaacgag ttcctgtaca gcaacaagtt caaggcgcgg | 420 |
| gtgatggtct cgcgcaagac ccccaacggg gtcacagtaa cagatggtag tcaggacgag | 480 |
| ctgacctacg agtgggtgga gtttgagctg cccgagggca acttctcggt gaccatgacc | 540 |
| atcgatctga tgaacaacgc cattatcgac aattacttgg cggtggggcg gcagaacggg | 600 |
| gtgctggaga gcgacatcgg cgtgaagttc gacacgcgca acttcaggct cggttgggac | 660 |
| cccgtgaccg agctggtcat gccgggcgtg tacaccaacg aggccttcca ccccgacatc | 720 |
| gtcctgctgc ccggctgcgg cgtggacttc accgagagcc gcctcagcaa cctgctgggc | 780 |
| attcgcaaga ggcagcccctt ccaggagggt ttccagatca tgtacgagga tctggagggg | 840 |
| ggcaacatcc ccgcgctcct ggatgtcgag gcctacgaga aaagcaagga ggatagcgcc | 900 |
| gccgcggcga ccgcagccgt ggccaccgcc tctaccgagg tgcggggcga taattttgct | 960 |
| agcgccgcgc cagtggccga ggcggctgaa accgaaagta agatagtgat ccagccggtg | 1020 |
| gagaaggaca gcaaggacag gagctacaac gtgctcgcgg acaagaaaaa caccgcctac | 1080 |
| cgcagctggt acctggccta caactacggc gaccccgaga agggcgtgcg ctcctggacg | 1140 |
| ctgctcacca cctcggacgt cacctgcggc gtggagcaag tctactggtc gctgcccgac | 1200 |
| atgatgcaag acccggtcac cttccgctcc acgcgtcaag ttagcaacta cccggtggtg | 1260 |
| ggcgccgagc tcctgcccgt ctactccaag agcttcttca acgagcaggc cgtctactcg | 1320 |
| cagcagctgc gcgccttcac ctcgctcacg cacgtcttca accgcttccc cgagaaccag | 1380 |
| atcctcgtcc gcccgcccgc gcccaccatt accaccgtca gtgaaaacgt tcctgctctc | 1440 |
| acagatcacg ggaccctgcc gctgcgcagc agtatccggg gagtccagcg cgtgaccgtc | 1500 |
| actgacgcca gacgccgcac ctgcccctac gtctacaagg ccctgggcgt agtcgcgccg | 1560 |
| cgcgtcctct cgagccgcac cttctaa | 1587 |

<210> SEQ ID NO 48
<211> LENGTH: 1608
<212> TYPE: DNA
<213> ORGANISM: Adenoviridae - Mastadenovirus

<400> SEQUENCE: 48

| | |
|---|---|
| atgatgaggc gtgcgtaccc ggagggtcct cctccctcgt acgagagcgt gatgcagcag | 60 |
| gcgatggcgg cggcggcggc gatgcagccc ccgctggagg ctccttacgt gccccgcgg | 120 |
| tacctggcgc ctacgagggg cggaacagc attcgttact cggagctggc acccttgtac | 180 |
| gataccaccc ggttgtacct ggtggacaac aagtcggcgg acatcgcctc gctgaactac | 240 |
| cagaacgacc acagcaactt cctgaccacc gtggtgcaga caatgacttc accccccacg | 300 |
| gaggccagca cccagaccat caactttgac gagcgctcgc ggtggggcgg ccagctgaaa | 360 |
| accatcatgc acaccaacat gcccaacgtg aacgagttca tgtacagcaa caagttcaag | 420 |
| gcgcgggtca tggtctcccg caagaccccc aacggggtga cagtgacaga ggattatgat | 480 |
| ggtagtcagg atgagctgaa atacgagtgg gtggagtttg agctgcccga aggcaacttc | 540 |

-continued

| | |
|---|---|
| tcggtgacca tgactatcga cctgatgaac aacgccatca tcgacaatta cttggcggtg | 600 |
| gggcggcaga acggggtgct ggagagcgac atcggcgtga agttcgacac taggaacttc | 660 |
| aggctgggct gggaccccgt gaccgagctg gtcatgcccg gggtgtacac caacgaggcc | 720 |
| ttccatcccg atattgtctt gctgcccggc tgcggggtgg acttcaccga gagccgcctc | 780 |
| agcaacctgc tgggcattcg caagaggcag cccttccagg agggcttcca gatcatgtac | 840 |
| gaggatctgg aggggggtaa catccccgcg ctcctggatg tcgacgccta tgagaaaagc | 900 |
| aaggaggaga gcgccgccgc ggcgaccgca gccgtagcca ccgcctctac cgaggtcagg | 960 |
| ggcgataatt ttgctagcgc cgcagcagtg gcagcggccg aggcggctga aaccgaaagt | 1020 |
| aagatagtca ttcagccggt ggagaaggat agcaaagaca ggagctacaa cgtgctgccg | 1080 |
| gacaagataa acaccgccta ccgcagctgg tacctggcct acaactatgg cgaccccgag | 1140 |
| aagggcgtgc gctcctggac gctgctcacc acctcggacg tcacctgcgg cgtggagcaa | 1200 |
| gtctactggt cgctgcccga catgatgcaa gacccggtca ccttccgctc cacgcgtcaa | 1260 |
| gttagcaact acccggtggt gggcgccgag ctcctgcccg tctactccaa gagcttcttc | 1320 |
| aacgagcagg ccgtctactc gcagcagctg gcgccttca cctcgctcac gcacgtcttc | 1380 |
| aaccgcttcc ccgagaacca gatcctcgtc cgcccgcccg cgcccaccat taccaccgtc | 1440 |
| agtgaaaacg ttcctgctct cacagatcac gggaccctgc cgctgcgcag cagtatccgg | 1500 |
| ggagtccagc gcgtgaccgt tactgacgcc agacgccgca cctgcccta cgtctacaag | 1560 |
| gccctgggca tagtcgcgcc gcgcgtcctc tcgagccgca ccttctaa | 1608 |

<210> SEQ ID NO 49
<211> LENGTH: 1743
<212> TYPE: DNA
<213> ORGANISM: Adenoviridae - Mastadenovirus

<400> SEQUENCE: 49

| | |
|---|---|
| atgcggcgcg cggcgatgta ccacgaggga cctcctccct cttatgagag cgtggtgggc | 60 |
| gcggcggcgg cctctcccttt tgcgtcgcag ctggagccgc cgtacgtgcc tccgcggtac | 120 |
| ctgcggccta cggggggaag aaacagcatc cgttactcgg agctggcgcc cctgtacgac | 180 |
| accacccggg tgtacctggt ggacaacaag tcggcggacg tggcctccct gaactaccag | 240 |
| aacgaccaca gcaattttttt gaccacggtc atccagaaca atgactacac cccgagcgag | 300 |
| gccagcaccc agaccatcaa tctggatgac cggtcgcact ggggcggcga cctgaaaacc | 360 |
| atcctgcaca ccaacatgcc caacgtgaac gagttcatgt tcaccaataa gttcaaggcg | 420 |
| cgggtgatgg tgtcgcgctc gcacaccaag gacgaccggg tggagctgaa gtacgagtgg | 480 |
| gtagagttcg agctgcccga gggcaactac tcggagacca tgaccataga cctgatgaac | 540 |
| aacgcgatcg tggagcacta tctgaaagtg ggcaggcaga acggggtcct ggagagcgac | 600 |
| atcggggtca agttcgacac caggaacttc gcctgggggc tggaccccgt caccgggctg | 660 |
| gttatgcccg gggtctacac caacgaggcc ttccaccccg acatcatcct gctgcccggc | 720 |
| tgcggggtgg acttcacccta cagccgcctg agcaacctgc tgggcatccg caagcggcag | 780 |
| cccttccagg agggcttcag gatcacctac gaggacctgg agggggcaa catccccgcg | 840 |
| ctcctggatg tggaggccta ccaggatagc ttgaaggaag aagaggcggg agagggcagc | 900 |
| ggcggtggcg ccggtcagga ggaggggcgg gcctcctctg aggcctctgc ggacccagcc | 960 |
| gctgccgccg aggcggaggc ggccgacccc gcgatggtgt tagaggaaga gaaggatatg | 1020 |

```
aacgacgagg cggtgcgcgg cgacaccttt gccactcggg gggaggagaa gaaagcggag    1080
gccgaggccg cggcagagga ggcggcagca gcggcggcgg cagtagaggc ggcggccgag    1140
gcggagaagc cccccaagga gcccgtgatt aagcccctga ccgaagatag caagaagcgc    1200
agttacaacg tgctcaagga cagcaccaac accgagtacc gcagctggta cctggcctac    1260
aactacggcg accggcgac gggggtgcgc tcctggaccc tgctgtgtac gccggacgtg    1320
acctgcggct cggagcaggt gtactggtcg ctgcccgaca tgatgcaaga ccccgtgacc    1380
ttccgctcca cgcggcaggt cagcaacttc ccggtggtgg gcgccgagct gctgcccgtg    1440
cactccaaga gcttctacaa cgaccaggcc gtctactccc agctcatccg ccagttcacc    1500
tctctgaccc acgtgttcaa tcgctttcct gagaaccaga ttctggcgcg cccgcccgcc    1560
cccaccatca ccaccgtcag tgaaaacgtt cctgctctca cagatcacgg gacgctaccg    1620
ctgcgcaaca gcatcggagg agtccagcga gtgaccgtaa ctgacgccag acgccgcacc    1680 tgccccctacg tttacaaggc cctgggcata gtctcgccgc gcgtcctttc cagccgcact    1740
ttt                                                                  1743

<210> SEQ ID NO 50
<211> LENGTH: 577
<212> TYPE: PRT
<213> ORGANISM: Adenoviridae - Mastadenovirus

<400> SEQUENCE: 50

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
        50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
        195                 200                 205

Ala Pro Leu His Val Val Asp Thr Leu Asn Ala Leu Thr Val Val Thr
    210                 215                 220

Gly Gln Gly Leu Thr Ile Asn Gly Arg Ala Leu Gln Thr Arg Val Thr
225                 230                 235                 240
```

```
Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
        260                 265                 270

Tyr Pro Phe Asp Ala Gln Asn Asn Leu Ser Leu Arg Leu Gly Gln Gly
            275                 280                 285

Pro Leu Ile Val Asn Ser Ala His Asn Leu Asp Leu Asn Leu Asn Arg
        290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
            325                 330                 335

Asn Ala Gly Asp Gly Leu Gln Phe Gly Ser Gly Ser Asp Thr Asn Pro
            340                 345                 350

Leu Gln Thr Lys Leu Gly Leu Gly Leu Glu Tyr Asp Ser Asn Lys Ala
        355                 360                 365

Ile Ile Thr Lys Leu Gly Thr Gly Leu Ser Phe Asp Asn Thr Gly Ala
        370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
        435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
        515                 520                 525

Thr Ile Thr Leu Asn Gly Thr Asn Glu Thr Gly Asp Ala Thr Val Ser
    530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 51
<211> LENGTH: 955
<212> TYPE: PRT
<213> ORGANISM: Adenoviridae - Mastadenovirus

<400> SEQUENCE: 51

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30
```

```
Arg Ala Thr Asp Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
 50                  55                  60

Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
            115                 120                 125

Ala Pro Asn Pro Cys Glu Trp Asp Glu Ala Val Thr Ala Val Asp Ile
130                 135                 140

Asn Leu Asp Glu Leu Gly Glu Asp Glu Asp Ala Glu Gly Glu Ala
145                 150                 155                 160

Glu Gln Gln Lys Ser His Val Phe Gly Gln Ala Pro Tyr Ser Gly Gln
                165                 170                 175

Asn Ile Thr Lys Glu Gly Ile Gln Ile Gly Val Asp Thr Thr Ser Gln
            180                 185                 190

Ala Gln Thr Pro Leu Tyr Ala Asp Lys Thr Phe Gln Pro Glu Pro Gln
        195                 200                 205

Val Gly Glu Ser Gln Trp Asn Glu Thr Glu Ile Asn Tyr Gly Ala Gly
        210                 215                 220

Arg Val Leu Lys Lys Thr Thr Leu Met Lys Pro Cys Tyr Gly Ser Tyr
225                 230                 235                 240

Ala Arg Pro Thr Asn Glu Asn Gly Gly Gln Gly Ile Leu Leu Glu Lys
                245                 250                 255

Glu Gly Gly Lys Pro Glu Ser Gln Val Glu Met Gln Phe Phe Ser Thr
            260                 265                 270

Thr Gln Ala Ala Ala Ala Gly Asn Ser Asp Asn Leu Thr Pro Lys Val
        275                 280                 285

Val Leu Tyr Ser Glu Asp Val His Leu Glu Thr Pro Asp Thr His Ile
        290                 295                 300

Ser Tyr Met Pro Thr Ser Asn Glu Ala Asn Ser Arg Glu Leu Leu Gly
305                 310                 315                 320

Gln Gln Ala Met Pro Asn Arg Pro Asn Tyr Ile Ala Phe Arg Asp Asn
                325                 330                 335

Phe Ile Gly Leu Met Tyr Tyr Asn Ser Thr Gly Asn Met Gly Val Leu
            340                 345                 350

Ala Gly Gln Ala Ser Gln Leu Asn Ala Val Val Asp Leu Gln Asp Arg
        355                 360                 365

Asn Thr Glu Leu Ser Tyr Gln Leu Leu Leu Asp Ser Met Gly Asp Arg
    370                 375                 380

Thr Arg Tyr Phe Ser Met Trp Asn Gln Ala Val Asp Ser Tyr Asp Pro
385                 390                 395                 400

Asp Val Arg Ile Ile Glu Asn His Gly Thr Glu Asp Glu Leu Pro Asn
                405                 410                 415

Tyr Cys Phe Pro Leu Gly Gly Ile Ile Asn Thr Glu Thr Leu Thr Lys
            420                 425                 430

Val Lys Pro Lys Thr Gly Gln Asp Ala Gln Trp Glu Lys Asp Thr Glu
        435                 440                 445

Phe Ser Glu Lys Asn Glu Ile Arg Val Gly Asn Asn Phe Ala Met Glu
```

```
            450                 455                 460
Ile Asn Leu Asn Ala Asn Leu Trp Arg Asn Phe Leu Tyr Ser Asn Val
465                 470                 475                 480

Ala Leu Tyr Leu Pro Asp Lys Leu Lys Tyr Thr Pro Ala Asn Val Gln
                    485                 490                 495

Ile Ser Ser Asn Ser Asn Ser Tyr Asp Tyr Met Asn Lys Arg Val Val
                500                 505                 510

Ala Pro Gly Leu Val Asp Cys Tyr Ile Asn Leu Gly Ala Arg Trp Ser
            515                 520                 525

Leu Asp Tyr Met Asp Asn Val Asn Pro Phe Asn His His Arg Asn Ala
530                 535                 540

Gly Leu Arg Tyr Arg Ser Met Leu Leu Gly Asn Gly Arg Tyr Val Pro
545                 550                 555                 560

Phe His Ile Gln Val Pro Gln Lys Phe Ala Ile Lys Asn Leu Leu
                    565                 570                 575

Leu Leu Pro Gly Ser Tyr Thr Tyr Glu Trp Asn Phe Arg Lys Asp Val
                580                 585                 590

Asn Met Val Leu Gln Ser Ser Leu Gly Asn Asp Leu Arg Val Asp Gly
                595                 600                 605

Ala Ser Ile Lys Phe Glu Ser Ile Cys Leu Tyr Ala Thr Phe Phe Pro
610                 615                 620

Met Ala His Asn Thr Ala Ser Thr Leu Glu Ala Met Leu Arg Asn Asp
625                 630                 635                 640

Thr Asn Asp Gln Ser Phe Asn Asp Tyr Leu Ser Ala Ala Asn Met Leu
                645                 650                 655

Tyr Pro Ile Pro Ala Asn Ala Thr Asn Val Pro Ile Ser Ile Pro Ser
                660                 665                 670

Arg Asn Trp Ala Ala Phe Arg Gly Trp Ala Phe Thr Arg Leu Lys Thr
                675                 680                 685

Lys Glu Thr Pro Ser Leu Gly Ser Gly Phe Asp Pro Tyr Tyr Thr Tyr
                690                 695                 700

Ser Gly Ser Ile Pro Tyr Leu Asp Gly Thr Phe Tyr Leu Asn His Thr
705                 710                 715                 720

Phe Lys Lys Val Ser Val Thr Phe Asp Ser Ser Val Ser Trp Pro Gly
                    725                 730                 735

Asn Asp Arg Leu Leu Thr Pro Asn Glu Phe Glu Ile Lys Arg Ser Val
                740                 745                 750

Asp Gly Glu Gly Tyr Asn Val Ala Gln Cys Asn Met Thr Lys Asp Trp
                755                 760                 765

Phe Leu Ile Gln Met Leu Ala Asn Tyr Asn Ile Gly Tyr Gln Gly Phe
770                 775                 780

Tyr Ile Pro Glu Ser Tyr Lys Asp Arg Met Tyr Ser Phe Phe Arg Asn
785                 790                 795                 800

Phe Gln Pro Met Ser Arg Gln Val Val Asp Glu Thr Lys Tyr Lys Asp
                    805                 810                 815

Tyr Gln Gln Val Gly Ile Ile His Gln His Asn Asn Ser Gly Phe Val
                820                 825                 830

Gly Tyr Leu Ala Pro Thr Met Arg Glu Gly Gln Ala Tyr Pro Ala Asn
                835                 840                 845

Phe Pro Tyr Pro Leu Ile Gly Lys Thr Ala Val Asp Ser Val Thr Gln
                850                 855                 860

Lys Lys Phe Leu Cys Asp Arg Thr Leu Trp Arg Ile Pro Phe Ser Ser
865                 870                 875                 880
```

Asn Phe Met Ser Met Gly Ala Leu Thr Asp Leu Gly Gln Asn Leu Leu
                885                 890                 895

Tyr Ala Asn Ser Ala His Ala Leu Asp Met Thr Phe Glu Val Asp Pro
            900                 905                 910

Met Asp Glu Pro Thr Leu Leu Tyr Val Leu Phe Glu Val Phe Asp Val
            915                 920                 925

Val Arg Val His Gln Pro His Arg Gly Val Ile Glu Thr Val Tyr Leu
        930                 935                 940

Arg Thr Pro Phe Ser Ala Gly Asn Ala Thr Thr
945                 950                 955

<210> SEQ ID NO 52
<211> LENGTH: 582
<212> TYPE: PRT
<213> ORGANISM: Adenoviridae - Mastadenovirus

<400> SEQUENCE: 52

Met Arg Arg Ala Ala Met Tyr His Glu Gly Pro Pro Ser Tyr Glu
1               5                   10                  15

Ser Val Val Gly Ala Ala Ala Ser Pro Phe Ala Ser Gln Leu Glu
            20                  25                  30

Pro Pro Tyr Val Pro Pro Arg Tyr Leu Arg Pro Thr Gly Gly Arg Asn
        35                  40                  45

Ser Ile Arg Tyr Ser Glu Leu Ala Pro Leu Tyr Asp Thr Thr Arg Val
    50                  55                  60

Tyr Leu Val Asp Asn Lys Ser Ala Asp Val Ala Ser Leu Asn Tyr Gln
65                  70                  75                  80

Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
            100                 105                 110

His Trp Gly Gly Asp Leu Lys Thr Ile Leu His Thr Asn Met Pro Asn
        115                 120                 125

Val Asn Glu Phe Met Phe Thr Asn Lys Phe Lys Ala Arg Val Met Val
    130                 135                 140

Ser Arg Ser His Thr Lys Asp Asp Arg Val Glu Leu Lys Tyr Glu Trp
145                 150                 155                 160

Val Glu Phe Glu Leu Pro Gly Asn Tyr Ser Glu Thr Met Thr Ile
                165                 170                 175

Asp Leu Met Asn Asn Ala Ile Val Glu His Tyr Leu Lys Val Gly Arg
            180                 185                 190

Gln Asn Gly Val Leu Glu Ser Asp Ile Gly Val Lys Phe Asp Thr Arg
        195                 200                 205

Asn Phe Arg Leu Gly Leu Asp Pro Val Thr Gly Leu Val Met Pro Gly
    210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
            260                 265                 270

Leu Glu Gly Gly Asn Ile Pro Ala Leu Leu Asp Val Glu Ala Tyr Gln
        275                 280                 285

Asn Ser Leu Lys Glu Glu Glu Ala Gly Glu Gly Ser Gly Gly Gly Gly

```
                290                 295                 300
Ala Gly Gln Glu Glu Gly Ala Ser Ser Glu Ala Ser Ala Asp Ala
305                 310                 315                 320

Ala Ala Ala Glu Ala Glu Ala Ala Asp Pro Ala Met Val Val Glu
                325                 330                 335

Glu Glu Lys Asp Met Asn Asp Glu Ala Val Arg Gly Asp Thr Phe Ala
                340                 345                 350

Thr Arg Gly Glu Glu Lys Lys Ala Glu Ala Glu Ala Ala Glu Glu
            355                 360                 365

Ala Ala Ala Ala Ala Ala Val Glu Ala Ala Glu Ala Glu Lys
        370                 375                 380

Pro Pro Lys Glu Pro Val Ile Lys Pro Leu Thr Glu Asp Ser Lys Lys
385                 390                 395                 400

Arg Ser Tyr Asn Val Leu Lys Asp Ser Thr Asn Thr Glu Tyr Arg Ser
                405                 410                 415

Trp Tyr Leu Ala Tyr Asn Tyr Gly Asp Pro Ala Thr Gly Val Arg Ser
                420                 425                 430

Trp Thr Leu Leu Cys Thr Pro Asp Val Thr Cys Gly Ser Glu Gln Val
            435                 440                 445

Tyr Trp Ser Leu Pro Asp Met Met Gln Asp Pro Val Thr Phe Arg Ser
            450                 455                 460

Thr Arg Gln Val Ser Asn Phe Pro Val Val Gly Ala Glu Leu Leu Pro
465                 470                 475                 480

Val His Ser Lys Ser Phe Tyr Asn Asp Gln Ala Val Tyr Ser Gln Leu
                485                 490                 495

Ile Arg Gln Phe Thr Ser Leu Thr His Val Phe Asn Arg Phe Pro Glu
                500                 505                 510

Asn Gln Ile Leu Ala Arg Pro Pro Ala Pro Thr Ile Thr Thr Val Ser
            515                 520                 525

Glu Asn Val Pro Ala Leu Thr Asp His Gly Thr Leu Pro Leu Arg Asn
530                 535                 540

Ser Ile Gly Gly Val Gln Arg Val Thr Val Thr Asp Ala Arg Arg Arg
545                 550                 555                 560

Thr Cys Pro Tyr Val Tyr Lys Ala Leu Gly Ile Val Ser Pro Arg Val
                565                 570                 575

Leu Ser Ser Arg Thr Phe
            580

<210> SEQ ID NO 53
<211> LENGTH: 542
<212> TYPE: PRT
<213> ORGANISM: Adenoviridae - Mastadenovirus

<400> SEQUENCE: 53

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
        50                  55                  60

Lys Met Gly Asn Gly Leu Ser Leu Asp Asp Ala Gly Asn Leu Thr Ser
65                  70                  75                  80
```

-continued

```
Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
                165                 170                 175

Thr Thr Pro Pro Ile Ser Val Ser Ser Gly Ser Leu Gly Leu Asp Met
            180                 185                 190

Glu Asp Pro Met Tyr Thr His Asp Gly Lys Leu Gly Ile Arg Ile Gly
        195                 200                 205

Gly Pro Leu Gln Val Val Asp Ser Leu His Thr Leu Thr Val Val Thr
    210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
                245                 250                 255

Gly Gly Met Arg Ile Asn Thr Gly Gly Gln Leu Ile Leu Asp Val Ala
            260                 265                 270

Tyr Pro Phe Asp Ala Gln Asn Asn Leu Ser Leu Arg Leu Gly Gln Gly
        275                 280                 285

Pro Leu Tyr Val Asn Thr Asn His Asn Leu Asp Leu Asn Cys Asn Arg
    290                 295                 300

Gly Leu Thr Thr Thr Ser Ser Asn Thr Thr Lys Leu Glu Thr Lys
305                 310                 315                 320

Ile Asp Ser Gly Leu Asp Tyr Asn Ala Asn Gly Ala Ile Ile Ala Lys
                325                 330                 335

Leu Gly Thr Gly Leu Thr Phe Asp Asn Thr Gly Ala Ile Thr Val Gly
            340                 345                 350

Asn Thr Gly Asp Asp Lys Leu Thr Leu Trp Thr Thr Pro Asp Pro Ser
        355                 360                 365

Pro Asn Cys Arg Ile His Ala Asp Lys Asp Cys Lys Phe Thr Leu Val
    370                 375                 380

Leu Thr Lys Cys Gly Ser Gln Ile Leu Ala Ser Val Ala Ala Leu Ala
385                 390                 395                 400

Val Ser Gly Asn Leu Ser Ser Met Thr Gly Thr Val Ser Ser Val Thr
                405                 410                 415

Ile Phe Leu Arg Phe Asp Gln Asn Gly Val Leu Met Glu Asn Ser Ser
            420                 425                 430

Leu Asp Lys Glu Tyr Trp Asn Phe Arg Asn Gly Asn Ser Thr Asn Ala
        435                 440                 445

Thr Pro Tyr Thr Asn Ala Val Gly Phe Met Pro Asn Leu Ser Ala Tyr
    450                 455                 460

Pro Lys Thr Gln Ser Gln Thr Ala Lys Asn Asn Ile Val Ser Glu Val
465                 470                 475                 480

Tyr Leu His Gly Asp Lys Ser Lys Pro Met Ile Leu Thr Ile Thr Leu
                485                 490                 495

Asn Gly Thr Asn Glu Ser Ser Glu Thr Ser Gln Val Ser His Tyr Ser
```

```
                  500                 505                 510
Met Ser Phe Thr Trp Ser Trp Asp Ser Gly Lys Tyr Ala Thr Glu Thr
                515                 520                 525

Phe Ala Thr Asn Ser Phe Thr Phe Ser Tyr Ile Ala Glu Gln
                530                 535                 540

<210> SEQ ID NO 54
<211> LENGTH: 964
<212> TYPE: PRT
<213> ORGANISM: Adenoviridae - Mastadenovirus

<400> SEQUENCE: 54

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Asp Ser Tyr Phe Ser Leu Ser Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ser Leu Ala Pro Lys Gly
            115                 120                 125

Ala Pro Asn Ser Cys Glu Trp Glu Gln Glu Glu Thr Gln Thr Ala Glu
        130                 135                 140

Glu Ala Gln Asp Glu Glu Glu Asp Glu Ala Glu Ala Glu Glu Glu Met
145                 150                 155                 160

Pro Gln Glu Glu Gln Ala Pro Val Lys Lys Thr His Val Tyr Ala Gln
                165                 170                 175

Ala Pro Leu Ser Gly Glu Lys Ile Thr Lys Asp Gly Leu Gln Ile Gly
                180                 185                 190

Thr Asp Ala Thr Ala Thr Glu Gln Lys Pro Ile Tyr Ala Asp Pro Thr
            195                 200                 205

Phe Gln Pro Glu Pro Gln Ile Gly Glu Ser Gln Trp Asn Glu Ala Asp
        210                 215                 220

Ala Ser Val Ala Gly Arg Val Leu Lys Lys Thr Thr Pro Met Lys
225                 230                 235                 240

Pro Cys Tyr Gly Ser Tyr Ala Arg Pro Thr Asn Ala Asn Gly Gly Gln
                245                 250                 255

Gly Val Leu Val Glu Lys Asp Gly Gly Lys Met Glu Ser Gln Val Asp
                260                 265                 270

Met Gln Phe Phe Ser Thr Ser Glu Asn Ala Arg Asn Glu Ala Asn Asn
            275                 280                 285

Ile Gln Pro Lys Leu Val Leu Tyr Ser Glu Asp Val His Met Glu Thr
        290                 295                 300

Pro Asp Thr His Ile Ser Tyr Lys Pro Ala Lys Ser Asp Asp Asn Ser
305                 310                 315                 320

Lys Val Met Leu Gly Gln Gln Ser Met Pro Asn Arg Pro Asn Tyr Ile
                325                 330                 335
```

```
Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
            355                 360                 365

Asp Leu Gln Asp Arg Asn Thr Glu Leu Ser Tyr Gln Leu Leu Leu Asp
        370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly Gly
        435                 440                 445

Asn Thr Thr Trp Thr Lys Asp Glu Thr Phe Ala Asp Arg Asn Glu Ile
        450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510

Tyr Asp Tyr Met Asn Lys Arg Val Val Ala Pro Gly Leu Val Asp Cys
            515                 520                 525

Tyr Ile Asn Leu Gly Ala Arg Trp Ser Leu Asp Tyr Met Asp Asn Val
        530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Pro Gly Ser Tyr Thr
            580                 585                 590

Tyr Glu Trp Asn Phe Arg Lys Asp Val Asn Met Val Leu Gln Ser Ser
            595                 600                 605

Leu Gly Asn Asp Leu Arg Val Asp Gly Ala Ser Ile Lys Phe Glu Ser
        610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
            660                 665                 670

Thr Asn Val Pro Ile Ser Ile Pro Ser Arg Asn Trp Ala Ala Phe Arg
        675                 680                 685

Gly Trp Ala Phe Thr Arg Leu Lys Thr Lys Thr Pro Ser Leu Gly
            690                 695                 700

Ser Gly Phe Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ser Val Thr
                725                 730                 735

Phe Asp Ser Ser Val Ser Trp Pro Gly Asn Asp Arg Leu Leu Thr Pro
            740                 745                 750

Asn Glu Phe Glu Ile Lys Arg Ser Val Asp Gly Glu Gly Tyr Asn Val
```

```
                    755                 760                 765
Ala Gln Cys Asn Met Thr Lys Asp Trp Phe Leu Ile Gln Met Leu Ala
770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                805                 810                 815

Val Val Asp Glu Thr Lys Tyr Lys Asp Tyr Gln Gln Val Gly Ile Ile
            820                 825                 830

His Gln His Asn Asn Ser Gly Phe Val Gly Tyr Leu Ala Pro Thr Met
        835                 840                 845

Arg Glu Gly Gln Ala Tyr Pro Ala Asn Phe Pro Tyr Pro Leu Ile Gly
    850                 855                 860

Lys Thr Ala Val Asp Ser Val Thr Gln Lys Lys Phe Leu Cys Asp Arg
865                 870                 875                 880

Thr Leu Trp Arg Ile Pro Phe Ser Ser Asn Phe Met Ser Met Gly Ala
                885                 890                 895

Leu Thr Asp Leu Gly Gln Asn Leu Leu Tyr Ala Asn Ser Ala His Ala
                900                 905                 910

Leu Asp Met Thr Phe Glu Val Asp Pro Met Asp Glu Pro Thr Leu Leu
            915                 920                 925

Tyr Val Leu Phe Glu Val Phe Asp Val Val Arg Val His Gln Pro His
        930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 55
<211> LENGTH: 584
<212> TYPE: PRT
<213> ORGANISM: Adenoviridae - Mastadenovirus

<400> SEQUENCE: 55

Met Arg Arg Ala Ala Met Tyr His Glu Gly Pro Pro Ser Tyr Glu
1               5                   10                  15

Ser Val Val Gly Ala Ala Ala Ser Pro Phe Ala Ser Gln Leu Glu
            20                  25                  30

Pro Pro Tyr Val Pro Pro Arg Tyr Leu Arg Pro Thr Gly Gly Arg Asn
        35                  40                  45

Ser Ile Arg Tyr Ser Glu Leu Ala Pro Leu Tyr Asp Thr Thr Arg Val
    50                  55                  60

Tyr Leu Val Asp Asn Lys Ser Ala Asp Val Ala Ser Leu Asn Tyr Gln
65                  70                  75                  80

Asn Asp His Ser Asn Phe Leu Thr Thr Val Ile Gln Asn Asn Asp Tyr
                85                  90                  95

Thr Pro Ser Glu Ala Ser Thr Gln Thr Ile Asn Leu Asp Asp Arg Ser
            100                 105                 110

His Trp Gly Gly Asp Leu Lys Thr Ile Leu His Thr Asn Met Pro Asn
        115                 120                 125

Val Asn Glu Phe Met Phe Thr Asn Lys Phe Lys Ala Arg Val Met Val
    130                 135                 140

Ser Arg Ser His Thr Lys Asp Asp Arg Val Glu Leu Lys Tyr Glu Trp
145                 150                 155                 160

Val Glu Phe Glu Leu Pro Glu Gly Asn Tyr Ser Glu Thr Met Thr Ile
```

```
                      165                 170                 175
Asp Leu Met Asn Asn Ala Ile Val Glu His Tyr Leu Lys Val Gly Arg
                180                 185                 190

Gln Asn Gly Val Leu Glu Ser Asp Ile Gly Val Lys Phe Asp Thr Arg
            195                 200                 205

Asn Phe Arg Leu Gly Leu Asp Pro Val Thr Gly Leu Val Met Pro Gly
        210                 215                 220

Val Tyr Thr Asn Glu Ala Phe His Pro Asp Ile Ile Leu Leu Pro Gly
225                 230                 235                 240

Cys Gly Val Asp Phe Thr Tyr Ser Arg Leu Ser Asn Leu Leu Gly Ile
                245                 250                 255

Arg Lys Arg Gln Pro Phe Gln Glu Gly Phe Arg Ile Thr Tyr Glu Asp
                260                 265                 270

Leu Glu Gly Gly Asn Ile Pro Ala Leu Leu Asp Val Glu Ala Tyr Gln
            275                 280                 285

Asp Ser Leu Lys Glu Glu Ala Gly Glu Gly Ser Gly Gly Gly Gly
        290                 295                 300

Gly Ala Gly Gln Glu Glu Gly Ala Ser Ser Glu Ala Ser Ala Asp
305                 310                 315                 320

Ala Ala Ala Ala Glu Ala Glu Ala Asp Pro Ala Met Val Val
                325                 330                 335

Glu Glu Glu Lys Asp Met Asn Asp Glu Ala Val Arg Gly Asp Thr Phe
            340                 345                 350

Ala Thr Arg Gly Glu Glu Lys Lys Ala Glu Ala Glu Ala Ala Ala Glu
            355                 360                 365

Glu Ala Ala Ala Ala Ala Ala Val Glu Ala Ala Ala Glu Ala
        370                 375                 380

Glu Lys Pro Pro Lys Glu Pro Val Ile Lys Ala Leu Thr Glu Asp Ser
385                 390                 395                 400

Lys Lys Arg Ser Tyr Asn Val Leu Lys Asp Ser Thr Asn Thr Ala Tyr
                405                 410                 415

Arg Ser Trp Tyr Leu Ala Tyr Asn Tyr Gly Asp Pro Ala Thr Gly Val
                420                 425                 430

Arg Ser Trp Thr Leu Leu Cys Thr Pro Asp Val Thr Cys Gly Ser Glu
            435                 440                 445

Gln Val Tyr Trp Ser Leu Pro Asp Met Met Gln Asp Pro Val Thr Phe
        450                 455                 460

Arg Ser Thr Arg Gln Val Ser Asn Phe Pro Val Val Gly Ala Glu Leu
465                 470                 475                 480

Leu Pro Val His Ser Lys Ser Phe Tyr Asn Asp Gln Ala Val Tyr Ser
                485                 490                 495

Gln Leu Ile Arg Gln Phe Thr Ser Leu Thr His Val Phe Asn Arg Phe
                500                 505                 510

Pro Glu Asn Gln Ile Leu Ala Arg Pro Pro Ala Pro Thr Ile Thr Thr
            515                 520                 525

Val Ser Glu Asn Val Pro Ala Leu Thr Asp His Gly Thr Leu Pro Leu
530                 535                 540

Arg Asn Ser Ile Gly Gly Val Gln Arg Val Thr Val Thr Asp Ala Arg
545                 550                 555                 560

Arg Arg Thr Cys Pro Tyr Val Tyr Lys Ala Leu Gly Ile Val Ser Pro
                565                 570                 575

Arg Val Leu Ser Ser Arg Thr Phe
                580
```

<210> SEQ ID NO 56
<211> LENGTH: 1734
<212> TYPE: DNA
<213> ORGANISM: Adenoviridae - Mastadenovirus

<400> SEQUENCE: 56

```
atgaagcgcg ccaaaacgtc tgacgagacc ttcaaccccg tgtacccccta tgacacggaa      60
aacgggcctc cctccgtccc tttcctcacc cctcccttcg tgtcccccga cggatttcaa     120
gaaagccccc caggggtcct gtctctgcgc ctgtcagagc cctggtcac ttcccacggc      180
atgcttgccc tgaaaatggg aaatggcctc tccctggatg acgccggcaa cctcacctct     240
caagatgtca ccaccgtcac ccctcccctc aaaaaaacca agaccaacct cagcctccag     300
acctcagccc cctgaccgt tagctctggg tccctcaccg tcgcggccgc cgctccactg      360
gcggtggccg gcacctctct caccatgcaa tctcaggccc ccttgacagt gcaagatgca     420
aaactcggcc tggccaccca gggacccctg accgtgtctg aaggcaaact caccttgcag     480
acatcggctc cactgacggc cgctgacagc agcactctca ctgttagtgc cacacctccc     540
ctcagcacaa gcaatggtag tttgagcatt gacatgcagg ccccgattta taccaccaat     600
ggaaaactgg cacttaacat tggtgctccc ctgcatgtgg tagacaccct aaatgcacta     660
actgtagtaa ctggccaggg tcttaccata aatggaagag ccctgcaaac tagagtcacg     720
ggtgccctca gttatgacac agaaggcaac atccaactgc aagccggagg gggtatgcgc     780
attgacaata atggccaact tatccttaat gtagcttatc catttgatgc tcaaaacaac     840
ctcagcctta gacttggcca aggtcccccta attgttaact ctgcccacaa cttggatctt     900
aaccttaaca gaggccttta cttatttaca tctggaaaca cgaaaaaact ggaagttaac     960
ataaaaacag ccaaaggtct attttacgat ggcaccgcta tagcaatcaa tgcaggtgac    1020
gggctacagt ttgggtctgg ttcagataca aatccattgc aaactaaact tggattgggg    1080
ctggaatatg actccaacaa agctataatc actaaacttg gaactggcct aagctttgac    1140
aacacaggtg ccatcacagt aggcaacaaa atgatgaca agcttacctt gtggaccaca    1200
ccagacccct ccccaaactg cagaattaat tcagaaaaag atgctaaact cacactagtt    1260
ttgactaaat gcggcagcca ggtgttagcc agcgtttctg ttttatctgt aaaaggcagc    1320
cttgccccca tcagcggcac agtaactagc gcccagattg ttttaagatt tgatgaaaac    1380
ggagttttat tgagcaattc ttctcttgac ccccaatact ggaactatag aaaaggcgat    1440
tctacagaag gcactgcata tactaatgct gtgggattta tgcccaacct cacagcatac    1500
cctaaaacac agagccagac tgctaaaagc aacattgtaa gtcaagttta cttgaatggg    1560
gacaaaacaa aacccatgac cctaaccatc accctcaatg aactaatga acagggat      1620
gctacagtaa gcacatactc catgtcattt tcatggaact ggaatggaag taattacatt    1680
aatgacacct tccaaaccaa ctccttacc ttctcctaca tcgcccaaga ataa           1734
```

<210> SEQ ID NO 57
<211> LENGTH: 2868
<212> TYPE: DNA
<213> ORGANISM: Adenoviridae - Mastadenovirus

<400> SEQUENCE: 57

```
atggcgaccc catcgatgat gccgcagtgg tcgtacatgc acatctcggg ccaggacgcc      60
tcggagtacc tgagccccgg gctggtgcag ttcgcccgcg ccaccgacag ctacttcagc     120
```

```
ctgagtaaca agtttaggaa ccccacggtg gcgcccacgc acgatgtgac caccgaccgg      180
tcccagcgcc tgacgctgcg gttcatcccc gtggaccgcg aggacaccgc gtactcttac      240
aaggcgcggt tcaccctggc cgtgggcgac aaccgcgtgc tggacatggc ctccacctac      300
tttgacatcc gcggcgtgct ggacaggggc cccacccttta agccctactc cggcactgcc     360
tacaactccc tggcccccaa gggcgccccc aaccctgtg agtgggatga agccgttact       420
gctgttgaca ttaacctgga tgagctcggc gaagatgaag acgacgccga aggggaagca      480
gaacagcaaa aaagtcatgt atttggtcaa gcgccctact caggacaaaa cattacgaag      540
gagggcatac aaattggggt agataccacc agccaagccc aaacaccttt atacgctgac      600
aaaacattcc aacccgaacc tcaggttgga gaatcccaat ggaatgagac agaaatcaat     660
tatggagcgg gacgagtgct aaaaaagacc accctcatga aaccatgcta tgggtcatat      720
gcaagaccta ctaatgaaaa cggcggtcag ggcatactgc tggagaaaga gggtggtaaa      780
ccagaaagtc aagttgaaat gcaattttttt tctactactc aggccgccgc ggctggtaat     840
tcagataatc ttactccaaa agttgttttg tatagcgagg atgttcacct ggaaacgcca      900
gatacacaca tttcatatat gcccactagc aacgaagcca attcaagaga actgttggga      960
caacaagcta tgcccaacag acccaactac attgccttca gagacaactt tattggcctt     1020
atgtattaca acagcactgg caacatggga gtgctggcag gtcaggcctc acagttgaat     1080
gcagtggtgg acttgcaaga cagaaacaca gaactgtcct accagctctt gcttgattcc     1140
atgggagaca gaaccagata cttttccatg tggaatcagg cggtggacag ttatgatcca     1200
gatgttagaa ttattgaaaa tcatggaact gaagatgagc tgcccaacta ttgtttcccc     1260
ctgggcggca taattaacac cgaaacttta actaaagtga aacctaagac tggacaagac     1320
gctcagtggg aaaaagatac tgagttttca gagaaaaatg aaataagggt gggaaacaac     1380
ttcgccatgg agattaacct caatgccaac ctgtggagga atttcctgta ctccaacgtg     1440
gccctgtacc tgccagacaa acttaagtac actccagcca acgtgcagat tccagcaac      1500 tccaactcct acgactacat gaacaagcga gtggtggccc cggggctggt ggactgctac     1560
atcaacctgg cgcgcgcctg gtccctggac tacatggaca acgtcaaccc cttcaaccac     1620
caccgcaatg cgggcctgcg ctaccgctcc atgcttctgg caacgggcg ctacgtgccc      1680 ttccacatcc aggtgcccca gaagttcttt gccatcaaga acctcctcct cctgccgggc     1740
tcctacacct acgagtggaa cttcaggaag gatgtcaaca tggtcctcca gagctctctg     1800
ggtaacgacc tcagggtcga cggggccagc atcaagttcg agagcatctg cctctacgcc     1860
accttcttcc ccatggccca aacacggcc tccacgctcg aggccatgct caggaacgac      1920
accaacgacc agtccttcaa cgactacctc tccgccgcca catgctcta ccccatcccc     1980 gccaacgcca ccaacgtccc catctccatc ccctcgcgca actgggcggc cttccgcggc     2040
tgggccttca ctcgcctcaa gaccaaggag acccctcc tgggctcggg tttcgacccc       2100
tactacacct actcgggctc catacctac ctggacggaa ccttctacct caaccacacc      2160
ttcaagaagg tctcggtcac cttcgactcc tcggtcagct ggccgggcaa cgaccgcctg     2220
ctcaccccca cgagttcga gatcaagcgc tcggtcgacg ggagggcta caacgtggcc      2280 cagtgcaaca tgaccaagga ctggttcctc atccagatgc tggccaacta caacatcggc     2340
tatcagggct tctacatccc agagagctac aaggacagga tgtactcctt ctttaggaac     2400
ttccagccca tgagccggca ggtggtgac gaaaccaagt acaaggacta ccagcaggtg      2460
ggcatcatcc accagcacaa caactcgggc ttcgtgggct acctcgcccc caccatgcgc    2520
```

```
gagggacagg cctaccccgc caacttcccc tacccgctca ttggcaagac cgcggtcgac    2580
agcgtcaccc agaaaaagtt cctctgcgac cgcaccctct ggcgcatccc cttctccagc    2640
aacttcatgt ccatgggtgc gctcacggac ctgggccaga acctgctcta tgccaactcc    2700
gcccacgcgc tcgacatgac cttcgaggtc gaccccatgg acgagcccac ccttctctat    2760
gttctgttcg aagtctttga cgtggtccgg gtccaccagc cgcaccgcgg cgtcatcgag    2820
accgtgtacc tgcgcacgcc cttctcggcc ggcaacgcca ccacctaa                 2868
```

<210> SEQ ID NO 58
<211> LENGTH: 1749
<212> TYPE: DNA
<213> ORGANISM: Adenoviridae - Mastadenovirus

<400> SEQUENCE: 58

```
atgcggcgcg cggcgatgta ccacgaggga cctcctccct cttatgagag cgtggtgggc     60
gcggcggcgg cctctcccct tgcgtcgcag ctggagccgc cgtacgtgcc tccgcggtac    120
ctgcggccta cgggggggaag aaacagcatc cgttactcgg agctggcgcc cctgtacgac    180
accacccggg tgtacctggt ggacaacaag tcggcggacg tggcctccct gaactaccag    240
aacgaccaca gcaattttttt gaccacggtc atccagaaca atgactacac cccgagcgag    300
gccagcaccc agaccatcaa tctggatgac cggtcgcact ggggcggcga cctgaaaacc    360
atcctgcaca ccaacatgcc caacgtgaac gagttcatgt tcaccaataa gttcaaggcg    420
cgggtgatgg tgtcgcgttc gcacaccaag gacgaccggg tggagctgaa gtacgagtgg    480
gtagagttcg agctgcccga gggcaactac tcggagacca tgaccataga cctgatgaac    540
aacgcgatcg tggagcacta tctgaaagtg ggcaggcaga acggggtcct ggagagcgac    600
atcggggtca agttcgacac caggaacttc cgcctggggc tggaccccgt caccgggctg    660
gtcatgcccg gggtctacac caacgaggcc ttccaccccg acatcatcct gctgcccggc    720
tgcggggtgg acttcaccta cagccgcctg agcaacctgc tgggcatccg caagcggcag    780
cccttccagg agggctttag gatcacctac gaggacctgg agggggcaa catccccgcg    840 ctcctggatg tggaggccta ccagaatagc ttgaaggaag aagaggcggg agagggcagc    900
ggcggcggcg cgccggtca ggaggaggc gggcctcct ctgaggcctc tgcggacgca    960
gctgccgccg aggcggagga gcggccgac cccgcgatgg tggtagagga agagaaggat    1020
atgaatgacg aggcggtgcg cggcgacacc tttgccaccc ggggggagga gaagaaagcg    1080
gaggccgagc ccgcggcaga ggaggcggca gcagcggcgg cggcagtaga ggcggcggcc    1140
gaggcggaga agcccccccaa ggagccgtg attaagcccc tgaccgaaga tagcaagaag    1200
cgcagttaca acgtgctcaa ggacagcacc aacaccgagt accgcagctg gtacctggcc    1260
tacaactacg gcgacccggc gacggggtg cgctcctgga ccctgctgtg tacgccggac    1320
gtgacctgcg ctcggagca ggtgtactgg tcgctgcccg acatgatgca agaccccgtg    1380
accttccgct ccacgcggca ggtcagcaac tttccggtgg tgggcgccga gctgctgccc    1440
gtgcactcca agagcttcta caacgaccag gccgtctact cccagctcat ccgccagttc    1500
acctctctga cccacgtgtt caatcgcttt cctgagaacc agattctggc gcgcccgccc    1560
gcccccacca tcaccaccgt cagtgaaaac gttcctgctc tcacagatca cgggacgcta    1620
ccgctgcgca acagcatcgg aggagtccag cgagtgaccg taactgacgc cagacgccgc    1680
acctgtccct acgtttacaa ggccctgggc atagtctcgc cgcgcgtcct ttccagccgc    1740
```

```
acttttaa                                                         1749

<210> SEQ ID NO 59
<211> LENGTH: 1629
<212> TYPE: DNA
<213> ORGANISM: Adenoviridae - Mastadenovirus

<400> SEQUENCE: 59
atgaagcgcg ccaaaacgtc tgacgagacc ttcaaccccg tgtaccccta tgacacggaa    60
aacgggcctc cctccgttcc tttcctcacc cctcccttcg tgtcccccga cggatttcaa   120
gaaagccccc caggggtcct gtctctgcgc ctgtcagagc ccctggtcac ttcccacggc   180
atgcttgccc tgaaaatggg aaatggcctc tccctggatg acgccggcaa cctcacctct   240
caagatgtca ccaccgtcac ccctcccctc aaaaaaacca agaccaacct cagcctccag   300
acctcagccc ccctgaccgt tagctctggg tccctcaccg tcgcggccgc cgctccactg   360
gcggtggccg gcacctctct caccatgcaa tctcaggccc ccttgacggt gcaagatgca   420
aaactgggtc tggccaccca gggacccctg accgtgtctg aaggcaaact caccttgcag   480
acatcggctc cactgacggc cgccgacagc agcactctca ctgttggcac cacaccgcca   540
atcagtgtga gcagtggaag tctaggctta gatatggaag accccatgta tactcacgat   600
ggaaaactgg gaatcagaat tggtggccca ctgcaagtag tagacagctt gcacacactc   660
actgtagtta ctgaaacgg aataactgta gctaacaatg cccttcaaac taaagttgcg   720
ggtgccctgg ttatgactc atctggcaat ctagaattgc gagccgcagg gggtatgcga   780
attaacacag ggggtcaact cattcttgat gtggcttatc catttgatgc tcagaacaat   840
ctcagcctta gactcggcca gggaccttta tatgtgaaca ccaatcacaa cctagattta   900
aattgcaaca gaggtctgac cacaaccacc agcagtaaca caaccaaact gaaactaaa    960 atcgattcgg gcttagacta taacgccaat ggggctatca ttgctaaact tggcactggg   1020
ttaacctttg acaacacagg tgccataact gtgggaaaca ctggggatga caaactcact   1080
ctgtggacta ccccagatcc ctctcctaac tgcagaattc acgcagacaa agactgcaag   1140
tttactctag tcctgactaa gtgtggaagt caaattctgg cctccgtcgc cgccctggcg   1200
gtgtctggaa acctatcatc aatgacaggc actgtctcca gcgttaccat ctttctcaga   1260
ttcgatcaga atggagttct tatggaaaat tcctcgctag acaaggagta ctggaacttc   1320
agaaatggta attccaccaa tgccaccccc tacaccaatg cggttgggtt catgcccaac   1380
ctcagcgcct accccaaaac ccagagtcaa actgcaaaaa acaacattgt aagtgaggtt   1440
tacttacatg gggacaaatc taaacccatg atccttacca ttacccttaa tggcacaaat   1500
gaatccagtg aaactagtca ggtgagtcac tactccatgt catttacatg gtcctgggac   1560
agtgggaaat atgccaccga aacctttgcc accaactctt ttaccttctc ctacattgct   1620
gaacaataa                                                         1629

<210> SEQ ID NO 60
<211> LENGTH: 2895
<212> TYPE: DNA
<213> ORGANISM: Adenoviridae - Mastadenovirus

<400> SEQUENCE: 60
atggcgaccc catcgatgat gccgcagtgg tcgtacatgc acatctcggg ccaggacgcc    60
tcggagtacc tgagccccgg gctggtgcag ttcgcccgcg ccaccgacag ctacttcagc   120
ctgagtaaca agtttaggaa ccccacggtg gcgcccacgc acgatgtgac caccgaccgg   180
```

```
tcccagcgcc tgacgctgcg gttcatcccc gtggaccgcg aggacaccgc gtactcttac    240
aaggcgcggt tcaccctggc cgtgggcgac aaccgcgtgc tggacatggc ctccacctac    300
tttgacatcc gcggcgtgct ggacagggc cccaccttca gccctactc cggcaccgcc     360 tacaactccc tggcccccaa gggcgcccc aactcctgcg agtgggagca agaggagact     420
cagacagctg aagaggcaca agacgaagaa gaagatgaag ctgaagctga ggaggaaatg    480
cctcaggaag agcaagcacc tgtcaaaaag actcatgtat atgctcaggc tccccttct    540 ggcgaaaaaa ttactaaaga cggtctgcag ataggaacgg acgctacagc taccgaacaa    600
aaacctattt atgcagatcc cacattccag ccagaacccc aaattggtga atctcagtgg    660
aatgaggcag atgcttcagt tgccggcggt agagtgctga agaaaactac tcccatgaaa    720
ccctgttatg gttcctatgc caggcccaca aatgccaatg gaggtcaggg tgtattggtg    780
gagaaagacg gtggaaagat ggaaagccaa gtagatatgc aattctttc gacttctgaa     840 aacgcccgta acgaggctaa caacattcag cccaaattgg tgctgtacag cgaggatgtg    900
catatggaga ccccagacac acacatttct tacaagcctg caaaaagcga tgataattcg    960
aaagtcatgc tgggtcagca gtccatgccc aacaggccaa attacatcgg cttcagagac    1020
aactttatcg ggctcatgta ttacaacagc actggcaaca tgggggtgct ggcaggtcag    1080
gcctcacagt tgaatgcggt ggtggacttg aagacagaa acacagaact gtcctaccag     1140
ctcttgcttg attccatggg agacagaacc agatactttt ccatgtggaa tcaggcggtg    1200
gacagttatg atccagatgt cagaattatt gaaaatcatg gaactgaaga tgagctgccc    1260
aactattgtt tccctctggg aggcatagg gtaactgaca cttaccaggc cattaagact     1320
aatggcaatg gcaacggcgg gggcaatacc acttggacca aggatgaaac ttttgcagac    1380
cgcaacgaga tagggtggg aaacaatttc gccatggaga tcaacctcag tgccaacctg    1440
tggaggaact tcctctactc caacgtggcc ctgtacctgc agacaagct taagtacaac     1500 ccctccaacg tggaaatctc tgacaacccc aacacctacg actacatgaa caagcgagtg    1560
gtggccccgg gctggtgga ctgctacatc aacctgggcg cgcgctggtc cctggactac     1620
atggacaacg tcaaccctt caaccaccac cgcaacgcgg gcctgcgcta ccgctccatg     1680
cttctgggca acgggcgcta cgtgcccttc cacatccagg tgccccagaa gttctttgcc    1740
atcaagaacc tcctcctcct gccgggctcc tacacctacg agtggaactt caggaaggat    1800
gtcaacatgg tcctccagag ctctctgggt aacgacctca gggtcgacgg ggccagcatc    1860
aagttcgaga gcatctgcct ctacgccacc ttcttcccca tgcccacaa cacggcctcc    1920 acgctcgagg ccatgctcag gaacgacacc aacgaccagt ccttcaacga ctacctctcc    1980
gccgccaaca tgctctaccc catccccgcc aacgccacca cgttccat ctccatccc      2040 tcgcgcaact gggcggcctt ccgcggctgg gccttcaccc gcctcaagac caaggagacc    2100
ccctccctgg gctcgggttt cgaccctac tacacctact cgggctccat acctacctg      2160 gacggaacct tctacctcaa ccacacttt aagaaggtct cggtcacctt cgactcctcg     2220
gtcagctggc cgggcaacga tcgcctgctc accccaacg agttcgagat caagcgctcg    2280
gtcgacgggg agggctacaa cgtggcccag tgcaacatga ccaaggactg gttcctcatc    2340
caaatgctgg ccaactacaa catcggctat cagggcttct acatcccaga gagctacaag    2400
gacaggatgt actccttctt taggaacttc cagcccatga gccggcaggt ggtggacgaa    2460
accaagtaca aggactacca gcaggtgggc atcatccacc agcacaacaa ctcgggcttc    2520
```

| | |
|---|---|
| gtgggctacc tcgcccccac catgcgcgag ggacaggcct accccgccaa cttcccctac | 2580 |
| ccgctcattg gcaagaccgc ggtcgacagc gtcacccaga aaagttcct ctgcgaccgc | 2640 |
| accctctggc gcatccccctt ctccagcaac ttcatgtcca tgggtgcgct cacggacctg | 2700 |
| ggccagaacc tgctctatgc caactccgcc cacgcgctcg acatgacctt cgaggtcgac | 2760 |
| cccatggacg agcccaccct tctctatgtt ctgttcgaag tctttgacgt ggtccgggtc | 2820 |
| caccagccgc accgcggcgt catcgagacc gtgtacctgc gcacgcccett ctcggccggc | 2880 |
| aacgccacca cctaa | 2895 |

<210> SEQ ID NO 61
<211> LENGTH: 1755
<212> TYPE: DNA
<213> ORGANISM: Adenoviridae - Mastadenovirus

<400> SEQUENCE: 61

| | |
|---|---|
| atgcggcgcg cggcgatgta ccacgaggga cctcctccct cttatgagag cgtggtgggc | 60 |
| gcggcggcgg cctctccctt tgcgtcgcag ctggagccgc cgtacgtgcc tccgcggtac | 120 |
| ctgcggccta cgggggggaag aaacagcatc cgttactcgg agctggcgcc cctgtacgac | 180 |
| accacccggg tgtacctggt ggacaacaag tcggcggacg tggcctccct gaactaccag | 240 |
| aacgaccaca gcaattttttt gaccacggtc atccagaaca atgactacac cccgagcgag | 300 |
| gccagcaccc agaccatcaa tctggatgac cggtcgcact ggggcggcga cctgaaaacc | 360 |
| atcctgcaca ccaacatgcc caacgtgaac gagttcatgt tcaccaataa gttcaaggcg | 420 |
| cgggtgatgg tgtcgcgttc gcacaccaag gacgaccggg tggagctgaa gtacgagtgg | 480 |
| gtagagttcg agctgcccga gggcaactac tcggagacca tgaccataga cctgatgaac | 540 |
| aacgcgatcg tggagcacta tctgaaagtg gcaggcagaa acgggtcct ggagagcgac | 600 |
| atcggggtca agttcgacac caggaacttc cgcctggggc tggacccggt caccgggctg | 660 |
| gtcatgcccg ggtctacac caacgaggcc ttccaccccg acatcatcct gctgcccggc | 720 |
| tgcgggggtgg acttcaccta cagccgcctg agcaacctgc tgggcatccg caagcggcag | 780 |
| cccttccagg agggctttag gatcacctac gaggacctgg aggggggcaa catccccgcg | 840 |
| ctcctggatg tggaggccta ccaggatagc ttgaaggaag aagaggcggg agagggcagc | 900 |
| ggcggcggcg gcgcgccgg tcaggaggag ggcggggcct cctctgaggc ctctgcggac | 960 |
| gccgccgctg ccgccgaggc ggaggcggcc gaccccgcga tggtggtaga ggaagagaag | 1020 |
| gatatgaatg acgaggcggt gcgcggcgac acctttgcca ccggggggga ggagaagaaa | 1080 |
| gcggaggccg aggccgcggc agaggaggcg gcagcggcgg cggcggcggc agtagaggcg | 1140 |
| gcggccgagg cggagaagcc ccccaaggag cccgtgatta aggccctgac cgaagatagc | 1200 |
| aagaagcgca gttacaacgt gctcaaggac agcaccaaca ccgcgtaccg cagctggtac | 1260 |
| ctggcctaca actacggcga cccggcgacg ggggtgcgct cctggaccct gctgtgtacg | 1320 |
| ccggacgtga cctgcggctc ggagcaggtg tactggtcgc tgcccgacat gatgcaagac | 1380 |
| cccgtgacct tccgctccac gcggcaggtc agcaacttcc cggtggtggg cgccgagctg | 1440 |
| ctgcccgtgc actccaagag cttctacaac gaccaggccg tctactccca gctcatccgc | 1500 |
| cagttcacct ctctgaccca cgtgttcaat cgctttcctg agaaccagat tctggcgcgc | 1560 |
| ccgccgccc ccaccatcac caccgtcagt gaaaacgttc ctgctctcac agatcacggg | 1620 |
| acgctaccgc tgcgcaacag catcggagga gtccagcgag tgaccgtaac tgacgccaga | 1680 |
| cgccgcacct gtccctacgt ttacaaggcc ctgggcatag tctcgccgcg cgtcctttcc | 1740 | agccgcactt tttaa     1755

<210> SEQ ID NO 62
<211> LENGTH: 37776
<212> TYPE: DNA
<213> ORGANISM: Adenoviridae - Mastadenovirus

<400> SEQUENCE: 62

| | | | | | |
|---|---|---|---|---|---|
| catcatcaat | aatatacctt | attttggatt | gaagccaata | tgataatgag | gtgggcggag | 60 |
| cggggcgggg | cggggaggag | cggcggcgcg | gggcgggccg | ggaggtgtgg | cggaagttga | 120 |
| gtttgtaagt | gtggcggatg | tgacttgcta | gcgccggatg | tggtaaaagt | gacgttttttg | 180 |
| gagtgcgaca | acgcccacgg | gaagtgacat | ttttcccgcg | gttttaccg | gatgtcgtag | 240 |
| tgaatttggg | cgttaccaag | taagatttgg | ccattttcgc | gggaaaactg | aaatggggaa | 300 |
| gtgaaatctg | attaatttcg | cgttagtcat | accgcgtaat | atttgccgag | ggccgaggga | 360 |
| ctttgaccga | ttacgtggag | gaatcgccca | ggtgttttt | gaggtgaatt | tccgcgttcc | 420 |
| gggtcaaagt | ctccgtttta | ttattatagt | cagctgacgc | ggagtgtatt | tatacccgct | 480 |
| gatctcgtca | agaggccact | cttgagtgcc | agcgagtaga | gttttctcct | ctgccgctcc | 540 |
| gctccgctct | gacaccgggg | gaaaaatgag | acatttcacc | tacgatggcg | gtgtgcttac | 600 |
| cggccagctg | gctgcctcgg | tcctggacgc | cctgattgag | gacgtattgg | ccgacaatta | 660 |
| tcctcctcca | gctcattttg | agccacctac | tcttcacgaa | ctgtatgatt | tggacgtggt | 720 |
| ggcacctagc | gacccgaacg | agcaggcggt | ttccagtttt | tttcctgact | ctatgctgtt | 780 |
| ggccagccag | gaggggtcg | agctcgagac | ccctcctcca | atcgccgttt | ctcctgagcc | 840 |
| tccgaccctg | accaggcagc | ccgatcgccg | tgttggacct | gcgactatgc | cccatctgct | 900 |
| gcccgaggtg | atcgatctca | cctgtaacga | gtctggtttt | ccacccagcg | aggatgagga | 960 |
| cgaagagggt | gagcagtttg | tgttagattc | tgtggaggaa | cccgggcgcg | gttgcagatc | 1020 |
| ttgtcaatac | catcggaaaa | atacaggaga | cccccaaatt | atgtgttccc | tgtgttatat | 1080 |
| gaagacgacc | tgtatgttta | tttacagtaa | gtttgtgatt | ggtgggtcgg | tgggctgtag | 1140 |
| tgtgggtagg | tggtctgtgg | ttttttttt | ttttaatatc | agcttgggct | aaaaaactgc | 1200 |
| tatggtaatt | ttttaaggt | ccggtgtctg | aacctgagca | ggaagctgaa | ccggagcctg | 1260 |
| agagtcgccc | caggagaagg | cctgcaattc | taactagacc | gagtgcacct | gtagcgaggg | 1320 |
| acctcagcag | tgcagagacc | accgattccg | gtccttcctc | atcccctcca | gagattcatc | 1380 |
| ccgtggtgcc | tttgtgtccc | ctcaagcccg | ttgccgtgag | agttagtggg | cggagggccg | 1440 |
| ccgtggagag | cattgaggac | ttgcttaatg | agacacagga | acctttggac | ttgagctgta | 1500 |
| aacgccctag | gcaataaacc | tgcttacctg | gactgaatga | gttgacgcct | atgtttgctt | 1560 |
| ttgaatgact | taatgtgtat | ataataaaga | gtgagataat | gtttaattgc | atggtgtgtt | 1620 |
| tgattggggc | ggggtttgtt | gggtatataa | gcttccctgg | gctaaacttg | gttacacttg | 1680 |
| acctcatgga | ggcctgggag | tgtttagaga | gctttgccga | agtgcgtgcc | ttgctggaag | 1740 |
| agagctctaa | taatacctct | gggtggtgga | ggtattttttg | gggctctccc | caggctaagt | 1800 |
| tagtttgtag | aatcaaggag | gattacaagt | gggaatttga | acagcttttg | aaatcctgtg | 1860 |
| gtgagctctt | ggattctttg | aatctggggcc | accaggctct | tttccaggac | aagatcatca | 1920 |
| ggactttgga | tttttccaca | ccggggcgca | ttgctgccgg | ggttgctttt | ctagcttttt | 1980 |
| tgaaggataa | atggagcgaa | gagacccact | tgagttcggg | atacgtcctg | gattttctgg | 2040 |

```
ccatacaact gtggagagca tggatcaggc acaagaacag aatgcaactg ttgtcttccg    2100
tccgtccgtt gctgattcag ccggaggagc agcagaccgg gccggaggac cgggctcgtc    2160
tggaaccaga agagagggcg ccggagagga gcgcgtggaa cctgggagcc ggcctgaacg    2220
gccatccaca tcgggagtga atgttggaca ggtggcggat ctctttccag aactgcgacg    2280
aatcttaact atcagggagg atggacaatt tgttaagggg cttaagaggg agcgggggggc    2340
ttctgaacat aacgaggagg ccagtaattt agcttttagt ctgatgacca gacaccgtcc    2400
cgagtgcatt acttttcagc agattaagga taattgtgcc aatgagttag atctgctggg    2460
tcagaagtac agcatagagc agttgaccac ttactggctg cagccgggtg atgatctgga    2520
ggaagctatt agggtgtatg ccaaggtggc cctgaggccc gattgcaagt acaagctcaa    2580
ggggctggtg aatatcagga attgttgcta catttctggg aacggggcgg aggtggagat    2640
agagaccgat gacagggtgg cctttaggtg cagcatgatg aatatgtggc ctggggtgct    2700
gggcatggac ggggtggtga ttatgaatgt gaggttcacg gggcccaatt ttaatggcac    2760
ggtgttcctg ggcaacacca acttggtgct gcacggggtg agcttctatg ctttaacaa    2820
cacctgtgtg gaggcctgga ccgatgtgaa ggtccgtggc tgtgccttct acggatgttg    2880
gaaggcggta gtgtgtcgcc ccaagagcag gagttccatt aaaaaatgct gtttgagag    2940
gtgcaccctg ggggtgctgg cggagggcaa ctgtcgggtg cgccacaatg tggcctcaga    3000
atgcggttgc ttcatgctag tcaagagcgt ggcggtcatc aagcataaca tggtgtgcgg    3060
caacagcgag gacaaggcct cgcagatgct gacctgctcg gatggcaact gccacttact    3120
gaagaccgta catataacca gccacagccg caaggcctgg cccgtgttcg agcacaacgt    3180
gttgacccgc tgctctttgc atctgggcaa caggaggggt gtgttcctgc cctatcaatg    3240
caacttgagc cacaccaaga tcttgctaga gcccgaaagc atgtccaagg tgaacctgaa    3300
cggggtgttt gacatgaccc tgaagatatg gaaggtgctg aggtacgacg agaccaggtc    3360
tcgatgcagg ccctgcgagt gcgggggcaa gcatatgagg aaccagcctg tgatgctgga    3420
tgtgaccgag gagctgaggc ctgaccactt ggttctggcc tgcaccaggg ccgagtttgg    3480
ttctagcgat gaagacacag actgaggtgg gtgagtgggc gtggtctggg ggtgggaagc    3540
aatatataag ttgggggtct tagggtctct gtgtctgttt tgcagaggga ccgccggcgc    3600
catgagcggg agcagtagca gcaacgcctt ggatggcagc atcgtgagcc cttatttgac    3660
gacgcgcatg ccccactggg ccggggtgcg tcagaatgtg atgggctcca gcatcgacgg    3720
acgaccgtg ctgcccgcaa attccgccac gctgacctac gcgaccgtcg cggggacccc    3780
gttggacgcc accgccgccg ccgccgccac cgccgccgcc tcggccgtgc gcagcctggc    3840
cacggacttt gcattcttgg gaccccttggc caccggggcg ccgcccgtg ccgccgttcg    3900
cgatgacaag ctgaccgccc tgctggcgca gttggatgcg cttacccggg aactgggtga    3960
cctttcgcag caggtcgtgg ccctgcgcca gcaggtctcc gccctgcagg ctagcgggaa    4020
tgcttctcct gcaaatgccg tttaagataa ataaaaccag actctgtttg gattaaagaa    4080
aagtagcaag tgcattgctc tctttatttc ataattttcc gcgcgcgata ggcccgagtc    4140
cagcgttctc ggtcgttgag ggtgcggtgt atcttctcca ggacgtggta gaggtggctc    4200
tggacgttga gatacatggg catgagcccg tcccgggggt ggaggtagca ccactgcaga    4260
gcttcatgct ccggggtggt gttgtagatg atccagtcgt agcaggagcg ctgggcatgg    4320
tgcctaaaaa tgtccttaag cagcaggccg atggccaggg gaggccctt ggtgtaagtg    4380
tttacaaaac ggttgagttg ggaagggtgc atgcggggtg agatgatgtg catcttagat    4440
```

-continued

```
tgtatttta  gattggcgat  gtttcctccc  agatcccttc  tgggattcat  gttgtggagg  4500
accaccagca  cagtatatcc  ggtgcacttg  ggaaatttgt  catgcagctt  agagggaaat  4560
gcgtggaaga  acttggagac  gcccttgtgg  cctcccagat  tctccatgca  ttcgtccatg  4620
atgatggcaa  tgggcccgcg  ggaggcggcc  tgggcaaaga  tgtttctggg  gtcactgaca  4680
tcgtagttgt  gttccagggt  gagatcgtca  taggccattt  ttataaagcg  cgggcggagg  4740
gtgcccgact  gggggatgat  ggttccctcg  gccccgggg   cgtagttgcc  ttcgcagatc  4800
tgcatttccc  aggccttaat  ctctgagggg  ggaatcatat  ccacttgcgg  ggcgatgaag  4860
aaaacggttt  ccggagccgg  ggagattaac  tgggatgaga  gcaggtttct  cagcagctgt  4920
gactttccac  agccggtggg  gccataaata  acacctataa  ccggctgcag  ctggtagttg  4980
agcgagctgc  agctgccgtc  gtcccggagg  agggggccca  cctcattgag  catgtcccgg  5040
acgcgcttgt  tctcctcgac  caggtccgcc  agaaggcgct  cgccgcccag  ggacagcagc  5100
tcttgcaagg  aagcaaagtt  tttcagcggc  ttgaggccgt  ccgccgtggg  catgttttc   5160
agggtctggc  cgagcagctc  caggcggtcc  cagagctcgg  tgacgtgctc  tacggcatct  5220
ctatccagca  tatctcctcg  tttcgcgggt  tggggcggct  ttcgctgtag  ggcaccaggc  5280
gatggtcgtc  cagcgcggcc  agagtcatgt  ccttccatgg  gcgcagggtc  ctcgtcaggg  5340
tggtctgggt  cacggtgaag  gggtgcgccc  cgggctgggc  gctggccagg  gtgcgcttga  5400
gactggtcct  gctggtgctg  aagcgctgcc  ggtcttcgcc  ctgcgcgtcg  gccaggtagc  5460
atttgaccat  ggtgtcgtag  tccagcccct  ccgcggcgtg  tcccttggcg  cgcagcttgc  5520
ccttggaggt  ggcgccgcac  gcggggcact  gcaggctctt  gagcgcgtag  agcttggggg  5580
cgaggaagac  cgattcgggg  gagtaggcgt  ccgcgccgca  ggccccgcac  acggtctcgc  5640
actccaccag  ccaggtgagc  tcgggcgct   cggggtcaaa  accaggtttt  ccccatgct   5700
ttttgatgcg  tttcttacct  cgggtctcca  tgaggcggtg  tccccgctcg  gtgacgaaga  5760
ggctgtccgt  gtctccgtag  accgacttga  ggggtctgtc  ctccagggg   gtccctcggt  5820
cctcttcgta  gagaaactcg  gaccactctg  agacgaaggc  ccgcgtccag  gccaggacga  5880
aggaggccag  gtgggagggg  tagcggtcgt  tgtccactag  ggggtccacc  ttctccaagg  5940
tgtgaagaca  catgtcgccc  tcctcggcgt  ccaggaaggt  gattggcttg  taggtgtagg  6000
ccacgtgacc  cggggttccg  gacggggggg  tataaaaggg  ggtgggggcg  cgctcgtcct  6060
cactctcttc  cgcatcgctg  tctgcgaggg  ccagctgctg  gggtgagtat  tccctctcga  6120
aggcgggcat  gacctcagcg  ctgaggctgt  cagtttctaa  aaacgaggag  gatttgatgt  6180
tcacctgtcc  cgagctgatg  cctttgaggg  tgcccgcgtc  catctggtca  gaaaacacga  6240
tctttttatt  gtccagcttg  gtggcgaacg  accgtagag   ggcgttggag  agcagcttgg  6300
cgatggagcg  cagggtctga  ttcttgtccc  ggtcggcgcg  ctccttggcc  gcgatgttga  6360
gctgcacgta  ctcgcgcgcg  acgcagcgcc  actcggggaa  gacggtggtg  cgctcgtcgg  6420
gcaccaggcg  cacgcgccag  ccgcggttgt  gcagggtgac  gaggtccacg  ctggtggcga  6480
cctcgccgcg  caggcgctcg  ttggtccagc  agaggcgccc  gcccttgcgc  gagcagaagg  6540
ggggcagggg  gtcgagttgg  gtttcgtccg  ggggtccgc   gtccaccgtg  aagacccgg   6600
ggcgcaggcg  cgcgtcgaag  tagtcgatct  tgcatccttg  caagtccagc  gcctgctgcc  6660
agtcgcgggc  ggcgagcgcg  cgctcgtagg  ggttgagcgg  cgggcccag   ggcatggggt  6720
gggtgagcgc  ggaggcgtac  atgccgcaga  tgtcatagac  gtagagggc   tcccggagga  6780
```

```
tgcccaggta ggtggggtag cagcggccgc cgcggatgct ggcgcgcacg tagtcgtaga    6840
gctcgtgcga gggggcgagg aggtcgggwc ccaggttggt gcgggcgggg cgctccgcgc    6900
ggaagacgat ctgcctgaag atggcatgcg agttggaaga gatggtgggg cgctggaaga    6960
cgttgaagct ggcgtcctgc aggccgacgg cgtcgcgcac gaaggaggcg taggactcgc    7020
gcagcttgtg caccagctcg gcggtgacct gcacgtcgag cgcgcagtag tcgagggtct    7080
cgcggatgat gtcatactta gcctgcccct tcttttttcca cagctcgcgg ttgaggacga    7140
actcttcgcg gtctttccag tactcttgga tcgggaaacc gtccggctcc gaacggtaag    7200
agcccagcat gtagaactgg ttgacggcct ggtaggcgca gcagcccttc tccacgggca    7260
gggcgtaggc ctgcgcggcc ttgcggagcg aggtgtgggt cagggcgaag gtgtccctga    7320
ccatgacctt gaggtactgg tgtttgaagt cggagtcgtc gcagccgccc cgctcccaga    7380
gcgagaagtc ggtgcgcttt ttggagcggg ggttgggcag cgcgaaggtg acatcgttgt    7440
agaggatctt gcccgcgcga ggcatgaagt tgcgggtgat gcggaagggc ccggcactt    7500 ccgagcggtt gttgatgacc tgggcggcga gcacgatctc gtcgaagccg ttgatgttgt    7560
ggcccacgat gtagagttcc aggaagcggg gccggccctt gacgctgggc agcttcttta    7620
gctcttcgta ggtgagctcc tcgggcgagg cgaggccgtg ctcggccagg cccagtccg    7680 ccaggtgcgg gttgtccgcg aggaaggacc gccagaggtc gcgggccagg agggtctgca    7740
ggcggtccct gaaggtcctg aactggcggc ctacggccat cttttcgggg gtgacgcagt    7800
agaaggtgag ggggtcttgc tgccagggt cccagtcgag ctccagggcg aggtcgcgcg    7860
cggcggcgac caggcgctcg tcgccccga atttcatgac cagcatgaag ggcacgagct    7920
gctttccgaa ggcgcccatc caagtgtagg tctctacatc gtaggtgaca aagagacgtt    7980
ccgtgcgagg atgcgagccg atcgggaaga actggatctc ccgccaccag ttggaggagt    8040
ggctgttgat gtggtgaaag tagaagtccc gtcggcgggc cgagcactcg tgctggcttt    8100
tgtaaaagcg agcgcagtac tggcagcgct gcacgggctg tacctcttgc acgagatgca    8160
cctgccgacc gcggacgagg aagctgagtg ggaatctgag cccccgcat ggctcgcggc    8220 ctggctggtc ctcttctact ttggatgcgt ggccgtcacc gtctggctcc tcagggtg    8280 ttacggtgga gcggatcacc acgccgcgcg agccgcaggt ccagatatcg gcgcgcggcg    8340
gtcggagttt gatgacgaca tcgcgcagct gggagctgtc catggtctgg agctcccgcg    8400
gcggcggcag gtcagccggg agttcttgca ggtttacctc gcagagacgg gccagggcgc    8460
ggggcaggtc caggtggtac ttgaattcga gaggcgtgtt ggtggcggcg tcgatggctt    8520
gcaggaggcc gcagcccgg gcgcgacga cggtgccccg cggggcggtg aagctcccgc    8580
cgccgctcct gctgtcgccg ccggtggcgg ggcttagaag cggtgccgcg gtcgggcccc    8640
cggaggtagg gggggctccg gtcccgcggg cagggcggc agcggcacgt cggcgccgcg    8700
cgcgggcagg agctggtgct gcgcccggag gttgctggcg aaggcgacga cgcggcggtt    8760
gatctcctgg atctggcgcc tctgcgtgaa gacgacgggt ccggtgagct tgaacctgaa    8820
agagagttcg acagaatcaa tctcggtgtc attgaccgcg acctggcgca ggatctcctg    8880
cacgtcgccc gagttgtctt ggtaggcgat ctcggccatg aactgttcga tctcttcctc    8940
ctggaggtct ccgcgtccgg cgcgctccac ggtgccgccc aggtcgttgg agatgcgcgc    9000
catgagctgc gagaaggcgt tgagtccgcc ctcgttccag actcggctgt agaccacgcc    9060
gccctggtcc tcgcgggcgc gcatgaccac ctgcgcgagg ttgagttcca cgtgcgcgc    9120 aaagacggcg tagttgcgca ggcgctggaa gaggtagttg agggtggtgg cggtgtgctc    9180
```

```
ggccacgaag aagtacatga cccagcggcg caacgtggat tcgttgatgt cccccaaggc   9240
ctccagtcgc tccatggcct cgtagaagtc cacggcgaag ttgaaaaact gggagttgcg   9300
cgccgacacg gtcaactcct cctccagaag acggatgagc tcggcgacgg tgtcgcgcac   9360
ctcgcgctcg aaggctatgg gaatctcttc ctccgccagc atcaccacct cttcctcttc   9420
ttcctcctct ggcacttcca tgatggcttc ctcctcttcg ggggtggcg gcggggagg     9480 gggcgctcgg cgccggcggc ggcgcaccgg gaggcggtcc acgaagcgct cgatcatctc   9540
cccgcggcgg cgacgcatgg tctcggtgac ggcgcggccg ttctctcggg gacgcagctg   9600
gaagacgccg ccggtcatct ggtgctgggg cgggtggccg tggggcagcg agaccgcgct   9660
gacgatgcat cttaacaatt gctgcgtagg tacgccgccg agggacctga gggagtccag   9720
atccaccgga tccgaaaacc tttcgaggaa ggcatctaac cagtcgcagt cgcaaggtag   9780
gctgagcacc gtggcgggcg gcggggggtg ggggagtgt ctggcggagg tgctgctgat    9840
gatgtaattg aagtaggcgg tcttgacacg gcggatggtc gacaggagca ccatatcttt   9900
gggcccggcc tgctggatgc ggaggcggtc ggccatgccc caggcttcgt tctggcatct   9960
gcgcaggtct ttgtagtagt cttgcatgag cctttccacc ggcacctctt ctccttcttc  10020
ttctgacatc tctgctgcat ctgcggccct ggggcgacgg cgcgcgcccc tgcccccat   10080 gcgcgtcacc ccgaaccccc tgagcggctg gagcagggcc aggtcggcga cgacgcgctc  10140
ggccaggatg gcctgctgga cctgcgtgag ggtggtttgg aagtcatcca agtccacgaa  10200
gcggtggtag gcgcccgtgt tgatggtgta ggtgcagttg gccatgacgg accagttgac  10260
ggtctggtgg cccggttgcg tcatctcggt gtacctgagg cgcgagtagg cgcgcgagtc  10320
gaagatgtag tcgttgcaag tccgcaccag gtactggtag cccaccagga agtgcggcgg  10380
cggctggcgg tagaggggcc agcggagggt ggcgggggct ccggggcca ggtcttccag   10440 catgaggcgg tggtattcgt agatgtacct ggacatccag gtgatgcccg cggcggtggt  10500
ggaggcgcgc gggaagtcgc gcacccggtt ccagatgttg cgcagcggca gaaagtgctc  10560
catggtaggc gtgctctggc cggtcaggcg cgcgcagtcg ttgatactct agaccaggga  10620
aaacgaaagc cggtcagcgg gcactcttcc gtggtctggt ggataaattc gcaagggtat  10680
catggcggag ggcctcggtt cgagccccgg gcccgggccg gacggtccgc catgatccac  10740
gcggttaccg cccgcgtgtc gaacccaggt ggcgacgtca gacaacggtg gagtgttcct  10800
tttgggtttt ttttaatttt tctggccggg cgccgacgcc gccgcgtaag agactagagt  10860
gcaaaagcga aagcagtaag tggctcgctc cctgtagccc ggaggatcct tgctaaggt   10920 tgcgttgcgg cgaaccccgg ttcgagtctg gctctcgctg ggccgctcgg gtcggccgga  10980
accgcggcta aggcgggatt ggcctccccc tcattaaaga ccccgcttgc ggattcctcc  11040
ggacacaggg gacgagcccc tttttacttt tgcttttctc agatgcatcc ggtgctgcgg  11100
cagatgcgcc ccccgcccca gcagcagcag cagcaacatc agcaagagcg gcaccagcag  11160
cagcgggagt catgcagggc cccctcgccc acgctcggcg gtccggcgac ctcggcgtcc  11220
gcggccgtgt ctggagccgg cggcggtggg ctggcggacg acccggagga gccccgcgg   11280 cgcagggcca gacagtacct ggacctggag gagggcgagg gcctggcgcg actggggcg    11340 ccgtcccccg agcgccaccc gcgggtgcag ctgaagcgcg actcgcgcga ggcgtacgtg  11400
cctcggcaga acctgttcag agaccgcgcg gcgaggagc ccgaggagat gcgggaccgc   11460
aggttcgccg cggggcggga gctgcggcag gggctgaacc gggagcggct gctgcgcgag  11520
```

```
gaggactttg agcccgacgc gcggacgggg atcagccccg cgcgcgcgca cgtggcggcc    11580
gccgacctgg tgacggcgta cgagcagacg gtgaaccagg agatcaactt ccaaaaaagc    11640
ttcaacaacc acgtgcgcac gctggtggcg cgcgaggagg tgaccatcgg cctgatgcac    11700
ctgtgggact tgtgagcgc gctggagcag aaccccaaca gcaagcctct gacgcgcag    11760 ctgttcctga tagtgcagca cagcagggac aacgaggcgt tcagggacgc gctgctgaac    11820
atcaccgagc ccgagggtcg gtggctcctg gacctgatta acatcttgca gagcatagtg    11880
gtgcaggagc gcagcctgag cctggccgac aaggtggcgg ccatcaatta ctcgatgctc    11940
agtctgggca gttttacgc gcgcaagatc taccagacgc cgtacgtgcc catagacaag    12000
gaggtgaaga tcgacggctt ctacatgcgc atggcgctga aggtgctgac cctgagcgac    12060
gacctgggcg tgtaccgcaa cgagcgcatc cacaaggccg tgagcgtgag ccggcggcgc    12120
gagctgagcg accgcgagct gatgcacagc ctgcagcggg cgctggcggg ggccggcagc    12180
ggcgacaggg aggccgagtc ctacttcgag gcggggcgg acctgcgctg ggtgcccagc    12240
cggagggccc tggaggccgc gggggcccgc cgcgaggact atgcagacga ggaggaggag    12300
gatgacgagg agtacgagct agaggagggc gagtacctgg actaaaccgc aggtggtgtt    12360
tttggtagat gcaagacccg aacgtggtgg acccggcgct gcgggcggct ctgcagagcc    12420
agccgtccgg ccttaactct acagacgact ggcgacaggt catggaccgc atcatgtcgc    12480
tgacggcgcg caatccggac gcgttccggc agcagccgca ggccaacagg ctctccgcca    12540
tcttggaggc ggtggtgcct gcgcgcgcga accccacgca cgagaaggtg ctggccatag    12600
tgaacgcgct cgccgagaac agggccatcc gcccggacga ggccgggctg gtgtacgacg    12660
cgctgctgca gcgcgtggcc cgctacaaca gcggcaacgt gcagaccaac ctggaccggc    12720
tggtggggga cgtgcgcgag gcggtggcgc agcgggagcg cgcggagcgg cagggaaacc    12780
tgggctccat ggtggcgctg aacgccttcc tgagcacgca gccggccaac gtgccgcggg    12840
ggcaggagga ctacaccaac tttgtgagcg cgctgcggct gatggtgacc gagacccccc    12900
agagcgaggt gtaccagtcg gggccggact actttttcca gaccagcaga cagggcctgc    12960
agacggtgaa cctgagccag gctttcaaga acctgcgggg gctgtgggc gtgaaggcgc    13020 ccaccgggga ccgggcgacg gtgtccagcc tgctgacgcc caactcgcgc ctgctgctgc    13080
tgctgatcgc gccgttcacg gacagcggca cgtgtcccg ggagacctac ctcgggcacc    13140
tgctgacgct gtaccgcgag gccatcgggc agacccaggt ggacgagcac accttccagg    13200
agatcaccag cgtgagccgc gcgctggggc aggaggacac gggcagcctg gaggcgaccc    13260
tgaactacct gctgaccaac cggcggcaga agatcccctc gctgcatagt ttgaccaccg    13320
aggaggagcg catcctgcgc tacgtgcagc agagcgtgag cctgaacctg atgcgcgacg    13380
gggtgacgcc cagcgtggcg ctggacatga ccgcgcgcaa catggaaccg ggcatgtacg    13440
ccgcgcatcg gccttacatc aaccgcctga tggactactt gcatcgcgcg gcggccgtga    13500 acccccgagta cttcaccaac gccatcctga accccgcactg ctcccgccg cccgggttct    13560 acagcggggg cttcgaggtc cccgaggcca cgacggcttc ctgtgggac gacatggacg    13620 acagcgtgtt ctccccgcgg ccgcaggcgc tggcggaggc gtcgctgctc cgcctccccca    13680 agaaagaaga gagccgccgg cccagcagcg cggcggcctc tctgtccgag ctgggggcgg    13740
cggccgcgcg gccgggtcc ctgggggca gccccttcc cagtctggtg gggtctctgc    13800
agagcgggcg caccacccgg ccccggctgc tgggcgagga cgagtacctg aacaactccc    13860
tgatgcagcc ggtgcgggag aaaaaacctgc cccccgcctt ccccaacaac gggatagaga    13920
```

```
gcctggtaga caagatgagc agatggaaga cctatgcgca ggagcacagg gactcgcccg   13980
tgctccgtcc gcccacgcgg cgccagcgcc acgaccggca gcgggggctg gtatgggatg   14040
acgaggactc cgcggacgat agcagcgtgc tggacctggg ggggagcggc ggtaacccgt   14100
tcgcgcacct gcgcccccgc ctggggagga tgtttcaata agaaaaatca agcatgatgc   14160
aaggtttttt aagcggataa ataaaaaact caccaaggcc atggcgaccg agcgttgttg   14220
gtttcttgtt gtgttccctt agtatgcggc gcgcggcgat gtaccacgag ggacctcctc   14280
cctcttatga gagcgtggtg ggcgcggcgg cggcctctcc ctttgcgtcg cagctggagc   14340
cgccgtacgt gcctccgcgg tacctgcggc ctacgggggg aagaaacagc atccgttact   14400
cggagctggc gcccctgtac gacaccaccc gggtgtacct ggtggacaac aagtcggcgg   14460
acgtggcctc cctgaactac cagaacgacc acagcaattt tttgaccacg gtcatccaga   14520
acaatgacta caccccgagc gaggccagca cccagaccat caatctggat gaccggtcgc   14580
actgggggcgg cgacctgaaa accatcctgc acaccaacat gcccaacgtg aacgagttca   14640
tgttcaccaa taagttcaag gcgcgggtga tggtgtcgcg ttcgcacacc aaggacgacc   14700
gggtggagct gaagtacgag tgggtagagt tcgagctgcc cgagggcaac tactcggaga   14760
ccatgaccat agacctgatg aacaacgcga tcgtggagca ctatctgaaa gtgggcaggc   14820
agaacggggt cctggagagc gacatcgggg tcaagttcga caccaggaac ttccgcctgg   14880
ggctggaccc ggtcaccggg ctggtcatgc ccggggtcta caccaacgag gccttccacc   14940
ccgacatcat cctgctgccc ggctgcgggg tggacttcac ctacagccgc ctgagcaacc   15000
tgctgggcat ccgcaagcgg cagccccttcc aggagggctt taggatcacc tacgaggacc   15060
tggaggggggg caacatcccc gcgctcctgg atgtggaggc ctaccagaat agcttgaagg   15120
aagaagaggc gggagagggc agcggcggcg gcggcgccgg tcaggaggag ggcggggcct   15180
cctctgaggc ctctgcggac gcagctgccg ccgaggcgga ggaggcggcc gaccccgcga   15240
tggtggtaga ggaagagaag gatatgaatg acgaggcggt gcgcggcgac acctttgcca   15300
cccgggggga ggagaagaaa gcggaggcca aggccgcggc agaggaggcg gcagcagcgg   15360
cggcggcagt agaggcggcg gccgaggcgg agaagccccc caaggagccc gtgattaagc   15420
ccctgaccga agatagcaag aagcgcagtt acaacgtgct caaggacagc accaacaccg   15480
agtaccgcag ctggtacctg gcctacaact acggcgaccc ggcgacgggg gtgcgctcct   15540
ggaccctgct gtgtacgccg gacgtgacct gcggctcgga gcaggtgtac tggtcgctgc   15600
ccgacatgat gcaagacccc gtgaccttcc gctccacgcg gcaggtcagc aactttccgg   15660
tggtgggcgc cgagctgctg cccgtgcact ccaagagctt ctacaacgac caggccgtct   15720
actccagct catccgccag ttcacctctc tgacccacgt gttcaatcgc tttcctgaga   15780
accagattct ggcgcgcccg cccgccccca ccatcaccac cgtcagtgaa aacgttcctg   15840
ctctcacaga tcacgggacg ctaccgctgc gcaacagcat cggaggagtc cagcgagtga   15900
ccgtaactga cgccagacgc cgcacctgtc cctacgttta caaggccctg gcatagtct   15960
cgccgcgcgt ccttttccagc cgcactttt aagcatgtcc atcctcatct cgcccagcaa   16020
taacaccggc tggggcctgc tgcgcgcgcc cagcaagatg ttcggagggg cgaggaagcg   16080
ctccgaccag cacccccgtgc gcgtgcgcgg gcactaccgc gcccccctggg gcgcgcacaa   16140
acgcgggcgc accggcaccg cggggcgcac caccgtggac gaagccatcg actcggtggt   16200
ggagcaggcg cgcaactaca cgcccgcggt ctccaccgtg gacgcggcta tcgagagcgt   16260
```

```
ggtgcgaggc gcgcggcggt acgccaaggc gaagagccgc cggaggcgcg tggcccgccg   16320
ccaccgccgc cgacccggga gcgccgccaa gcgcgccgcc gccgccttgc ttcgccgggc   16380
cagacgcacg ggccgccgcg ccgccatgag ggccgcgcgc cgcctggccg ccggcatcac   16440
caccgtggcc ccccgcgcca gaagacgcgc ggccgctgcc gccgctgcgg ccatcagcga   16500
cctggccacc aggcgccggg gcaacgtgta ctgggtgcgc gactcggtga gcggcacgcg   16560
cgtgcccgtg cgcttccgcc ccccgcggac ttgagaggag aggacaggaa aaaagcatca   16620
acaacaacac cactgagtct cctgctgttg tgtgtatccc agcggcgcgc gcgcacacgg   16680
cgacatgtcc aagcgcaaaa tcaaagaaga gatgctccag gtcgtcgcgc cggagatcta   16740
tgggcccccg aagaaggaag agcaggattt caagccccgc aagataaagc gggtcaaaaa   16800
gaaaaagaaa gatgacgatg atggcgaggt ggagtttctg cgcgccacgg cgcccaggcg   16860
cccgctgcag tggaagggtc ggcgcgtaaa gcgcgttctg cgccccggca ccgcggtggt   16920
cttcacgccc ggcgagcgct ccacccgcac tttcaagcgc gtctatgacg aggtgtacgg   16980
cgacgaagac ctgctggagc aggccaacga tcgctccgga gagtttgctt acgggaagcg   17040
gcaccgggcg atggagaagg acgaggtgct ggcgctgccg ctggaccggg gcaaccccac   17100
ccccagcctg aagcccgtga ccttgcagca ggtgctgccg agcagcgcgc cctccgagat   17160
gaagcggggc ctgaagcgcg agggcggcga cctggcgccc accgtgcagc tgatggtgcc   17220
caagcggcag aggctggagg acgtgctgga gaaaatgaaa gtagaccccg gcctgcagcc   17280
ggacatcagg gtccgcccca tcaagcaggt ggcgccgggc ctcggcgtgc agaccgtgga   17340
cgtggtcatc cccaccggcg cctcctcttc cagcgccgcc gccgccacta gcaccgcgga   17400
catggagacg cagactagct ccgccctcgc cgccccgcg gccgccgccg ccgccgccac   17460
ctcctcggcg gaggtacaga cggacccctg gatgccgccg ccggcggccg cccctcgcg   17520 cgcacgccgc gggcgcagga agtacggtgc cgccagcgcg ctcatgcccg agtacgcctt   17580
gcatccttcc atcgcgccca cccccggcta ccgaggctac agctaccgcc cgcgaagagc   17640
caagggctcc acccgccgca ccgccgcgc cgccacctct acccgccgcc gcagtcgccg   17700
ccgccgccgc cggcagcccg cgctggctcc gatctccgtg aggagagtgg cgcgcaacgg   17760
ggacaccttg gtgctgccca gggcgcgcta ccaccccagc atcgtttaaa agcctgttgt   17820
ggttcttgca gatatggccc tcacttgccg cctccgtttc ccggtgccgg gataccgagg   17880
aagatcgcgc cgtagaaggg gtatggccgg acgcggcctg agcggaggca gccgccgtgc   17940
gcaccggcgg cgacgcgcca ccagccgacg catgcgcggc ggggtgctgc ctctgctgat   18000 cccctgatc gccgcggcga tcggcgccgt gcccgggatc gcctccgtgg ccttgcaggc   18060
gtcccagagg cgttgacaca gacttcttgc aagcttgcaa atatggaaa aaatccccc    18120 aataaaaaag tctagactct cacgctcgct tggtcctgtg actattttgt agaaaaaga   18180 tggaagacat caactttgcg tcgctggccc cgcgtcacgg ctcgcgcccg ttcctgggac   18240
actgaaacga tatcggcacc agcaacatga gcggtggcgc cttcagttgg ggctctctgt   18300
ggagcggcat taaaaatatc ggttctgccg ttaagaatta cggcaccaag gcctggaaca   18360
gcagcacggg ccagatgttg agagacaagt tgaaagagca gaacttccag cagaaggtgg   18420
tggagggcct ggcctccggc atcaacgggg tggtggacct ggccaatcag gccgtgcaaa   18480
ataagatcaa cagcaaactg gaccccccgg cgccggtgga agagctgccg ccggcgctgg   18540
agacggtgtc ccccgatggg cggggcgaaa agcgcccgcg gcccgacagg gaagagacca   18600
ctctggtcac gcacaccgat gagccgcccc cctacgagga agccctgaag caaggcttgc   18660
```

```
ccaccactcg gcccatcgcg cccatggcca ccggggtggt gggccgccac accccgcca    18720
cgctggacct gcctcctcct cctgtttctt cttcggccgc cgatgcgcag cagcagaagg    18780
cggcgctgcc cggtccgccc gcggccgccc cccgtcccac cgccagtcga gcgccctgc    18840
gtcgcgcggc cagcggcccc cgcggggtcg cgaggcacag cagcggcaac tggcagaaca    18900
cgctgaacag catcgtgggt ctgggggtgc agtccgtgaa gcgccgccga tgctactgaa    18960
tagcttagct aacggtgttg tatgtgtgta tgcgtcctat gtcaccgcca gaggagctgc    19020
tgagtcgccg ccgttcgcgc gcccaccgcc actaccaccg ccggtactac tccagcgccc    19080
ctcaagatgg cgaccccatc gatgatgccg cagtggtcgt acatgcacat ctcgggccag    19140
gacgcctcgg agtacctgag ccccgggctg gtgcagttcg cccgcgccac cgacagctac    19200
ttcagcctga gtaacaagtt taggaacccc acggtggcgc ccacgcacga tgtgaccacc    19260
gaccggtccc agcgcctgac gctgcggttc atccccgtgg accgcgagga caccgcgtac    19320
tcttacaagg cgcggttcac cctggccgtg gcgacaacc gcgtgctgga catggcctcc    19380
acctactttg acatccgcgg cgtgctggac aggggcccca cctttaagcc ctactccggc    19440
actgcctaca actccctggc ccccaagggc gcccccaacc cctgtgagtg ggatgaagcc    19500
gttactgctg ttgacattaa cctggatgag ctcggcgaag atgaagacga cgccgaaggg    19560
gaagcagaac agcaaaaaac tcatgtattt ggtcaagcgc cctactcagg acaaaacatt    19620
acgaaggagg gcatacaaat tggggtagat accaccagcc aagcccaaac acctttatac    19680
gctgacaaaa cattccaacc cgaacctcag gttggagaat cccaatggaa tgagacagaa    19740
atcaattatg gagcgggacg agtgctaaaa aagaccaccc tcatgaaacc atgctatggg    19800
tcatatgcaa gacctactaa tgaaaacggc ggtcagggca tactgctgga gaaagagggt    19860
ggtaaaccag aaagtcaagt tgaaatgcaa ttttttttcta ctactcaggc cgccgcggct    19920
ggtaattcag ataatcttac tccaaaagtt gttttgtata gcgaggatgt tcacctggaa    19980
acgccagata cacacatttc atatatgccc actagcaacg aagccaattc aagagaactg    20040
ttgggacaac aagctatgcc caacagaccc aactacattg ccttcagaga caactttatt    20100
ggccttatgt attacaacag cactggcaac atgggagtgc tggcaggtca ggcctcacag    20160
ttgaatgcag tggtggactt gcaagacaga aacacagaac tgtcctacca gctcttgctt    20220
gattccatgg gagacagaac cagatacttt tccatgtgga atcaggcggt ggacagttat    20280
gatccagatg ttagaattat tgaaaatcat ggaactgaag atgagctgcc caactattgt    20340
ttcccctgg gcgcataat taacaccgaa actttaacta aagtgaaacc taagactgga    20400
caagacgctc agtgggaaaa agatactgag ttttcagaga aaaatgaaat aagggtggga    20460
aacaacttcg ccatggagat taacctcaat gccaacctgt ggaggaattt cctgtactcc    20520
aacgtggccc tgtacctgcc agacaaactt aagtacactc cagccaacgt gcagatttcc    20580
agcaactcca actcctacga ctacatgaac aagcgagtgg tggccccggg gctggtggac    20640
tgctacatca acctgggcgc gcgctggtcc ctggactaca tggacaacgt caacccttc    20700
aaccaccacc gcaatgcggg cctgcgctac cgctccatgc ttctgggcaa cgggcgctac    20760
gtgcccttcc acatccaggt gccccagaag ttctttgcca tcaagaacct cctcctcctg    20820
ccgggctcct acacctacga gtggaacttc aggaaggatg tcaacatggt cctccagagc    20880
tctctgggta cgacctcag ggtcgacggg gccagcatca agttcgagag catctgcctc    20940
tacgccacct tcttccccat ggcccacaac acggcctcca cgctcgaggc catgctcagg    21000
```

```
aacgacacca acgaccagtc cttcaacgac tacctctccg ccgccaacat gctctacccc  21060
atccccgcca acgccaccaa cgtccccatc tccatcccct cgcgcaactg ggcggccttc  21120
cgcggctggg ccttcactcg cctcaagacc aaggagaccc cctccctggg ctcgggtttc  21180 gaccccact acacctactc gggctccata ccctacctgg acggaacctt ctacctcaac  21240
cacaccttca agaaggtctc ggtcaccttc gactcctcgg tcagctggcc gggcaacgac  21300
cgcctgctca cccccaacga gttcgagatc aagcgctcgg tcgacgggga gggctacaac  21360
gtggcccagt gcaacatgac caaggactgg ttcctcatcc agatgctggc caactacaac  21420
atcggctatc agggcttcta catcccagag agctacaagg acaggatgta ctccttcttt  21480
aggaacttcc agcccatgag ccggcaggtg gtggacgaaa ccaagtacaa ggactaccag  21540
caggtgggca tcatccacca gcacaacaac tcgggcttcg tgggctacct cgcccccacc  21600
atgcgcgagg acaggcctac ccccgccaac ttccctacc cgctcattgg caagaccgcg  21660
gtcgacagcg tcacccagaa aaagttcctc tgcgaccgca ccctctggcg catcccttc  21720 tccagcaact tcatgtccat gggtgcgctc acggacctgg ccagaacct gctctatgcc  21780 aactccgccc acgcgctcga catgaccttc gaggtcgacc ccatggacga gcccacccTt  21840
ctctatgttc tgttcgaagt cttTTgacgtg gtccgggtcc accagccgca ccgcggcgtc  21900
atcgagaccg tgtacctgcg cacgcccttc tcggccggca acgccaccac ctaaagaagc  21960
aagccgccac cgccaccacc tgcatgtcgt cgggttccac cgagcaggag ctcaaggcca  22020
tcgtcagaga cctgggatgc gggccctatt ttttgggcac cttcgacaaa cgcttcccgg  22080
gcttcgtcgc cccgcacaag ctggcctgcg ccatcgtcaa cacggccggc cgcgagaccg  22140
ggggcgtgca ctggctggcc ttcgcctgga cccgcgctc caaaacatgc tacctctttg  22200
accccttcgg attctcggac cagcggctca agcagatcta ccagttcgag tacgagggcc  22260
tgctgcgccg cagcgccatc gcctcctcgc ccgaccgctg cgtcaccctc gagaagtcca  22320
cccagaccgt gcaggggccc gactcggccg cctgcggtct cttctgctgc atgttcctgc  22380
atgcctttgt gcgctggccc cagagtccca tggaccgcaa ccccaccatg aacttgctga  22440
cggggatccc caactccatg ctccagagcc ccaggccgc gcccaccctg cgccgcaatc  22500
aggagcgact ctacagcttc ctggagcgcc actcgcccta cttccgccgc cacagcgcgc  22560
agatcagggg ggccacctct ttctgccgca tgcaagagat gcaagggaaa atgcaatgat  22620
gtacacagac acttttTtctt ttctcaataa atggcaactt tatttataca tgctctctct  22680
ctcgggtatt catttcccca ccacccacca cccgccgccg ccgtaaccat ctgctgctgg  22740
ctttttTaaa aatcgaaagg gttctgccgg gaatcgccgt gcgccacggg cagggacacg  22800
ttgcggaact ggtagcgggt gccccacttg aactcgggca ccaccatgcg gggcaagtcg  22860
gggaagttgt cggcccacag gccgcgggtc agcaccagcg cgttcatcag gtcgggcgcc  22920
gagatcttga gtcgcagtt ggggccgccg ccctgcgcgc gcgagttgcg gtacaccggg  22980
ttgcaacact ggaacaccag cagcgccgga taattcacgc tggccagcac gctccggtcg  23040
gagatcagct cggcgtccag gtcctccgcg ttgctcagcg cgaacggggt cagcttgggc  23100
acctgccgcc ccaggaaggg agcgtgtccc ggcttggaat tgcagtcgca gcgcagcggg  23160
atcagcaggt gcccgcggcc ggactcggcg ttggggtaca gcgcgcgcat gaaggcctcc  23220
atctggcgga aggccatctg ggccttggcg ccctccgaga aaaacatgcc gcaggacttg  23280
cccgagaact ggttcgcggg gcagctcgcg tcgtgcaggc agcagcgcgc gtcggtgttg  23340
gcgatctgca ccacgttgcg cccccaccgg ttcttcacga tcttggcctt ggaagcctgc  23400
```

```
tccttcagcg cgcgctgccc gttctcgctg gtcacatcca tctcgatcac gtgctccttg   23460
ttcaccatgc tgctgccgtg cagacacttc agctcgccct ccacctcggt gcagcggtgc   23520
tgccacagcg cgcagcccgt gggctcgaaa tgcttgtagg tcacctccgc gtaggactgc   23580
aggtaggcct gcaggaagcg ccccatcatg gtcacgaagg tcttgttgct gctgaaggtc   23640
agctgcagcc cgcggtgctc ctcgttcagc caggccttgc acacggccgc cagcgcctcc   23700
acctggtcgg gcagcatctt gaagttcagc ttcagctcat tctccacatg gtacttgtcc   23760
atcagcgcgc gcgcagcctc catgcccttc tcccaggccg acaccagcgg caggctcaag   23820
gggttcacca ccgtcgcagt cgccgccgcg ctttcgcttt ccgctccgct gttctcttct   23880
tcctcctcct cctcttcttc ctcgccgccc gcgcgcagcc cccgcaccac ggggtcgtct   23940
tcctgcaggc gccgcaccga gcgcttgccg ctcctgccct gcttgatgcg cacgggcggg   24000
ttgctgaagc ctaccatcac cagcgcggcc tcttcttgct cgtcctcgct gtccactatg   24060
acctcggggg agggcgacct cagtaccgtg gcgcgctgcc tcttctttt cctggggcg    24120 tttgcaagct ccgcggccgc ggccgccgcc gaggtcgaag gccgagggct gggcgtgcgc   24180
ggcaccagcg cgtcctgcga gccgtcctcg tcctcggact cgaggcggca gcgagcccgc   24240
ttcttcgggg gcgcgcgggg cggcggcggc ggggcggcg gcgacggaga cggggacgag     24300
acatcgtcca gggtgggagg acggcgggcc gcgccgcgtc cgcgctcggg ggtggtttcg   24360
cgctggtcct cttcccgact ggccatctcc cactgctcct tctcctatag gcagaaagag   24420
atcatggagt ctctcatgca agtcgagaag gaggaggaca gcctaaccac caccgccccc   24480
tctgagccct ccgccgccgc cgccgcggac gacgcgccca ccaccgccgc cgccaccacc   24540
accattacca ccctacccgg cgacgcagcc ccgatcgaga aggaagtgtt gatcgagcag   24600
gacccgggtt ttgtgagcga agaggaggat gaggaggatg aaaaggagaa ggataccgcc   24660
gcctcagtgc caaaagagga taaaaagcaa gaccaggacg acgcagagac agatgaggca   24720
gcagtcgggg gggggacga gaggcatgat gatgatgacg ctacctaga cgtgggagac    24780 gacgtgctgc ttaagcacct gcaccgccag tgcgtcatcg tctgcgacgc gctgcaggag   24840
cgctgcgaag tgcccctgga cgtggcgag gtcagccgcg cctacgagcg gcacctcttc    24900
gcgccacacg tgccccccaa gcgcggggag aacggcacct gcgagcccaa cccgcgcctc   24960
aacttctacc cggtcttcgc ggtacccgag gtgctggcca cctaccacat cttcttccaa   25020
aactgcaaga tccccctctc ctgccgcgcc aaccgcaccc gcgccgacaa gacgctggcc   25080
ctgcggcagg gcgcccacat acctgatatc gcctctctgg aggaggtgcc caagatcttc   25140
gagggtctcg gtcgcgacga gaaacgggcg gcgaacgctc tgcaaggaga cagcgaaaac   25200
gagagtcact cggggggtgct ggtggagctc gagggcgaca acgcgcgcct ggccgtgctc   25260
aagcgcagca tcgaagtcac ccacttcgcc taccgggcgc tcaacctgcc ccccaaggtc   25320
atgagtgtgg tcatgagcga gctcatcatg cgccgcgccc agcccctgga cgcggatgca   25380
aacttgcaag agccctccga ggaaggcctg cccgcggtca gcgacgagca gctggcgcgc   25440
tggctggaga cccgcgaccc cgcccagctg gaggagcggc gcaagctcat gatggccgcg   25500
gtgctcgtca ccgtggagct cgagtgtctg cagcgcttct tcggggaccc cgagatgcag   25560
cgcaagctcg aggagaccct gcactacacc ttccgccagg gctacgtgcg ccaggcctgc   25620
aagatctcca acgtggagct ctgcaacctg gtctcctacc tgggcatcct gcacgagaac   25680
cgcctcgggc agaacgtcct gcactccacc ctcaaagggg aggcgcgccg cgactacgtc   25740
```

```
cgcgactgcg tctacctctt cctctgctac acgtggcaga cagccatggg ggtctggcag   25800
cagtgcctgg aggagcgcaa cctcaaggag ctggagaagc tcctccggcg cgccctcagg   25860
gacctctgga cgggcttcaa cgagcgctcg gtggccgccg cgctggcgga catcatcttc   25920
cccgagcgcc tgctcaaaac cctgcagcag ggcctgcccg acttcaccag ccagagcatg   25980
ctgcagaact tcaggacctt catcctggag cgctcgggca tcctgccggc cacctgctgc   26040
gcgctgccca cgacttcgt gcccatcagg tacaggagt gcccgccgcc gctctggggc    26100
cactgctacc tcttccagct ggccaactac ctcgcctacc actcggatct catggaagac   26160
gtgagcggcg agggcctgct cgagtgccac tgccgctgca acctgtgcac gccccaccgc   26220
tctctagtct gcaacccgca gctgctcagc gagagtcaga ttatcggtac ctttgagctg   26280
cagggtccct cgcccgacga aaagtccgcg gctccggggt tgaaactcac tccggggctg   26340
tggacttccg cctacctacg caaatttgta cctgaagact accacgccca cgagatcagg   26400
ttttacgaag accaatcccg cccgcccaag gcggagctca ccgcctgcgt cattacccag   26460
ggccacatcc tgggccaatt gcaagccatc aacaaagccc gccaagagtt cttgctgaaa   26520
aagggtcggg gggtgtacct ggaccccag tccggcgagg agctaaaccc gctaccccg    26580
ccgccgcccc agcagcggga ccttgcttcc caggatggca cccagaaaga agcagccgcc   26640
gccgccgcca gcatacatgc ttctggagga agaggaggac tgggacagtc aggcagagga   26700
ggtttcggac gaggacgagg aggaggagat gatggaagac tgggaggagg acagcctaga   26760
cgaggaagct tcagaggccg aagaggtggc agacgcaaca ccatcaccct cggccgcagc   26820
cccctcgccg gcgcccccga aatcctccga ccccagcagc agcgctataa cctccgctcc   26880
tccggcgccg gcgcccaccc gcagcagacc caaccgtaga tgggacacta caggaaccgg   26940
ggtcggtaag tccaagtgcc ccccagcgcc gcccccgcaa caggagcaac agcagcagca   27000
gcggcgacag ggctaccgct cgtggcgcgg acacaaaaac gccatagtcg cctgcttgca   27060
agactgcggg ggcaacatct ccttcgcccg ccgcttcctg ctcttccacc acggggtggc   27120
tttttccccgc aatgtcctgc attactaccg tcatctctac agccctact gcggcggcag   27180
cggcgaccca gagggagcgg cggcagcagc agcgccagcc acagcggcga ccacctagga   27240
agacctccgc gggcaagacg gcgggagccg ggagacccgc ggcggcggcg gtagcggcgg   27300
cggcgggcgc actgcgcctc tcgcccaacg aaccctctc gacccgggag ctcagacaca   27360
ggatcttccc cactctgtat gctatcttcc agcagagcag aggccaggaa caggagctga   27420
aaataaaaaa cagatctctg cgctccctca cccgcagctg tctgtatcac aaaagcgaag   27480
atcagcttcg gcgcacgctg gaggacgcgg aggcactctt cagcaaatac tgcgcgctga   27540
ctcttaagga ctagccgcgc gcccttctcg aatttaggcg ggagaaagac tacgtcatcg   27600
ccgaccgccg cccagcccac ccagccgaca tgagcaaaga gattcccacg ccctacatgt   27660
ggagctacca gccgcagatg ggactcgcgg cgggagcggc ccaagactac tccacccgca   27720
tgaactacat gagcgcgggg ccccacatga tctcacgggt taatgggatc cgcgcccagc   27780
gaaaccaaat actgctggaa caggcggcca taaccgccac accccgtcat gacctcaatc   27840
cccgaaattg gccgcgcgcc ctcgtgtacc aggaaacccc ctctgccacc accgtggtac   27900
ttccgcgtga cacccaggcc gaagtccaga tgactaactc aggggcgcag ctcgcgggcg   27960
gctttcgtca cggggtgcgg ccgcaccggc cgggtatatt acacctggcg atcagaggcc   28020
gaggtattca gctcaacgac gagtcggtga gctcttcgct cggtctccgt ccggacgaa   28080
ccttccagat cgccggatca ggtcgctcct cattcacgcc tcgccaggcg tatctgactc   28140
```

```
tgcagacctc ctcctcggag cctcgctccg gcggcatcgg caccctccag ttcgtggagg   28200
agttcgtgcc ctcggtctac ttcaacccct tctcgggacc tcccgacgc tacccgacc    28260 agttcatccc gaactttgac gcggtgaagg actcggcgga cggctacgac tgaatgtcaa   28320
gtgctgaggc agagagcgtt cgcctgaaac acctccagca ctgccgccgc ttcgcctgct   28380
tcgcccgcag ctccggtgag ttctgctact ttcagctgcc cgaggagcat accgaggggc   28440
cggcgcacgg cgtccgccta accacccagg gcgaggttac ctgtacccctt atccgggagt  28500 ttaccctccg tcccctgcta gtggagcggg agcggggttc ttgtgtcata actatcgcct   28560
gcaactgccc taaccctgga ttacatcaag atctttgttg tcacctgtgc gctgagtata   28620
ataaacgctg agatcagact ctactggggc tcctgtcgcc atcctgtgaa cgccaccgtc   28680
ttcacccacc ccgagcagcc ccaggcgaac ctcacctgcg gcctgcgtcg gagggccaag   28740
aagtacctca cctggtactt caacggcacc cccctttgtgg tttacaacag cttcgaccag  28800
gacggagttg ccttgagaga cgacctttcc ggtctcagct actccattca caagaacacc   28860
accctccacc tcttccctcc ctacctgccg ggaacctacg agtgcgtcac cggccgctgc   28920
acccacctcc tccgcctgat cgtaaaccag acctttccgg gaacacacct cttccccaga   28980
acaggaggtg agctcaggaa accccctggg gcccagggcg gagacttacc ttcgacccctt  29040 gtggggttag gatttttat cgccgggttg ctggctctcc tgatcaaagc ttccttcaga    29100
tttgttctct ccctttactt ttatgaacag ctcaacttct aataacacta ccttttctca   29160
ggaatcgggt agtgacttct cttctgaaat cgggctgggt gtgctgctta ctctgttgat   29220
ttttttcctt atcatactta gccttctgtg cctcaggctc gccgcctgct gcgcacatat   29280
ctacatctac agccggttgc ttaactgctg gggtcgccat ccaagatgaa cggggctcag   29340
gtgctatgtc tgctggccct ggtggcctgc agtgccgccc tcaattttga ggaacccgct   29400
tgcaatgtga ctttcaagcc tgagggcgca cattgcacca ctctggttaa atgtgtgacc   29460
tctcatgaaa aactgctcat cgcctacaaa aacaaaacag gcgagttcgc ggtctatagt   29520
gtgtggcaac ccggagacca taataactac tcagtcaccg tcttcgaggg tgcggagtct   29580
aagaaattcg attacaccctt tcccttcgag agatgtgtg atgcggtcat gtacctgtcc   29640
aaacagcaca agctgtggcc ccccacccc gaggcgtgtg tggaaaacac tgggtcttc    29700 tgctgtctct ctctggcaat cactgtgctt gctctaatct gcacgctgct atacatgaga   29760
ttcaggcaga ggcgaatctt tatcgatgag aaaaaaatgc cttgatcgct aacaccggct   29820
ttctgtctgc agaatgaaag caatcacctc cctactaatc agcaccaccc tccttgcgat   29880
tgcccatggg ttgacacgaa tcgaagtgcc agtggggtcc aatgtcacca tggtgggccc   29940
cgccggcaat tcctccctga tgtgggaaaa atatgtccgt aatcaatggg atcattactg   30000
ctctaatcga atctgtatca agcccagagc catctgcgac gggcaaaatc taactttgat   30060
tgatgtgcaa atgacggatg ctgggtacta ttacgggcag cggggagaaa tgattaatta   30120
ctggcgaccc cacaaggact acatgctgca tgtagtcaag gcagtcccca ctactaccac   30180
ccccaccact accactccca ctactaccac cccactact accactagca ctgctactac   30240
cgctgcccgc aaagctatta cccgcaaaag caccatgctt agcaccaagc ccattctca    30300 ctcccacgcc ggcgggccca ccggtgcggc ctcagaaacc accgagcttt gcttctgcca   30360
atgcactaac gccagcgccc acgaactgtt cgacctggag aatgaggacg atgaccagct   30420
gagctccgct tgcccggtcc cgctgcccgc agagccggtc gccctgaagc agctcggtga   30480
```

```
tccatttaat gactctcctg tttatccctc tcccgaatac ccgcccgact ctaccttcca    30540
catcacgggc accaacgacc ccaacctctc cttctacctg atgctgctgc tttgtatctc    30600
tgtggtatct tccgcgctca tgttactggg catgttctgc tgcctcatct gccgcagaaa    30660
gagaaagtct cgctctcagg gccaaccact gatgcccttc ccctaccccc cagattttgc    30720
agataacaag atatgagcac gctgctgaca ctaaccgctt tactcgcctg cgctctaacc    30780
cttgtcgctt gcgaatccag ataccacaat gtcacagttg tgacaggaga aaatgttaca    30840
ttcaactcca cggccgacac ccagtggtcg tggagcggcc acggtagcta tgtatacatc    30900
tgcaatagct ccacctcccc tagcatgtcc tctcccaagt accactgcaa tgccagcctg    30960
ttcaccctca tcaacgcctc cacctcggac aatggactct atgtaggcta tgtgacaccc    31020
ggtgggcggg gaaagaccca cgcctacaac ctgcaagttc gccacccctc caccaccgcc    31080
accacctctg ccgcccctac ccgcagcagc agcagcatca gcagcagcag cagcagcagc    31140
agattcctga ctttaatcct agccagctca acaaccaccg ccaccgctga gaccaccac    31200 agctccgcgc ccgaaaccac ccacccccac cacccagaga cgaccgcggc ctccagtgac    31260
cagatgtcgg ccaacatcac cgcctcgggt cttgaacttg cttcaacccc cacccaaaa    31320 ccagtggatg cagccgacgt ctccgccctc gtcaatgact gggcggggct gggaatgtgg    31380
tggttcgcca taggcatgat ggcgctctgc ctgcttctgc tctggctcat ctgctgcctc    31440
aaccgcaggc gggccagacc catctataga cccatcattg ttctcaaccc cgctgatgat    31500
gggatccata gattggatgg tctgaaaaac ctactttttct cttttacagt atgataaatt    31560
gagacatgcc tcgcatttc atgtacttga cacttctccc actttttctg gggtgttcta    31620
cgctggccgc cgtctctcac ctcgaggtag actgcctcac acccttcact gtctacctga    31680
tttacggatt ggtcaccctc actctcatct gcagcctaat cacagtagtc atcgccttca    31740
tccagtgcat tgactacatc tgtgtgcgcc tcgcatacct gagacaccac ccgcagtacc    31800
gagacaggaa cattgcccaa ctcctaagac tgctctaatc atgcataaga ctgtgatctg    31860
cctcctcatc ctcctctccc tgcccgctct cgtctcatgc cagcccacca caaaacctcc    31920
acgaaaaaga catgcctcct gtcgcttgag ccaactgtgg aatattccca aatgctacaa    31980
tgaaaagagc gagctttccg aagcctggct atatgcggtc atgtgtgtcc ttgtcttctg    32040
cagcacaatc tttgccctca tgatctaccc ccactttgat ttgggatgga atgcggtcga    32100
tgccatgaat taccctacct ttcccgcgcc cgatatgatt ccactccgac aggttgtggt    32160
gcccgtcgcc ctcaatcaac gcccccatc ccctacaccc actgaggtca gctactttaa    32220
tctaacaggc ggagatgact gacactctag atctagaaat ggacggcatc ggcaccgagc    32280
agcgtctcct acagaggcgc aagcaggcgg ctgaacaaga gcgcctcaat caggagctcc    32340
gagatctcat taacctgcac cagtgcaaaa aaggcatctt ttgcctggtc aagcaggccg    32400
atgtcaccta cgagaaaacc ggtaacagcc accgcctcag ctacaagctg cccacccaac    32460
gccagaagtt ggtgctcatg gtgggtcaga atcccatcac cgtcacccag cactcggtgg    32520
agaccgaggg gtgtctgcac tcccctgtc agggtccgga agacctctgc accctggtaa    32580
agaccctgtg tggtcttaga gatttaatcc cctttaacta atcaaacact ggaatcaata    32640
aaaagaatca cttactttaa atcagtcagc aggtctctgt ccactttatt cagcagcacc    32700
tccttcccct cctcccaact ctggtactcc aaacgcctcc tggcggcaaa cttcctccac    32760
accctgaagg gaatgtcaga ttcttgctcc tgtccctccg cacccactat cttcatgttg    32820
ttgcagatga agcgcgccaa aacgtctgac gagaccttca accccgtgta ccctatgac    32880
```

```
acggaaaacg ggcctccctc cgtccctttc ctcacccctc ccttcgtgtc cccgacgga   32940 tttcaagaaa gcccccagg ggtcctgtct ctgcgcctgt cagagcccct ggtcacttcc   33000
cacggcatgc ttgccctgaa aatgggaaat ggcctctccc tggatgacgc cggcaacctc   33060
acctctcaag atgtcaccac cgtcacccct cccctcaaaa aaaccaagac caacctcagc   33120
ctccagacct cagcccccct gaccgttagc tctgggtccc tcaccgtcgc ggccgccgct   33180
ccactggcgg tggccggcac ctctctcacc atgcaatctc aggccccctt gacagtgcaa   33240
gatgcaaaac tcggcctggc cacccaggga cccctgaccg tgtctgaagg caaactcacc   33300
ttgcagacat cggctccact gacggccgct gacagcagca ctctcactgt tagtgccaca   33360
cctcccctca gcacaagcaa tggtagtttg agcattgaca tgcaggcccc gatttatacc   33420
accaatggaa aactggcact taacattggt gctcccctgc atgtggtaga caccctaaat   33480
gcactaactg tagtaactgg ccagggtctt accataaatg gaagagccct gcaaactaga   33540
gtcacgggtg ccctcagtta tgacacagaa ggcaacatcc aactgcaagc cggagggggt   33600
atgcgcattg acaataatgg ccaacttatc cttaatgtag cttatccatt tgatgctcaa   33660
aacaacctca gccttagact tggccaaggt cccctaattg ttaactctgc ccacaacttg   33720
gatcttaacc ttaacagagg ccttttactta tttacatctg gaaacacgaa aaaactggaa   33780
gttaacataa aaacagccaa aggtctattt tacgatggca ccgctatagc aatcaatgca   33840
ggtgacgggc tacagtttgg gtctggttca gatacaaatc cattgcaaac taaacttgga   33900
ttggggctgg aatatgactc caacaaagct ataatcacta aacttggaac tggcctaagc   33960
tttgacaaca caggtgccat cacagtaggc aacaaaatg atgacaagct taccttgtgg   34020
accacaccag accctcccc aaactgcaga attaattcag aaaagatgc taaactcaca   34080 ctagttttga ctaaatgcgg cagccaggtg ttagccagcg tttctgtttt atctgtaaaa   34140
ggcagccttg cccccatcag cggcacagta actagcgccc agattgtttt aagatttgat   34200
gaaaacggag ttttattgag caattcttct cttgaccccc aatactggaa ctatagaaaa   34260
ggcgattcta cagaaggcac tgcatatact aatgctgtgg gatttatgcc caaccctcaca   34320 gcatacccta aaacacagag ccagactgct aaaagcaaca ttgtaagtca agtttacttg   34380
aatggggaca aaacaaaacc catgacccta accatcaccc tcaatggaac taatgaaaca   34440
ggggatgcta cagtaagcac atactccatg tcattttcat ggaactggaa tggaagtaat   34500
tacattaatg acaccttcca aaccaactcc tttaccttct cctacatcgc ccaagaataa   34560
aaaagcatga cgctttgttc tctgattcag tgtgtttctt ttattttttt ttcaattaca   34620
acagaatcat tcaagtcatt ctccatttag cttaatagac ccagtagtgc aaagccccat   34680
actagcttat ttcagacagt ataaattaaa ccataccttt tgatttcaat attaaaaaaa   34740
tcatcacagg atcctagtcg tcaggccgcc ccctccctgc caagacacag aatacacaat   34800 cctctcccc cggctggctt taaacaacac catctggttg gtgacagaca ggttcttcgg   34860
ggttatattc cacacggtct cctggcgggc caggcgctcg tcggtgatgc tgataaactc   34920
tcccggcagc tcgctcaagt tcacgtcgct gtccagcggc tgaacctcat gctgacgcgg   34980
taactgcgcg accggctgct gaacaaacgg aggccgcgcc tacaagggg tagagtcata   35040 atcctccgtc aggatagggc ggttatgcag cagcagcgag cgaatcatct gctgccgccg   35100
ccgctccgtc cggcaggaaa acaacatccc ggtggtctcc tccgctataa tccgcaccgc   35160
ccgcagcata agcctcctcg ttctccgcgc gcagcaccgc accctgatct cgctcaggtt   35220
```

```
ggcgcagtag gtacagcaca tcaccacgat gttattcatg atcccacagt gcaaggcgct   35280
gtatccaaag ctcatgcccg ggaccaccgc ccccacgtga ccgtcgtacc agaagcgcag   35340
gtaaatcaag tgacgacccc tcatgaacgt gctggacata acatcacct ccttgggcat    35400 gttgtaattc accacctccc ggtaccagat gaatctctga ttgaacacgg ccccttccac   35460
caccatcctg aaccaagagg ctaggacctg cccaccggct atgcactgca gggaacccgg   35520
gttggaacaa tgacaatgca gactccaggg ctcgtaaccg tggatcatcc ggctgctgaa   35580
gacatcgatg ttggcgcaac acagacacac gtgcatacac ttcctcatga ttagcagctc   35640
ctccctcgtc aggatcatat cccaaggat aacccattct tgaatcaacg taaagcccac    35700
agagcaggga aggcctcgca cataactcac gttgtgcatg gtcagcgtgt tgcattccgg   35760
aaacagcgga tgatcctcca gtatcgaggc gcgggtctcg ttctcacagg gaggtaaagg   35820
ggccctgctg tacggactgt ggcgggacga ccgagatcgt gttgagcgta acgtcatgga   35880
aaagggaacg ccggacgtgg tcatacttct tgaagcagaa ccaggctcgc gcgtgacaga   35940
cctccttgcg tctacggtct cgccgcttag ctcgctccgt gtgatagttg tagtacagcc   36000
actctctcaa agcgtcgagg cgacacctgg cgtcaggatg tatgtagact ccgtcttgca   36060
ccgcggccct gataatatcc accaccgtag aataagccac accaagccaa gcaatacact   36120
cgctttgcga gcggcagaca ggaggagcgg ggagagacgg aaggaccatc ataaaatttt   36180
aaagaatatt ttccaatatt tcgaaatcaa gatctaccaa atggcagcgc tcccctccac   36240
tggcgcggtc aaactctacg gccaaagaac agataacggc attttttaaga tgttcccgga   36300 cggcgtctaa aagacaaacc gctctcaagt cgacataaat tataagccaa aagccatcgg   36360
gttcaagatc cactatggac gcgccggcgg cgtccaccaa acccaaataa ttttcttctc   36420
tccagcgctg caaaatccca gtaagcaact ccctgatatt aagatgaacc atgccaaaaa   36480
tctgttcaag agcgccctcc accttcattc tcaagcagcg catcatgatt gcaaaaattc   36540
aggttcctca gacacctgta tgagattcaa aacgggaata ttaacaaaaa ttcctctgtc    36600
gcgcagatcc cttcgcaggg caagctgaac ataatcagac aggtctgaac gaaccagcga   36660
ggccaaatcc ccgccaggaa ccagatccag agaccctatg ctgattatga cgcgcatact   36720
cggggctatg ctaaccagcg tagcgccgat gtaggcgtgc tgcatgggcg gcgaaataaa   36780
atgcaaggtg ctggttaaaa aatcaggcaa agcctcgcgc aaaaaagcta agacatcata   36840
atcatgctca tgcaggtagt tgcaggtaag ctcaggaacc aaaacggaat aacacacgat   36900
tttcctctca aacatgactt ccaggtgact gcataagaaa aaaattataa ataataaata   36960
ttaattaaat aaattaaaca ttggaagcct gtctcacaac aggaaaaacc actctgatca   37020
acataagacg ggccacgggc atgcccgcgt gaccataaaa aaatcggtct ccgtgattac   37080
aaagcaccac agatagctcc ccggtcatgt cgggggtcat catgtgagac tgtgtataca   37140
cgtccgggct gttgacatcg gtcaaagaaa gaaatcgagc tacatagccc ggaggaatca   37200
acacccgcac gcggaggtac agcaaaacgg tccccatagg aggaatcaca aaattagtag   37260
gagaaaaaaa aacataaaca ccagaaaaac cctcttgccg aggcaaaaca gcgccctccc   37320
gttccaaaac aacataaagc gcttccacag gagcagccat gacaaagacc cgagtcttac   37380
caggaaaatt ttaaaaaaga ttcctcaacg cagcaccagc accaacacct gtcagtgtaa   37440
aatgccaagc gccgagcgag tatatatagg aataaaaagt gacgtaaacg gttaaagtcc   37500
agaaaacgcc cagaaaaacc gcacgcgaac ctacgccccg aaacgaaagc caaaaaacag   37560
tgaacacgcc ctttcggcgt caacttccgg tttcccacgg tacgtcactt ccgcatataa   37620
```

| | | |
|---|---|---|
| gaaaactacg ctacccaaca tgcaagaagc cacgccccaa aaaacgtcac acctcccggc | 37680 |
| ccgcccgcg ccgccgctcc tccccgcccc gccccgctcc gcccacctca ttatcatatt | 37740 |
| ggcttcaatc caaaataagg tatattattg atgatg | 37776 |

<210> SEQ ID NO 63
<211> LENGTH: 37713
<212> TYPE: DNA
<213> ORGANISM: Adenoviridae - Mastadenovirus

<400> SEQUENCE: 63

| | |
|---|---|
| catcatcaat aatataccct attttggatt gaagccaata tgataatgag gtgggcggag | 60 |
| cggggcgggg cggggaggag cggcggcgcg gggcgggccg ggaggtgtgg cggaagttga | 120 |
| gtttgtaagt gtggcggatg tgacttgcta gcgccggatg tggtaaaagt gacgttttttg | 180 |
| gagtgcgaca acgcccacgg gaagtgacat ttttcccgcg gttttttaccg gatgtcgtag | 240 |
| tgaatttggg cgttaccaag taagatttgg ccattttcgc gggaaaactg aaatggggaa | 300 |
| gtgaaatctg attaatttcg cgttagtcat accgcgtaat atttgccgag ggccgaggga | 360 |
| ctttgaccga ttacgtggag gaatcgccca ggtgtttttg aggtgaattt ccgcgttccg | 420 |
| ggtcaaagtc tccgtttttat tattatagtc agctgacgcg gagtgtatttt atacccgctg | 480 |
| atctcgtcaa gaggccactc ttgagtgcca gcgagtagag ttttctcctc tgccgctccg | 540 |
| ctccgctctg acaccggggg aaaaaaatga gacatttcac ctacgatggc ggtgtgctta | 600 |
| ccggccagct ggctgcctcg gtcctggacg ccctgattga ggacgtattg gccgacaatt | 660 |
| atcctcctcc agctcatttt gagccaccta ctcttcacga actgtatgat ttggacgtgg | 720 |
| tggcacctag cgacccgaac gagcaggcgg tttccagttt ttttcctgac tctatgctgt | 780 |
| tggccagcca ggaggggggtc gagctcgaga cccctcctcc aatcgccgtt tctcctgagc | 840 |
| ctccgaccct gaccaggcag cccgatcgcc gtgttggacc tgcgactatg ccccatctgc | 900 |
| tgcccgaggt gatcgatctc acctgtaacg agtctggttt tccacccagc gaggatgagg | 960 |
| acgaagaggg tgagcagttt gtgttagatt ctgtggagga acccgggcgc ggttgcagat | 1020 |
| cttgtcaata ccatcggaaa aatacaggag accccccaaat tatgtgttcc ctgtgttata | 1080 |
| tgaagacgac ctgtatgttt atttacagta agtttgtgat tggtgggtcg gtgggctgta | 1140 |
| gtgtgggtaa gtgtctctgt gttttttttt tttaatatca gcttgggcta aaaaactgct | 1200 |
| atggtaattt ttttaaggtc cggtgtctga acctgagcag gaagctgaac cggagcctga | 1260 |
| gagtcgcccc aggagaaggc ctgcaattct aactagaccg agtgcacctg tagcgaggga | 1320 |
| cctcagcagt gcagagacca ccgattctgg tccttcctca tccctccag agattcatcc | 1380 |
| cgtggtgcct ttgtgtcccc tcaagcccgt tgccgtgaga gttagtgggc ggagggccgc | 1440 |
| cgtggagagc attgaggact tgcttaatga gacacaggaa cctttggact tgagctgtaa | 1500 |
| acgccctagg caataaacct gcttacctgg actgaatgag ttgacgccta tgtttgcttt | 1560 |
| tgaatgactt aatgtgtata taataaagag tgagataatg tttaattgca tggtgtgttt | 1620 |
| gattggggcg gggtttgttg ggtatataag cttccctggg ctaaacttgg ttacacttga | 1680 |
| cctcatggag gcctgggagt gttagagag ctttgccgaa gtgcgtgcct tgctggaaga | 1740 |
| gagctctaat aatacctctg ggtggtggag gtatttttgg ggctctcccc aggctaagtt | 1800 |
| agtttgtaga atcaaggagg attacaagtg ggaatttgaa cagcttttga aatcctgtgg | 1860 |
| tgagctcttg gattctttga atctgggcca ccaggctctt ttccaggaca agatcatcag | 1920 |

```
gactttggat ttttccacac cggggcgcat tgctgccggg gttgcttttc tagctttttt     1980
gaaggataaa tggagcgaag agacccactt gagttcggga tacgtcctgg attttctggc     2040
catacaactg tggagagcat ggatcaggca caagaacaga atgcaactgt tgtcttccgt     2100
ccgtccgttg ctgattcagc ggaggagca gcagaccggg ccggaggacc gggctcgtct      2160
ggaaccagaa gagagggcac cggagaggag cgcgtggaac ctgggagccg gcctgaacgg     2220
ccatccacat cgggagtgaa tgttggacag gtggcggatc tctttccaga actgcgacga     2280
atcttaacta tcagggagga tggacaattt gttaaggggc ttaagaggga gcggggggct     2340
tctgaacata acgaggaggc cagtaattta gcttttagtc tgatgaccag acaccgtccc     2400
gagtgcatta cttttcagca gattaaggat aattgtgcca atgagttaga tctgctgggt     2460
cagaagtaca gcatagagca gttgaccact tactggctgc agccgggtga tgatctggag     2520
gaagctatta gggtgtatgc caaggtggcc ctgaggcccg attgcaagta caagctcaag     2580
gggctggtga atatcaggaa ttgttgctac atttctggga acggggcgga ggtggagata     2640
gagaccgatg acagggtggc ctttaggtgt agcatgatga atatgtggcc tggggtgctg     2700
ggcatggacg gggtggtgat tatgaatgtg aggttcacgg ggcccaattt taatggcacg     2760
gtgttcctgg gcaacaccaa cttggtgctg cacggggtga gcttctatgg ctttaacaac     2820
acctgtgtgg aggcctggac cgatgtgaag gtccgtggct gtgccttcta cggatgttgg     2880
aaggcggtag tgtgtcgccc caagagcagg agttccatta aaaatgctt gtttgagagg      2940 tgcaccctgg gggtgctggc ggagggcaac tgtcgggtgc gccacaatgt ggcctcagaa     3000
tgcggttgct tcatgctagt caagagcgtg gcggtcatca agcataacat ggtgtgcggc     3060
aacagcgagg acaaggcctc gcagatgctg acctgctcgg atggcaactg ccacttactg     3120
aagaccgtac atataaccag ccacagccgc aaggcctggc ccgtgttcga gcacaacgtg     3180
ttgacccgct gctctttgca tctgggcaac aggagggtg tgttcctgcc ctatcaatgc      3240
aacttgagcc acaccaagat cttgctagag cccgaaagca tgtccaaggt gaacctgaac     3300
ggggtgtttg acatgaccct gaagatatgg aaggtgctga ggtacgacga gaccaggtct     3360
cgatgcaggc cctgcgagtg cggggggcaag catatgagga accagcctgt gatgctggat     3420
gtgaccgagg agctgaggcc tgaccacttg gttctggcct gcaccagggc cgagtttggt     3480
tctagcgatg aagacacaga ctgaggtggg tgagtgggcg tggtctgggg gtgggaagca     3540
atatataagt tgggggtctt agggtctctg tgtctgtttt gcagagggac cgccggcgcc     3600
atgagcggga gcagtagcag caacgccttg gatggcagca tcgtgagccc ttatttgacg     3660
acgcgcatgc cccactgggc cggggtgcgt cagaatgtga tgggctccag catcgacgga     3720
cgacccgtgc tgcccgcaaa ttccgccacg ctgacctacg cgaccgtcgc ggggaccccg     3780
ttggacgcca ccgccgccgc cgccgccacc gccgccgcct cggccgtgcg cagcctggcc     3840
acggactttg cattcttggg acccttggcc accggggcgg ccgcccgtgc cgccgttcgc     3900
gatgacaagc tgaccgccct gctggcgcag ttggatgcgc ttacccggga actgggtgac     3960
ctttcgcagc aggtcgtggc cctgcgccag caggtctccg ccctgcaggc tagcgggaat     4020
gcttctcctg caaatgccgt ttaagataaa taaaaccaga ctctgtttgg attaaagaaa     4080
agtagcaagt gcattgctct ctttatttca taattttccg cgcgcgatag gcccgagtcc     4140
agcgttctcg gtcgttgagg gtgcggtgta tcttctccag gacgtggtag aggtggctct     4200
ggacgttgag atacatgggc atgagcccgt cccggggtg gaggtagcac cactgcagag      4260
cttcatgctc cggggtggtg ttgtagatga tccagtcgta gcaggagcgc tgggcatggt     4320
```

```
gcctaaaaat gtccttaagc agcaggccga tggccagggg gaggcccttg gtgtaagtgt    4380
ttacaaaacg gttgagttgg gaagggtgca tgcggggtga gatgatgtgc atcttagatt    4440
gtatttttag attggcgatg tttcctccca gatcccttct gggattcatg ttgtggagga    4500
ccaccagcac agtatatccg gtgcacttgg gaaatttgtc atgcagctta gagggaaatg    4560
cgtggaagaa cttggagacg cccttgtggc ctcccagatt ctccatgcat tcgtccatga    4620
tgatggcaat gggcccgcgg gaggcggcct gggcaaagat gtttctgggg tcactgacat    4680
cgtagttgtg ttccagggtg agatcgtcat aggccatttt tataaagcgc gggcggaggg    4740
tgcccgactg ggggatgatg gttccctcgg gccccggggc gtagttgcct tcgcagatct    4800
gcatttccca ggccttaatc tctgaggggg gaatcatatc cacttgcggg gcgatgaaga    4860
aaacggtttc cggagccggg gagattaact gggatgagag caggtttctc agcagctgtg    4920
actttccaca gccggtgggt ccataaataa cacctataac cggctgcagc tggtagttga    4980
gcgagctgca gctgccgtcg tcccggagga ggggggccac ctcattgagc atgtcccgga    5040
cgcgcttgtt ctcctcgacc aggtccgcca gaaggcgctc gccgcccagg acagcagct    5100
cttgcaagga agcaaagttt ttcagcggtt tgaggccgtc cgccgtgggc atgttttttca    5160
gggtctggcc gagcagctcc aggcggtccc agagctcggt gacgtgctct acggcatctc    5220
tatccagcat atctcctcgt ttcgcggggtt ggggcggctt tcgctgtagg gcaccaggcg    5280
atggtcgtcc agcgcggcca gagtcatgtc cttccatggg cgcagggtcc tcgtcagggt    5340
ggtctgggtc acggtgaagg ggtgcgcccc gggctgggcg ctggccaggg tgcgcttgag    5400
actggtcctg ctggtgctga agcgctgccg gtcttcgccc tgcgcgtcgg ccaggtagca    5460
tttgaccatg gtgtcgtagt ccagcccctc cgcggcgtgt cccttggcgc gcagcttgcc    5520
cttggaggtg gcgccgcacg cggggcactg caggctcttg agcgcgtaga gcttggggggc    5580
gaggaagacc gattcggggg agtaggcgtc cgcgccgcag gccccgcaca cggtctcgca    5640
ctccaccagc caggtgagct cggggcgctc ggggtcaaaa accaggtttc ccccatgctt    5700
tttgatgcgt ttcttacctc gggtctccat gaggcggtgt cccgttcgg tgacgaagag    5760
gctgtccgtg tctccgtaga ccgacttgag gggtctgtcc tccagggggg tccctcggtc    5820
ctcttcgtag agaaactcgg accactctga gacaaaggcc cgcgtccagg ccaggacgaa    5880
ggaggccagg tgggagggggt accggtcgtt gtccactagg gggtccacct tctccaaggt    5940
gtgaagacac atgtcgccct cctcggcgtc caggaaggtg attggcttgt aggtgtaggc    6000
cacgtgaccc ggggttccgg acgggggggt ataaaagggg gtggggcgc gctcgtcctc    6060
actctcttcc gcatcgctgt ctgcgagggc cagctgctgg ggtgagtatt ccctctcgaa    6120
ggcgggcatg acctcagcgc tgaggctgtc agtttctaaa aacgaggagg atttgatgtt    6180
cacctgtccc gagctgatgc ctttgagggt gcccgcgtcc atctggtcag aaaacacgat    6240
cttttttattg tccagcttgg tggcgaacga cccgtagagg gcgttggaga gcagcttggc    6300
gatggagcgc agggtctgat tcttgtcccg gtcggcgcgc tccttggccg cgatgttgag    6360
ctgcacgtac tcgcgcgcga cgcagcgcca ctcggggaag acggtggtgc gctcgtcggg    6420
caccaggcgc acgcgccagc cgcggttgtg cagggtgacg aggtccacgc tggtggcgac    6480
ctcgccgcgc aggcgctcgt tggtccagca gaggcgcccg cccttgcgcg agcagaaggg    6540
gggcaggggg tcgagtttggg tttcgtccgg ggggtccgcg tccaccgtga agaccccggg    6600
gcgcaggcgc gcgtcgaagt agtcgatctt gcatccttgc aagtccagcg cccgctgcca    6660
```

-continued

| | |
|---|---|
| gtcgcgggcg gcgagcgcgc gctcgtaggg gttgagcggc gggccccagg gcatgggg tg | 6720 |
| ggtgagcgcg gaggcgtaca tgccgcagat gtcatagacg tagaggggct cccggaggat | 6780 |
| gcccaggtag gtggggtagc agcggccgcc gcggatgctg gcgcgcacgt agtcgtagag | 6840 |
| ctcgtgcgag ggggcgagga ggtcggggcc caggttggtg cgggcggggc gctccgcgcg | 6900 |
| gaagacgatc tgcctgaaga tggcatgcga gttggaagag atggtggggc gctggaagac | 6960 |
| gttgaagctg gcgtcctgca ggccgacggc gtcgcgcacg aaggaggcgt aggactcgcg | 7020 |
| cagcttgtgc accagctcgg cggtgacctg cacgtcgagc gcgcagtagt cgagggtctc | 7080 |
| gcggatgatg tcatacttag cctgccccttt cttttccac agctcgcggt tgaggacgaa | 7140 |
| ctcttcgcgg tctttccagt actcttggat cgggaaaccg tccggctccg aacggtaaga | 7200 |
| gcccagcatg tagaactggt tgacggcctg gtaggcgcag cagcccttct ccacgggcag | 7260 |
| ggcgtaggcc tgcgcggcct tgcggagcga ggtgtgggtc agggcgaagg tgtccctgac | 7320 |
| catgaccttg aggtactggt gtttgaagtc ggagtcgtcg cagccgcccc gctcccagag | 7380 |
| cgagaagtcg gtgcgctttt tggagcgggg gttgggcagc gcgaaggtga catcgttgta | 7440 |
| gaggatcttg cccgcgcgag gcatgaagtt gcgggtgatg cggaagggcc ccggcacttc | 7500 |
| cgagcggttg ttgatgacct gggcggcgag cacgatctcg tcgaagccgt tgatgttgtg | 7560 |
| gcccacgatg tagagttcca ggaagcgggg ccggcccttg acgctgggca gcttctttag | 7620 |
| ctcttcgtag gtgagctcct cgggcgaggc gaggccgtgc tcggccaggg cccagtccgc | 7680 |
| caggtgcggg ttgtccgcga ggaaggaccg ccagaggtcg cgggccagga gggtctgcag | 7740 |
| gcggtccctg aaggtcctga actggcgccc tacggccatc ttttcggggg tgacgcagta | 7800 |
| gaaggtgagg gggtcttgct gccaggggtc ccagtcgagc tccagggcga ggtcgcgcgc | 7860 |
| ggcggcgacc aggcgctcgt cgcccccgaa tttcatgacc agcatgaagg gcacgagctg | 7920 |
| ctttccgaag gcgcccatcc aagtgtaggt ctctacatcg taggtgacaa agagacgttc | 7980 |
| cgtgcgagga tgcgagccga tcgggaagaa ctggatctcc cgccaccagt tggaggagtg | 8040 |
| gctgttgatg tggtgaaagt agaagtcccg tcggcgggcc gagcactcgt gctggctttt | 8100 |
| gtaaaagcga gcgcagtact ggcagcgctg cacgggctgt acctcttgca cgagatgcac | 8160 |
| ctgccgaccg cggacgagga agctgagtgg gaatctgagc ccccgcatg gctcgcggcc | 8220 |
| tggctggtgc tcttctactt tggatgcgtg gccgtcaccg tctggctcct cgaggggtgt | 8280 |
| tacggtggag cggatcacca cgccgcgcga gccgcaggtc cagatatcgg cgcgcggcgg | 8340 |
| tcggagtttg atgacgacat cgcgcagctg ggagctgtcc atggtctgga gctcccgcgg | 8400 |
| cggcggcagg tcagccggga gttcttgcag gtttacctcg cagagacggg ccagggcgcg | 8460 |
| gggcaggtcc agtggtact tgaattcgag aggcgtgttg gtggcggcgt cgatggcttg | 8520 |
| cagtatgccg cagccccggg gcgcgacgac ggtgccccgc ggggcggtga agctcccgcc | 8580 |
| gccgctcctg ctgtcgccgc cggtggcggg gcttagaagc ggtgccgcgg tcgggccccc | 8640 |
| ggaggtaggg ggggctccgg tcccgcgggc aggggcggca gcggcacgtc ggcgccgcgc | 8700 |
| gcgggcagga gctggtgctg cgcccggagg ttgctggcga aggcgacgac gcggcggttg | 8760 |
| atctcctgga tctggcgcct ctgcgtgaag acgacgggtc cggtgagctt gaacctgaaa | 8820 |
| gagagttcga cagaatcaat ctcggtgtca ttgaccgcga cctggcgcag gatctcctgc | 8880 |
| acgtcgcccg agttgtcttg gtaggcgatc tcggccatga actgttcaat ctcttcctcc | 8940 |
| tggaggtctc cgcgtccggc gcgctccacg gtggccgcca ggtcgttgga gatgcgcgcc | 9000 |
| atgagctgcg agaaggcgtt gagtccgccc tcgttccaca ctcggctgta gaccacgccg | 9060 |

```
ccctggtcgt cgcgggcgcg catgaccacc tgcgcgaggt tgagttccac gtggcgcgca    9120
aagacggcgt agttgcgcag gcgctggaag aggtagttga gggtggtggc ggtgtgctcg    9180
gccacaaaga agtacatgac ccagcggcgc aacgtggatt cgttgatgtc ccccaaggcc    9240
tccagtcgct ccatggcctc gtagaagtcc acggcgaagt tgaaaaactg ggagttgcgc    9300
gccgacacgg tcaactcctc ctccagaaga cggatgagct cggcgacggt gtcgcgcacc    9360
tcgcgctcga aggctatggg aatctcttcc tccgccagca tcaccacctc ttcctcttct    9420
tcctcctctg gcacttccat gatggcttcc tcctcttcgg ggggtggcgg cggggagggg    9480
ggcgctcggc gccggcggcg gcgcaccggg aggcggtcca cgaagcgctc gatcatctcc    9540
ccgcggcggc gacgcatggt ctcggtgacg gcgcggccgt tctctcgggg acgcagctgg    9600
aagacgccgc cggtcatctg gtgctgggc gggtggccgt ggggcagcga gaccgcgctg    9660
acgatgcatc ttaacaattg ctgcgtaggt acgccgccga gggacctgag ggagtccaga    9720
tccaccggat ccgaaaacct ttcgaggaag gcatctaacc agtcgcagtc gcaaggtagg    9780
ctgagcaccg tggcgggcgg cggggggtgg ggggagtgtc tggcggaggt gctgctgatg    9840
atgtaattga agtaggcggt cttgacacgg cggatggtcg acaggagcac catgtctttg    9900
ggcccggcct gctggatgcg gaggcggtcg gccatgcccc aggcttcgtt ctggcatctg    9960
cgcaggtctt tgtagtagtc ttgcatgagc ctttccaccg gcacctcttc tccttcttct   10020
tctgacatct ctgctgcatc tgcggccctg gggcgacggc gcgcgcccct gcccccccatg   10080 cgcgtcaccc cgaaccccct gagcggctgg agcagggcca ggtcggcgac gacgcgctcg   10140
gccaggatgg cctgctggac ctgcgtgagg gtggtttgga agtcatccaa gtccacgaag   10200
cggtggtagg cgcccgtgtt gatggtgtag gtgcagttgg ccatgacgga ccagttgacg   10260
gtctggtggc ccggttgcgt catctcggtg tacctgaggc gcgagtaggc gcgcgagtcg   10320
aagatgtagt cgttgcaagt ccgcaccagg tactggtagc ccaccaggaa gtgcggcggc   10380
ggctggcggt agaggggcca gcggagggtg gcggggctc cggggccag gtcttccagc   10440 atgaggcggt ggtattcgta gatgtacctg gacatccagg tgatgcccgc ggcggtggtg   10500
gaggcgcgcg ggaagtcgcg caccggttc cagatgttgc gcagcggcag aaagtgctcc   10560
atggtaggcg tgctctggcc ggtcaggcgc gcgcagtcgt tgatactcta gaccagggaa   10620
aacgaaagcc ggtcagcggg cactcttccg tggtctggtg gataaattcg caagggtatc   10680
atggcggagg gcctcggttc gagccccggg cccgggccgg acggtccgcc atgatccacg   10740
cggttaccgc ccgcgtgtcg aacccaggtg gcgacgtcag acaacggtgg agtgttcctt   10800
ttgggttttt ttccaaattt ttctggccgg gcgccgacgc cgccgcgtaa gagactagag   10860
tgcaaaagcg aaagcagtaa gtggctcgct ccctgtagcc cggaggatcc ttgctaaggg   10920
ttgcgttgcg gcgaaccccg gttcgagtct ggctctcgct gggccgctcg gtcggccgg    10980 aaccgcggct aaggcgggat tggcctcccc ctcattaaag accccgcttg cggattcctc   11040
cggacacagg ggacgagccc cttttttactt ttgcttttct cagatgcatc cggtgctgcg   11100
gcagatgcgc ccccgcccc agcagcagca gcagcaacat cagcaagagc ggcaccagca   11160 gcagcggggag tcatgcaggg cccctcgcc cacgctcggc ggtccggcga cctcggcgtc   11220
cgcggccgtg tctggagccg gcggcggtgg gctggcggac gacccggagg agccccgcg    11280 gcgcagggca agacagtacc tggacctgga ggagggcgag ggcctggcgc gactgggggc   11340
gccgtccccc gagcgccacc cgcggggtgca gctgaagcgc gactcgcgcg aggcgtacgt   11400
```

```
gcctcggcag aacctgttca gagaccgcgc gggcgaggag cccgaggaga tgcgggaccg    11460
caggttcgcc gcggggcggg agctgcggca ggggctgaac cgggagcggc tgctgcgcga    11520
ggaggacttt gagcccgacg cgcggacggg gatcagcccc gcgcgcgcgc acgtggcggc    11580
cgccgacctg gtgacggcgt acgagcagac ggtgaaccag gagatcaact tccaaaaaag    11640
cttcaacaac cacgtgcgca cgctggtggc gcgcgaggag gtgaccatcg gcctgatgca    11700
cctgtgggac tttgtgagcg cgctggagca gaaccccaac agcaagcctc tgacggcgca    11760
gctgttcctg atagtgcagc acagcaggga caacgaggcg ttcagggacg cgctgctgaa    11820
catcaccgag cccgagggtc ggtggctgct ggacctgatt aacatcttgc agagcatagt    11880
ggtgcaggag cgcagcctga gcctggccga caaggtggcg gccatcaatt actcgatgct    11940
cagtctgggc aagttttacg cgcgcaagat ctaccagacg ccgtacgtgc ccatagacaa    12000
ggaggtgaag atcgacggct tctacatgcg catggcgctg aaggtgctga ccctgagcga    12060
cgacctgggc gtgtaccgca acgagcgcat ccacaaggcc gtgagcgtga gccggcggcg    12120
cgagctgagc gaccgcgagc tgatgcacag cctcagcgg gcgctggcgg gggccggcag    12180
cggcgacagg gaggccgagt cctacttcga ggcggggcg gacctgcgct gggtgcccag    12240
ccggagggcc ctggaggccg cggggcccg ccgcgaggac tatgcagacg aggaggagga    12300
ggatgacgag gagtacgagc tagaggaggg cgagtacctg gactaaaccg caggtggtgt    12360
ttttggtaga tgcaagaccc gaacgtggtg gacccggcgc tgcgggcggc tctgcagagc    12420
cagccgtccg gccttaactc tacagacgac tggcgacagg tcatggaccg catcatgtcg    12480
ctgacggcgc gcaatccgga cgcgttccgg cagcagccgc aggccaacag gctctccgcc    12540
atcttggagg cggtggtgcc tgcgcgcgcg aaccccacgc acgagaaggt gctggccata    12600
gtgaacgcgc tggccgagaa cagggccatc cgcccgacg aggccgggct ggtgtacgac    12660
gcgctgctgc agcgcgtggc ccgctacaac agcggcaacg tgcagaccaa cctggaccgg    12720
ctggtggggg acgtgcgcga gcggtggcg cagcgggagc gcgcggagcg gcagggaaac    12780
ctgggctcca tggtggcgct gaacgccttc ctgagcacgc agccggccaa cgtgccgcgg    12840
gggcaggagg actacaccaa ctttgtgagc gcgctgcggc tgatggtgac cgagaccccc    12900
cagagcgagg tgtaccagtc ggggccggac tactttttcc agaccagcag acagggcctg    12960
cagacggtga acctgagcca ggcttttcaag aacctgcggg ggctgtgggg cgtgaaggcg    13020
cccaccgggg accgggcgac ggtgtccagc ctgctgacgc ccaactcgcg cctgctgctg    13080
ctgctgatcg cgccgttcac ggacagcggc agcgtgtccc gggagaccta cctcgggcac    13140
ctgctgacgc tgtaccgcga ggccatcggg cagacccagg tggacgagca caccttccag    13200
gagatcacca gcgtgagccg cgcgctgggg caggaggaca cgggcagcct ggaggcgacc    13260
ctgaactacc tgctgaccaa ccggcggcag aagatcccct cgctgcatag tttgaccacc    13320
gaggaggagc gcatcctgcg ctacgtgcag cagagcgtga gcctgaacct gatgcgcgac    13380
ggggtgacgc ccagcgtggc gctggacatg accgcgcgca catggaacc gggcatgtac    13440 gccgcgcatc ggccttacat caaccgcctg atggactact tgcatcgcgc ggcggccgtg    13500
aaccccgagt acttcaccaa cgccatcctg aacccgcact ggctcccgcc gcccgggttc    13560
tacagcgggg gcttcgaggt ccccgaggcc aacgacggct tcctgtggga cgacatggac    13620
gacagcgtgt tctccccgcg gccgcaggcg ctggcggagg cgtcgctgct ccgcctcccc    13680
aagaaagaag agagccgccg gcccagcagc gcggcggcct ctctgtccga gctggggcg    13740 gcggccgcgc ggcccgggtc cctgggggc agccccttc ccagtctggt ggggtctctg    13800
```

```
cagagcgggc gcaccacccg gccccggctg ctgggcgagg acgagtacct gaacaactcc   13860
ctgatgcagc cggtgcggga gaaaaacctg ccccccgcct tccccaacaa cgggatagag   13920
agcctggtag acaagatgag cagatggaag acctatgcgc aggagcacag ggactcgccc   13980
gtgctccgtc cgcccacgcg cgccagcgc cacgaccggc agcgggggct ggtatgggat    14040
gacgaggact ccgcggacga tagcagcgtg ctggacctgg ggggagcgg cggtaacccg    14100 ttcgcgcacc tgcgccccg cctggggagg atgtttcaat aagaaaaatc aagcatgatg    14160
caaggttttt taagcggata aataaaaaac tcaccaaggc catggcgacc gagcgttgtt   14220
ggtttcttgt tgtgttccct tagtatgcgg cgcgcggcga tgtaccacga gggacctcct   14280
ccctcttatg agagcgtggt gggcgcggcg gcggcctctc cctttgcgtc gcagctggag   14340
ccgccgtacg tgcctccgcg gtacctgcgg cctacggggg gaagaaacag catccgttac   14400
tcggagctgg cgcccctgta cgacaccacc cgggtgtacc tggtggacaa caagtcggcg   14460
gacgtggcct ccctgaacta ccagaacgac cacagcaatt ttttgaccac ggtcatccag   14520
aacaatgact acaccccgag cgaggccagc acccagacca tcaatctgga tgaccggtcg   14580
cactggggcg gcgacctgaa aaccatcctg cacaccaaca tgcccaacgt gaacgagttc   14640
atgttcacca ataagttcaa ggcgcgggtg atggtgtcgc gttcgcacac caaggacgac   14700
cgggtggagc tgaagtacga gtgggtagag ttcgagctgc ccgagggcaa ctactcggag   14760
accatgacca tagacctgat gaacaacgcg atcgtggagc actatctgaa agtgggcagg   14820
cagaacgggg tcctggagag cgacatcggg gtcaagttcg acaccaggaa cttccgcctg   14880
gggctggacc cggtcaccgg gctggtcatg cccggggtct acaccaacga ggccttccac   14940
cccgacatca tcctgctgcc cggctgcggg gtggacttca cctacagccg cctgagcaac   15000
ctgctgggca tccgcaagcg gcagcccttc caggagggct ttaggatcac ctacgaggac   15060 ctggagggg gcaacatccc cgcgctcctg gatgtggagg cctaccagga tagcttgaag    15120
gaagaagagg cgggagaggg cagcggcggc ggcggcggcg ccggtcagga ggagggcggg   15180
gcctcctctg aggcctctgc ggacgccgcc gctgccgccg aggcggaggc ggccgacccc   15240
gcgatggtgg tagaggaaga gaaggatatg aatgacgagg cggtgcgcgg cgacaccttt   15300
gccacccggg gggaggagaa gaaagcggag gccgaggccg cggcagagga ggcggcagcg   15360
gcggcggcgg cggcagtaga ggcggcggcc gaggcggaga gccccccaa ggagcccgtg    15420 attaaggccc tgaccgaaga tagcaagaag cgcagttaca acgtgctcaa ggacagcacc   15480
aacaccgcgt accgcagctg gtacctggcc tacaactacg gcgacccggc gacggggcgtg   15540 cgctcctgga ccctgctgtg tacgccggac gtgacctgcg gctcggagca ggtgtactgg   15600
tcgctgcccg acatgatgca agaccccgtg accttccgct ccacgcggca ggtcagcaac   15660
ttcccggtgg tgggcgccga gctgctgccc gtgcactcca agagcttcta caacgaccag   15720
gccgtctact cccagctcat ccgccagttc acctctctga cccacgtgtt caatcgcttt   15780
cctgagaacc agattctggc gcgcccgccc gccccacca tcaccaccgt cagtgaaaac   15840
gttcctgctc tcacagatca cgggacgcta ccgctgcgca acagcatcgg aggagtccag   15900
cgagtgaccg taactgacgc cagacgccgc acctgtccct acgtttacaa ggccctgggc   15960
atagtctcgc cgcgcgtcct ttccagccgc acttttttaag catgtccatc ctcatctcgc   16020
ccagcaataa caccggctgg ggcctgctgc gcgcgcccag caagatgttt ggaggggcga   16080
ggaagcgctc cgaccagcac cccgtgcgcg tgcgcgggca ctaccgcgcc ccctgggggcg   16140
```

```
cgcacaaacg cgggcgcacc ggcaccgcgg ggcgcaccac cgtggacgaa gccatcgact   16200
cggtggtgga gcaggcgcgc aactacacgc ccgcggtctc caccgtggac gcggctatcg   16260
agagcgtggt gcgaggcgcg cggcggtacg ccaaggcgaa gagccgccgg aggcgcgtgg   16320
cccgccgcca ccgccgtcga cccggaagcc ccgccaagcg cgccgccgcc gccttgcttc   16380
gtcgggccag acgcacgggc cgccgcgccg ccatgagggc cgcgcgccgc ctggccgccg   16440
gcatcaccac cgtggccccc cgcgccagaa gacgcgcggc cgctgccgcc gccgcggcca   16500
tcagcgacct ggccaccagg cgccggggca acgtgtactg ggtgcgcgac tcggtgagcg   16560
gcacgcgcgt gcccgtgcgc ttccgccccc cgcggacttg agaggagagg acaggaaaaa   16620
agcatcaaca acaccaccac tgagtctcct gctgttgtgt gtatcccagc ggcgcgcgcg   16680
cacacgcgca catgtccaag cgcaaaatca aagaagagat gctccaggtc gtcgcgccgg   16740
aaatctatgg gcccccgaag aaggaagagc aggatttcaa gccccgcaag ataaagcggg   16800
tcaaaaagaa aaagaaagat gacgatgatg gcgaggtgga gtttctgcgc gccacggcgc   16860
ccaggcgccc gctgcagtgg aagggtcggc gcgtaaagcg cgttctgcgc cccggcaccg   16920
cggtggtctt cacgcccggc gagcgctcca cccgcacttt caagcgcgtc tatgacgagg   16980
tgtacgcgca cgaagacctg ctggagcagg ccaacgatcg ctccggagag tttgcttacg   17040
ggaagcggca ccgggcgatg gagaaggacg aggtgctggc gctgccgctg accggggca   17100 accccacccc cagcctgaag cccgtgaccc tgcagcaggt gctgccggcc agcgcgccct   17160
ccgagatgaa gcggggcctg aagcgcgagg gcggcgacct ggcgcccacc gtgcagctga   17220
tggtgcccaa gcggcagagg ctggaggacg tgctggagaa aatgaaagta daccccggcc   17280
tgcagccgga catcagggtc cgccccatca agcaggtggc gccgggcctc ggcgtgcaga   17340
ccgtggacgt ggtcatcccc accggcgcct cctcttccag cgccgccgcc gccactagca   17400
ccgcggacat ggagacgcag actagctccg ccctcgccgc cccgcggcc gccgccgccg   17460 ccacctcctc ggcggaggta cagacggacc cctggatgcc gccgccggcg gccgcccct   17520 cgcgcgcacg ccgcgggcgc aggaagtacg gcgccgccag cgcgctcatg cccgagtacg   17580
ccttgcatcc ttccatcgcg cccacccccg gctaccgagg ctacagctac cgcccgcgaa   17640
gagccaaggg ctccacccgc cgcagccgcc gcgccgccac ctctaccccgc cgccgcagtc   17700 gccgccgccg ccggcagccc gcgctggctc cgatctccgt gaggagagtg cgcgcaacg   17760 gggacaccct ggtgctgccc agggcgcgct accaccccag catcgtttaa aagcctgttg   17820
tggttcttgc agatatggcc ctcacttgcc gcctccgttt cccggtgccg ggataccgag   17880
gaagatcgcg ccgtagaagg ggtatggccg gacgcggcct gagcggaggc agccgccgtg   17940
cgcaccggcg gcgacgcgcc accagccgac gcatgcgcgg cggggtgctg cctctgctga   18000
tccccctgat cgccgcggcg atcggcgccg tgcccgggat cgcctccgtg gccttgcagg   18060
cgtcccagag gcgttgacac agacttcttg caagcttgca aaaatatgga aaaaatcccc   18120
ccaataaaaa agtctagact ctcacgctcg cttggtcctg tgactatttt gtagaaaaaa   18180
agatggaaga catcaacttt gcgtcgctgg ccccgcgtca cggctcgcgc ccgttcctgg   18240
gacactggaa cgatatcggc accagcaaca tgagcgtgg cgccttcagt tggggctctc   18300
tgtggagcgg cattaaaaat atcggttctg ccgttaagaa ttacggctcc aaggcctgga   18360
acagcagcac gggccagatg ttgagagaca agttgaaaga gcagaacttc cagcagaagg   18420
tggtggaggg cctggcctcc ggcatcaacg gggtggtgga cctggccaat caggccgtgc   18480
aaaataagat caacagcaga ctggaccccc ggccgccggt ggaagagctg ccgccggcgc   18540
```

```
tggagacggt gtccccccgat gggcggggcg aaaagcgccc gcggcccgac agggaagaga   18600
ccactctggt cacgcacacc gatgagccgc cccctacga ggaagctctg aagcaaggct   18660
tgcccaccac tcggcccatc gcgcccatgg ccaccggggt ggtgggccgc cacaccccg    18720 ccaggctgga cctgcctcct cctcctgttt cttcttcggc cgccgatgcg cagcagcaga   18780
aggcggcgct gcccggtccg cccgcggccg cccccgtcc caccgccagt cgagcgcccc    18840
tgcgtcgcgc ggccagcggc ccccgcgggg tcgcgaggca cagcagcggc aactggcaga   18900
acacgctgaa cagcatcgtg ggtctggggg tgcagtccgt gaagcgccgc cgatgctact   18960
gaatagctta gctaacggtg ttgtatgtgt gtatgcgtcc tatgtcaccg ccagaggagc   19020
tgctgagtcg ccgccgttcg cgcgcccacc gccactacca ccgccggtac cactccagcg   19080
cccctcaaga tggcgacccc atcgatgatg ccgcagtggt cgtacatgca catctcgggc   19140
caggacgcct cggagtacct gagcccgggg ctggtgcagt tcgcccgcgc caccgacagc   19200
tacttcagcc tgagtaacaa gtttaggaac cccacggtgg cgcccacgca cgatgtgacc   19260
accgaccggt cccagcgcct gacgctgcgg ttcatccccg tggaccgcga ggacaccgcg   19320
tactcttaca aggcgcggtt caccctggcc gtgggcgaca accgcgtgct ggacatggcc   19380
tccacctact ttgacatccg cggcgtgctg gacaggggcc ccaccttcaa gccctactcc   19440
ggcaccgcct acaactccct ggccccaag ggcgccccca actcctgcga gtgggagcaa   19500
gaggagactc agacagctga agaggcacaa gacgaagaag aagatgaagc tgaagctgag   19560
gaggaaatgc ctcaggaaga gcaagcacct gtcaaaaaga ctcatgtata tgctcaggct   19620
cccctttctg gcgaaaaaat tactaaagac ggtctgcaga taggaacgga cgctacagct   19680
accgaacaaa aacctattta tgcagatccc acattccagc cagaaccca aattggtgaa    19740 tctcagtgga atgaggcaga tgcttcagtt gccggcggta gagtgctgaa gaaaactact   19800
cccatgaaac cctgttatgg ttcctatgcc aggcccacaa atgccaatgg aggtcagggt   19860
gtattggtgg agaaagacgg tggaaagatg gaaagccaag tagatatgca attcttttcg   19920
acttctgaaa acgcccgtaa cgaggctaac aacattcagc ccaaattggt gctgtacagc   19980
gaggatgtgc atatggagac cccagacaca cacatttctt acaagcctgc aaaaagcgat   20040
gataattcga aagtcatgct gggtcagcag tccatgccca acaggccaaa ttacatcggc   20100
ttcagagaca actttatcgg gctcatgtat tacaacagca ctggcaacat ggggggtgctg  20160 gcaggtcagg cctcacagtt gaatgcggtg gtggacttgc aagacagaaa cacagaactg   20220
tcctaccagc tcttgcttga ttccatggga gacagaacca gatacttttc catgtggaat   20280
caggcggtgg acagttatga tccagatgtc agaattattg aaaatcatgg aactgaagat   20340
gagctgccca ctattgtttt ccctctggga ggcatagggg taactgacac ttaccaggcc   20400
attaagacta atggcaatgg caacggcggg ggcaatacca cttggaccaa ggatgaaact   20460
tttgcagacc gcaacgagat agggtggga aacaatttcg ccatggagat caacctcagt    20520
gccaacctgt ggaggaactt cctctactcc aacgtggccc tgtacctgcc agacaagctt   20580
aagtacaacc cctccaacgt ggaaatctct gacaacccca acacctacga ctacatgaac   20640
aagcgagtgg tgcccccggg gctggtggac tgctacatca acctgggcgc gcgctggtcc   20700
ctggactaca tggacaacgt caaccccttc aaccaccacc gcaacgcggg cctgcgctac   20760
cgctccatgc ttctgggcaa cgggcgctac gtgcccttcc acatccaggt gccccagaag   20820
ttctttgcca tcaagaacct cctcctcctg ccgggctcct acacctacga gtggaacttc   20880
```

-continued

```
aggaaggatg tcaacatggt cctccagagc tctctgggta acgacctcag ggtcgacggg    20940
gccagcatca agttcgagag catctgcctc tacgccacct tcttccccat ggcccacaac    21000
acggcctcca cgctcgaggc catgctcagg aacgacacca acgaccagtc cttcaacgac    21060
tacctctccg ccgccaacat gctctacccc atccccgcca acgccaccaa cgttcccatc    21120
tccatcccct cgcgcaactg gcggccttc cgcggctggg ccttcacccg cctcaagacc    21180
aaggagaccc cctccctggg ctcgggtttc gacccctact acacctactc gggctccata    21240
ccctacctgg acggaacctt ctacctcaac cacactttca agaaggtctc ggtcaccttc    21300
gactcctcgg tcagctggcc gggcaacgat cgcctgctca cccccaacga gttcgagatc    21360
aagcgctcgg tcgacgggga gggctacaac gtggcccagt gcaacatgac caaggactgg    21420
ttcctcatcc aaatgctggc caactacaac atcggctatc agggcttcta catcccagag    21480
agctacaagg acaggatgta ctccttcttt aggaacttcc agcccatgag ccggcaggtg    21540
gtggacgaaa ccaagtacaa ggactaccag caggtgggca tcatccacca gcacaacaac    21600
tcgggcttcg tgggctacct cgccccccacc atgcgcgagg acaggccta ccccgccaac    21660 ttcccctacc cgctcattgg caagaccgcg gtcgacagcg tcacccagaa aaagttcctc    21720
tgcgaccgca ccctctggcg catcccccttc tccagcaact tcatgtccat gggtgcgctc    21780
acggacctgg ccagaacct gctctatgcc aactccgccc acgcgctcga catgaccttc    21840
gaggtcgacc ccatggacga gcccacccttt ctctatgttc tgttcgaagt cttttgacgtg    21900 gtccgggtcc accagccgca ccgcggcgtc atcgagaccg tgtacctgcg cacgcccttc    21960
tcggccggca acgccaccac ctaaagaagc aagccgccac cgccaccacc tgcatgtcgt    22020
cgggttccac cgagcaggag ctcaaggcca tcgtcagaga cctgggatgc gggccctatt    22080
ttttgggcac cttcgacaaa cgcttccccgg gcttcgtcgc cccgcacaag ctggcctgcg    22140
ccatcgtcaa cacggccggc cgcgagaccg ggggcgtgca ctggctggcc ttcgcctgga    22200
acccgcgctc caaaacatgc tacctcttg accccttcgg attctcggac cagcggctca    22260
agcagatcta ccagttcgag tacgagggcc tgctgcgccg cagcgccatc gcctcctcgc    22320
ccgaccgctg cgtcaccctc gagaagtcca cccagaccgt gcagggggccc gactcggccg    22380 cctgcggtct cttctgctgc atgttcctgc atgcctttgt gcactggccc cagagtccca    22440
tggaccgcaa ccccaccatg aacttgctga cggggatccc caactccatg ctccagagcc    22500
cccaggtcgc gcccaccctg cgccgcaacc aggagcggct ctacagcttc ctggaacgcc    22560
actcgcccta cttccgccgc cacagcgcgc agatcagggg ggccaccctct ttctgccgca    22620 tgcaagagat gcaagggaaa atgcaatgat gtacacagac actttttctt ttctcaataa    22680
atggcaactt tatttataca tgctctctct cgggtattca tttcccccacc cccaccacc    22740 cgccgccgcc gtaaccatct gctgctggct ttttttttt tttttaaaaa tcgaaagggt    22800
tctgccggga atcgccgtgc gccacgggca gggacacgtt gcggaactgg tagcgggtgc    22860
cccacttgaa ctcgggcacc accatgcggg gcaagtcggg gaagttgtcg cccacaggc    22920 tgcgggtcag caccagcgcg ttcattaggt cgggcgccga gatcttgaag tcgcagttgg    22980
ggccgccgcc ctgcgcgcgc gagttgcggt acaccgggtt gcaacactgg aacaccagca    23040
gcgccggata attcacactg gccagcacgc tccggtcgga gatcagctcg gcgtccaggt    23100
cctccgcgtt gctcagcgcg aacggggtca gcttgggcac ctgccgcccc aggaagggag    23160 cgtgcccgc cttcgagttg cagtcgcagc gcagcgggat cagcaggtgc ccgcggccgg    23220
actcggcgtt ggggtacagc gcgcgcatga aggcctccat ctggcggaag gccatctggg    23280
```

```
ccttggcgcc ctccgagaag aacatgccgc aggacttgcc cgagaactgg ttcgcggggc   23340
agctagcgtc gtgcaggcag cagcgcgcgt cggtgttggc gatctgcacc acgttgcgcc   23400
cccaccggtt cttcacgatt ttggccttgg aagcctgctc cttcagcgcg cgctgcccgt   23460
tctcgctggt cacatccatc tcgatacgt gctccttgtt caccatgctg ctgccgtgca    23520
gacacttcag ctcgccctcc acctcggtgc agcggtgctg ccatagcgcg cagcccgtgg   23580
gctcgaaatg cttgtaggtc acctccgcgt aggactgcag gtaggcctgc aggaagcgcc   23640
ccatcatggt cacgaaggtc ttgttgctgc tgaaggtcag ctgcagcccg cggtgctcct   23700
cgttcagcca ggccttgcac acggccgcca gcgcctccac ctggtcgggc agcatcttga   23760
agttcagctt cagctcattc tccacatggt acttgtccat cagcgcgcgc gcagcctcca   23820
tgcccttctc ccaggccgac accagcggca ggctcaaggg gttcaccacc gtcgcagccg   23880
ccgctgcgct ttcgctttcc gctccgctgt tctcttcttc ctcctcctct tcttcctcgc   23940
cgcccgcgcg cagcccccgc accacggggt cgtcttcctg caggcgccgc accgagcgct   24000
tgccgctcct gccctgcttg atacgcacgg gcgggttgct gaagcctacc atcaccagcg   24060
cggcctcttc ttgctcgtcc tcgctgtcca ctatgacctc gggggagggc gacctcagaa   24120
ccgtggcgcg ctgcctcttc ttttcctgg gggcgtttgc cagctccgcg ccgcggccg    24180 ccgccgaggt cgaaggccga gggctgggcg tgcgcggcac cagcgcgtcc tgcgagccgt   24240
cctcgtcctc ggactcgagg cggcagcgag cccgcttctt cgggggcgcg cggggcggcg   24300
gcggcggggg cggcggcgac ggagacgggg acgagacatc gtccagggtg ggaggacggc   24360
gggccgcgcc gcgtccgcgc tcgggggtgg tttcgcgctg gtcctcttcc cgactggcca   24420
tctcccactg ctccttctcc tataggcaga aagagatcat ggagtctctc atgcaagtcg   24480
agaaggagga ggacagccta accaccaccg cccctctga gccctccgcc gccgccgcgg   24540
acgacgcgcc caccaccacc gccgccgcca ccaccaccat taccacccta cccggcgacg   24600
cagccccgat cgagaaggaa gtgttgatcg agcaggaccc gggttttgtg agcgaagagg   24660
aggatgagga ggatgaaaag gagaaggata ccgccgcctc agtgccaaaa gaggataaaa   24720
agcaagacca ggacgacgca gagacagatg aggcagcagt cgggcggggg gacggaaggc   24780
atgatgatga tgacggctac ctagacgtgg gagacgacgt gctgcttaag cacctgcacc   24840
gccagtgcgt catcgtctgc gacgcgctgc aggagcgctg cgaagtgccc ctggacgtgg   24900
cggaggtcag ccgcgcctac gagcggcacc tcttcgcgcc acacgtgccc cccaagcgcc   24960
gggagaacgc cacctgcgag cccaacccgc gcctcaactt ctacccggtc ttcgcggtac   25020
ccgaggtgct ggccacctac cacatcttct tccaaaactg caagatcccc ctctcctgcc   25080
gcgccaaccg caccccgcgc cacaagacgc tggccctgcg gcagggcgcc cacatacctg   25140
atatcgcctc tctggaggag gtgcccaaga tcttcgaggg tctcggtcgc gacgagaaac   25200
gggcggcgaa cgctctgcaa ggagacagcg aaaacgagag tcactcgggg gtgctggtgg   25260
agctcgaggg cgacaacgcg cgcctggccg tgctcaagcg cagcatcgaa gtcacccact   25320
tcgcctaccc ggcgctcaac ctgccccccca aggtcatgag tgtggtcatg agtgagctca   25380
tcatgcgccc cgcccagccc ctggacgcgg atgcaaactt gcaagagccc tccgaggaag   25440
gcctgcccgc ggtcagcgac gagcagctgg cgcgctggct ggagacccgc gacccccgccc  25500 agctggagga gcgcgcaag ctcatgatgg ccgcggtgct cgtcaccgtg agctcgagt     25560 gtctgcagcg cttcttcggg gaccccgaga tgcagcgcaa gctcgaggag accctgcact   25620
```

```
acaccttccg ccagggctac gtgcgccagg cctgcaagat ctccaacgtg gagctctgca   25680
acctggtctc ctacctgggc atcctgcacg agaaccgcct cgggcagaac gtcctgcact   25740
ccaccctcaa aggggaggcg cgccgcgact acgtccgcga ctgcgtctac ctcttcctct   25800
gctacacgtg gcagacggcc atgggggtct ggcagcagtg cctggaggag cgcaacctca   25860
aggagctgga gaagctcctc cggcgcgccc tcagggacct ctggacgggc ttcaacgagc   25920
gctcggtggc cgccgcgctg gcggacatca tcttccccga gcgcctgctc aaaaccctgc   25980
agcagggcct gcccgacttc accagccaga gcatgctgca gaacttcagg accttcatcc   26040
tggagcgctc gggcatcctg ccggccacct gctgcgcgct gcccagcgac ttcgtgccca   26100
tcaggtacag ggagtgcccg ccgccgctct ggggccactg ctacctcttc cagctggcca   26160
actacctcgc ctaccactcg gatctcatgg aagacgtgag cggcgagggc ctgctcgagt   26220
gccactgccg ctgcaacctg tgcacgcccc accgctctct agtctgcaat ccgcagctgc   26280
tcagcgagag tcagattatc ggtaccttcg agctgcaggg tccctcgccc gacgaaaagt   26340
ccgcggctcc gggggttgaaa ctcactccgg ggctgtggac ttccgcctac ctacgcaaat   26400
ttgtacctga agactaccac gcccacgaga tcaggtttta cgaagaccaa tcccgcccgc   26460
ccaaggcgga gctcaccgcc tgcgtcatta cccagggcca catcctgggc caattgcaag   26520
ccatcaacaa agcccgccaa gagttcttgc tgaaaaaggg tcgggggggtg tacctggacc   26580
cccagtccgg cgaggagcta aaccccgctac ccccgccgcc gccccagcag cgggaccttg   26640
cttcccagga tggcacccag aaagaagcag ccgccgccgc cgccagcata catgcttctg   26700
gaggaagagg aggactggga cagtcaggca gaggaggttt cggacgagga cgaggaggag   26760
gagatgatgg aagactggga ggaggacagc ctagacgagg aagcttcaga ggccgaagag   26820
gtggcagacg caacaccatc accctcggcc gcagcccct cgccgcgcc cccgaaatcc   26880
tccgaccca gcagcagcgc tataacctcc gctcctccgg cgccggcgcc cacccgcagc   26940
agacccaacc gtagatggga cactacagga accggggtcg gtaagtccaa gtgcccccca   27000
gcgccgcccc cgcaacagga gcaacagcag cagcagcggc gacagggcta ccgctcgtgg   27060
cgcggacaca agaacgccat agtcgcctgc ttgcaagact gcggggggcaa catctccttc   27120
gcccgccgct tcctgctctt ccaccacggg gtggcttttc cccgcaatgt cctgcattac   27180
taccgtcatc tctacagccc ctactgcggc ggcagcggcg acccagaggg agcggcggca   27240
gcagcagcgc cagccacagc ggcgaccacc taggaagacc tccgcgggca agacggcggg   27300
agccgggaga cccgcggcgg cggcggtagc ggcggcggcg ggcgcactgc gcctctcgcc   27360
caacgaaccc ctctcgaccc gggagctcag acacaggatc ttccccactc tgtatgctat   27420
cttccagcag agcagaggcc aggaacagga gctcaaaata aaaaacagat ctctgcgctc   27480
cctcacccgc agctgtctgt atcacaaaag cgaagatcag cttcggcgca cgctggagga   27540
cgcggaggca ctcttcagca aatactgcgc gctgactctt aaggactagc cgcgcgccct   27600
tctcgaattt aggcgggaga aagactacgt catcgccgac cgccgcccag cccacccagc   27660
cgacatgagc aaaagagattc ccacgcccta catgtggagc taccagccgc agatgggact   27720
cgcggcggga gcggcccaag actactccac ccgcatgaac tacatgagcg cggggcccca   27780
catgatctca cgggttaatg ggatccgcgc ccagcgaaac caaatactgc tggaacaggc   27840
ggccataacc gccacacccc gtcatgacct caatccccga aattggcccg ccgccctcgt   27900
gtaccaggaa acccctctg ccaccaccgt ggtacttccg cgtgacaccc aggccgaagt   27960
ccagatgact aactcagggg cgcagctcgc gggcggcttt cgtcacgggg tgcggccgca   28020
```

```
ccggccgggt atattacacc tggcgatcag aggccgaggt attcagctca acgacgagtc    28080
ggtgagctct tcgctcggtc tccgtccgga cggaaccttc cagatcgccg gatcaggtcg    28140
ctcctcattc acgcctcgcc aggcgtatct gactctgcag acctcctcct cggagcctcg    28200
ctccggcggc atcggcaccc tccagttcgt ggaggagttc gtgccctcgg tctacttcaa    28260
ccccttctcg ggacctcccg gacgctaccc cgaccagttc atcccgaact ttgacgcggt    28320
gaaggactcg gcggacggct acgactgaat gtcaagtgct gaggcagaga gcgttcgcct    28380
gaaacacctc cagcactgcc gccgcttcgc ctgctttgcc cgcagctccg gtgagttctg    28440
ctactttcag ctgcccgagg agcataccga agggccggcg cacggcgtcc gcctaaccac    28500
ccagggcgag gttacctgta cccttatccg ggagtttacc ctccgtcccc tgctagtgga    28560
gcgggagcgg ggttcttgtg tcataactat cgcctgcaac tgccctaacc ctggattaca    28620
tcaagatctt tgttgtcacc tgtgcgctga gtaataaaa cgctgagatc agactctact    28680
ggggctcctg tcgccatcct gtgaacgcca ccgtcttcac ccaccccgag cagccccagg    28740
cgaacctcac ctgcggcctg cgtcggaggg ccaagaagta cctcacctgg tacttcaacg    28800
gcaccccctt tgtggtttac aacagcttcg accaggacgg agttgccttg agagacgacc    28860
tttccggtct cagctactcc attcacaaga acaccaccct ccacctcttc cctccctacc    28920
tgccgggaac ctacgagtgc gtcaccggcc gctgcaccca cctcctccgc ctgatcgtaa    28980
accagacctt tccgggaaca cacctcttcc ccagaacagg aggtgagctc aggaaacccc    29040
ctggggccca gggcggagac ttaccttcga cccttgtggg gttaggattt tttatcgccg    29100
ggttgctggc tctcctgatc aaagcttcct tcagatttgt tctctccctt tacttttatg    29160
aacagctcaa cttctaataa cgctaccttt tctcaggaat cgagtagtaa cttctcttcc    29220
gaaatcgggc tgggtgtgct gcttactctg ttgatttttt tccttatcat acttagcctt    29280
ctgtgcctca ggctcgccgc ctgctgcgca catatctaca tctacagccg gttgcttaac    29340
tgctggggtc gccatccaag atgaacgggg ctcaggtgct atgtctgctg gccctggtgg    29400
cctgcagtgc cgccgtcaat tttgaggaac ccgcttgcaa tgtgactttc aagcctgagg    29460
gcgcacattg caccactctg gttaaatgtg tgacctctca tgaaaaactg ctcatcgcct    29520
acaaaaacaa aacaggccag atcgcagtct atagcgagtg gctacccgga gaccataata    29580
actactcagt caccgtcttc gagggtgcgg agtctaagaa attcgattac acctttccct    29640
tcgaggagat gtgtgatgcg gtcatgtacc tgtccaaaca gtacaagctg tggccccca    29700 cccccaaggc gtgtgtggaa aacactgggt ctttctgctg tctctctctg gcaatcactg    29760
tgcttgctct aatctgcacg ctgctataca tgagattcag gcagaggcga atctttatcg    29820
atgagaaaaa aatgccttga tcgctaacac cggctttctg tctgcagaat gaaagcaatc    29880
acctccctac taatcagcac caccctcctt gcgattgccc atgggttgac acgaatcgaa    29940
gtgccagtgg ggtccaatgt caccatggtg ggccccgccg gcaattcctc cctgatgtgg    30000
gaaaaatatg tccgtaatca atgggatcat tactgctcta atcgaatctg tatcaagccc    30060
agagccacct gcgacgggca aaatctaact ttgattgatg tgcaaatgac ggatgctggg    30120
tactattacg ggcagcgggg agaaatgatt aattactggc gaccccacaa ggactacatg    30180
ctgcatgtag tcaaggcagt cccaactact accaccccca ccactaccac tcccactacc    30240
accaccccca ccactaccac tagcactgct actaccgctg cccgcaaagc tattcccgc    30300 aaaagcacca tgcttagcac caagccccat tctcactccc acgccggcgg gcccaccggt    30360
```

```
gcggcctcag aaaccaccga gctttgcttc tgccaatgca ctaacgccag cgcccacgaa    30420
ctgttcgacc tggagaatga ggacgatgac cagctgagct ccgcttgccc ggtcccgctg    30480
cccgcagagc cggtcgccct gaagcagctc ggtgatccat ttaatgactc tcctgtttat    30540
ccctctcccg aataccctcc cgactctacc ttccacatca cgggcaccaa agaccccaac    30600
ctctccttct acctgatgct gctgctctgt atctctgtgg tatcttccgc gctcatgtta    30660
ctgggcatgt tctgctgcct catctgccgc agaaaaagaa agtctcgctc tcagggccaa    30720
ccactgatgc ccttccccta ccccccagat tttgcagata caagatatg agcacgctgc     30780 tgacactaac cgctttactc gcctgcgctc taacccttgt cgcttgcgaa tccagatacc    30840
acaatgtcac agttgtgaca ggagaaaatg ttacattcaa ctccacggcc gacacccagt    30900
ggtcgtggag tggccacggt agctatgtat acatctgcaa tagctccacc tcccctagca    30960
tgtcctctcc caagtaccac tgcaatgaca gcctgttcac cctcatcaac gcctccacct    31020
cggacaatgg actctatgta ggctatgtga cacccgtggg gcaggaaaag acccacgcct    31080
acaacctgca agttcgccac ccctccacca ccgccaccac ctctgccgcc ctacccgca    31140 gcagcagcag cagcagcagc agcagcagca gcagcagcag cagattcctg actttaatcc    31200
tagccagctc aacaaccacc gccaccgctg agaccaccca cagctccgcg cccgaaacca    31260
cccacaccca ccacccagag acgaccgcgg cctccagcga ccagatgtcg gccaacatca    31320
ccgcctcggg tcttgaactt gcttcaaccc ccaccccaaa accagtggat gcagccgacg    31380
tctccgccct cgtcaatgac tgggcggggc tgggaatgtg gtggttcgcc ataggcatga    31440
tggcgctctg cctgcttctg ctctggctca tctgctgcct caaccgcagg cgggccagac    31500
ccatctatag acccatcatt gttctcaacc ccgctgatga tgggatccat agattggatg    31560
gtctgaaaaa cctactttc tcttttacag tatgataaat tgagacatgc ctcgcatttt     31620
catgtacttg acacttctcc cacttttct ggggtgttct acgctggccg ccgtctctca     31680
cctcgaggta gactgcctca cacccttcac tgtctacctg atttacggat tggtcaccct    31740
cactctcatc tgcagcctaa tcacagtagt catcgccttc atccagtgca ttgactacat    31800
ctgtgtgcgc ctcgcatacc tgagacacca cccgcagtac cgagacagga acattgccca    31860
actcctaaga ctgctctaat catgcataag actgtgatct gcctcctcat cctcctctcc    31920
ctgcccgctc tcgtctcatg ccagcccacc acaaaacctc cacgaaaaag acatgcctcc    31980
tgtcgcttga gccaactgtg aatattccc aaatgctaca atgaaaagag cgagctttcc      32040
gaagcctggc tatatgcggt catgtgtgtc cttgtcttct gcagcacaat cttttgccctc    32100 atgatctacc cccactttga tttgggatgg aatgcggtcg atgccatgaa ttaccctacc    32160
tttcccgcgc ccgatatgat tccactccga caggttgtgg tgcccgtcgc cctcaatcaa    32220
cgccccccat cccctacacc cactgaggtc agctacttta atctaacagg cggagatgac    32280
tgacactcta gatctagaaa tggacggcat cggcaccgag cagcgtctcc tacagaggcg    32340
caagcaggcg gctgaacaag agcgcctcaa tcaggagctc cgagatctca ttaacctgca    32400
ccagtgcaaa aaaggcatct tttgcctggt caagcaggcc gatgtcacct acgagaaaac    32460
cggtaacagc caccgcctca gctacaagct gcccacccaa cgccagaagt tggtgctcat    32520
ggtgggtcag aatcccatca ccgtcaccca gcactcggtg gagaccgagg ggtgtctgca    32580 ctcccccctgt cagggtccgg aagacctctg caccctggta aagaccctgt gtggtcttag    32640
agatttaatc ccctttaact aatcaaacac tggaatcaat aaaaagaatc acttactta     32700 aatcagtcag caggtctctg tccactttat tcagcagcac ctccttcccc tcctcccaac    32760
```

```
tctggtactc caaacgcctc ctggcggcaa acttcctcca caccctgaag ggaatgtcag    32820
attcttgctc ctgtccctcc gcacccacta tcttcatgtt gttgcagatg aagcgcgcca    32880
aaacgtctga cgagaccttc aaccccgtgt accccctatga cacggaaaac gggcctccct    32940
ccgttccttt cctcacccct cccttcgtgt ccccgacgg atttcaagaa agccccccag    33000
gggtcctgtc tctgcgcctg tcagagcccc tggtcacttc ccacggcatg cttgccctga    33060
aaatgggaaa tggcctctcc ctggatgacg ccggcaacct cacctctcaa gatgtcacca    33120
ccgtcacccc tccctcaaa aaaaccaaga ccaacctcag cctccagacc tcagcccccc    33180
tgaccgttag ctctgggtcc ctcaccgtcg cggccgccgc tccactggcg gtggccggca    33240
cctctctcac catgcaatct caggcccct tgacggtgca agatgcaaaa ctgggtctgg    33300
ccacccaggg accctgacc gtgtctgaag gcaaactcac cttgcagaca tcggctccac    33360
tgacggccgc cgacagcagc actctcactg ttggcaccac accgccaatc agtgtgagca    33420
gtggaagtct aggcttagat atggaagacc ccatgtatac tcacgatgga aaactgggaa    33480
tcagaattgg tggcccactg caagtagtag acagcttgca cacactcact gtagttactg    33540
gaaacggaat aactgtagct aacaatgccc ttcaaactaa agttgcgggt gccctgggtt    33600
atgactcatc tggcaatcta gaattgcgag ccgcaggggg tatgcgaatt aacacagggg    33660
gtcaactcat tcttgatgtg gcttatccat ttgatgctca gaacaatctc agccttagac    33720
tcggccaggg accttttatat gtgaacacca atcacaacct agatttaaat tgcaacagag    33780
gtctgaccac aaccaccagc agtaacacaa ccaaacttga aactaaaatc gattcgggct    33840
tagactataa cgccaatggg gctatcattg ctaaacttgg cactgggtta accttttgaca    33900 acacaggtgc cataactgtg ggaaacactg gggatgacaa actcactctg tggactaccc    33960
cagatccctc tcctaactgc agaattcacg cagacaaaga ctgcaagttt actctagtcc    34020
tgactaagtg tggaagtcaa attctggcct ccgtcgccgc cctggcggtg tctggaaacc    34080
tatcatcaat gacaggcact gtctccagcg ttaccatctt tctcagattc gatcagaatg    34140
gagttcttat ggaaaattcc tcgctagaca aggagtactg gaacttcaga aatggtaatt    34200
ccaccaatgc cacccccta accaatgcgg ttgggttcat gcccaacctc agcgcctacc    34260
ccaaaaccca gagtcaaact gcaaaaaaca acattgtaag tgaggtttac ttacatgggg    34320
acaaatctaa acccatgatc cttaccatta cccttaatgg cacaaatgaa tccagtgaaa    34380
ctagtcaggt gagtcactac tccatgtcat ttacatggtc ctgggacagt gggaaatatg    34440
ccaccgaaac ctttgccacc aactctttta ccttctccta cattgctgaa caataaagaa    34500
gcataacgct gctgttcatt tgtaatcaag tgttactttt ttattttca attacaacag    34560 aatcattcaa gtcattctcc atttagctta atagacccca gtagtgcaaa gccccatact    34620
agcttatttc agacagtata aattaaacca tacctttga tttcaacatt aaaaaaatca    34680
tcacaggatc ctagtcgtca ggccgccccc tccttccaa gacacagaat acacaatcct    34740 ctcccccgg ctagctttaa acaacaccat ctgattggtg acagacaggt tcttcgggt    34800 tatattccac acggtctcct ggcgggccag gcgctcgtcg gtgatgctga taaactctcc    34860
cggcagctcg ctcaagttca cgtcgctgtc cagcggctga acctcatgct gacgcggtaa    34920
ctgcgcgacc ggctgctgaa caaacggagg ccgcgcctac aagggggtag agtcataatc    34980
ctccgtcagg atagggcggt tatgcagcag cagcgagcga atcatctgct gccgccgccg    35040
ctccgtccgg caggaaaaca acatcccggt ggtctcctcc gctataatcc gcaccgcccg    35100
```

```
cagcataagc ctcctcgttc tccgcgcgca gcaccgcacc ctgatctcgc tcaggttggc    35160
gcagtaggta cagcacatca ccacgatgtt attcatgatc ccacagtgca aggcgctgta    35220
tccaaagctc atgcccggga ccaccgcccc cacgtgaccg tcgtaccaga agcgcaggta    35280
aatcaagtgc cgacccctca tgaacgtgct ggacataaac atcacctcct tgggcatgtt    35340
gtaattcacc acctcccggt accagatgaa tctctgattg aacacggccc cttccaccac    35400
catcctgaac caagaggcta ggacctgccc accggctatg cactgcaggg aacccggggtt   35460 agaacaatga caatgcagac tccagggctc gtaaccgtgg atcatccggc tgctgaagac    35520
atcgatgttg gcgcaacaca gacacacgtg catacacttc ctcatgatta gcagctcctc    35580
cctcgtcagg atcatatccc aagggataac ccattcttga atcaacgtaa agcccacaga    35640
gcagggaagg cctcgcacat aactcacgtt gtgcatggtt agcgtgttgc attccggaaa    35700
cagcggatga tcctccagta tcgaggcgcg ggtctcgttc tcacagggag gtaaggggc     35760 cctgctgtac ggactgtggc gggacgaccg agatcgtgtt gagcgtaacg tcatggaaaa    35820
gggaacgccg gacgtggtca tacttcttga agcagaacca ggctcgcgcg tgacagacct    35880
ccttgcgtct acggtctcgc cgcttagctc gctccgtgtg atagttgtag tacagccact    35940
ctctcaaagc gtcgaggcga cacctggcgt caggatgtat gtagactccg tcttgcaccg    36000
cggccctgat aatatccacc accgtagaat aagccacacc aagccaagca atacactcgc    36060
tttgcgagcg gcagacagga ggagcgggga gagacggaag gaccatcata aaattttaaa    36120
gaatattttc caatacttcg aaatcaagat ctaccaaatg gcaacgctcc cctccactgg    36180
cgcggtcaaa ctctacggcc aaagaacaga taacggcatt tttaagatgt tcccggacgg    36240
cgtctaaaag acaaaccgct ctcaagtcga cataaattat aagccaaaag ccatcgggat    36300
ccatatccac tatggacgcg ccggcggcgt ccaccaaacc caaataattt tcttctctcc    36360
agcgcagcaa aatcccagta agcaactccc tgatattaag atgaaccatg ccaaaaatct    36420
gttcaagagc gccctccacc ttcattctca agcagcgcat catgattgca aaaattcagg    36480
ttcctcagac acctgtatga gattcaaaac gggaatatta acaaaaattc ctctgtcgcg    36540
cagatccctt cgcagggcaa gctgaacata atcagacagg tctgaacgaa ccagcgaggc    36600
caaatccccg ccaggaacca gatccagaga ccctatgctg attatgacgc gcatactcgg    36660
ggctatgcta accagcgtag cgccgatgta ggcgtgctgc atgggcggcg aaataaaatg    36720
caaggtgctg gttaaaaaat caggcaaagc ctcgcgcaaa aaagctaaga catcataatc    36780
atgctcatgc aggtagttgc aggtaagctc aggaaccaaa acggaataac acacgatttt    36840
cctctcaaac atgacttcca ggtgactgca taagaaaaaa attataaata ataaatatta    36900
attaaataaa ttaaacattg gaagcctgtc tcacaacagg aaaaaccact ctgatcaaca    36960
taagacgggc cacgggcatg cccgcgtgac cataaaaaaa tcggtctccg tgattacaaa    37020
gcaccacaga tagctccccg gtcatgtcgg gggtcatcat gtgagactgt gtatacacgt    37080
ccgggctgtt gacatcggtc aaagaaagaa atcgagctac atagcccgga ggaatcaaca    37140
cccgcacgcg gaggtacagc aaaacggtcc ccataggagg aatcacaaaa ttagtaggag    37200
aaaaaaaaac ataaacacca gaaaaaccct cttgccgagg caaacagcg ccctcccgtt     37260 ccaaaacaac ataaagcgct tccacaggag cagccatgac aaagacccga gtcttaccag    37320
gaaaatttta aaaagattc ctcaacgcag caccagcacc aacacctgtc agtgtaaaat      37380 gccagcgcc gagcgagtat atataggaat aaaaagtgac gtaaacggtt aaagtccaga     37440
aaacgcccag aaaaaccgca cgcgaaccta cgccccgaaa cgaaagccaa aaaacagtga    37500
```

```
acacgccctt tcggcgtcaa cttccgcttt cccacggtac gtcacttccg catatagtaa    37560
aactacgcta cccaacatgc aagaagccac gccccaaaaa acgtcacacc tcccggcccg    37620
ccccgcgccg ccgctcctcc ccgccccgcc ccgctccgcc cacctcatta tcatattggc    37680
ttcaatccaa aataaggtat attattgatg atg                                 37713
```

<210> SEQ ID NO 64
<211> LENGTH: 882
<212> TYPE: DNA
<213> ORGANISM: Adenoviridae - Mastadenovirus

<400> SEQUENCE: 64

```
atgactacgt ccggcgttcc atttggcatg acactacgac caacacgatc tcggttgtct      60
cggcgcactc cgtacagtag ggatcgtcta cctccttttg agacagaaac ccgcgctacc     120
atactggagg atcatccgct gctgcccgaa tgtaacactt tgacaatgca caacgtgagt     180
tacgtgcgag gtcttccctg cagtgtggga tttacgctga ttcaggaatg ggttgttccc     240
tgggatatgg ttctaacgcg ggaggagctt gtaatcctga ggaagtgtat gcacgtgtgc     300
ctgtgttgtg ccaacattga tatcatgacg agcatgatga tccatggtta cgagtcctgg     360
gctctccact gtcattgttc cagtcccggt tccctgcagt gtatagccgg cgggcaggtt     420
ttggccagct ggtttaggat ggtggtggat ggcgccatgt ttaatcagag gtttatatgg     480
taccgggagg tggtgaatta acacatgcca aaagaggtaa tgtttatgtc cagcgtgttt     540 atgagggtc gccacttaat ctacctgcgc ttgtggtatg atggccacgt gggttctgtg     600
gtccccgcca tgagctttgg atacagcgcc ttgcactgtg ggattttgaa caatattgtg     660
gtgctgtgct gcagttactg tgctgattta agtgagatca gggtgcgctg ctgtgcccgg     720
aggacaaggc gccttatgct gcgggcggtg cgaatcatcg ctgaggagac cactgccatg     780
ttgtattcct gcaggacgga gcggcggcg cagcagttta ttcgcgcgct gctgcagcac     840
caccgcccta tcctgatgca cgattatgac tctaccccca tg                        882
```

<210> SEQ ID NO 65
<211> LENGTH: 36571
<212> TYPE: DNA
<213> ORGANISM: Adenoviridae - Mastadenovirus

<400> SEQUENCE: 65

```
catcatcaat aatatacctc aaacttttgg tgcgcgttaa tatgcaaatg agctgtttga      60
atttggggat gcggggcgct gattggctgc gggagcggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc aggaggagt atttgccgag     360 ggccgagtag actttgaccg attacgtggg ggtttcgatt accgtatttt tcacctaaat     420
ttccgcgtac ggtgtcaaag tccggtgttt ttacgtaggc gtcagctgat cgccagggta     480
tttaaacctg cgctcactag tcaagaggcc actcttgagt gccagcgagt agagttttct     540
cctccgcgcc gcgagtcaga tctacacttt gaaagatgag gcacttgaga gacctgcccg     600
gtaatgtttt cctggctact gggaacgaga ttctggaatt ggtggtggac gccatgatgg     660
gtgacgaccc tcccgagccc cctaccccat ttgaggcgcc ttcgctgtac gatttgtatg     720
```

```
atctggaggt ggatgtgccc gagaacgacc ccaacgagga ggcggtgaat gatttgttta    780
gcgatgccgc gctgctggct gccgagcagg ctaatacgga cttttggctca gacagcgatt    840
cttctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca gcgaaccagg gagtgaaagc tgcgggcgaa agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgttttta tgtgtaggtc ccgtctctga cgcagatgag accccccactt   1260
cagagtgcat ttcatcaccc ccagaaattg gcgaggaacc gcccgaagat attattcata   1320
gaccagttgc agtgagagtc accgggcgga gagcagctgt ggagagtttg gatgacttgc   1380
tacagggtgg ggatgaacct ttggacttgt gtacccggaa acgccccagg cactaagtgc   1440
cacacatgtg tgtttactta aggtgatgtc agtatttata gggtgtggag tgcaataaaa   1500
tccgtgttga ctttaagtgc gtggtttatg actcaggggt ggggactgtg ggtatataag   1560
caggtgcaga ccctgtgtggt cagttcagag caggactcat ggagatctgg acggtcttgg   1620
aagactttca ccagactaga cagctgctag agaactcatc ggagggagtc tcttacctgt   1680
ggagattctg cttcggtggg cctctagcta agctagtcta tagggccaag caggattata   1740
aggatcaatt tgaggatatt ttgagagagt gtcctggtat ttttgactct ctcaacttgg   1800
gccatcagtc tcacttaac cagagtattc tgagagccct tgacttttcc actcctggca   1860
gaactaccgc cgcggtagcc ttttttgcct ttatccttga caaatggagt caagaaaccc   1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacccga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agtcacagaa ctgaactgac   2280
tgtcagtctg atgagccgca ggcgcccaga atcggtgtgg tggcatgagg tgcagtcgca   2340
ggggatagat gaggtctcgg tgatgcatga gaaatattcc ctagaacaag tcaagacttg   2400
ttggttggag cctgaggatg attgggaggt agccatcagg aattatgcca agctagctct   2460
gaagccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcaccttta tgaacgcgag   2640
gttcaggggc gatgggtata tgggtggt ctttatggcc aacaccaagc tgacagtgca   2700
cggatgctcc ttctttggct tcaataacat gtgcatcgag gctgggca gtgtttcagt   2760
gagggggatgc agttttcag ccaactggat ggggtcgtg gcagaacca agagcaaggt   2820
gtcagtgaag aaatgcctgt tcgagaggtg ccacctgggg gtgatgagcg agggcgaagc   2880
caaagtcaaa cactgcgcct ctactgagac gggctgcttt gtgctgatca agggcaatgc   2940
ccaagtcaag cataacatga tctgtggggc ctcggatgag cgcggctacc agatgctgac   3000
ctgcgccggt gggaacagcc atatgctggc caccgtgcat gtgacctcgc accccgcaa   3060
gacatggccc gagttcgagc acaacgtcat gacccgctgc aatgtgcacc tgggctcccg   3120
```

```
ccgaggcatg ttcatgccct accagtgcaa catgcaattt gtgaaggtgc tgctggagcc    3180
cgatgccatg tccagagtga gcctgacggg ggtgtttgac atgaatgtgg agatgtggaa    3240
aattctgaga tatgatgaat ccaagaccag gtgccgggcc tgcgaatgcg gaggcaagca    3300
cgccaggctt cagcccgtgt gtgtggaggt gacggaggac ctgcgacccg atcatttggt    3360
gttgtcctgc aacgggacgg agttcggctc cagcgggaa gaatctgact agagtgagta    3420
gtgtttgggg gaggtggagg gcctggatga ggggcagaat gactaaaatc tgtgtttttc    3480
tgcgcagcag catgagcgga agcgcctcct ttgagggagg ggtattcagc ccttatctga    3540
cggggcgtct ccctcctgg gcgggagtgc gtcagaatgt gatgggatcc acggtggacg    3600
gccggcccgt gcagcccgcg aactcttcaa ccctgaccta cgcgaccctg agctcctcgt    3660
ccgtggacga agctgccgcc gcagctgctg cttccgccgc cagcgccgtg cgcggaatgg    3720
ccctgggcgc cggctactac agctctctgg tggccaactc gagttccacc aataatcccg    3780
ccagcctgaa cgaggagaag ctgctgctgc tgatggccca gctcgaggcc ctgacccagc    3840
gcctgggcga gctgacccag caggttgctc agctgcaggc ggagacgcgg ccgcggttg    3900
ccacggtgaa aaccaaataa aaatgaatc aataaataaa cggagacggt tgttgatttt    3960
aacacagagt cttgaatctt tatttgattt ttcgcgcgcg gtaggccctg gaccaccggt    4020
ctcgatcatt gagcacccgg tggatctttt ccaggacccg gtagaggtgg gcttggatgt    4080
tgaggtacat gggcatgagc ccgtcccggg ggtggaggta gctccattgc agggcctcgt    4140
gctcgggggt ggtgttgtaa atcacccagt catagcaggg gcgcagggcg tggtgctgca    4200
cgatgtcctt gaggaggaga ctgatggcca cgggcagccc cttggtgtag gtgttgacga    4260
acctgttgag ctgggaggga tgcatgcggg gggagatgag atgcatcttg gcctggatct    4320
tgagattggc gatgttcccg cccagatccc gccgggggtt catgttgtgc aggaccacca    4380
gcacggtgta tccggtgcac ttggggaatt tgtcatgcaa cttggaaggg aaggcgtgaa    4440
agaatttgga gacgcccttg tggccgccca ggttttccat gcactcatcc atgatgatgg    4500
cgatgggccc gtgggcggcg gcctgggcaa agacgtttcg ggggtcggac acatcgtagt    4560
tgtggtcctg ggtgagctcg tcataggcca ttttaatgaa tttggggcgg agggtgcccg    4620
actggggac gaaggtgccc tcgatcccgg gggcgtagtt gccctcgcag atctgcatct    4680
cccaggcctt gagctcggag gggggatca tgtccacctg cggggcgatg aaaaaaacgg    4740
tttccggggc gggggagatg agctgcgccg aaagcaggtt ccggagcagc tgggacttgc    4800
cgcagccggt ggggccgtag atgaccccga tgaccggctg caggtggtag ttgagggaga    4860
gacagctgcc gtcctcgcgg aggagggggg ccacctcgtt catcatctcg cgcacatgca    4920
tgttctcgcg cacgagttcc gccaggaggc gctcgccccc cagcgagagg agctcttgca    4980
gcgaggcgaa gttttcagc ggcttgagcc cgtcggccat gggcattttg gagagggtct    5040
gttgcaagag ttccagacgg tcccagagct cggtgatgtg ctctagggca tctcgatcca    5100
gcagacctcc tcgtttcgcg ggttggggcg actgcgggag tagggcacca ggcgatgggc    5160
gtccagcgag gccagggtcc ggtccttcca gggtcgcagg gtccgcgtca gcgtggtctc    5220
cgtcacggtg aagggtgcg cgccgggctg ggcgcttgcg agggtgcgct tcaggctcat    5280
ccggctggtc gagaaccgct cccggtcggc gccctgtgcg tcggccaggt agcaattgag    5340
catgagttcg tagttgagcg cctcggccgc gtggcccttg gcgcggagct tacctttgga    5400
agtgtgtccg cagacgggac agaggaggga cttgagggcg tagagcttgg gggcgaggaa    5460
```

```
gacggactcg ggggcgtagg cgtccgcgcc gcagctggcg cagacggtct cgcactccac    5520
gagccaggtg aggtcgggc ggtcgggtc aaaaacgagg tttcctccgt gcttttttgat    5580 gcgtttctta cctctggtct ccatgagctc gtgtccccgc tgggtgacaa agaggctgtc    5640
cgtgtccccg tagaccgact ttatgggccg gtcctcgagc ggggtgccgc ggtcctcgtc    5700
gtagaggaac cccgcccact ccgagacgaa ggcccgggtc caggccagca cgaaggaggc    5760
cacgtgggag gggtagcggt cgttgtccac cagcgggtcc accttctcca gggtatgcaa    5820
gcacatgtcc ccctcgtcca catccaggaa ggtgattggc ttgtaagtgt aggccacgtg    5880
accgggggtc ccggccgggg gggtataaaa ggggcgggc ccctgctcgt cctcactgtc    5940
ttccggatcg ctgtccagga gcgccagctg ttggggtagg tattccctct cgaaggcggg    6000
catgacctcg gcactcaggt tgtcagtttc tagaaacgag gaggatttga tattgacggt    6060
gccgttggag acgcctttca tgagcccctc gtccatctgg tcagaaaaga cgatcttttt    6120
gttgtcgagc ttggtggcga aggagccgta gagggcgttg gagagcagct tggcgatgga    6180
gcgcatggtc tggttctttt ccttgtcggc gcgctccttg gcggcgatgt tgagctgcac    6240
gtactcgcgc gccacgcact tccattcggg gaagacggtg gtgagctcgt cgggcacgat    6300
tctgacccgc cagccgcggt tgtgcagggt gatgaggtcc acgctggtgg ccacctcgcc    6360 gcgcagggc tcgttggtcc agcagaggcg cccgcccttg cgcgagcaga agggggcag    6420 cgggtccagc atgagctcgt cgggggggtc ggcgtccacg tgaagatgc cgggcaggag    6480 ctcggggtcg aagtagctga tgcaggtgcc cagatcgtcc agcgccgctt gccagtcgcg    6540
cacggccagc gcgcgctcgt aggggctgag gggcgtgccc cagggcatgg ggtgcgtgag    6600
cgcggaggcg tacatgccgc agatgtcgta cgtagagg ggctcctcga ggacgccgat    6660
gtaggtgggg tagcagcgcc ccccgcggat gctggcgcgc acgtagtcgt acagctcgtg    6720
cgagggcgcg aggagccccg tgccgaggtt ggagcgttgc ggcttttcgg cgcggtagac    6780
gatctggcgg aagatggcgt gggagttgga ggagatggtg ggcctctgga agatgttgaa    6840
gtgggcgtgg ggcaggccga ccgagtccct gatgaagtgg gcgtaggagt cctgcagctt    6900
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgaggggga cccgtcctga tcggcacggt aagagcccac    7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
tttgaggaac tggtgcttga agtcgaggtc gtcgcagccg ccctgctccc agagttggaa    7260
gtccgtgcgc ttcttgtagg cggggttggg caaagcgaaa gtaacatcgt tgaagaggat    7320
cttgcccgcg cggggcatga agttgcgagt gatgcggaaa ggctgggca cctcggcccg    7380 gttgttgatg acctgggcgg cgaggacgat ctcgtcgaag ccgttgatgt tgtgcccgac    7440
gatgtagagt tccacgaatc gcgggcagcc cttgacgtgg ggcagcttct tgagctcgtc    7500
gtaggtgagc tcggcggggt cgctgagccc gtgctgctcg agggcccagt cggcgacgtg    7560 ggggttggc ctgaggaagg aagtccgagag atccacggcc agggcggtct gcaagcggtc    7620
ccggtactga cggaactgct ggcccacggc catttttcg ggggtgacgc agtagaaggt    7680 gcggggggtcg ccgtgccagc ggtcccactt gagttggagg gcgaggtcgt gggcgagctc    7740
gacgagcggc gggtccccgg agagtttcat gaccagcatg aaggggacga gctgcttgcc    7800
gaaggacccc atccaggtgt aggtttccac atcgtaggtg aggaagagcc tttcggtgcg    7860
```

```
aggatgcgag ccgatgggga agaactggat ctcctgccac cagttggagg aatggctgtt    7920
gatgtgatgg aagtagaaat gccgacggcg cgccgagcac tcgtgcttgt gtttatacaa    7980
gcgtccgcag tgctcgcaac gctgcacggg atgcacgtgc tgcacgagct gtacctgggt    8040
tcctttgacg aggaatttca gtgggcagtg gagcgctggc ggctgcatct ggtgctgtac    8100
tacgtcctgg ccatcggcgt ggccatcgtc tgcctcgatg gtggtcatgc tgacgagccc    8160
gcgcgggagg caggtccaga cctcggctcg acgggtcgg agagcgagga cgagggcgcg     8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggcgg cggcggctcc atgcttagaa gcggcggcga    8460
ggacgcgcgc cgggcggcag gggcggctcg gggcccggag gcaggggcgg caggggcacg    8520
tcggcgccgc gcgcgggcag gttctggtac tgcgcccgga gaagactggc gtgagcgacg    8580
acgcgacggt tgacgtcctg gatctgacgc ctctgggtga aggccacggg acccgtgagt    8640
ttgaacctga aagagagttc gacagaatca atttcggtat cgttgacggc ggcctgccgc    8700
aggatctctt gcacgtcgcc cgagttgtcc tggtaggcga tctcggtcat gaactgctcg    8760
atctcctcct cctgaaggtc tccgcggccg gcgcgctcga cggtggccgc gaggtcgttg    8820
gagatgcggc ccatgagctg cgagaaggcg ttcatgccgg cctcgttcca gacgcggctg    8880
tagaccacgg ctccgttggg gtcgcgcgcg cgcatgacca cctgggcgag gttaagctcg    8940
acgtggcgcg tgaagaccgc gtagttgcag aggcgctggt agaggtagtt gagcgtggtg    9000
gcgatgtgct cggtgacgaa gaagtacatg atccagcggc ggagcggcat ctcgctgacg    9060
tcgcccaggg cttccaagcg ctccatggtc tcgtagaagt ccacggcgaa gttgaaaaac    9120
tgggagttgc gcgccgagac ggtcaactcc tcctccagaa gacggatgag ctcggcgatg    9180
gtggcgcgca cctcgcgctc gaaggccccg gggggctcct cttcttccat ctcctcctcc    9240
tcttcctcct ccactaacat ctcttctact tcctcctcag gaggcggcgg cggggagggg    9300
gccctgcgtc gccggcggcg cacgggcaga cggtcgatga agcgctcgat ggtctccccg    9360
cgccggcgac gcatggtctc ggtgacggcc gcccgtcct cgcggggccg cagcgtgaag      9420
acgccgccgc gcatctccag gtggccgccg gggggtctc cgttgggcag ggagagggcg      9480
ctgacgatgc atcttatcaa ttggcccgta gggactccgc gcaaggacct gagcgtctcg    9540
agatccacgg gatccgaaaa ccgctgaacg aaggcttcga gccagtcgca gtcgcaaggt    9600
aggctgagcc cggtttcttg ttcttcgggt atttggtcgg gaggcgggcg ggcgatgctg    9660
ctggtgatga agttgaagta ggcggtcctg agacggcgga tggtggcgag gagcaccagg    9720
tccttgggcc cggcttgctg gatgcgcaga cggtcggcca tgccccaggc gtggtcctga    9780
cacctggcga ggtccttgta gtagtcctgc atgagccgct ctacgggcac gtcctcctcg    9840
cccgcgcggc cgtgcatgcg cgtgagcccg aacccgcgct gcggctggac gagcgccagg    9900
tcggcgacga cgcgctcggc gaggatggcc tgctggatct gggtgagggt ggtctggaag    9960
tcgtcgaagt cgacgaagcg gtggtaggct ccggtgttga tggtgtagga gcagttggcc    10020
atgacggacc agttgacggt ctggtggccg gggcgcacga gctcgtggta cttgaggcgc    10080
gagtaggcgc gcgtgtcgaa gatgtagtcg ttgcaggtgc gcacgaggta ctggtatccg    10140
acgaggaagt gcggcggcgg ctggcggtag agcggccatc gctcggtggc gggggcgccg    10200
```

-continued

```
ggcgcgaggt cctcgagcat gaggcggtgg tagccgtaga tgtacctgga catccaggtg    10260
atgccggcgg cggtggtgga ggcgcgcggg aactcgcgga cgcggttcca gatgttgcgc    10320
agcggcagga agtagttcat ggtggccgcg gtctggcccg tgaggcgcgc gcagtcgtgg    10380
atgctctaga catacgggca aaaacgaaag cggtcagcgg ctcgactccg tggcctggag    10440
gctaagcgaa cgggttgggc tgcgcgtgta ccccggttcg aatctcgaat caggctggag    10500
ccgcagctaa cgtggtactg gcactcccgt ctcgacccaa gcctgctaac gaaacctcca    10560
ggatacggag gcgggtcgtt ttttggcctt ggtcgctggt catgaaaaac tagtaagcgc    10620
ggaaagcggc cgcccgcgat ggctcgctgc cgtagtctgg agaaagaatc gccagggttg    10680
cgttgcggtg tgccccggtt cgagcctcag cgctcggtgc cggccggatt ccgcggctaa    10740
cgtgggcgtg gctgccccgt cgtttccaag accccttagc cagccgactt ctccagttac    10800
ggagcgagcc cctcttttc ttgtgttttt gccagatgca tcccgtactg cggcagatgc    10860
gcccccaccc tccaccacaa ccgccctac cgcagcagca gcaacagccg gcgcttctgc    10920
ccccgcccca gcagcagcag ccagccacta ccgcggcggc cgccgtgagc ggagccggcg    10980
ttcagtatga cctggccttg aagaggggcg aggggctggc gcggctgggg gcgtcgtcgc    11040
cggagcggca cccgcgcgtg cagatgaaaa gggacgctcg cgaggcctac gtgcccaagc    11100
agaacctgtt cagagacagg agcggcgagg agcccgagga gatgcgcgcc tcccgcttcc    11160
acgcggggcg ggagctgcgg cgcggcctgg accgaaagcg ggtgctgagg gacgaggatt    11220
tcgaggcgga cgagctgacg gggatcagcc ccgcgcgcgc gcacgtggcc gcggccaacc    11280
tggtcacggc gtacgagcag accgtgaagg aggagagcaa cttcaaaaa tccttcaaca    11340
accacgtgcg cacgctgatc gcgcgcgagg aggtgaccct gggcctgatg cacctgtggg    11400
acctgctgga ggccatcgtg cagaacccca cgagcaagcc gctgacggcg cagctgtttc    11460
tggtggtgca gcacagtcgg acaacgaga cgttcaggga ggcgctgctg aatatcaccg    11520
agcccgaggg ccgctggctc ctggacctgg tgaacattct gcagagcatc gtggtgcagg    11580
agcgcgggct gccgctgtcc gagaagctgg cggccatcaa cttctcggtg ctgagcctgg    11640
gcaagtacta cgctaggaag atctacaaga ccccgtacgt gcccatagac aaggaggtga    11700
agatcgacgg gttttacatg cgcatgaccc tgaaagtgct gaccctgagc gacgatctgg    11760
gggtgtaccg caacgacagg atgcaccgcg cggtgagcgc cagccgccgg gcgcgagctga    11820
gcgaccagga gctgatgcac agcctgcagc gggccctgac cggggccggg accgagggg    11880
agagctactt tgacatgggc gcggacctgc gctggcagcc cagccgccgg gccttggaag    11940
ctgccggcgg cgtgccctac gtggaggagg tggacgatga ggaggaggag ggcgagtacc    12000
tggaagactg atggcgcgac cgtatttttg ctagatgcag caacagccac cgccgcctcc    12060
tgatcccgcg atgcgggcgg cgctgcagag ccagccgtcc ggcattaact cctcggacga    12120
ttggacccag gccatgcaac gcatcatggc gctgacgacc cgcaatcccg aagcctttag    12180
acagcagcct caggccaacc ggctctcggc catcctggag gccgtggtgc cctcgcgctc    12240
gaaccccacg cacgagaagg tgctggccat cgtgaacgcg ctggtggaga caaggccat    12300
ccgcggcgac gaggccgggc tggtgtacaa cgcgctgctg agcgcgtgg cccgctacaa    12360
cagcaccaac gtgcagacga acctggaccg catggtgacc gacgtgcgcg aggcggtgtc    12420
gcagcgcgag cggttccacc gcgagtcgaa cctgggctcc atggtggcgc tgaacgcctt    12480
cctgagcacg cagcccgcca acgtgccccg gggccaggag gactacacca acttcatcag    12540
cgcgctgcgg ctgatggtgg ccgaggtgcc ccagagcgag gtgtaccagt cggggccgga    12600
```

```
ctacttcttc cagaccagtc gccagggctt gcagaccgtg aacctgagcc aggctttcaa   12660
gaacttgcag ggactgtggg gcgtgcaggc cccggtcggg gaccgcgcga cggtgtcgag   12720
cctgctgacg ccgaactcgc gcctgctgct gctgctggtg gcgcccttca cggacagcgg   12780
cagcgtgagc cgcgactcgt acctgggcta cctgcttaac ctgtaccgcg aggccatcgg   12840
gcaggcgcac gtggacgagc agacctacca ggagatcacc cacgtgagcc gcgcgctggg   12900
ccaggaggac ccgggcaacc tggaggccac cctgaacttc ctgctgacca accggtcgca   12960
gaagatcccg ccccagtacg cgctgagcac cgaggaggag cgcatcctgc gctacgtgca   13020
gcagagcgtg gggctgttcc tgatgcagga ggggccacg cccagcgccg cgctcgacat   13080
gaccgcgcgc aacatggagc ccagcatgta cgcccgcaac cgcccgttca tcaataagct   13140
gatggactac ttgcatcggg cggccgccat gaactcggac tactttacca cgccatctt   13200 gaacccgcac tggctcccgc cgcccgggtt ctacacgggc gagtacgaca tgcccgaccc   13260
caacgacggg ttcctgtggg atgacgtgga cagcagcgtg ttctcgccgc gtcccaccac   13320
caccgtgtgg aagaaagagg gcggggaccg gcggccgtcc tcggcgctgt ccggtcgcgc   13380
gggtgctgcc gcggcggtgc ccgaggccgc cagccccttt ccgagcctgc cttttcgct   13440 gaacagcgtg cgcagcagcg agctgggtcg gctgacgcgg ccgcgcctgc tgggcgagga   13500
ggagtacctg aacgactcct tgttgaggcc cgagcgcgaa aagaacttcc ccaataacgg   13560
gatagagagc ctggtggaca agatgagccg ctggaagacg tacgcgcacg agcacaggga   13620
cgagccccga gctagcagcg caggcacccg tagacgccag cggcacgaca ggcagcgggg   13680
tctggtgtgg gacgatgagg attccgccga cgacagcagc gtgttggact gggtgggag   13740 tggtggtggt aacccgttcg ctcacttgcg cccccgtatc gggcgcctga tgtaagaatc   13800
tgaaaaataa aaacggtac tcaccaaggc catggcgacc agcgtgcgtt cttctctgtt   13860
gtttgtagta gtatgatgag gcgcgtgtac ccggagggtc ctcctccctc gtacgagagc   13920
gtgatgcagc aggcggtggc ggcggcgatg cagccccgc tggaggcgcc ttacgtgccc   13980
ccgcggtacc tggcgcctac ggaggggcgg aacagcattc gttactcgga gctggcaccc   14040
ttgtacgata ccacccggtt gtacctggtg gacaacaagt cggcggacat cgcctcgctg   14100
aactaccaga cgaccacag caacttcctg accaccgtgg tgcagaacaa cgatttcacc   14160
cccacggagg ccagcaccca gaccatcaac tttgacgagc gctcgcggtg gggcggccag   14220
ctgaaaacca tcatgcacac caacatgccc aacgtgaacg agttcatgta cagcaacaag   14280
ttcaaggcgc gggtgatggt ctcgcgcaag accccaacg gggtcacagt aacagatggt   14340
agtcaggacg agctgaccta cgagtgggtg gagtttgagc tgcccgaggg caacttctcg   14400
gtgaccatga ccatcgatct gatgaacaac gccatcatcg acaactactt ggcggtgggg   14460
cggcagaacg gggtgctgga gagcgacatc ggcgtgaagt tcgacacgcg caacttccgg   14520
ctgggctggg accccgtgac cgagctggtg atgccgggcg tgtacaccaa cgaggccttc   14580
caccccgaca tcgtcctgct gcccggctgc ggcgtggact tcaccgagag ccgcctcagc   14640
aacctgctgg gcatccgcaa gcggcagccc ttccaggagg gcttccagat cctgtacgag   14700
gacctggagg ggggcaacat ccccgcgctc ttggatgtcg aagcctacga gaaaagcaag   14760
gaggatagca ccgccgtggc taccgccgcg actgtggcag atgccactgt caccagggc   14820 gatacattcg ccacccaggc ggaggaagca gccgccctag cggcgaccga tgatagtgaa   14880
agtaagatag ttatcaagcc ggtggagaag gacagcaagg acaggagcta caacgttcta   14940
```

```
tcggatggaa agaacaccgc ctaccgcagc tggtacctgg cctacaacta cggcgacccc   15000
gagaagggcg tgcgctcctg gacgctgctc accacctcgg acgtcacctg cggcgtggag   15060
caagtctact ggtcgctgcc cgacatgatg caagacccgg tcaccttccg ctccacgcgt   15120
caagttagca actacccggt ggtgggcgcc gagctcctgc ccgtctactc caagagcttc   15180
ttcaacgagc aggccgtcta ctcgcagcag ctgcgcgcct tcacctcgct cacgcacgtc   15240
ttcaaccgct tccccgagaa ccagatcctc gtccgcccgc ccgcgcccac cattaccacc   15300
gtcagtgaaa acgttcctgc tctcacagat cacgggaccc tgccgctgcg cagcagtatc   15360
cggggagtcc agcgcgtgac cgtcactgac gccagacgcc gcacctgccc ctacgtctac   15420
aaggccctgg gcgtagtcgc gccgcgcgtc ctctcgagcc gcaccttcta aaaaatgtcc   15480
attctcatct cgcccagtaa taacaccggt tggggcctgc gcgcgcccag caagatgtac   15540
ggaggcgctc gccaacgctc cacgcaacac cccgtgcgcg tgcgcgggca cttccgcgct   15600
ccctggggcg ccctcaaggg tcgcgtgcgc tcgcgcacca ccgtcgacga cgtgatcgac   15660
caggtggtgg ccgacgcgcg caactacacg cccgccgccg cgcccgcctc caccgtggac   15720
gccgtcatcg acagcgtggt ggccgacgcg cgccggtacg cccgcgccaa gagccggcgg   15780
cggcgcatcg cccggcggca ccggagcacc cccgccatgc gcgcggcgcg agccttgctg   15840
cgcagggcca ggcgcacggg acgcagggcc atgctcaggg cggccagacg cgcggcctcc   15900
ggcagcagca gcgccggcag gacccgcaga gcgcggcca cggcggcggc ggcggccatc   15960
gccagcatgt cccgcccgcg gcgcggcaac gtgtactggg tgcgcgacgc cgccaccggt   16020
gtgcgcgtgc ccgtgcgcac ccgccccct cgcacttgaa gatgctgact cgcgatgtt   16080 gatgtgtccc agcggcgagg aggatgtcca agcgcaaata caaggaagag atgctccagg   16140
tcatcgcgcc tgagatctac ggcccgcgg cggcggtgaa ggaggaaaga aagccccgca   16200
aactgaagcg ggtcaaaaag gacaaaaagg aggaggaaga tgtggacgga ctggtggagt   16260
ttgtgcgcga gttcgccccc cggcggcgcg tgcagtggcg cgggcggaaa gtgaaaccgg   16320
tgctgcggcc cggcaccacg gtggtcttca cgcccggcga gcgttccggc tccgcctcca   16380
agcgctccta cgacgaggtg tacggggacg aggacatcct cgagcaggcg ccgagcgtc   16440 tgggcgagtt tgcttacggc aagcgcagcc gcccgcgcc cttgaaagag gaggcggtgt   16500
ccatcccgct ggaccacggc aaccccacgc cgagcctgaa gccggtgacc ctgcagcagg   16560
tgctgccgag cgcggcgccg cgccggggct tcaagcgcga gggcggcgag gatctgtacc   16620
cgaccatgca gctgatggtg cccaagcgcc agaagctgga ggacgtgctg gagcacatga   16680
aggtggaccc cgaggtgcag cccgaggtca aggtgcggcc catcaagcag gtggccccgg   16740
gcctgggcgt gcagaccgtg gacatcaaga tccccacgga gcccatggaa acgcagaccg   16800
agcccgtgaa gcccagcacc agcaccatgg aggtgcagac ggatccctgg atgccggcgc   16860
cggcttccac caccactcgc cgaagacgca agtacggcgc ggccagcctg ctgatgccca   16920
actacgcgct gcatccttcc atcatcccca cgccgggcta ccgcggcacg cgcttctacc   16980
gcggctacag cagccgccgc aagaccacca cccgccgccg ccgtcgccgc acccgccgca   17040
gcaccaccgc gacttccgcc gccgccttgg tgcgagagt gtaccgcagc gggcgtgagc   17100
ctctgaccct gccgcgcgcg cgctaccacc cgagcatcgc catttaactc tgccgtcgcc   17160
tccttgcaga tatggccctc acatgccgcc tccgcgtccc cattacgggc taccgaggaa   17220
gaaagccgcg ccgtagaagg ctgacgggga acgggctgcg tcgccatcac caccggcggc   17280
ggcgcgccat cagcaagcgg ttgggggag gcttcctgcc cgcgctgatc cccatcatcg   17340
```

```
ccgcggcgat cggggcgatc cccggcatag cttccgtggc ggtgcaggcc tctcagcgcc   17400
actgagacac agcttggaaa atttgtaata aaaaaatgga ctgacgctcc tggtcctgtg   17460
atgtgtgttt ttagatggaa gacatcaatt tttcgtccct ggcaccgcga cacggcacgc   17520
ggccgtttat gggcacctgg agcgacatcg gcaacagcca actgaacggg ggcgccttca   17580
attggagcag tctctggagc gggcttaaga atttcgggtc cacgctcaaa acctatggca   17640
acaaggcgtg gaacagcagc acagggcagg cgctgaggga aaagctgaaa gagcagaact   17700
tccagcagaa ggtggtcgat ggcctggcct cgggcatcaa cggggtggtg gacctggcca   17760
accaggccgt gcagaaacag atcaacagcc gcctggacgc ggtcccgccc gcggggtccg   17820
tggagatgcc ccaggtggag gaggagctgc ctcccctgga caagcgcggc gacaagcgac   17880
cgcgtcccga cgcggaggag acgctgctga cgcacacgga cgagccgccc cgtacgagg   17940 aggcggtgaa actgggtctg cccaccacgc ggcccgtggc gcctctggcc accggggtgc   18000
tgaaacccag cagcagcagc agccagcccg cgaccctgga cttgcctcca cctcgccccct   18060 ccacagtggc taagcccctg ccgccggtgg ccgtcgcgtc gcgcgccccc cgaggccgcc   18120
cccaggcgaa ctggcagagc actctgaaca gcatcgtggg tctgggagtg cagagtgtga   18180
agcgccgccg ctgctattaa aagacactgt agcgcttaac ttgcttgtct gtgtgtatat   18240
gtatgtccgc cgaccagaag gaggaggaag aggcgcgtcg ccgagttgca agatggccac   18300
cccatcgatg ctgccccagt gggcgtacat gcacatcgcc ggacaggacg cttcggagta   18360
cctgagtccg ggtctggtgc agttcgcccg cgccacagac acctacttca gtctggggaa   18420
caagtttagg aaccccacgg tggcacccac gcacgatgtg accaccgacc gcagccagcg   18480
gctgacgctg cgcttcgtgc ccgtggaccg cgaggacaac acctactcgt acaaagtgcg   18540
ctacacgctg gccgtgggcg acaaccgcgt gctggacatg gccagcacct actttgacat   18600
ccgcggcgtg ctggatcggg gccccagctt caaaccctac tccggcaccg cctacaacag   18660
cctggctccc aagggagcgc ccaacacctc acagtggata accaaagaca atggaactga   18720
taagacatac agttttggaa atgctccagt cagaggattg acattacag aagagggtct   18780 ccaaatagga accgatgagt caggggtga agcaagaaa attttttgcag acaaaaccta   18840 tcagcctgaa cctcagcttg gagatgagga atggcatgat actattggag ctgaagacaa   18900
gtatggaggc agagcgctta aacctgccac caacatgaaa ccctgctatg ggtctttcgc   18960
caagccaact aatgctaagg gaggtcaggc taaaagcaga accaaggacg atggcactac   19020
tgagcctgat attgacatgg ccttctttga cgatcgcagt cagcaagcta gtttcagtcc   19080
agaacttgtt ttgtatactg agaatgtcga tctggacacc ccggataccc acattattta   19140
caaacctggc actgatgaaa caagttcttc tttcaacttg ggtcagcagt ccatgcccaa   19200
cagacccaac tacattggct tcagagacaa ctttatcggg ctcatgtact acaacagcac   19260
tggcaatatg ggtgtactgg ccggtcaggc ctcccagctg aatgctgtgg tggacttgca   19320
ggacagaaac actgaactgt cctaccagct cttgcttgac tctctgggtg acagaaccag   19380
gtatttcagt atgtggaatc aggcggtgga cagctatgac cccgatgtgc gcattattga   19440
aaatcacggt gtggaggatg aactccccaa ctattgcttc cctttgaatg tgtgggcttt   19500
tacagataca ttccagggaa ttaaggttaa aactacaaat aacggaacag caaatgctac   19560
agagtgggaa tctgataccc tgtcaataa tgctaatgag attgccaagg gcaatccttt   19620
cgccatggag atcaacatcc aggccaacct gtggcggaac ttcctctacg cgaacgtggc   19680
```

```
gctgtacctg cccgactcct acaagtacac gccggccaac atcacgctgc ccaccaacac   19740
caacacctac gattacatga acggccgcgt ggtggcgccc tcgctggtgg acgcctacat   19800
caacatcggg gcgcgctggt cgctggaccc catggacaac gtcaacccct caaccacca    19860 ccgcaacgcg ggcctgcgct accgctccat gctcctgggc aacgggcgct acgtgccctt   19920
ccacatccag gtgccccaaa agttttccgc catcaagagc ctcctgctcc tgcccgggtc   19980
ctacacctac gagtggaact tccgcaagga cgtcaacatg atcctgcaga gctccctcgg   20040
caacgacctg cgcacggacg ggcctccat cgccttcacc agcatcaacc tctacgccac    20100
cttcttcccc atggcgcaca acaccgcctc cacgctcgag gccatgctgc gcaacgacac   20160
caacgaccag tccttcaacg actacctctc ggcggccaac atgctctacc ccatcccggc   20220
caacgccacc aacgtgccca tctccatccc ctcgcgcaac tgggccgcct tccgcggatg   20280
gtccttcacg cgcctcaaga cccgcgagac gccctcgctc ggctccgggt cgacccccta   20340
cttcgtctac tcgggctcca tcccctacct cgacggcacc ttctacctca accacacctt   20400
caagaaggtc tccatcacct tcgactcctc cgtcagctgg cccggcaacg accgcctcct   20460
gacgcccaac gagttcgaaa tcaagcgcac cgtcgacgga gaggggtaca acgtggccca   20520
gtgcaacatg accaaggact ggttcctggt ccagatgctg ccccactaca catcggcta   20580 ccagggcttc tacgtgcccg agggctacaa ggaccgcatg tactccttct ccgcaactt    20640 ccagcccatg agccgccagg tcgtggacga ggtcaactac aaggactacc aggccgtcac   20700
cctggcctac cagcacaaca actcgggctt cgtcggctac ctcgcgccca ccatgcgcca   20760
gggccagccc taccccgcca actaccccta cccgctcatc ggcaagagcg ccgtcgccag   20820
cgtcacccag aaaaagttcc tctgcgaccg ggtcatgtgg cgcatcccct ctccagcaa    20880 cttcatgtcc atgggcgcgc tcaccgacct cggccagaac atgctctacg ccaactccgc   20940
ccacgcgcta gacatgaatt tcgaagtcga ccccatggat gagtccaccc ttctctatgt   21000
tgtcttcgaa gtcttcgacg tcgtccgagt gcaccagccc caccgcggcg tcatcgaggc   21060
cgtctacctg cgcacgccct tctcggccgg caacgccacc acctaagcct cttgcttctt   21120
gcaagatgac ggcctgtggc tccggcgagc aggagctcag ggccatcctc cgcgacctgg   21180
gctgcgggcc ctacttcctg ggcaccttcg acaagcgctt cccgggattc atggccccgc   21240
acaagctggc ctgcgccatc gtcaacacgg ccggccgcga accgggggc gagcactggc    21300 tggccttcgc ctggaacccg cgcacccaca cctgctacct cttcgacccc ttcgggttct   21360
cggacgagcg cctcaagcag atctaccagt tcgagtacga gggcctgctg cgccgcagcg   21420
ccctggccac cgaggaccgc tgcgtcaccc tggaaaagtc cacccagacc gtgcagggtc   21480
cgcgctcggc cgcctgcggg ctcttctgct gcatgttcct gcacgccttc gtgcactggc   21540
ccgaccgccc catggacaag aaccccacca tgaacttgct gacggggtg cccaacggca    21600 tgctccagtc gccccaggtg gaaccccaccc tgcgccgcaa ccaggaggcg ctctaccgct   21660
tcctcaacgc ccactccgcc tactttcgct cccaccgcgc gcgcatcgag aaggccaccg   21720
ccttcgaccg catgaatcaa gacatgtaaa ctgtgtgtat gtgaatgctt tattcataat   21780
aaacagcaca tgtttatgcc accttctctg aggctctgac tttatttaga aatcgaaggg   21840
gttctgccgg ctctcggcgt gccccgcggg cagggatacg ttgcggaact ggtacttggg   21900
cagccacttg aactcgggga tcagcagctt cggcacgggg aggtcgggga acagagtcgct   21960 ccacagcttg cgcgtgagtt gcagggcgcc cagcaggtcg ggcgcggata tcttgaaatc   22020
acagttggga cccgcgttct gcgcgcgaga gttgcggtac acggggttgc agcactggaa   22080
```

```
caccatcagg gccgggtgct tcacgctcgc cagcaccgtc gcgtcggtga tgccctccac    22140
gtccagatcc tcggcgttgg ccatcccgaa gggggtcatc ttgcaggtct gccgcccat     22200 gctgggcacg cagccgggct tgtggttgca atcgcagtgc aggggatca gcatcatctg     22260 ggcctgctcg gagctcatgc ccgggtacat ggccttcatg aaagcctcca gctggcggaa    22320
ggcctgctgc gccttgccgc cctcggtgaa gaagaccccg caggacttgc tagagaactg    22380
gttggtggcg cagccggcgt cgtgcacgca gcagcgcgcg tcgttgttgg ccagctgcac    22440
cacgctgcgc ccccagcggt tctgggtgat cttggcccgg tcggggttct ccttcagcgc    22500
gcgctgcccg ttctcgctcg ccacatccat ctcgatcgtg tgctccttct ggatcatcac    22560
ggtcccgtgc aggcaccgca gcttgccctc ggcttcggtg catccgtgca gccacagcgc    22620
gcagccggtg cactcccagt tcttgtgggc gatctgggag tgcgagtgca cgaagccctg    22680
caggaagcgg cccatcatcg cggtcagggt cttgttgctg gtgaaggtca gcgggatgcc    22740
gcggtgctcc tcgttcacat acaggtggca gatgcgcgcg gacacctcgc cctgctcggg    22800
catcagctgg aaggcggact tcaggtcgct ctccacgcgg taccgctcca tcagcagcgt    22860
catgacttcc atgcccttct cccaggccga aacgatcggc aggctcaggg ggttcttcac    22920
cgttgtcatc ttagtcgccg ccgccgaggt caggggggtcg ttctcgtcca gggtctcaaa   22980
cactcgcttg ccgtccttct cggtgatgcg cacggggggg aagctgaagc ccacggccgc    23040
cagctcctcc tcggcctgcc tttcgtcctc gctgtcctgg ctgatgtctt gcaaaggcac    23100
atgcttggtc ttgcggggtt tctttttggg cggcagaggc ggcggcggag acgtgctggg    23160
cgagcgcgag ttctcgctca ccacgactat ttcttcttct tggccgtcgt ccgagaccac    23220
gcggcggtag gcatgcctct tctggggcag aggcggaggc gacgggctct cgcggttcgg    23280
cgggcggctg gcagagcccc ttccgcgttc gggggtgcgc tcctggcggc gctgctctga    23340
ctgacttcct ccgcggccgg ccattgtgtt ctcctaggga gcaagcatgg agactcagcc    23400
atcgtcgcca acatcgccat ctgccccgc cgccgccgac gagaaccagc agcagcagaa     23460
tgaaagctta accgccccgc cgcccagccc cacctccgac gccgcggccc cagacatgca    23520
agagatggag gaatccatcg agattgacct gggctacgtg acgcccgcgg agcacgagga    23580
ggagctggca gcgcgctttt cagccccgga agagaaccac caagagcagc cagagcagga    23640
agcagagagc gagcagagcc aggctgggct cgagcatggc gactacctga gcggggcaga    23700
ggacgtgctc atcaagcatc tggcccgcca atgcatcatc gtcaaggatg cgctgctcga    23760
ccgcgccgag gtgcccctca gcgtggcgga gctcagccgc gcctacgagc gcaacctctt    23820
ctcgccgcgc gtgcccccca agcgccagcc caacggcacc tgcgagccca cccgcgcct    23880 caacttctac ccggtcttcg cggtgcccga ggccctggcc acctaccacc tcttttttcaa    23940 gaaccaaagg atccccgtct cctgccgcgc caaccgcacc cgcgccgacg ccctgctcaa    24000
cctgggcccc ggcgcccgcc tacctgatat cgcctccttg gaagaggttc ccaagatctt    24060
cgagggtctg ggcagcgacg agactcgggc cgcgaacgct ctgcaaggaa gcggagagga    24120
gcatgagcac cacagcgccc tggtggagtt ggaaggcgac aacgcgcgcc tggcggtcct    24180
caagcgcacg gtcgagctga cccacttcgc ctacccggcg ctcaacctgc cccccaaggt    24240
catgagcgcc gtcatggacc aggtgctcat caagcgcgcc tcgcccctct cggaggagga    24300
gatgcaggac cccgagagct cggacagaggg caagcccgtg gtcagcgacg agcagctggc    24360
gcgctggctg ggagcgagta gcaccccccca gagcctggaa gagcggcgca agctcatgat    24420
```

```
ggccgtggtc ctggtgaccg tggagctgga gtgtctgcgc cgcttcttcg ccgacgcgga    24480
gaccctgcgc aaggtcgagg agaacctgca ctacctcttc aggcacgggt tcgtgcgcca    24540
ggcctgcaag atctccaacg tggagctgac caacctggtc tcctacatgg gcatcctgca    24600
cgagaaccgc ctggggcaga acgtgctgca caccaccctg cgcggggagg cccgccgcga    24660
ctacatccgc gactgcgtct acctgtacct ctgccacacc tggcagacgg gcatgggcgt    24720
gtggcagcag tgcctggagg agcagaacct gaaagagctc tgcaagctcc tgcagaagaa    24780
cctgaaggcc ctgtggaccg ggttcgacga gcgcaccacc gcctcggacc tggccgacct    24840
catcttcccc gagcgcctgc ggctgacgct gcgcaacggg ctgcccgact ttatgagcca    24900
aagcatgttg caaaactttc gctctttcat cctcgaacgc tccgggatcc tgcccgccac    24960
ctgctccgcg ctgccctcgg acttcgtgcc gctgaccttc cgcgagtgcc cccgccgct    25020 ctggagccac tgctacctgc tgcgtctggc caactacctg gcctaccact cggacgtgat    25080
cgaggacgtc agcggcgagg tctgctcga gtgccactgc cgctgcaacc tctgcacgcc    25140
gcaccgctcc ctggcctgca accccagct gctgagcgag acccagatca tcggcacctt    25200
cgagttgcaa ggccccggcg aggagggcaa gggggtctg aaactcaccc cggggctgtg    25260
gacctcggcc tacttgcgca agttcgtgcc cgaggactac catccctccg agatcaggtt    25320
ctacgaggac caatcccagc cgcccaaggc cgagctgtcg gcctgcgtca tcacccaggg    25380
ggccatcctg gcccaattgc aagccatcca gaaatcccgc caagaatttc tgctgaaaaa    25440
gggccacggg gtctacttgg accccagac cggagaggag ctcaaccca gcttccccca    25500 ggatgcccag aggaagcagc aagaagctga aagtggagct gccgctgccg ccggaggatt    25560
tggaggaaga ctgggagagc agtcaggcag aggaggagga gatggaagac tgggacagca    25620
ctcaggcaga ggaggacagc ctgcaagaca gtctggaaga cgaggtggag gaggaggcag    25680
aggaagaagc agccgccgcc agaccgtcgt cctcggcgga gaaagcaagc agcacggata    25740
ccatctccgc tccgggtcgg ggtctcggcg gccgggccca cagtaggtgg gacgagaccg    25800
ggcgcttccc gaaccccacc acccagaccg gtaagaagga gcggcaggga tacaagtcct    25860 ggcggggca caaaaacgcc atcgtctcct gcttgcaagc ctgcggggc aacatctcct    25920 tcacccggcg ctacctgctc ttccaccgcg gggtgaactt ccccgcaac atcttgcatt    25980 actaccgtca cctccacagc ccctactact gttttccaaga agaggcagaa acccagcagc    26040
agcagaaaac cagcagcagc tagaaaatcc acagcggcgg cggcggcagg tggactgagg    26100
atcgcggcga acgagccggc gcagaccggg gagctgagga accggatctt tcccacctc    26160 tatgccatct tccagcagag tcgggggcag gagcaggaac tgaaagtcaa gaaccgttct    26220
ctgcgctcgc tcacccgcag ttgtctgtat cacaagagcg aagaccaact tcagcgcact    26280
ctcgaggacg ccgaggctct cttcaacaag tactgcgcgc tcactcttaa agagtagccc    26340
gcgcccgccc acacacggaa aaaggcggga attacgtcac cacctgcgcc cttcgcccga    26400
ccatcatcat gagcaaagag attcccacgc cttacatgtg gagctaccag ccccagatgg    26460
gcctggccgc cggcgccgcc caggactact ccacccgcat gaactggctc agtgccgggc    26520
ccgcgatgat ctcacgggtg aatgacatcc gcgcccgccg aaaccagata tcctagaac    26580 agtcagcgat caccgccacg ccccgccatc accttaatcc gcgtaattgg cccgccgccc    26640
tggtgtacca ggaaattccc cagcccacga ccgtactact tccgcgagac gcccaggccg    26700
aagtccagct gactaactca ggtgtccagc tggccggcgg cgccgccctg tgtcgtcacc    26760
gccccgctca gggtataaag cggctggtga tccgaggcag aggcacacag ctcaacgacg    26820
```

```
aggtggtgag ctcttcgctg ggtctgcgac ctgacggagt cttccaactc gccggatcgg   26880
ggagatcttc cttcacgcct cgtcaggccg tcctgacttt ggagagttcg tcctcgcagc   26940
cccgctcggg tggcatcggc actctccagt tcgtggagga gttcactccc tcggtctact   27000 tcaaccccctt ctccggctcc cccggccact acccggacga gttcatcccg aacttcgacg   27060
ccatcagcga gtcggtggac ggctacgatt gaatgtccca tggtggcgcg gctgacctag   27120
ctcggcttcg acacctggac cactgccgcc gcttccgctg cttcgctcgg gatctcgccg   27180
agtttgccta ctttgagctg cccgaggagc accctcaggg cccggcccac ggagtgcgga   27240
tcatcgtcga aggggggcctc gactcccacc tgcttcggat cttcagccag cgtccgatcc   27300
tggtcgagcg cgagcaagga cagacccgtc tgaccctgta ctgcatctgc aaccaccccg   27360
gcctgcatga aagtctttgt tgtctgctgt gtactgagta taataaaagc tgagatcagc   27420
gactactccg gacttccgtg tgttcctgaa tccatcaacc agtccctgtt cttcaccggg   27480
aacgagaccg agctccagct ccagtgtaag ccccacaaga agtacctcac ctggctgttc   27540
cagggctccc cgatcgccgt tgtcaaccac tgcgacaacg acggagtcct gctgagcggc   27600
cctgccaacc ttacttttc cacccgcaga agcaagctcc agctcttcca acccttcctc   27660
cccgggacct atcagtgcgt ctcgggaccc tgccatcaca ccttccacct gatcccgaat   27720
accacagcgt cgctccccgc tactaacaac caaactaccc accaacgcca ccgtcgcgac   27780 cttctcctctg aatctaatac cactaccgga ggtgagctcc gaggtcgacc aacctctggg   27840
atttactacg gcccctggga ggtggtgggg ttaatagcgc taggcctagt tgtgggtggg   27900
cttttggctc tctgctacct atacctccct tgctgttcgt acttagtggt gctgtgttgc   27960
tggtttaaga aatggggcag atcacctag tgagctgcgg tgtgctggtg gcggtggtgc   28020
tttcgattgt gggactgggc ggcgcggctg tagtgaagga gaaggccgat ccctgcttgc   28080
atttcaatcc cgacaaatgc cagctgagtt ttcagcccga tggcaatcgg tgcgcggtgc   28140
tgatcaagtg cggatgggaa tgcgagaacg tgagaatcga gtacaataac aagactcgga   28200
acaatactct cgcgtccgtg tggcagcccg gggaccccga gtggtacacc gtctctgtcc   28260
ccggtgctga cggctccccg cgcaccgtga ataatacttt cattttgcg cacatgtgcg   28320 acacggtcat gtggatgagc aagcagtacg atatgtggcc ccccacgaag gagaacatcg   28380
tggtcttctc catcgcttac agcctgtgca cggtgctaat taccgctatc gtgtgcctga   28440
gcattcacat gctcatcgct attcgcccca gaaataatgc cgaaaagag aaacagccat   28500 aacacgtttt ttcacacacc ttgttttttac agacaatgcg tctgttaaat tttttaaaca   28560
ttgtgctcag tattgcttat gcctctggct atgcaaacat acagaaaacc ctctatgtag   28620
gatctgatga tacactagag ggtacccaat cacaagctag ggtttcatgg tatttttata   28680
aaagctcaga taatcctatt actctttgca aaggtgatca ggggcggaca acaaagccgc   28740
ctatcacatt tagctgtacc agaacaaatc tcacgctttt ctcaattaca aaacaatatg   28800 ctggtatttta ttacagtaca aactttcata gtgggcaaga taaatattat actgttaagg   28860
tagaaaatcc taccactcct agaactacca ccaccaccac caccaccacc actactgcga   28920
agcccactaa acctaaaact accaagaaaa ccactgtgaa aactcaaact agaaccacca   28980
caactacaga aaccaccacc agcacaacac ttgctgcaac tacacacaca cactgagc   29040 taaccttaca gaccactaat gatttgatag ccctgttgca aagggggat aacagcacca   29100 cttccaatga ggagataccc aaatccatga ttggcattat tgttgctgta gtggtgtgca   29160
```

```
tgttgatcat cgccttgtgc atggtgtact atgccttctg ctacagaaag cacagactga   29220
acgacaagct ggaacactta ctaagtgttg aattttaatt ttttagaacc atgaagatcc   29280
taggccttt  agtttttct atcattacct ctgctctatg caattctgac aatgaggacg    29340
ttactgtcgt tgtcggatca aattatacac tgaaaggtcc agcgaagggt atgctttcgt   29400
ggtattgctg gtttggaact gacactgatc aaactgagct ttgcaatgca atgaaaggtc   29460
aaataccaac ctcaaaaatt aaacataaat gcaatggtac tgacttagta ctactcaata   29520
tcacgaaatc atatgctggc agctattcat gccctggaga tgatgctgag aacatgattt   29580
tttacaaagt aactgttgtt gatcccacta ctccaccacc caccaccaca actactcaca   29640
ccacacacac agaacaaaca ccagaggcag cagaagcaga gttggccttc caggttcacg   29700
gagattcctt tgctgtcaat accctacac ccgatcatcg gtgtccgggg ctgctagtca    29760
gcggcattgt cggtgtgctt tcgggattag cagtcataat catctgcatg ttcatttttg   29820
cttgctgcta tagaaggctt taccgacaaa aatcagaccc actgctgaac ctctatgttt   29880
aattttttcc agagccatga aggcagttag cgctctagtt ttttgttctt tgattggcat   29940
tgttttttgc aatcctatta ctagagttag ctttattaaa gatgtgaatg ttactgaggg   30000
gggcaatgtg acactggtag gtgtagaggg tgctaaaaac accacctgga caaaatacca   30060
ccttgggtgg aaagatattt gcaattggag tgtcactgtg tacacatgtg agggagttaa   30120
tcttaccatt gtcaatgcca cctcagctca aaatggtaga attcaaggac aaagtgttag   30180
tgtgaccagt gatgggtatt ttacccaaca tactttttatc tatgacgtta agtcataac   30240
actgcctacg cctagcccac ctagcaccac tacacaaaca acccacacta cacagacaac   30300
cacatacagt acatcaaatc agcctaccac cactacagca gcagaggttg ccagctcgtc   30360
tggagttcaa gtggcatttt tgttgttgcc cccatctagc agtccactg ctattaccaa    30420
tgagcagact actgcatttt tgtccactgt cgagagccac accacagcta cctccagtgc   30480
cttctctagc accgccaatc tctcctcgct ttcctctaca ccaatcagtc ccgctactac   30540
tactaccccc gctattcttc ccactcccct gaagcaaaca gacggcggca tgcaatggca   30600
gatcaccctg ctcattgtga tcgggttggt catcctagcc gtgttgctct actacatctt   30660
ctgccgccgc attcccaacg cgcaccgcaa gccggtctac aagcccatca ttgtcgggca   30720
gccggagccg cttcaggtgg aagggggtct aaggaatctt ctcttctctt ttacagtatg   30780
gtgattgaac tatgattcct agacaattct tgatcactat tcttatctgc ctcctccaag   30840
tctgtgccac cctcgctctg gtggccaacg ccagtccaga ctgtattggg cccttcgcct   30900
cctacgtgct cttctgccttc atcacctgca tctgctgctg tagcatagtc tgcctgctta   30960
tcaccttctt ccagttcatt gactggatct ttgtgcgcat cgcctacctg cgccaccacc   31020
cccagtaccg cgaccagcga gtggcgcagc tgctcaggct cctctgataa gcatgcgggc   31080
tctgctactt ctcgcgcttc tgctgttagt gctcccccgt cccgttgacc cccgccccc    31140
cactcagtcc cccgaggagg tccgcaaatg caaattccaa gaaccctgga aattcctcaa   31200
atgctaccgc caaaaatcag acatgcatcc cagctggatc atgatcattg ggatcgtgaa   31260
cattctggcc tgcaccctca tctccttttgt gatttacccc tgctttgact ttggttgaa    31320
ctcgccagag gcgctctatc tcccgcctga acctgacaca ccaccacagc aacctcaggc   31380
acacgcacta ccaccaccac agcctaggcc acaatacatg cccatattag actatgaggc   31440
cgagccacag cgacccatgc tccccgctat tagttacttc aatctaaccg gcggagatga   31500
ctgacccact ggccaacaac aacgtcaacg accttctcct ggacatggac ggccgcgcct   31560
```

```
cggagcagcg actcgcccaa cttcgcattc gccagcagca ggagagagcc gtcaaggagc  31620
tgcaggacgg catagccatc caccagtgca agaaaggcat cttctgcctg gtgaaacagg  31680
ccaagatctc ctacgaggtc acccagaccg accatcgcct ctcctacgag ctcctgcagc  31740
agcgccagaa gttcacctgc ctggtcggag tcaaccccat cgtcatcacc cagcagtcgg  31800
gcgataccaa ggggtgcatc cactgctcct gcgactcccc cgactgcgtc cacactctga  31860
tcaagaccct ctgcggcctc cgcgacctcc tccccatgaa ctaatcaccc acttatccag  31920
tgaaataaaa aaataatcat ttgatttgaa ataaagatac aatcatattg atgatttgag  31980
tttaacaaaa ataaagaatc acttacttga aatctgatac caggtctctg tccatatttt  32040
ctgccaacac cacctcactc ccctcttccc agctctggta ctgcaggccc cggcgggctg  32100
caaacttcct ccacacgctg aaggggatgt caaattcctc ctgcccctca atcttcattt  32160
tatcttctat cagatgtcca aaaagcgcgt ccgggtggat gatgacttcg accccgtcta  32220
cccctacgat gcagacaacg caccgaccgt gcccttcatc aaccccccct tcgtctcttc  32280
agatggattc caagagaagc ccctgggggt gttgtccctg cgactggccg accccgtcac  32340
caccaagaac ggggaaatca ccctcaagct gggagagggg gtggacctcg actcctcggg  32400
aaaactcatc tccaacacgg ccaccaaggc cgctgcccct ctcagttttt ccaacaacac  32460
catttccctt aacatggatc accccttttta cactaaagat ggaaaattag ccttacaagt  32520
ttctccacca ttaaatatac tgagaacaag cattctaaac acactagctt taggttttgg  32580
atcaggttta ggactccgtg gctctgcctt ggcagtacag ttagtctctc cacttacatt  32640
tgatactgat ggaaacataa agcttacctt agacagaggt ttgcatgtta caacaggaga  32700
tgcaattgaa agcaacataa gctgggctaa aggtttaaaa tttgaagatg agccatagc  32760 aaccaacatt ggaaatgggt tagagtttgg aagcagtagt acagaaacag gtgtcgatga  32820
tgcttaccca atccaagtta aacttggatc tggcctagc tttgacagta caggagccat  32880
aatggctggt aacaaagaag acgataaact cactttgtgg acaacacctg atccatcacc  32940
aaactgtcaa atactcgcag aaaatgatgc aaaactaaca ctttgcttga ctaaatgtgg  33000
tagtcaaata ctggccactg tgtcagtctt agttgtagga agtggaaacc taaacccccat  33060 tactggcacc gtaagcagtg ctcaggtgtt tctacgtttt gatgcaaacg gtgttctttt  33120
aacagaacat tctacactaa aaaaatactg ggggtatagg cagggagata gcatagatgg  33180
cactccatat gtcaatgctg taggattcat gcccaattta aaagcttatc caaagtcaca  33240
aagttctact actaaaaata atatagtagg gcaagtatac atgaatggag atgtttcaaa  33300
acctatgctt ctcactataa ccctcaatgg tactgatgac agcaacagta catattcaat  33360
gtcattttca tacacctgga ctaatggaag ctatgttgga gcaacatttg gagctaactc  33420
ttataccttc tcctacatcg cccaagaatg aatactgtat cccaccctgc atgcccaacc  33480
ctcccccacc tctgtctata tggaaaactc tgaaacacaa aataaaataa agttcaagtg  33540
ttttattgat tcaacagttt tacaggattc gagcagttat ttttcctcca ccctcccagg  33600
acatggaata caccaccctc tcccccgca cagccttgaa catctgaatg ccattggtga  33660
tggacatgct tttggtctcc acgttccaca cagtttcaga gcgagccagt ctcgggtcgg  33720
tcagggagat gaaaccctcc gggcactccc gcatctgcac ctcacagctc aacagctgag  33780
gattgtcctc ggtggtcggg atcacggtta tctggaagaa gcagaagagc ggcggtggga  33840
atcatagtcc gcgaacggga tcggccggtg gtgtcgcatc aggccccgca gcagtcgctg  33900
```

```
ccgccgccgc tccgtcaagc tgctgctcag ggggtccggg tccagggact ccctcagcat   33960
gatgcccacg gccctcagca tcagtcgtct ggtgcggcgg gcgcagcagc gcatgcggat   34020
ctcgctcagg tcgctgcagt acgtgcaaca caggaccacc aggttgttca acagtccata   34080
gttcaacacg ctccagccga aactcatcgc gggaaggatg ctacccacgt ggccgtcgta   34140
ccagatcctc aggtaaatca agtggcgccc cctccagaac acgctgccca tgtacatgat   34200
ctccttgggc atgtggcggt tcaccacctc ccggtaccac atcaccctct ggttgaacat   34260
gcagccccgg atgatcctgc ggaaccacag ggccagcacc gccccgcccg ccatgcagcg   34320
aagagacccc gggtcccggc aatgcaatg gaggacccac cgctcgtacc cgtggatcat   34380
ctgggagctg aacaagtcta tgttggcaca gcacaggcac acgctcatgc atctcttcag   34440
cactctcagc cctcgggggg tcaaaaccat atcccagggc acgggaaact cttgcaggac   34500
agcgaagccc gcagaacagg gcaatcctcg cacataactt acattgtgca tggacagggt   34560
atcgcaatca ggcagcaccg ggtgatcctc caccagagaa gcgcgggtct cggtctcctc   34620
acagcgtggt aaggggccg gccgatacgg gtgatggcgg gacgcggctg atcgtgttcg   34680
cgaccgtgtc atgatgcagt tgctttcgga cattttcgta cttgctgaag cagaacctgg   34740
tccgggcgct gcacaccgat cgccggcggc ggtctcggcg cttggaacgc tcggtgttga   34800
agttgtaaaa cagccactct ctcagaccgt gcagcagatc tagggcctca ggagtgatga   34860
agatcccatc atgcctgatg gctctgatca catcgaccac cgtggaatgg gccagaccca   34920
gccagatgat gcaattttgt tgggtttcgg tgacggcggg ggagggaaga acaggaagaa   34980
ccatgattaa cttttaatcc aaacggtctc ggagcacttc aaaatgaagg tcgcggagat   35040
ggcacctctc gcccccgctg tgttggtgga aaataacagc caggtcaaag gtgatacggt   35100
tctcgagatg ttccacggtg gcttccagca aagcctccac gcgcacatcc agaaacaaga   35160
caatagcgaa agcgggaggg ttctctaatt cctcaatcat catgttacac tcctgcacca   35220
tccccagata attttcattt ttccagcctt gaatgattcg aactagttcc tgaggtaaat   35280
ccaagccagc catgataaag agctcgcgca gagcgccctc caccggcatt cttaagcaca   35340
ccctcataat tccaagatat tctgctcctg gttcacctgc agcagattga caagcgggat   35400
atcaaaatct ctgccgcgat ccctgagctc ctccctcagc aataactgta agtactcttt   35460
catatcctct ccgaaatttt tagccatagg accccagga ataagagaag ggcaagccac   35520
attacagata aaccgaagtc cccccagtg agcattgcca aatgtaagat tgaaataagc   35580
atgctggcta gacccggtga tatcttccag ataactggac agaaaatcgg gcaagcaatt   35640
tttaagaaaa tcaacaaaag aaaaatcttc caggtgcacg tttagggcct cgggaacaac   35700
gatggagtaa gtgcaagggg tgcgttccag catggttagt tagctgatct gtaaaaaaac   35760
aaaaaataaa acattaaacc atgctagcct ggcgaacagg tgggtaaatc gttctctcca   35820
gcaccaggca ggcacgggg tctccggcgc gaccctcgta aaaattgtcg ctatgattga   35880
aaaccatcac agagagacgt tcccggtggc cggcgtgaat gattcgagaa gaagcataca   35940
cccccggaac attggagtcc gtgagtgaaa aaagcggcc gaggaagcaa tgaggcacta   36000
caacgctcac tctcaagtcc agcaaagcga tgccatgcgg atgaagcaca aaattttcag   36060
gtgcgtaaaa aatgtaatta ctcccctcct gcacaggcag cgaagctccc gatccctcca   36120
gatacacata caaagcctca gcgtccatag cttaccgagc ggcagcagca gcggcacaca   36180
acaggcgcaa gagtcagaga aaagactgag ctctaacctg tccgcccgct ctctgctcaa   36240
tatatagccc cagatctaca ctgacgtaaa ggccaaagtc taaaaatacc cgccaaataa   36300
```

```
tcacacacgc ccagcacacg cccagaaacc ggtgacacac tcaaaaaaat acgcgcactt    36360
cctcaaacgc ccaaactgcc gtcatttccg ggttcccacg ctacgtcatc aaaacacgac    36420
tttcaaattc cgtcgaccgt taaaaacgtc acccgccccg cccctaacgg tcgccgctcc    36480
cgcagccaat cagcgccccg catccccaaa ttcaaacagc tcatttgcat attaacgcgc    36540
accaaaagtt tgaggtatat tattgatgat g                                  36571
```

RECOMBINANT SIMIAN ADENOVIRAL VECTORS ENCODING A HETEROLOGOUS FIBER PROTEIN AND USES THEREOF

CROSS-REFERENCE TO RELATED APPLICATIONS

This application is a Continuation of application Ser. No. 15/623,723 filed Jun. 15, 2017, now U.S. Pat. No. 10,544,192, which issued Jan. 28, 2020, which is a Divisional of application Ser. No. 13/147,193, filed Sep. 30, 2011, now U.S. Pat. No. 9,718,863 which issued Aug. 1, 2017, which is a U.S. National Phase of PCT/EP2010/000616, entitled "SIMIAN ADENOVIRUS NUCLEIC ACID- AND AMINO ACID-SEQUENCES, VECTORS CONTAINING SAME, AND USES THEREOF," filed on Feb. 2, 2010, which claims the benefit of PCT patent application PCT/EP2009/000672, filed Feb. 2, 2009, U.S. provisional patent application Ser. No. 61/266,342, filed on Dec. 3, 2009, U.S. provisional patent application Ser. No. 61/174,852, filed on May 1, 2009, and U.S. provisional application Ser. No. 61/172,624, filed on Apr. 24, 2009, the disclosures of which are incorporated herein by reference in their entirety for all purposes.

FIELD OF INVENTION

The present invention relates to novel adenovirus strains with an improved seroprevalence. In one aspect, the present invention relates to isolated polypeptides of adenoviral capsid proteins such as hexon, penton and fiber protein and fragments thereof and polynucleotides encoding the same. Also provided is a vector comprising the isolated polynucleotide according to the invention and adenoviruses comprising the isolated polynucleotides or polypeptides according to the invention and a pharmaceutical composition comprising said vector, adenovirus, polypeptide and/or polynucleotide. The invention also relates to the use of the isolated polynucleotides, the isolated polypeptides, the vector, the adenoviruses and/or the pharmaceutical composition for the therapy or prophylaxis of a disease.

BACKGROUND OF THE INVENTION

The adenoviruses (Ads) comprise a large family of double-stranded DNA viruses found in amphibians, avians, and mammals which have a nonenveloped icosahedral capsid structure (Straus, Adenovirus infections in humans; *The Adenoviruses,* 451-498, 1984; Hierholzer et. al, J. Infect. Dis., 158: 804-813, 1988; Schnurr and Dondero, *Intervirology,* 36: 79-83, 1993; Jong et al., *J. Cline Mierobiol.,* 37: 3940-3945: 1999). In contrast to retroviruses, adenoviruses can transduce numerous cell types of several mammalian species, including both dividing and nondividing cells, without integrating into the genome of the host cell.

Generally speaking, adenoviral DNA is typically very stable and remains episomal (e.g., extrachromosomal), unless transformation or tumorigenesis has occurred. In addition, adenoviral vectors can be propagated to high yields in well-defined production systems which are readily amenable to pharmaceutical scale production of clinical grade compositions. These characteristics and their well-characterized molecular genetics make recombinant adenoviral vectors good candidates for use as vaccine carriers. The production of recombinant adenoviral vectors may rely on the use of a packaging cell line which is capable of complementing the functions of adenoviral gene products that have been either deleted or engineered to be nonfunctional.

Presently, two well-characterized human subgroup C adenovirus serotypes (i.e., hAd2 and hAd5) are widely used as the sources of the viral backbone for most of the adenoviral vectors that are used for gene therapy. Replication-defective human adenoviral vectors have also been tested as vaccine carriers for the delivery of a variety of immunogens derived from a variety of infectious agents. Studies conducted in experimental animals (e.g. rodents, canines and nonhuman primates) indicate that recombinant replication-defective human adenoviral vectors carrying transgenes encoding immunogens as well as other antigens elicit both humoral and cell-mediated immune responses against the transgene product. Generally speaking, investigators have reported success using human adenoviral vectors as vaccine carriers in nonhuman experimental systems by either using immunization protocols that utilizes high doses of recombinant adenoviral vectors that are predicted to elicit immune responses; or by using immunization protocols which employ the sequential administration of adenoviral vectors that are derived from different serotypes but which carry the same transgene product as boosting immunizations (Mastrangeli, et. al., Human Gene Therapy, 7: 79-87 (1996).

Viral vectors based on human adenovirus type 5 (Ad5) have been developed for different gene therapy and vaccine applications. Although Ad5-based vectors are extremely efficient in animal models, the presence of a pre-existing immunity in humans against Ads wild type virus has been demonstrated in clinical trials to reduce the efficiency of gene transduction. In particular, a clear reduction of the immunization efficiency was demonstrated in subjects with titers of neutralizing antibodies over 200 enrolled in vaccine clinical trial based on Ad5 vectors. The most extensive characterization of an Ads vectored vaccine was obtained in the HIV vaccine STEP trial conducted by Merck (Moore J P et al. Science. 2008 May 9; 320(5877):753-5). The vaccine study was based on the co-injection of 3 Ad5 vectors expressing different HIV antigens as proof of concept study in subjects with high risk of HIV infection. Surprisingly, the data revealed an increase of HIV infection rate in vaccinated subjects with anti-Ad5 pre-existing immunity rather then a protective effect. Although the mechanism of this paradoxical observation is not clear yet, the results raised additional questions on the safety and efficiency of vectors based on adenovirus of human origin for vaccine application in healthy subjects. Taken together all results obtained so far in different vaccine and gene therapy clinical trials such as the trials with Ad5 vectors increased the need for an adenovirus characterized in a very low or absent pre-existing immunity in humans.

SUMMARY OF THE INVENTION

In a first aspect the present invention provides an isolated polynucleotide that encodes an adenoviral fiber protein or a functional derivative thereof and that is selected from the group consisting of:
(a) a polynucleotide encoding a polypeptide having the amino acid sequence according to any of SEQ ID NOs: 14-19, 50 and 53;
(b) a polynucleotide encoding the functional derivative of a polypeptide according to any of SEQ ID NOs: 14-19, 50 and 53, wherein said functional derivative comprises the deletion, insertion and/or substitution of one or more amino acid residues; and (c) a polynucleotide encoding a functional derivative having an amino acid sequence which is at least 85% identical over its entire length to the amino acid sequence of any of SEQ ID NOs: 14-19, 50 and 53.

In a further aspect the present invention relates to an isolated polynucleotide that encodes an adenoviral hexon protein or a functional derivative thereof and that is selected from the group consisting of:

(a) a polynucleotide encoding a polypeptide having the amino acid sequence according to any of SEQ ID NOs: 20-25, 51 and 54;
(b) a polynucleotide encoding the functional derivative of a polypeptide according to any of SEQ ID NOs: 20-25, 51 and 54, wherein said functional derivative comprises the deletion, insertion and/or substitution of one or more amino acid residues; and
(c) a polynucleotide encoding a functional derivative having an amino acid sequence which is at least 95% identical over its entire length to the amino acid sequence of any of SEQ ID NOs: 20-25, 51 and 54.

Also provided is an isolated polynucleotide that encodes an adenoviral penton protein or a functional derivative thereof and that is selected from the group consisting of:

(a) a polynucleotide encoding a polypeptide having the amino acid sequence according to any of SEQ ID NOs: 26-31, 52 and 55;
(b) a polynucleotide encoding the functional derivative of a polypeptide according to any of SEQ ID NOs: 26-31, 52 and 55, wherein said functional derivative comprises the deletion, insertion and/or substitution of one or more amino acid residues; and
(c) a polynucleotide encoding a functional derivative having an amino acid sequence which is at least 85% identical over its entire length to the amino acid sequence of any of SEQ ID NOs: 26-31, 52 and 55.

The invention also relates to a polynucleotide comprising at least one of the isolated polynucleotide according to the invention as outlined above. The invention further provides an isolated adenoviral capsid polypeptide encoded by the isolated polynucleotide according to the invention or a functional derivative thereof.

In a further aspect the invention provides a vector comprising the isolated polynucleotide according to the invention.

Also provided is a recombinant adenovirus, preferably a replication-incompetent adenovirus, comprising an isolated polynucleotide according to the invention and/or at least one isolated adenoviral capsid polypeptide according to the invention.

A further aspect of the invention is a composition comprising an adjuvant and at least one of the following (i) through (iv):
(i) one or more isolated adenoviral capsid polypeptides according to the invention;
(ii) an isolated polynucleotide according to the invention;
(iii) a vector according to the invention;
(iv) a recombinant adenovirus according to the invention; and, optionally, a pharmaceutically acceptable excipient.

The invention further relates to a cell comprising at least one of the following:
(i) one or more isolated adenoviral capsid polypeptides according to the invention;
(ii) an isolated polynucleotide according to the invention;
(iii) a vector according to the invention;
(iv) a recombinant adenovirus according to the invention.

A further aspect of the invention relates to the use of an isolated adenoviral capsid polypeptide according to the invention; an isolated polynucleotide according to the invention; a vector according to the invention; a recombinant adenovirus according to the invention; and/or the composition according to the invention for the therapy or prophylaxis of a disease.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Throughout this specification and the claims which follow, unless the context requires otherwise, the word "comprise", and variations such as "comprises" and "comprising", will be understood to imply the inclusion of a stated feature, integer or step or group of features, integers or steps but not the exclusion of any other feature, integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or in ra, are hereby incorporated by reference in their entirety. Nothing herein is to be construed as an admission that the invention is not entitled to antedate such disclosure by virtue of prior invention.

In the following, some definitions of terms frequently used in this specification are provided. These terms will, in each instance of its use, in the remainder of the specification have the respectively defined meaning and preferred meanings.

Generally speaking, the adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITRs), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles are activated.

The following Table 1 provides an overview over the sequences referred to herein:

TABLE 1

| Designation/Strain | SEQ ID NO: | Protein | Polynucleotide |
| --- | --- | --- | --- |
| HIV gag | 1 | | HIV gag |
| TLR9 agonist | 2 | | TLR9 agonist |
| HVR7 primer1 | 3 | | HVR7 primer1 |
| HVR7 primer2 | 4 | | HVR7 primer2 |
| HVR1-6fd | 5 | | HVR1-6fd |
| HVR1-6rev | 6 | | HVR1-6rev |
| PanAd1 left end P1 | 7 | | PanAd1 left end P1 |
| PanAd1 left end P2 | 8 | | PanAd1 left end P2 |
| PanAd1 right end P1 | 9 | | PanAd1 right end P1 |
| PanAd1 right end P2 | 10 | | PanAd1 right end P2 |
| pIX P1 | 11 | | pIX P1 |
| pIX P2 | 12 | | pIX P2 |
| Bonobo Adenovirus type 1 (PanAd1). Complete genome | 13 | | Bonobo Adenovirus type 1 (PanAd1). Complete genome |
| ChAd55 | 14 | Fiber | |
| ChAd73 | 15 | Fiber | |
| ChAd83 | 16 | Fiber | |
| ChAd146 | 17 | Fiber | |
| ChAd147 | 18 | Fiber | |
| PanAd1 | 19 | Fiber | |
| ChAd55 | 20 | Hexon | |
| ChAd73 | 21 | Hexon | |
| ChAd83 | 22 | Hexon | |
| ChAd146 | 23 | Hexon | |
| ChAd147 | 24 | Hexon | |
| PanAd1 | 25 | Hexon | |
| ChAd55 | 26 | Penton | |
| ChAd73 | 27 | Penton | |
| ChAd83 | 28 | Penton | |
| ChAd146 | 29 | Penton | |
| ChAd147 | 30 | Penton | |
| PanAd1 | 31 | Penton | |
| ChAd55 | 32 | | Fiber |
| ChAd73 | 33 | | Fiber |
| ChAd83 | 34 | | Fiber |
| ChAd146 | 35 | | Fiber |
| ChAd147 | 36 | | Fiber |
| PanAd1 | 37 | | Fiber |
| ChAd55 | 38 | | Hexon |
| ChAd73 | 39 | | Hexon |
| ChAd83 | 40 | | Hexon |
| ChAd146 | 41 | | Hexon |
| ChAd147 | 42 | | Hexon |
| PanAd1 | 43 | | Hexon |
| ChAd55 | 44 | | Penton |
| ChAd73 | 45 | | Penton |
| ChAd83 | 46 | | Penton |
| ChAd146 | 47 | | Penton |
| ChAd147 | 48 | | Penton |
| PanAd1 | 49 | | Penton |
| PanAd2 | 50 | Fiber | |
| PanAd2 | 51 | Hexon | |
| PanAd2 | 52 | Penton | |
| PanAd3 | 53 | Fiber | |
| PanAd3 | 54 | Hexon | |
| PanAd3 | 55 | Penton | |
| PanAd2 | 56 | | Fiber |
| PanAd2 | 57 | | Hexon |
| PanAd2 | 58 | | Penton |
| PanAd3 | 59 | | Fiber |
| PanAd3 | 60 | | Hexon |
| PanAd3 | 61 | | Penton |
| Bonobo Adenovirus type 2 (PanAd2). Complete genome | 62 | | Bonobo Adenovirus type 2 (PanAd2). Complete genome |
| Bonobo Adenovirus type 3 (PanAd3). Complete genome | 63 | | Bonobo Adenovirus type 3 (PanAd3). Complete genome |
| Ad5 E4 ORF6 coding sequence | 64 | | Ad5 E4 ORF6 coding sequence |
| ChAd83 Complete genome | 65 | | ChAd83 Complete genome |

As used herein, the term "isolated" refers to a molecule which is substantially free of other molecules with which it is naturally associated with. An isolated molecule is thus free of other molecules that it would encounter or contact in a living animal in nature, i.e. outside an experimental setting.

As used herein, the term "protein", "peptide", "polypeptide", "peptides" and "polypeptides" are used interchangeably throughout. These terms refers to both naturally occurring peptides, e.g. naturally occurring proteins and synthesized peptides that may include naturally or non-naturally occurring amino acids. Peptides can be also chemically modified by modifying a side chain or a free amino or carboxy-terminus of a natural or non-naturally occurring amino acid. This chemical modification includes the addition of further chemical moieties as well as the modification of functional groups in side chains of the amino acids, such as a glycosylation. A peptide is a polymer preferably having at least 3, 4, 5, 6, 7, 8, 9, 10, 15, 20, 25, 30, 35, 40, 45, 50, 55, 60, 65, 70, 75, 80, 85, 90, 95, or at least 100 amino acids, most preferably at least 8 or at least 30 amino acids. As the polypeptides and proteins disclosed herein are derived from adenovirus, it is preferred that the molecular mass of an isolated polypeptide or protein as used herein does not exceed 200 kDa.

The term "vector" as used herein includes any vectors known to the skilled person including plasmid vectors, cosmid vectors, phage vectors such as lambda phage, viral vectors such as adenovirus (Ad) vectors (e.g., non-replicating Ad5, Ad11, Ad26, Ad35, Ad49, ChAd3, ChAd4, ChAd5, ChAd7, ChAd8, ChAd9, ChAd10, ChAd11, ChAd16, ChAd17, ChAd19, ChAd20 ChAd22, ChAd24, ChAd26, ChAd30, ChAd31, ChAd37, ChAd38, ChAd44, ChAd63 and ChAd82 vectors or replication-competent Ad4 and Ad7 vectors known from the prior art, e.g. WO 2005/071093 A2), adeno-associated virus (AAV) vectors e.g., AAV type 5), alphavirus vectors e.g., Venezuelan equine encephalitis virus (VEE), sindbis virus (SIN), semliki forest virus (SFV), and VEE-SIN chimeras), herpes virus vectors, measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), and vesicular stomatitis virus vectors, viral like particles, or bacterial spores. A vector also includes expression vectors, cloning vectors and vectors that are useful to generate recombinant adenoviruses in host cells.

The term "expression cassette" refers to a nucleic acid molecule which comprises at least one nucleic acid sequence that is to be expressed, along with its transcription and translation control sequences. Changing the expression cassette will cause the vector in which it is incorporated to direct the expression of a different sequence or combination of sequences. Because of the restriction sites being preferably engineered to be present at the 5' and 3' ends, the cassette can be easily inserted, removed, or replaced with another cassette. Preferably, an expression cassette includes cis-regulating elements for efficient expression of a given gene, such as promoter, initiation-site and/or polyadenylation-site, as further described below.

The term "antibody" refers to both monoclonal and polyclonal antibodies, i.e., any immunoglobulin protein or portion thereof which is capable of binding an antigen or hapten. Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) variants, single-chain antibodies (scFv), chimeric antibodies, humanized antibodies, diabodies, and polypeptides that contain at least a portion of an antibody that is sufficient to confer specific antigen binding to the polypeptide.

The administration of an immunogen/antigen for inducing/generating an immune response in a mammal in the context of the present invention is termed "priming", and the administration of an immunogen/antigen for enhancing an immune response against said immunogen/antigen, e.g. a particular pathogen (such as a virion or a virus pathogen, an antigen of a pathogenic bacterium or a tumorantigen) in a mammal is termed "boosting". The phrase "heterologous prime-boost" means that the vector for inducing/generating an immune response (priming) in a mammal and the vector for enhancing the immune response (boosting) in a mammal are different. "Heterologous prime-boost" is useful if a subject, e.g. patient has developed antibodies against a first vector and a boosting is required. Thus, in a preferred embodiment of heterologous prime-boost two different adenoviruses may be used, e.g. for vaccination and/or gene therapy. In this context, a first and a second adenovirus are sufficiently different, if the antibody response induced during priming by the first adenovirus does not prevent more than 70% or preferably more than 80% of the second adenovirus particles administered for boosting from entering the nucleus of cells of the animal that has been subjected to priming and boosting.

The term "replication-competent" recombinant adenovirus (AdV) refers to an adenovirus which can replicate in a host cell in the absence of any recombinant helper proteins comprised in the cell. Preferably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-defective" recombinant AdV refers to an adenovirus that has been rendered to be incapable of replication because it has been engineered to comprise at least a functional deletion, i.e. a deletion which impairs the function of a gene without removing it entirely, e.g. introduction of artificial stop codons, deletion or mutation of active sites or interaction domains, mutation or deletion of a regulatory sequence of a gene etc., or a complete removal of a gene encoding a gene product that is essential for viral replication, such as one or more of the adenoviral genes selected from E1, E2, E3 and E4. The recombinant chimpanzee adenoviral vectors of the invention are preferably replication-defective.

The term "identity" or "identical" in the context of polynucleotide, polypeptide or protein sequences refers to the number of residues in the two sequences that are identical when aligned for maximum correspondence. Specifically, the percent sequence identity of two sequences, whether nucleic acid or amino acid sequences, is the number of exact matches between two aligned sequences divided by the length of the shorter sequence and multiplied by 100. Alignment tools that can be used to align two sequences are well known to the person skilled in the art and can, for example, be obtained on the World Wide Web, e.g., ClustalW (www.ebi.ac.uk/clustalw) or Align (http://www.ebi.ac.uk/emboss/align/index.html). The alignments between two sequences may be carried out using standard settings, for Align EMBOSS::needle preferably: Matrix: Blosum62, Gap Open 10.0, Gap Extend 0.5. Those skilled in the art understand that it may be necessary to introduce gaps in either sequence to produce a satisfactory alignment. The "best sequence alignment" between two polypeptides is defined as the alignment that produces the largest number of aligned identical residues.

Adenoviruses

An adenovirus (Ad) is a non-enveloped, icosahedral virus that has been identified in several avian and mammalian hosts. Human adenoviruses (hAds) belong to the Mastadenovirus genus which includes all known human and many Ads of animal (e.g., bovine, porcine, canine, marine, equine, simian and ovine) origin. Human adenoviruses are generally divided into six subgroups (A-F) based on a number of biological, chemical, immunological and structural criteria which include hemagglutination properties of rat and rhesus monkey erythrocytes, DNA homology, restriction enzyme cleavage patterns, percentage G+C content and oncogenicity (Straus, 1984, in *The Adenoviruses*, ed. H. Ginsberg, pps. 451-498, New York: Plenus Press, and Horwitz, 1990; in *Virology*, eds. B. N. Fields and D. M. Knipe, pps. 1679-1721).

The adenoviral virion has an icosahedral symmetry and, depending on the serotype, a diameter of 60-90 nm. The icosahedral capsid comprises three major proteins, hexon (II), penton base (III) and a knobbed fiber (IV) protein (W. C. Russel, J. Gen. Virol., 81: 2573-2604 (2000)). One aspect of the preexisting immunity that is observed in humans is humoral immunity, which can result in the production and persistence of antibodies that are specific for adenoviral proteins. The humoral response elicited by adenovirus is mainly directed against the three major structural proteins: hexon, penton and fiber.

To date, 51 distinct human adenovirus serotypes have been recognized and grouped into subgroups on the basis of their hemagglutination properties and biophysical and biochemical criteria. Published reports have established that titers comprising antibodies against multiple serotypes are common (Dambrosio, E. (1982) J. Hyg. (London) 89: 209-219) and that a substantial portion of the titers have neutralizing activity.

As mentioned, recombinant adenoviruses are useful in gene-therapy and as vaccines. Viral vectors based on chimpanzee adenovirus represent an alternative to the use of human derived Ad vectors for the development of genetic vaccines (Farina S F, J Virol. 2001 December; 75(23): 11603-13; Fattori E, Gene Ther. 2006 July; 13(14):1088-96). Adenoviruses isolated from chimpanzees are closely related to adenoviruses isolated from humans as demonstrated by their efficient propagation in cells of human origin. However, since human and chimp adenoviruses are close relatives, a serologic cross reactivity between the two virus species can be expected.

This presumption has been confirmed when chimpanzee adenoviruses were isolated and characterized. Nevertheless, adenovirus isolates from chimpanzees showed a reduced cross reactivity with the common serotypes of human adenovirus epitopes. Thus, a chimpanzee adenovirus (also abbreviated herein as "ChAd" for common chimpanzee adenovirus and "PanAd" for bonobo chimpanzee adenovirus) provides a basis for reducing the adverse effects associated with the preexisting immunity in humans to common serotypes of human adenoviruses. However, a low to intermediate neutralizing titer against chimp adenoviruses isolated so far is detected in subsets of human sera and, thus, all known serotypes of chimpanzee adenoviruses are still neutralized by human blood sera to some degree.

The present invention comprises the unexpected finding that novel chimpanzee adenovirus strains could be isolated, namely ChAd55, ChAd73, ChAd83, ChAd146, ChAd147 isolated from the Common Chimpanzee (Pan troglodytes) and PanAd1, PanAd2 and PanAd3 isolated from bonobos (Pan paniseus). All these novel strains show no measurable seroprevalence in humans, i.e. these adenovirus strains represent an exception among chimpanzee adenoviruses described so far in that all human sera tested completely negative for the presence of neutralizing antibodies. In this context, a neutralizing antibody refers to an antibody that binds to an epitope of the adenovirus and prevents it from producing a productive infection in a host cell or prevents the transduction of a target cell with a replication incompentent vector expressing a transgene, e.g. the adenovirus DNA is capable of entering a host cell. While neutralizing antibodies were observed for all prior-art chimpanzee-derived adenoviruses, the novel adenovirus types ChAd55, ChAd73, ChAd83, ChAd146, ChAd147 PanAd1, PanAd2 and PanAd3 are characterized by a complete absence of preexisting neutralizing antibody in humans directed against these adenovirus types. Thus, these adenoviruses provide a valuable medical tool that can e.g. be used for immunization and/or gene therapy.

As detailed further below, the invention provides, in one aspect, novel sequences of adenovirus capsid proteins that represent the most surface exposed adenovirus epitopes, namely hexon, penton and fiber protein. As already mentioned, no neutralizing antibodies specific for the viruses according to the invention are comprised in human blood sera. Thus, one advantage of the aforementioned novel chimpanzee hexon, penton and fiber protein sequences is that the sequences of these proteins can be used to enhance prior art adenoviruses, which have been engineered for e.g. medical purposes. For example, the capsid proteins or functional fragments thereof of the present invention can be used to e.g. replace/substitute one or more of the major structural capsid proteins or functional fragments thereof, respectively, of a different adenovirus, e.g. a prior art adenovirus, to obtain improved recombinant adenoviruses with a reduced seroprevalence in humans. As the novel adenoviruses of the invention but also adenoviruses which have been re-engineered as described will not encounter any significant inhibitory immune response in humans when administered, their overall transduction efficiency and infectivity will be enhanced. Thus, such improved adenoviruses are expected to be, e.g., more effective vaccines as the entry into host cells and the expression of the antigen cassette will not be hampered by any significant titer of neutralizing antibodies. In addition, as shown in the examples, a potent immune response against HIV gag was elicited even in naïve mice vaccinated with a recombinant HIV-gag encoding adenovirus that comprises hexon, penton and fiber proteins of the ChAd55, ChAd73, ChAd83, ChAd146, ChAd147, PanAd1, PanAd2 or PanAd3 isolate. The immune response elicited by ChAd55-gag, ChAd73-gag, ChAd83-gag, ChAd146-gag, ChAd147-gag, PanAd1-gag, PanAd2-gag and PanAd3-gag adenoviruses is comparable with the response observed with the most potent vectors developed so far based on recombinant human Ad5 vector of the prior art expressing HIV gag protein (see data of an ELIspot assay in FIG. 5A, 5B, 5C).

As mentioned before, the humoral response elicited by an adenovirus is mainly directed against the three major adenoviral structural proteins: hexon, penton and fiber, all of which comprise polypeptide sequences that are part of the adenoviral capsid and that are exposed to the outside of the virus particle (see also: Madisch I, et al., J. Virol. 2005 December; 79(24):15265-76; and also: Madisch I, et al., J Virol. 2007 August; 81(15):8270-81; and Pichla-Gollon S L, et al., J. Virol. 2007 February; 81(4): 1680-9).

As depicted in the multiple sequence alignment shown in FIG. 1, the novel adenovirus isolates of the group of PanAd1, PanAd2, PanAd3, ChAd55, ChAd73, ChAd83, ChAd146 and ChAd147 of the present invention share a very similar hexon protein sequence. In the alignment also the hypervariable regions (HVRs) are labeled which occur in loops at the top of the hexon molecule that lie on the exterior of the virion and cover a large amount of its surface (see Jophn J. Rux et. Al, J. of Virology, September 2003, vol. 77, no. 17), The sequence relatedness of the further capsid proteins fiber and penton of the novel chimpanzee adenoviruses is provided in FIGS. 2 and 3, respectively. All three structural capsid proteins are expected to contribute to the low seroprevalence and can, thus, be used independently from each other or in combination to suppress the affinity of an adenovirus to preexisting neutralizing antibodies, e.g. to manufacture a recombinant chimeric adenovirus with a reduced seroprevalence.

Thus, in a first aspect the invention provides an isolated polynucleotide that encodes an adenoviral fiber protein or a functional derivative thereof and that is selected from the group consisting of:

(a) a polynucleotide encoding a polypeptide having the amino acid sequence according to any of SEQ ID NOs: 14-19, 50 and 53; i.e. SEQ ID NO: 14, 15, 16, 17, 18, 19, 50 or 53;

(b) a polynucleotide encoding the functional derivative of a polypeptide according to any of SEQ ID NOs: 14-19, 50 and 53, i.e. SEQ ID NO: 14, 15, 16, 17, 18, 19, 50 o 53; wherein said functional derivative comprises the deletion, insertion and/or substitution of one or more amino acid residues; and (c) a polynucleotide encoding a functional derivative having an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of any of SEQ ID NOs: 14-19, 50 and 53, i.e. SEQ ID NO: 14, 15, 16, 17, 18, 19, 50 or 53.

By "adenoviral fiber protein" is meant the knobbed fiber (IV) protein comprised in an adenovirus. In a preferred embodiment, the isolated polynucleotide comprised in the first aspect of the invention and preferred embodiments thereof described below encodes a fiber protein or a functional derivative thereof that has the same function as a fiber protein or a fragment thereof in an infectious adenovirus virion. Thus, a recombinant adenovirus comprising said fiber or functional fiber derivative preferably as a capsid protein is capable of entering a host cell. It can be easily determined if a recombinant adenovirus can enter a host cell. For example, after contacting a host cell with the adenovirus, the recombinant host cell can be washed and lysed and it can be determined whether adenoviral RNA and/or DNA is found in the host cell using, e.g. an appropriate hybridization probe specific for adenoviral RNA andlor DNA. Alternatively or additionally, the host cell after having been brought into contact with the recombinant adenovirus may be washed, lysed and probed with adenovirus specific antibodies, e.g. using a Western blot. In yet another alternative, it is observed, e.g. in vivo, whether the host cell expresses a gene product, for example a fluorescent protein upon infection with a recombinant adenovirus that comprises a suitable expression cassette to express the gene product in the host cell.

It is further preferred that the fiber protein and functional derivative thereof has an affinity to an adenoviral penton protein, such as to SEQ ID NOs: 26-31, 52 and/or 55. The average skilled person is well aware of how to test protein-protein affinities. To determine if a first protein is capable of binding a second protein, such as a penton protein of a chimpanzee derived adenovirus, he may use, for example, a genetic yeast two-hybrid assay or a biochemical assay such as a pull-down, an enzyme-linked immunosorbent assay (ELISA), a fluorescence-activated cell sorting (FACS)-based assay or a Plasmon resonance assay. When using pull-down or Plasmon resonance assays, it is useful to fuse at least one of the proteins to an affinity tag such as HIS-tag, GST-tag or other, as is well known in the art of biochemistry. An adenoviral fiber protein in its glycosylated form is further capable of trimerizing. Thus, it is also preferred that the fiber protein or a fragment thereof encoded by the polynucleotide according to the first aspect of the invention is capable of being glycosylated and/or of forming a trimer.

As used throughout this application, the phrase "functional derivative" of a protein or polypeptide generally refers to a modified version of the protein or polypeptide, e.g. one or more amino acids of the protein or polypeptide may be deleted, inserted, modified and/or substituted. The derivative is functional, if, as mentioned also above, a chimeric adenovirus comprising the functional derivative in its capsid is capable of infecting a host cell. Furthermore, in the context of a "functional derivative", an insertion refers to the insertion of one or more amino acids into the original polypeptide or protein. It is preferred that a functional derivative does not comprise more than 1, 2, 3, 4, 5, 6, 7, 8, 9, 10, 15, 20, 25, 30, 35, 40, 45, 50, 60, 70, 80, 90 or more than 100 amino acid changes (i.e. deleted, inserted, modified and/or substituted amino acids). In another embodiment, it is preferred that not more than 1%, 2%, 3%, 4%, 5%, 6%, 7%, 8%, 9%, 10%, 15%, or more than 20% (most preferably not more than 5%) of all amino acids of the protein or polypeptide are changed (i.e. are deleted, inserted, modified and/or substituted amino acids). Amino acids of the protein or polypeptide may also be modified, e.g. chemically modified. For example, the side chain or a free amino or carboxy-terminus of an amino acid of the protein or polypeptide may be modified by e.g. glycosylation, amidation, phosphoration, uhiquitination, e.t.c. The chemical modification can also take place in vivo, e.g. in a host-cell, as is well known in the art. For examples, a suitable chemical modification motif, e.g. glycosylation sequence motif present in the amino acid sequence of the protein will cause the protein to be glycosylated. A substitution in a derivative may be a conservative or a non-conservative substitution, preferably a conservative substitution. In some embodiments, a substitution also includes the exchange of a naturally occurring amino acid with a not naturally occurring amino acid. A conservative substitution comprises the substitution of an amino acid with another amino acid having a chemical property similar to the amino acid that is substituted. Preferably, the conservative substitution is a substitution selected from the group consisting of:
(i) a substitution of a basic amino acid with another, different basic amino acid;
(ii) a substitution of an acidic amino acid with another, different acidic amino acid;
(iii) a substitution of an aromatic amino acid with another, different aromatic amino acid;
(iv) a substitution of a non-polar, aliphatic amino acid with another, different non-polar, aliphatic amino acid; and
(v) a substitution of a polar, uncharged amino acid with another, different polar, uncharged amino acid.

A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

If a functional derivative comprises a deletion, then in the derivative one or several amino acids that are present in the reference polypeptide or protein sequence have been removed. The deletion may, however, not be so extensive that the derivative comprises less than 200 amino acids in total.

Means for determining sequence identity have been described already above. In addition, the determination of percent identity between two sequences can also be determined using the mathematical algorithm of Karlin and Altschul (1993) Proc. Natl. Acad. Sci. USA 90: 5873-5877. Such an algorithm is also incorporated into the BLASTN and BLASTP programs of Altschul et al. (1990) J. Mol. Biol. 215: 403-410. When utilizing BLASTN and BLASTP it is preferred that the default parameters of these programs are used.

As mentioned before, the hyper variable domains of an adenoviral hexon protein are exposed to the outside of the adenovirus. Thus, these regions of the adenoviral capsid can be recognized and bound by neutralizing antibodies. Thus, an adenovirus with a capsid comprising a hexon protein derived from one of the novel adenovirus isolates of the present invention will exhibit an improved, i.e. smaller seroprevalence in humans. Thus, in a second aspect the invention provides an isolated polynucleotide that encodes an adenoviral hexon protein or a functional derivative thereof and that is selected from the group consisting of:
(a) a polynucleotide encoding a polypeptide having the amino acid sequence according to any of SEQ ID NOs: 20-25, 51 and 54, i.e. SEQ ID NO: 20, 21, 22, 23, 24, 25, 51 or 54;
(b) a polynucleotide encoding the functional derivative of a polypeptide according to any of SEQ ID NOs: 20-25, 51 and 54, i.e. SEQ ID NO: 20, 21, 22, 23, 24, 25, 51 or 54 wherein said functional derivative comprises the deletion, insertion and/or substitution of one or more amino acid residues; and (c) a polynucleotide encoding a functional derivative having an amino acid sequence which is at least 95%, 98%, 99%, 99.5%, 99.9% or at least 99.95%, more preferably at least 98% and most preferable at least 99.95% identical over its entire length to the amino acid sequence of any of SEQ ID NOs: 20-25, 51 and 54, i.e. SEQ ID NO: 20, 21, 22, 23, 24, 25, 51 or 54.

In a preferred embodiment, the isolated polynucleotide comprised in the second aspect of the invention and preferred embodiments thereof described below encodes a hexon protein or a functional derivative thereof that has the same function as a hexon protein or a functional fragment thereof in an inti ctious adenovirus virion. Thus, a recombinant adenovirus comprising said hexon or functional derivative thereof preferably as a capsid protein is capable of entering a host cell. One suitable method for generating functional derivatives of a hexon protein is described in U.S. Pat. No. 5,922,315, which is incorporated by reference. In this method, at least one loop region of the adenovirus hexon is changed with at least one loop region of another adenovirus serotype. For example, a loop region of a hexon protein of the invention can be used to substitute the corresponding hexon loop of an adenovirus of the prior art to generate an improved hybrid adenovirus. Analogously also derivatives of penton and fiber proteins of the invention can be generated.

In a third aspect, the invention provides an isolated polynucleotide that encodes an adenoviral penton protein or a functional derivative thereof and that is selected from the group consisting of:

(a) a polynucleotide encoding a polypeptide having the amino acid sequence according to any of SEQ ID NOs: 26-31, 52 and 55, i.e. SEQ ID NO: 26, 27, 28, 29, 30, 31, 52 or 55;

(b) a polynucleotide encoding the functional derivative of a polypeptide according to any of SEQ ID NOs: 26-31, 52 and 55, i.e. SEQ ID NO: 26, 27, 28, 29, 30, 31, 52 or 55; wherein said functional derivative comprises the deletion, insertion and/or substitution of one or more amino acid residues; and (c) a polynucleotide encoding a functional derivative having an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of any of SEQ ID NOs: 26-31, 52 and 55, i.e. SEQ ID NO: 26, 27, 28, 29, 30, 31, 52 or 55.

It is preferred that the penton protein and functional derivative thereof has an affinity to an adenoviral fiber protein, such as to SEQ ID NOs: 14-19, 50 and/or 53. The average skilled person is well aware of how to test protein-protein affinities as described above. By "adenoviral penton protein" is meant the penton base (III) protein comprised in an adenovirus. An adenoviral penton protein is characterized in that it localizes to the corners of the icosahedral symmetry of the capsid. As mentioned, in a preferred embodiment of the polynucleotide of the first, second and/or third aspect of the invention and preferred embodiments thereof described herein below, the polynucleotide encodes one or more polypeptides, wherein a recombinant adenovirus comprising said one or more polypeptides preferably as a capsid protein(s) is capable to infect, i.e. enter a host cell.

In the following, preferred embodiments of the first, second and third aspect of the invention will be specified for each of the novel chimpanzee adenovirus isolates disclosed herein.

Adenovirus ChAd55

In a preferred embodiment of the first aspect of the invention, the isolated polynucleotide encodes an adenoviral fiber protein with an amino acid sequence according to SEQ ID NO: 14 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 14.

In a preferred embodiment of the second aspect of the invention, the isolated polynucleotide encodes an adenoviral hexon protein with an amino acid sequence according to SEQ ID NO: 20 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 20.

In a preferred embodiment of the third aspect of the invention, the isolated polynucleotide encodes an adenoviral penton protein with an amino acid sequence according to SEQ ID NO: 26 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99.9% identical over its entire length to the amino acid sequence of SEQ ID NO: 26.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus ChAd73

In a preferred embodiment of the first aspect of the invention, the isolated polynucleotide encodes an adenoviral fiber protein with an amino acid sequence according to SEQ ID NO: 15 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99% or at least 99.9% more preferably at least 99% and most preferable at least 99.9% identical over its entire length to the amino acid sequence of SEQ ID NO: 15.

In a preferred embodiment of the second aspect of the invention, the isolated polynucleotide encodes an adenoviral hexon protein with an amino acid sequence according to SEQ ID NO: 21 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 21.

In a preferred embodiment of the third aspect of the invention, the isolated polynucleotide encodes an adenoviral penton protein with an amino acid sequence according to SEQ ID NO: 27 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 27.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus ChAd83

In a preferred embodiment of the first aspect of the invention, the isolated polynucleotide encodes an adenoviral fiber protein with an amino acid sequence according to SEQ ID NO: 16 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has the amino acid sequence of SEQ ID NO: 16.

In a preferred embodiment of the second aspect of the invention, the isolated polynucleotide encodes an adenoviral hexon protein with an amino acid sequence according to SEQ ID NO: 22 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 22.

In a preferred embodiment of the third aspect of the invention, the isolated polynucleotide encodes an adenoviral penton protein with an amino acid sequence according to SEQ ID NO: 28 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 28.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 65 or to a sequence that consists of SEQ ID NO: 65 but lacks any of the genomic regions E1A, E1B, E2A, E2B, E3 and/or E4 of SEQ ID NO: 65, most preferably that lacks the genomic regions E1, E3 and E4 of SEQ ID NO: 65.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the ChAd83 genome as set out in SEQ ID NO: 65. It is preferred that the polynucleotide also comprises sequences required for packaging of the polynucleotide into an adenoviral particle.

Adenovirus ChAd146

In a preferred embodiment of the first aspect of the invention, the isolated polynucleotide encodes an adenoviral fiber protein with an amino acid sequence according to SEQ ID NO: 17 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has the amino acid sequence of SEQ ID NO: 17.

In a preferred embodiment of the second aspect of the invention, the isolated polynucleotide encodes an adenoviral hexon protein with an amino acid sequence according to SEQ ID NO: 23 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 23.

In a preferred embodiment of the third aspect of the invention, the isolated polynucleotide encodes an adenoviral penton protein with an amino acid sequence according to SEQ ID NO: 29 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 99% identical over its entire length to the amino acid sequence of SEQ ID NO: 29.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus ChAd147

In a preferred embodiment of the first aspect of the invention, the isolated polynucleotide encodes an adenoviral fiber protein with an amino acid sequence according to SEQ ID NO: 18 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 18.

In a preferred embodiment of the second aspect of the invention, the isolated polynucleotide encodes an adenoviral hexon protein with an amino acid sequence according to SEQ ID NO: 24 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% identical over its entire length to the amino acid sequence of SEQ ID NO: 24.

In a preferred embodiment of the third aspect of the invention, the isolated polynucleotide encodes an adenoviral penton protein with an amino acid sequence according to SEQ ID NO: 30 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 98%, 99%, 99.5%, 99.9% or at least 99.95%, more preferably at least 98% and most preferable at least 990 identical over its entire length to the amino acid sequence of SEQ ID NO: 30.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the Ad5 genome as a reference. It is preferred that the polynucleotide also comprises sequences required for packaging of the polynucleotide into an adenoviral particle.

Adenovirus PanAd1

In a preferred embodiment of the first aspect of the invention, the isolated polynucleotide encodes an adenoviral fiber protein with an amino acid sequence according to SEQ ID NO: 19 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 19.

In a preferred embodiment of the second aspect of the invention, the isolated polynucleotide encodes an adenoviral hexon protein with an amino acid sequence according to SEQ ID NO: 25 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 25.

In a preferred embodiment of the third aspect of the invention, the isolated polynucleotide encodes an adenoviral penton protein with an amino acid sequence according to SEQ ID NO: 31 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 31.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 13 or to a sequence that consists of SEQ ID NO: 13 but lacks any of the genomic regions E1A, E1B, E2A, E2B, E3 and/or E4 of SEQ ID NO: 13, most preferably that lacks the genomic regions E1, E3 and E4 of SEQ ID NO: 13.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using thelPanAdi genome as set out in SEQ ID NO: 13. It is preferred that the polynucleotide also comprises sequences required for packaging of the polynucleotide into an adenoviral particle.

Adenovirus PanAd2

In a preferred embodiment of the first aspect of the invention, the isolated polynucleotide encodes an adenoviral fiber protein with an amino acid sequence according to SEQ ID NO: 50 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94% 95%, 96%, 97%, 98% or at least 99%, more preferably at least 85% and most preferable at least 99% identical over its entire length to the amino acid sequence of SEQ ID NO: 50.

In a preferred embodiment of the second aspect of the invention, the isolated polynucleotide encodes an adenoviral hexon protein with an amino acid sequence according to SEQ ID NO: 51 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 51.

In a preferred embodiment of the third aspect of the invention, the isolated polynucleotide encodes an adenoviral penton protein with an amino acid sequence according to SEQ ID NO: 52 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 52.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 62 or to a sequence that consists of SEQ ID NO: 62 but lacks any of the genomic regions E1A, E1B, E2A, E2B, E3 and/or E4 of SEQ ID NO: 62, most preferably that lacks the genomic regions E1, E3 and E4 of SEQ ID NO: 62.

In a further aspect the invention relates to a polynucleotide comprising the first, the second, the third, the first and second, the first and third, the second and third or the first, second and third aspect. It is preferred that the polynucleotide comprising this or these polynucleotide(s) comprises other adenoviral genes and nucleotide segments, which are adjacent to the hexon, penton and/or fiber gene in the adenovirus genome, e.g. using the PanAd1 genome as set out in SEQ ID NO: 62. It is preferred that the polynucleotide also comprises sequences required for packaging of the polynucleotide into an adenoviral panicle.

Adenovirus PanAd3

In a preferred embodiment of the first aspect of the invention, the isolated polynucleotide encodes an adenoviral fiber protein with an amino acid sequence according to SEQ ID NO: 53 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 99% identical over its entire length to the amino acid sequence of SEQ ID NO: 53.

In a preferred embodiment of the second aspect of the invention, the isolated polynucleotide encodes an adenoviral hexon protein with an amino acid sequence according to SEQ ID NO: 54 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 95%, 98%, 99%, 99.5%, 99.9% or at least 99.95%, more preferably at least 98% and most preferably at least 99% identical over its entire length to the amino acid sequence of SEQ ID NO: 54.

In a preferred embodiment of the third aspect of the invention, the isolated polynucleotide encodes an adenoviral penton protein with an amino acid sequence according to SEQ ID NO: 55 or a functional derivative thereof, wherein the functional derivative (i) does not comprise more than 1, 2, 3, 4, 5, 6, 7, 8, 9, 10, 15, 20, 25, 30, 35, 40, 45, 50, 60, 70, 80, 90 or more than 100, preferably not more than 10 deleted, inserted, modified and/or substituted amino acids or (ii) has an amino acid sequence which is at least 85%, 86%, 87%, 88%, 89%, 90%, 91%, 92%, 93%, 94%, 95%, 96%, 97%, 98% or at least 99%, more preferably at least 85% and most preferable at least 90% identical over its entire length to the amino acid sequence of SEQ ID NO: 55.

In a most preferred embodiment, the polynucleotide of the invention consists of or comprises a polynucleotide which is at least 90%, 91%, 92%, 93%, 94%, 95%, 96%, 97%, 98% identical and most preferably at least 99% or 100% identical over its entire length to a sequence that consists of SEQ ID NO: 63 or to a sequence that consists of SEQ ID NO: 63 but lacks any of the genomic regions E1A, E1B, E2A, E2B, E3 and/or E4 of SEQ ID NO: 63, most preferably that lacks the genomic regions E1, E3 and E4 of SEQ ID NO: 63.

In a further aspect the invention relates to a polynucleotide comprising the first, the second, the third, the first and second, the first and third, the second and third or the first, second and third aspect and most preferably the first, second and third aspect of the invention. It is preferred that the polynucleotide comprising this or these polynucleotide(s) comprises other adenoviral genes and nucleotide segments, which are adjacent to the hexon, penton and/or fiber gene in the adenovirus genome, e.g. using the PanAd1 genome as set out in SEQ ID NO: 63. It is preferred that the polynucleotide also comprises sequences required for packaging of the polynucleotide into an adenoviral particle.

In a recombinant adenovirus, a fiber, hexon and penton protein according to the first, second and third aspect of the invention, and according to the respective preferred embodiments disclosed herein, contributes each individually to reduce the interaction of said recombinant adenovirus with human and/or rodent neutralizing antibodies. Accordingly, polynucleotides which encode said fiber, hexon and/or penton protein of the present invention are useful to construct enhanced recombinant adenoviruses. Thus, in a further, fourth aspect the invention provides a polynucleotide comprising at least one, preferably at least two and most preferably three isolated polynucleotides selected from the group of polynucleotides consisting of a polynucleotide according to the first aspect of the invention, the second aspect of the invention and the third aspect of the invention. Thus, most preferably, the fourth aspect is an isolated polynucleotide comprising the first, second and third aspect of the invention. In a preferred embodiment, the polynucleotide according to the fourth aspect of the invention is a polynucleotide selected from the group consisting of:

(i) a polynucleotide comprising one polynucleotide according to the first, second or third aspect of the invention;

(ii) a polynucleotide comprising a polynucleotide according to the first aspect of the invention and a polynucleotide according to the second aspect of the invention;

(iii) a polynucleotide comprising a polynucleotide according to the first aspect of the invention and a polynucleotide according to the third aspect of the invention;

(iv) a polynucleotide comprising a polynucleotide according to the second aspect of the invention and a polynucleotide according to the third aspect of the invention; and (v) a polynucleotide comprising a polynucleotide according to the first, second and third aspect of the invention;

wherein it is preferred that said polynucleotides comprised in the polynucleotide according to (i) through (v) are selected from the same adenovirus isolate, e.g. all three polynucleotides encoding fiber, hexon and penton protein or functional derivative thereof, respectively, are from only one of the following adenoviruses: ChAd55, ChAd73, ChAd83, ChAd146, ChAd147 PanAd1, PanAd2 or PanAd3. Furthermore, it is preferred that in the fourth aspect of the invention or in a preferred embodiment thereof, e.g. as outlined above, each "functional derivative" does not comprise more than 10, more than 5 or more than 3 amino acid changes (i.e. deleted, inserted, modified and/or substituted amino acids).

Table 2 below lists a number of particularly preferred embodiments of the polynucleotide of the fourth aspect of invention outlined above. Preferred is a polynucleotide selected from polynucleotides A1 through AF1 shown in Table 2, wherein the polynucleotide comprises three polynucleotides according to alternative (c) of the first, second and third aspect of the invention, each of which respectively encodes an adenoviral fiber, hexon and penton protein or a functional derivative thereof. Table 2 below shows the minimal sequence identity (i.e. at least the indicated sequence identity) which each of said three encoded proteins has to have over its entire length to the amino acid sequence according to the SEQ ID NO which is also shown in Table 2:

TABLE 2

| Preferred embodiment | Fiber Protein | | Hexon Protein | | Penton Protein | |
|---|---|---|---|---|---|---|
| | Minimal %-Identity | to SEQ ID NO: | Minimal %-Identity | to SEQ ID NO: | Minimal %-Identity | to SEQ ID NO: |
| A1 - ChAd55 | 85% | 14 | 95% | 20 | 98% | 26 |
| B1 - ChAd73 | 98% | 15 | 95% | 21 | 98% | 27 |
| C1 - ChAd83 | 100% | 16 | 95% | 22 | 98% | 28 |
| D1 - ChAd146 | 100% | 17 | 95% | 23 | 98% | 29 |
| E1 - ChAd147 | 85% | 18 | 95% | 24 | 98% | 30 |
| F1 - PanAd1 | 85% | 19 | 95% | 25 | 98% | 31 |
| G1 - ChAd55 | 90% | 14 | 95% | 20 | 100% | 26 |
| H1 - ChAd73 | 90% | 15 | 95% | 21 | 98% | 27 |
| I1 - ChAd83 | 90% | 16 | 95% | 22 | 98% | 28 |
| J1 - ChAd146 | 90% | 17 | 95% | 23 | 98% | 29 |
| K1 - ChAd147 | 90% | 18 | 95% | 24 | 98% | 30 |
| L1 - PanAd1 | 90% | 19 | 95% | 25 | 90% | 31 |
| M1 - ChAd55 | 98% | 14 | 98% | 20 | 98% | 26 |
| N1 - ChAd73 | 98% | 15 | 98% | 21 | 98% | 27 |
| O1 - ChAd83 | 98% | 16 | 98% | 22 | 98% | 28 |
| P1 - ChAd146 | 98% | 17 | 98% | 23 | 98% | 29 |
| Q1 - ChAd147 | 98% | 18 | 98% | 24 | 98% | 30 |
| R1 - PanAd1 | 98% | 19 | 98% | 25 | 98% | 31 |
| S1 - ChAd55 | 99% | 14 | 99% | 20 | 99% | 26 |
| T1 - ChAd73 | 99% | 15 | 99% | 21 | 99% | 27 |
| U1 - ChAd83 | 99% | 16 | 99% | 22 | 99% | 28 |
| V1 - ChAd146 | 99% | 17 | 99% | 23 | 99% | 29 |
| W1 - ChAd147 | 99% | 18 | 99% | 24 | 99% | 30 |
| X1 - PanAd1 | 99% | 19 | 99% | 25 | 99% | 31 |
| Y1 - PanAd2 | 80% | 50 | 95% | 51 | 85% | 52 |
| Z1 - PanAd2 | 90% | 50 | 95% | 51 | 90% | 52 |
| AA1 - PanAd2 | 98% | 50 | 98% | 51 | 98% | 52 |
| AB1 - PanAd2 | 99% | 50 | 99% | 51 | 99% | 52 |
| AC1 - PanAd3 | 75% | 53 | 95% | 54 | 85% | 55 |
| AD1 - PanAd3 | 90% | 53 | 95% | 54 | 90% | 55 |
| AE1 - PanAd3 | 98% | 53 | 98% | 54 | 98% | 55 |
| AF1 - PanAd3 | 99% | 53 | 99% | 54 | 99% | 55 |

For example, preferred polynucleotide A1 as shown in Table 1 above comprises:
(i) a polynucleotide encoding a polypeptide having an amino acid sequence which is at least 85% identical over its entire length to SEQ ID NO: 14;
(ii) a polynucleotide encoding a polypeptide having an amino acid sequence which is at least 95% identical over its entire length to SEQ ID NO: 20; and
(iii) a polynucleotide encoding a polypeptide having an amino acid sequence which is at least 98% identical over its entire length to SEQ ID NO: 26;

As mentioned above it is most preferred that said "functional derivative" of a polynucleotide listen in table 2 does not comprise more than 10 amino acid changes (i.e. deleted, inserted, modified and/or substituted amino acids).

Table 3 below lists further preferred embodiments of the polynucleotide of the fourth aspect of the invention. Preferred is a polynucleotide selected from polynucleotides A2 through J2 selected from Table 3, wherein the polynucleotide comprises three polynucleotides designated, "Polynucleotide 1", "Polynucleotide 2" and "Polynucleotide 3", wherein each respective polynucleotide has at least the indicated sequence identity over its entire length to the corresponding polynucleotide according to the SEQ ID NO shown in Table 3:

TABLE 3

| Preferred embodiment | Polynucleotide 1 | | Polynucleotide 2 | | Polynucleotide 3 | |
|---|---|---|---|---|---|---|
| | Minimal %-Identity | to SEQ ID NO: (polynucleotide encoding Fiber protein) | Minimal %-Identity | to SEQ ID NO: (polynucleotide encoding Hexon protein) | Minimal %-Identity | to SEQ ID NO: (polynucleotide encoding Penton protein) |
| A2 - ChAd55 | 98% | 32 | 98% | 38 | 98% | 44 |
| B2 - ChAd73 | 98% | 33 | 98% | 39 | 98% | 45 |
| C2 - ChAd83 | 98% | 34 | 98% | 40 | 98% | 46 |
| D2 - ChAd146 | 98% | 35 | 98% | 41 | 98% | 47 |
| E2 - ChAd147 | 98% | 36 | 98% | 42 | 98% | 48 |
| F2 - PanAd1 | 98% | 37 | 98% | 43 | 98% | 49 |
| G2 - ChAd55 | 99% | 32 | 99% | 38 | 99% | 44 |
| H2 - ChAd73 | 99% | 33 | 99% | 39 | 99% | 45 |
| I2 - ChAd83 | 99% | 34 | 99% | 40 | 99% | 46 |
| J2 - ChAd146 | 99% | 35 | 99% | 41 | 99% | 47 |
| K2 - ChAd147 | 99% | 36 | 99% | 42 | 99% | 48 |
| L2 - PanAd1 | 99% | 37 | 99% | 43 | 99% | 49 |
| G2 - PanAd2 | 98% | 56 | 98% | 57 | 98% | 58 |
| H2 - PanAd2 | 99% | 56 | 99% | 57 | 99% | 58 |
| I2 - PanAd3 | 98% | 59 | 98% | 60 | 98% | 61 |
| J2 - PanAd3 | 99% | 59 | 99% | 60 | 99% | 61 |

Thus, as an example, preferred embodiment A2 ("A2-ChAd55") of Table 3 above is a polynucleotide comprising:
(i) a polynucleotide that is at least 98% identical to SEQ ID NO: 32 over its entire length;
(ii) a polynucleotide that is at least 98% identical to SEQ ID NO: 38 over its entire length; and
(iii) a polynucleotide that is at least 98% identical to SEQ ID NO: 44 over its entire length.

Table 4 below lists a number of further particularly preferred embodiments of the polynucleotide of the fourth aspect of invention outlined above. Preferred is a polynucleotide selected from polynucleotides A3 through H3 shown in Table 4, wherein the polynucleotide encodes an adenoviral fiber, hexon and penton protein according to the indicated SEQ ID NO or a functional derivative thereof, wherein all three proteins and/or encoded functional derivatives in total comprises equal or less than 1, 2, 3, 4, 5, 6, 7, 8, 9, 10, 15, 20, 25, 30, 35, 40, 45, 50, 60, 70, 80, 90 or more than 100, preferably not more than 20 deleted, inserted, modified and/or substituted amino acids:

TABLE 4

| Preferred embodiment | Fiber Protein according to SEQ ID NO: | Hexon Protein according to SEQ ID NO: | Penton Protein according to SEQ ID NO: |
|---|---|---|---|
| A3 - ChAd55 | 14 | 20 | 26 |
| B3 - ChAd73 | 15 | 21 | 27 |
| C3 - ChAd83 | 16 | 22 | 28 |
| D3 - ChAd146 | 17 | 23 | 29 |
| E3 - ChAd147 | 18 | 24 | 30 |
| F3 - PanAd1 | 19 | 25 | 31 |
| G3 - PanAd2 | 50 | 51 | 52 |
| H3 - PanAd3 | 53 | 54 | 55 |

In another embodiment of the polynucleotide of the fourth aspect of invention, the polynucleotide encodes an adenoviral fiber and hexon protein of the same strain according to the respective SEQ ID NO as shown in Table 4 or functional derivatives thereof. In a further embodiment of the polynucleotide of the fourth aspect of invention, the polynucleotide encodes an adenoviral fiber and penton protein of the same strain according to the respective SEQ ID NO as shown in Table 4 or functional derivatives thereof. In a further embodiment of the polynucleotide of the fourth aspect of invention, the polynucleotide encodes an adenoviral hexon and penton protein of the same strain according to the respective SEQ ID NO as shown in Table 4 or functional derivatives thereof. In this context, said functional derivative comprises in each instance less than 1, 2, 3, 4, 5, 6, 7, 8, 9 or less than 10, most preferably less than 3 deleted, inserted, modified and/or substituted amino acids.

In a further preferred embodiment of the fourth aspect of the invention, the polynucleotide consists of or comprises a polynucleotide which is at least 90%, 91%, 92%, 94%, 95%, 96%, 97%, 98%, 99%, 99.9% or 100%, preferably 98% identical over its entire length to a sequence that (i) consists of any one of SEQ If) NO: 13, 62, 63 or 65 or to (ii) a sequence that consists of any one of SEQ ID NO: 13, 62, 63 or 65 that lacks one or more of the genomic regions E1A, E1B, E2A, E2B, E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and/or E4 ORF1. Thus, the aforementioned one or more genomic regions will preferably not be considered in the alignment when determining the percent identity. In another preferred embodiment of the isolated polynucleotide of the invention, the polynucleotide comprises or consists of SEQ ID NO: 13, 62, 63 or 65, wherein one or more of the genomic regions E1A, E1B, E2A, E2B, E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF5, E4 ORF4, E4 ORF3, E4 ORF2 and E4 ORF1 are deleted from SEQ ID NO: 13, 62, 63 or 65, respectively, or substituted with a transgene or an expression cassette encoding a heterologous protein as described herein. In a most preferred embodiment adenoviral regions E1, E3 and/or E4 are deleted as also exemplified in example 2. The aforementioned preferred polynucleotides, which lack one or more of the indicated genomic regions may further comprise a polynucleotide sequence encoding for a heterologous protein or an expression cassette comprising such a polynucleotide sequence encoding for a heterologous protein. Said polynucleotide sequence encoding for a heterologous protein and said expression cassette comprising such a polynucleotide sequence encoding for a heterologous protein may be inserted into e.g. the deleted regions of the polynucleotide of the invention as is well known in the art and also described in the examples below. Said heterologous protein may be a molecule for delivery into a target cell such as described herein, e.g. a polynucleotide encoding an antigenic protein or a fragment thereof, preferably an antigenic protein or a fragment of a pathogen such as HIV gag protein, a tumour antigen or a protein of the herpes simplex virus as described in the examples. Thus, in a preferred embodiment, the isolated polynucleotide according to the invention further comprises a polynucleotide encoding an antigen selected from the group consisting of a virus antigen, an antigen of a pathogenic bacterium and a tumorantigen. In one embodiment, said heterologous protein can thus be an antigen selected from the group consisting of an RNA virus antigen, an antigen of a pathogenic bacterium and a tumorantigen. An antigen refers to any protein or peptide capable of eliciting an immune response in a mammal. An antigen comprises preferably at least 8 amino acids and most preferably comprises between 8 and 12 amino acids. Thus, when determining the sequence identity, the genomic regions E1A, E1B, E2A, E2B, E3 and/or E4 are preferably not considered in the alignment, i.e. the alignment is done using a sequence that consists of the entire sequence SEQ ID NO: 13, 62 63 or 65 but excluding the genomic regions E1A, E1B, E2A, E2B, E3, E4 and/or any polynucleotide encoding a heterologous polypeptide or expression cassette comprising such polynucleotide. As also mentioned above, it is preferred that the polynucleotide according to the fourth aspect of the invention and all its preferred embodiments encodes functional hexon, penton and/or fiber capsid proteins or functional derivatives thereof, e.g. the encoded proteins have the same function as the respective capsid proteins or fragments thereof in an infectious adenovirus virion. Thus, a recombinant adenovirus comprising in its capsid said encoded recombinant penton, hexon and/or fiber proteins or functional derivatives thereof is capable of entering a host cell. It is further preferred that the capsid proteins or functional derivatives thereof according to the invention or encoded by polynucleotides of the invention have no seroprevalence in human.

The invention further provides an isolated protein encoded by the isolated polynucleotide according to the invention, i.e. an isolated adenoviral capsid polypeptide encoded by the isolated polynucleotide according to the first, second and/or third aspect of the invention or a functional derivative thereof. In this context, the "functional derivative" in one embodiment does not comprise more than 5, 10 or not more than 25 amino acid changes (i.e. deleted, inserted, modified and/or substituted amino acids).

The invention further relates to a vector comprising an isolated polynucleotide according to the invention.

Preferably, the vector does not comprise a gene in a genomic region selected from the group of genomic regions consisting of E1A, E1B, E2A, E2B, E3 and E4, and/or comprises at least one gene of a genomic region selected from the group of E1A, E1B, E2A, E2B, E3 and E4, wherein said at least one gene comprises a deletion and/or mutation which renders the at least one gene non-functional. One possibility to render one of these gene products non-functional is to introduce one or more artificial stop-codons (e.g. TAA) into the open reading frame of these genes. Methods of rendering the virus replication-defective are well known in the art (see e.g. Brody et al, 1994 Ann NY Acad Sci., 716: 90-101).

In some embodiments the polynucleotide of the invention comprises a polynucleotide encoding a hexon protein; penton protein; fiber protein; hexon protein and penton protein; hexon protein and fibre protein; penton protein and fibre protein; or hexon protein, penton protein and fibre protein of the invention and further comprises additional adenoviral polynucleotides. Thus, in one preferred embodiment, the isolated polynucleotide according to the invention comprises at least one of the following:

(a) an adenoviral 5'-inverted terminal repeat (ITR);
(b) an adenoviral E1a region, or a fragment thereof selected from among the 13S, 12S and 9S regions;
(c) an adenoviral E1b region, or a fragment thereof selected from among the group consisting of the small T, large T and IX regions;
(d) an adenoviral E2b region; or a fragment thereof selected from among the group consisting of the small pTP, Polymerase and IVa2 regions;
(e) an adenoviral L1 region, or a fragment thereof, said fragment encoding an adenoviral protein selected from the group consisting of the 28.1 kD protein, polymerase, agnoprotein, 52/55 kDa protein, and IIIa protein;
(f) an adenoviral L2 region or a L2 region comprising a polynucleotide encoding the penton protein of the invention, or a fragment thereof, said fragment encoding an adenoviral protein selected from the group consisting of a penton protein or the penton protein of the invention, VII, V, and Mu protein;
(g) an adenoviral L3 region or a L3 region comprising a polynucleotide encoding the hexon protein of the invention, or a fragment thereof, said fragment encoding an adenoviral protein selected from the group consisting of the VI protein, hexon protein or the hexon protein of the invention and endoprotease;
(h) an adenoviral E2a region;
(i) an adenoviral L4 region, or a fragment thereof said fragment encoding an adenoviral protein selected from the group consisting of the 100 kD protein, the 33 kD homology, and protein VIII;

(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region or a L5 region comprising a polynucleotide encoding the fibre protein of the invention, or a fragment thereof said fragment encoding the fiber protein or the fiber protein of the invention;
(l) an adenoviral E4 region, or a fragment thereof selected from the group consisting of E4 ORF7, E4 ORF6, E4 ORF5, E4 ORF4, E4 ORF3, E4 ORF2, and E4 ORF1; in particular ORF6 of said E4 region;
and/or
(m) an adenoviral 3'-ITR.

In some embodiments of the aforementioned polynucleotide it may be desirable as also described above that preferably, the polynucleotide does not comprise an ORF of a genomic region as outlined above (such as e.g. region E3 and/or E4 as defined in example 2) and/or comprises an adenoviral gene which comprises a deletion and/or mutation which renders the at least one gene non-functional. In these preferred embodiments the suitable adenoviral regions will be modified to not include the aforementioned gene(s) or to render the selected gene(s) non-functional. Any adenoviral gene deletions will make space to insert transgenes such as a minigene cassette as described herein. Furthermore, gene deletions can be used to generate adenoviral vectors which are incapable to replicate without the use of a packaging cell line or a helper virus as is well known in the art. Thus, the final recombinant adenovirus comprising a polynucleotide as outlined above which comprises one or more of the specified gene/region deletions or loss-of-function mutations can provide a safer recombinant adenovirus for e.g. gene therapy or vaccination. In a particularly preferred embodiment, the polynucleotide of the invention comprises at least one of the following:

(a) the 5'-inverted terminal repeat (ITR) region of any one of SEQ ID NO: 13, 62, 63 or 65;
(b) the adenovirus E1a region of any one of SEQ ID NO: 13, 62, 63 or 65, or a fragment thereof selected from among the 13S, 12S and 9S regions;
(c) the adenovirus E1b region of any one of SEQ ID NO: 13, 62, 63 or 65, or a fragment thereof selected from among the group consisting of the small T, large T and IX regions;
(d) the adenovirus E2b region of any one of SEQ ID NO: 13, 62, 63 or 65; or a fragment thereof selected from among the group consisting of the small pTP, Polymerase and IVa2 regions;
(e) the adenovirus L1 region of any one of SEQ ID NO: 13, 62, 63 or 65, or a fragment thereof, said fragment encoding an adenoviral protein selected from the group consisting of the 28.1 kD protein, polymerase, agnoprotein, 52/55 kDa protein, and IIIa protein;
(f) the adenovirus L2 region of any one of SEQ ID NO: 13, 62, 63 or 65, or a fragment thereof, said fragment encoding an adenoviral protein selected from the group consisting of the penton protein with the amino acid sequence of SEQ ID NO: 31, 52 or 55, VII, V, and Mu protein;
(g) the adenovirus L3 region of any one of SEQ ID NO: 13, 62, 63 or 65, or a fragment thereof, said fragment encoding an adenoviral protein selected from the group consisting of the VI protein, hexon protein with the amino acid sequence of SEQ ID NO: 25, 51 or 54 and endoprotease;
(h) the adenovirus E2a region of any one of SEQ ID NO: 13, 62, 63 or 65;
(i) the adenovirus L4 region of any one of SEQ ID NO: 13, 62, 63 or 65, or a fragment thereof said fragment encoding an adenoviral protein selected from the group consisting of the 100 kD protein, the 33 kD homolog, and protein VIII;
(l) the adenovirus E3 region of any one of SEQ ID NO: 13, 62, 63 or 65, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) the adenovirus L5 region of any one of SEQ ID NO: 13, 62, 63 or 65, or a fragment thereof said fragment encoding the fiber protein with the amino acid sequence of SEQ ID NO:19, 50 or 53;
(l) the adenovirus E4 region of any one of SEQ ID NO: 13, 62, 63 or 65, or a fragment thereof selected from the group consisting of E4 ORF7, E4 ORF6, E4 ORF5, E4 ORF4, E4 ORF3, E4 ORF2, and E4 ORF1; or ORF6 of Ad5 E4 region (SEQ ID NO: 64); and
(m) the 3'-ITR of any one of SEQ ID NO: 13, 62, 63 or 65.

In one embodiment the isolated polynucleotide of the invention further encodes one or more, preferably all of the following adenoviral proteins: protein VI, protein VIII, protein IX, protein IIIa and protein IVa2. Preferably these proteins are encoded by from the respective open reading frames of the PanAd1, PanAd2 or PanAd3 genomic sequence disclosed herein. An average person skilled in the art of recombinant adenoviruses is well aware of how to determine the open reading frames that encode for the above specified adenoviral proteins. He is also aware of the structure of adenoviral genomes and can map, without undue burden, the individual adenoviral regions and ORFs outlined herein to e.g. any of the novel adenoviral genomes PanAd1, PanAd2 or PanAd3 of the invention.

In order to express a polynucleotide, preferably a cDNA, encoding one or more adenoviral proteins of the invention, one can subclone said polynucleotide into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available.

In addition to the promoter, the expression vector typically contains a transcription unit or expression cassette that contains all the additional elements required for the expression of the adenoviral protein-encoding nucleic acid in host cells. A typical expression cassette thus contains a promoter operatively linked to the nucleic acid sequence encoding the adenoviral protein/polypeptide and signals required for efficient polyadenylation of the transcript, ribosome binding sites, and translation termination. Additional elements of the cassette may include, for example enhancers. An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g. SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of e.g. the HCMV immediate-early promoter, SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that may also be included in expression vectors include a replicon that functions in $E.$ $coli$, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical—any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines. Any of the well-known procedures for introducing foreign polynucleotide sequences into host cells may be used. For example, commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (hiolistic), electroporation, or viral infection and any of the other well known methods for introducing cloned genomic DNA, cDNA, synthetic DNA or other foreign genetic material into a host cell may be used. It is only necessary that the particular genetic engineering procedure used be capable of successfully introducing at least one gene into the host cell capable of expressing the receptor.

An expressed adenoviral protein can be optionally purified using standard techniques. For example, the cells may be lysed either mechanically or by osmotic shock before being subject to precipitation and chromatography steps, the nature and sequence of which will depend on the particular recombinant material to be recovered. Alternatively, the recombinant protein may be secreted and recovered from the culture medium in which the recombinant cells had been cultured as is known in the art of protein expression.

In one preferred embodiment the vector of the invention is a plasmid vector, e.g. an expression vector. A plasmid vector according to the invention can also be used to generate a recombinant adenovirus.

Thus, a further aspect of the present invention is a recombinant adenovirus, preferably a replication-incompetent adenovirus, comprising an isolated polynucleotide according to the invention and/or at least one isolated adenoviral capsid polypeptide according to the invention. Preferably the recombinant adenovirus of the invention comprises a hexon a fiber and a penton protein of the present invention, e.g. a combination as outlined in Table 2 above. In a preferred embodiment, the recombinant adenovirus is characterized in that it is capable of infecting a human cell—preferably capable of infecting a human cell after said adenovirus was incubated for one hour in a human blood serum derived from a human that has not previously been exposed to a chimpanzee adenovirus.

As the sequence information of the novel hexon, penton and fiber proteins of the invention are provided, said recombinant adenovirus is obtainable e.g. by constructing a recombinant adenovirus which is composed of the usual adenoviral proteins but which has a capsid that comprises at least one isolated adenoviral capsid polypeptide according to the invention or a functional derivative thereof. In this regard it is preferred that the recombinant adenovirus comprises an L2 region which comprises a polynucleotide sequence encoding the penton protein of the invention, an L3 region which comprises a polynucleotide sequence encoding the hexon protein of the invention and/or an L5 region which comprises a polynucleotide sequence encoding the fiber protein of the invention. Most preferably said recombinant adenovirus comprises an L2 region, an L3 region and an L5 region encoding, respectively, at least for the penton, hexon and fiber protein of the invention.

Methods for the construction of recombinant adenoviruses are well known in the art. Useful techniques for the preparation of recombinant adenoviruses are, for example, reviewed in Graham & Prevec, 1991 In Methods in Molecular Biology: Gene Transfer and Expression Protocols, (Ed. Murray, E J.), p. 109; and Hitt et al., 1997 "Human Adenovirus Vectors for Gene Transfer into Mammalian Cells" Advances in Pharmacology 40:137-206. Further methods are described in WO 2006/086284. For the preparation of replication deficient adenoviruses, one or several of the E1A, E1B, E2A, E2B, E3 and E4 gene products may be expressed in a complementing cell line that can be used for the propagation and rescue of recombinant adenoviruses that are replication-incompetent, because they lack e.g. one of the aforementioned gene products. The use of such cell-lines is also described in the references outlined above.

In one embodiment, the polynucleotides of the invention (or vectors comprising said polynucleotides of the invention as described herein) are used to produce recombinant adenoviral particles. The recombinant adenoviruses are preferably functionally deleted as mentioned above in one or more adenoviral regions such as e.g. the E1a or E1b regions, and optionally bearing other mutations, e.g., temperature-sensitive mutations or deletions in other adenoviral genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of adenovirus vectors for delivery of a gene to a host, e.g. human (or other mammalian) cell, a range of adenovirus nucleic acid sequences can be employed in the vectors of the invention. For example, all or a portion of the adenovirus delayed early gene E3 may be eliminated from the adenovirus sequence which forms a part of the recombinant virus. The function of simian E3 is believed to be irrelevant to the function and production of the recombinant virus particle. In some embodiments, adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and IVa2 may be useful for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector according to the invention, the adenovirus sequence may have deletions of the E1 and the E4 region, or of the E1, E2a and E3 region, or of the E1 and E3 regions, or of E1, E2a and E4 regions, with or without deletion of E3, and so on. As discussed above, such deletions may be used in combination with other adenoviral gene mutations, such as temperature-sensitive mutations, to achieve a desired result.

An adenoviral vector lacking any essential adenoviral sequences (e.g., a region selected from E1a, E1b, E2a, E2b, E4 ORF6, L1 or L4) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell (complementing cell line as also described above). See, for example, the examples included herein and the techniques described for preparation of a "minimal" human adenovirus vector in International Patent Application WO96/13597 published May 9, 1996, and incorporated herein by reference.

Useful helper viruses contain selected adenovirus gene sequences that complement the respective genes that are deleted in preferred embodiments of the adenovirus vector of the invention and/or that are not expressed by the packaging cell line in which the vector is transfected. In one embodiment, the helper virus is replication-defective and contains a variety of adenovirus genes in addition to the sequences described above.

Helper viruses may also be formed into poly-cation conjugates as described in Wu et al, J. Biol. Chem., 264: 16985-16987 (1989); K. J. Fisher and J. M. Wilson, Biochem. J., 299: 49 (Apr. 1, 1994). A helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter may be used to facilitate separation between the resulting recombinant virus and the helper virus upon purification.

To generate recombinant adenoviruses (Ad) deleted in any of the genes described in the context of preferred embodiments herein, the function of the deleted gene region, if essential to the replication and infectivity of the virus, is preferably supplied to the recombinant virus by a helper virus or cell line, i.e., a complementation or packaging cell line. In many circumstances, a cell line expressing the human E1 can be used to transcomplement the vector used to generate recombinant adenoviruses. This is particularly advantageous because, due to the diversity between the polynucleotide sequences of the invention and the human adenoviral E1 sequences found in currently available packaging cells, the use of the current human E1-containing cells will prevent the generation of replication-competent adenoviruses during the replication and production process. However, in certain circumstances, it will be desirable to utilize a cell line which expresses the E1 gene products for the production of an E1-deleted recombinant adenovirus.

If desired, one may utilize the sequences provided herein to generate a packaging cell or cell line that expresses, at a minimum, the adenovirus E1 gene from a ChAd55, ChAd73, ChAd83, ChAd146, ChAd147, PanAd1, PanAd2 or PanAd3 adenovirus under the transcriptional control of a promoter for expression in a selected parent cell line, such as e.g. a HeLa cell. Inducible or constitutive promoters may be employed for this purpose. Examples of promoters are provided e.g. in the examples described herein. Such E1-expressing cell lines are useful in the generation of recombinant adenovirus E1 deleted vectors. Additionally, or alternatively, the invention provides cell lines that express one or more adenoviral gene products, e.g., E1a, E1b, E2a, and/or E4 ORF6, preferably Ad5 E4 ORF6 (see also the examples below), which can be constructed using essentially the same procedures for use in the generation of recombinant adenoviral vectors. Such cell lines can be utilized to transcomplement adenovirus vectors deleted in essential genes that encode those products, or to provide helper functions necessary for packaging of a helper-dependent virus (e.g., adeno-associated virus).

Generally, when delivering a vector of the invention comprising e.g. a minigene by transfection, the vector is delivered in an amount from about 0.1 μg to about 100 μg DNA, and preferably about 10 to about 50 μg DNA to about $1 \times 10^4$ cells to about $1 \times 10^3$ cells, and preferably about $10^5$ cells. However, the relative amounts of vector DNA to host cells may be adjusted, taking into consideration such factors as the selected vector, the delivery method and the host cells selected. Introduction of the vector into a host cell may be achieved by any means known in the art or as disclosed herein, including transfection, and infection, e.g. using $CaPO_4$ transfection or electroporation.

For the construction and assembly of the desired minigene-containing recombinant adenovirus, the vector can in one example be transfected in-vitro in the presence of a helper virus into the packaging cell line, allowing homologous recombination to occur between the helper and the vector sequences, which permits the adenovirus-transgene sequences in the vector to be replicated and packaged into virion capsids, resulting in the recombinant viral vector particles as is well known in the art. A recombinant adenoviruses of the invention is useful e.g. in transferring a selected transgene into a selected host cell.

In a preferred embodiment of the adenovirus of the invention, the adenovirus has a seroprevalence of less than 5% in human subjects and preferably no seroprevalence in human subjects, most preferably no seroprevalence in human subjects that have not previously been in contact with a chimpanzee adenovirus. In this context it is preferred that the human subjects belong to an ethnic group selected from Europeans, indigenous people of Africa, Asians, indigenous people of America and indigenous people of Oceania. Methods for the identification of the ethnic origin of a human subject are comprised in the art (see e.g. WO2003/102236).

In a further preferred embodiment of the recombinant adenovirus according to the invention, the adenovirus DNA is capable of entering a mammalian target cell, i.e. it is infectious. An infectious recombinant adenoviruses of the invention can be used as a vaccine and for gene therapy as also described below. Thus, in another embodiment it is preferred that the recombinant adenovirus comprises a molecule for delivery into a target cell. Preferably, the target cell is a mammalian cell, e.g. a chimpanzee cell, a rodent cell or a human cell. For example, the molecule for delivery into a target cell can be an expression cassette as defined herein. Methods to introduce an expression cassette into the genome of an adenovirus are well known in the art (see for example the literature citations provided above). In one example a recombinant adenovirus of the present invention that comprises an expression cassette, encoding e.g. a minigene or an antigen, can be generated by replacing a genomic region of the adenovirus selected from E1A, E1B, E2A, E2B, E3 and E4 with said expression cassette. The genomic regions E1A, E1B, E2A, E2B, E3 and E4 of the adenoviruses of the invention can easily be identified by an alignment with known and annotated adenoviral genomes such as from human Ads (see: Birgitt Täuber and Thomas Dobner, Oncogene (2001) 20, p. 7847-7854; and also: Andrew J. Davison, et al., "Genetic content and evolution of adenoviruses", Journal of General Virology (2003), 84, p. 2895-2908). Non-limiting examples of how to generate modified adenoviruses comprising a molecule for delivery into a target cell are also provided in examples 1 and 2 and FIG. 4 below.

The molecule for delivery into a target cell is preferably a polynucleotide but may also be a polypeptide or a small chemical compound, preferably having a therapeutic or diagnostic activity. In one particularly preferred embodiment, the molecule for delivery into a target cell is a polynucleotide that comprises an adenovirus 5' inverted terminal repeat sequence (ITR), a gene, e.g. SEQ ID NO: 1 and a 3' ITR. It will be evident to the skilled person that the molecular size of the molecule has to be chosen such that the capsid can form around and package the molecule, when the recombinant adenovirus is produced, e.g. in a packaging cell line. Thus, preferably the gene is a minigene which can have e.g. up to 7000 and maximally up to 8000 base pairs.

In a preferred embodiment, the molecule for delivery into a target cell comprised in the recombinant adenovirus according to the invention is a polynucleotide encoding an antigenic protein or a fragment thereof. An antigenic protein or fragment thereof is capable of eliciting an immune response in a mammal and may be in a particularly preferred embodiment the gag protein of HIV as shown in the examples and being encoded by a polynucleotide according to SEQ ID NO: 1.

In a particularly preferred embodiment, the recombinant adenovirus of the invention is an adenovirus that has been deposited at ECACC (European Collection of Cell Culture, Porton Down, Salisbury, SP4 OJG, UK) and has a deposit number selected from the group consisting of 08110601 (ChAd83), 08110602 (ChAd73), 08110603 (ChAd55), 08110604 (ChAd147) and 08110605 (ChAd146). The deposits of the aforementioned adenoviral strains (Latin name: Masiodenovirus, Adenoviridae) have been made on Nov. 6, 2008 by Okairos AG, Elisabethenstr, 3, 4051 Basel, Switzerland.

These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U. S. C. 112. All restrictions on the availability to the public of the deposited material will be irrevocably removed, except for the requirements specified in 37 C. F. R. 1. 808 (h), upon the granting of a patent.

Another preferred embodiment of the recombinant adenovirus of the invention is an adenovirus derived from an adenovirus selected from the group consisting of 08110601 (ChAd83), 08110602 (ChAd73), 08110603 (ChAd55), 08110604 (ChAd147) and 08110605 (ChAd146). Preferably the adenovirus derived of one of the aforementioned deposited adenoviruses has been altered by introducing a functional deletion, deletion or modification in its genome, e.g. to obtain a replication incompetent adenovirus and/or an adenovirus that is capable of expressing a transgene in a host cell. For example, one or more genes selected from the group consisting of E1A, E1B, E2A, E2B, E3 and E4 gene can be deleted, rendered non-functional, and/or can be replaced by an expression cassette as outlined above. Additionally, one or more genes of another adenovirus may be introduced, preferably for a deleted gene. A skilled person is well aware of how to introduce these genomic alterations in the deposited strains. In this respect, methods of generating modified adenoviruses comprising a molecule for delivery into a target cell, which is a preferred modification of the deposited strains, have been described above.

In a further aspect a composition is provided that comprises an immunological adjuvant and at least one of the following (i) through (iv):
(i) an isolated protein according to the invention;
(ii) an isolated polynucleotide according to the invention;
(iii) a vector according to the invention;
(iv) a recombinant adenovirus according to the invention;
and, optionally, a pharmaceutically acceptable excipient.

A composition according to the invention that comprises an adjuvant can be used as a vaccine, e.g. for human subjects. The immunological adjuvant also referred to herein in short as "adjuvant", accelerates, prolongs and/or enhances the quality and/or strength of an immune response to an antigen/immunogen, in comparison to the administration of the antigen alone, thus, reducing the quantity of antigen/immunogen necessary in any given vaccine, and/or the frequency of injection necessary in order to generate an adequate immune response to the antigen/immunogen of interest.

Examples of adjuvants that may be used in the context of the composition according to the present invention are gel-like precipitates of aluminum hydroxide (alum); AlPO4; athydrogel; bacterial products from the outer membrane of Gram-negative bacteria, in particular monophosphoryl lipid A (MPLA), lipopolysaccharides muramyl dipeptides and derivatives thereof; Freund's incomplete adjuvant; liposomes, in particular neutral liposomes, liposomes containing the composition and optionally cytokines; non-ionic block copolymers; ISCOMATRIX adjuvant (Drane et al., 2007); unmethylated DNA comprising CpG dinucleotides (CpG motif), in particular CpG ODN with a phosphorothioate (PTO) backbone (CpG PTO ODN) or phosphodiester (PO) backbone (CpG PO ODN); synthetic lipopeptide derivatives, in particular PamsCys; lipoarabinomannan; peptidoglycan; zymosan; heat shock proteins (HSP), in particular HSP 70; dsRNA and synthetic derivatives thereof, in particular Poly I:poly C; polycationic peptides, in particular poly-L-arginine; taxol; fibronectin; flagellin; imidazoquinoline; cytokines with adjuvant activity, in particular GM-CSF, interleukin- (IL-)2, IL-6, IL-7, IL-18, type I and II interferons, in particular interferon-gamma, TNF-alpha; 25-dihydroxyvitamin D3 (calcitriol); and synthetic oligopeptides, in particular MHCII-presented peptides. Non-ionic block polymers containing polyoxyethylene (POE) and polyoxypropylene (POP), such as POE-POP-POE block copolymers may be used as an adjuvant (Newman et al., 1998). This type of adjuvant is particularly useful for compositions comprising nucleic acids as active ingredient.

Optionally, various pharmaceutically acceptable excipients may be used. Preferred pharmaceutically acceptable excipients are mentioned below when discussing the uses according to the invention.

Activation of specific receptors can stimulate an immune response. Such receptors are known to the skilled artisan and comprise, for example, cytokine receptors, in particular type I cytokine receptors, type II cytokine receptors, TNF receptors; and vitamin D receptor acting as transcription factor; and the Toll-like receptors 1 (TLR1), TLR-2, TLR 3, TLR4, TLR5, TLR-6, TLR7, and TLR9. Agonists to such receptors have adjuvant activity, i.e., are immunostimulatory. In a preferred embodiment, the adjuvant of the composition of the present invention may be one or more Toll-like receptor agonists. In a more preferred embodiment, the adjuvant is a Toll-like receptor 4 agonist. In a particular preferred embodiment, the adjuvant is a Toll-like receptor 9 agonist, preferably being encoded by the nucleotide tccatgacgttcctgacgtt (SEQ ID NO: 2).

In a further aspect the invention provides a cell, preferably a non-simian cell, comprising at least one of the following:
(i) an isolated protein according to the invention;
(ii) an isolated polynucleotide according to the invention;
(iii) a vector according to the invention;
(iv) a recombinant adenovirus according to the invention;

The cell may be selected of a bacterial cell such as an *E. coli* cell, a yeast cell such as *Sacchararnyces cerevisiae* or *Pichia pastoris*, a plant cell, an insect cell such as SF9 or Hi5 cells, or a mammalian cell. Preferred examples of mammalian cells are Chinese hamster ovary (CHO) cells, human embryonic kidney (HEK 293) cells, HELA cells, human hepatoma cells (e.g. Huh7.5), Hep G2 human hepatoma cells, Hep 3B human hepatoma cells and the like.

If the cell comprises an isolated polyucleotide according to (ii), this polynucleotide may be present in the cell either (i) freely dispersed as such, or (ii) integrated into the host cell genome or mitochondrial DNA.

In a further preferred embodiment, the cell is a host cell, preferably a 293 cell or a PER.C6™ cell, that expresses at least one adenoviral gene selected from the group consisting of E1a, E1b, E2a, E2b, E4, L1, L2, L3, L4 and L5.

Also provided is the use of the isolated polynucleotide according to the invention, the isolated protein according to the invention, the vector according to the invention, the recombinant adenovirus according to the invention and/or the pharmaceutical composition according to the invention for the therapy or prophylaxis of a disease.

Adenoviral vectors have demonstrated great potential as vaccine vectors. Preclinical and clinical studies have demonstrated the feasibility of vector design, robust antigen expression and protective immunity using this system. Thus, a preferred embodiment is the use according to the invention, wherein the therapy or prophylaxis is a vaccination, e.g. for human subjects. Detailed instructions of how adenoviruses are used and prepared for vaccination are provided as ample literature comprised in the art and known to the skilled person.

If the use is a vaccination, a recombinant adenovirus of the invention can be administered in an immunologically and/or prophylactically effective dose which is preferably $1\times10^8$ to $1\times10^{11}$ viral particles $1\times10^8$, $5\times10^8$, $1\times10^9$, $5\times10^9$, $1\times10^{10}$, $2.5\times10^{10}$ or $5\times10^{10}$ particles). Furthermore, for a vaccination which requires a boosting, it is preferred to apply a "heterologous prime-boost" methodology, as defined above. Furthermore, when using the isolated polynucleotide according to the invention, the isolated protein according to the invention, the vector according to the invention, the recombinant adenovirus according to the invention and/or the pharmaceutical composition according to the invention in a vaccine, it is preferred that the vaccine comprises an adjuvant. Preferred immunological adjutants have been mentioned herein and can be used in such vaccine.

A recombinant adenovirus prepared using a polynucleotide or recombinant adenoviral protein or fragment thereof according to the invention can be used to transduce a host cell with a polynucleotide, e.g. DNA. Thus, a preferably replication deficient, albeit infectious, i.e., capable of entering a host cell, adenovirus can be prepared to express any custom protein or polypeptide in a host cell. Thus, in a preferred embodiment, the therapy recited in the use according to the invention is gene therapy. If an isolated polynucleotide, an isolated protein, a vector, a recombinant adenovirus and/or a pharmaceutical composition according to the invention is used for gene therapy and is administered to a subject to be treated, it is preferred that it is administered in a sufficiently large dose such that the treatment results in one or more cells of the patient being transfected, i.e. transduced. If a recombinant adenovirus and/or a pharmaceutical composition according to the invention is administered by any of the preferred means of administrations disclosed herein, it is preferred that an effective dose which is preferably $1\times10^8$ to $5\times10^{11}$ viral particles (i.e., $1\times10^8$, $5\times10^8$, $1\times10^9$, $5\times10^9$, $1\times10^{10}$, $2.5\times10^{10}$, $5\times10^{10}$, $1\times10^{11}$ or, most preferably, $5\times10^{11}$ particles) is administered. In preferred embodiments, the preferably heterologous polynucleotide that is comprised in the recombinant adenovirus of the invention is capable of expressing a protein or polypeptide in a host cell of the subject, wherein the protein or polypeptide comprises a signal peptide which effects secretion of the protein or polypeptide from said host cell. For example, a patient in need of a certain protein can be treated using an adenovirus of the present invention which comprises a cDNA that encodes a secretable form of that protein.

In a further embodiment of the use of the present invention, the isolated polynucleotide, isolated protein, vector, adenovirus and/or pharmaceutical composition according to the invention (in the following referred to as pharmaceutical according to the invention) formulated to further comprise one or more pharmaceutically acceptable diluents; carriers; excipients, including fillers, binders, lubricants, glidants, disintegrants, and adsorbents; and/or preservatives.

The pharmaceutical according to the invention can be administered by various well known routes, including oral, rectal, intragastrical and parenteral administration, e.g. intravenous, intramuscular, intranasal, intradermal, subcutaneous and similar administration routes. Parenteral-, intramuscular- and intravenous administration is preferred. Preferably the pharmaceutical according to the invention is formulated as syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

Particular preferred pharmaceutical forms for the administration of the pharmaceutical according to the invention during the use of the present invention are forms suitable for injectable use and include sterile aqueous solutions or dispersions and sterile powders for the extemporaneous preparation of sterile injectable solutions or dispersion. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils.

Infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride may be incorporated in infusion or injection solutions.

Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of the pharmaceutical according to the invention can be chosen from the following non-limiting list:
a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscaramellose, sodium methyl cellulose, agar, bentonite, alginic acid, carboxymethyl cellulose, polyvinyl pyrrolidone and the like.

Other suitable excipients can be found in the Handbook of Pharmaceutical Excipients, published by the American Pharmaceutical Association, which is herein incorporated by reference.

Certain amounts of the pharmaceutical according to the invention are preferred for the therapy or prophylaxis of a disease. It is, however, understood that depending on the severity of the disease, the type of the disease, as well as on the respective patient to be treated, e.g. the general health status of the patient, etc., different doses of the pharmaceutical according to the invention are required to elicit a therapeutic or prophylactic effect. The determination of the appropriate dose lies within the discretion of the attending physician.

If the pharmaceutical according to the invention is to be used prophylactically, it may be formulated as a vaccine. In this case the pharmaceutical according to the invention is preferably administered in above outlined preferred and particular preferred doses. Preferably, the administration of the vaccine is repeated at least two, three, four, five, six, seven, eight nine or at least 10 times over the course of a defined period of time, until the vaccinated subject has generated sufficient antibodies against the pharmaceutical according to the invention so that the risk of developing the respective disease has lessened. The period of time in this case is usually variable depending on the antigenicity of the vaccine. Preferably the period of time is not more than four weeks, three months, six months or three years. In one embodiment, if an adenovirus according to the invention is used for vaccination purposes, at least one of the hyper variable domains of the hexon protein can be replaced by an immunogenic epitope of the respective disease agent that the vaccination is directed against. Vaccines typically contain one or more adjuvants as outlined above. A detailed summary of the use of adenoviruses for vaccination and methods pertaining thereto is provided in: Bangari D S and Mittal S K (2006) Vaccine, 24(7), p. 849-862; see also: Zhou D, et al., Expert Opin Biot Ther. 2006 January; 6(1):63-72; and: Folgori A, et al., Nat Med. 2006 February; 12(2):190-7; see also: Draper S J. et al., Nat Med. 2008 August; 14(8):819-21. Epub 2008 Jul. 27.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following figures are merely illustrative of the present invention and should not be construed to limit the scope of the invention as indicated by the appended claims in any way.

BRIEF DESCRIPTION OF THE FIGURES

FIGS. 1A-1D Multiple sequence alignment between hexon proteins of various adenovirus isolates of the invention, using Clustal-W with default settings. Hlexon proteins of said novel chimpanzee adenovirus isolates are shown (designated as PanAd1, PanAd2, PanAd3, ChAd55, ChAd73, ChAd83, ChAd146 and ChAd147). The hypervariable domains 1 through 7 are designated as "HVR 1-6" and "HVR 7", respectively.

FIGS. 2A-2C Multiple sequence alignment between fiber proteins of adenovirus ChAd55 and of further novel chimpanzee adenovirus isolates (designated as PanAd1, PanAd2, PanAd3, ChAd73, ChAd83, ChAd146 and ChAd147), using Clustal-W with default settings.

FIGS. 3A-3C Multiple sequence alignment between penton proteins of adenovirus ChAd55 and of further novel chimpanzee adenovirus isolates (designated as PanAd1, PanAd2, PanAd3, ChAd73, ChAd83, ChAd146 and ChAd147), using Clustal-W with default settings.

FIGS. 7A-7B PanAd HSV immunization of BALB/c mice is shown in FIG. 7A and PanAd cancer Ag immunization of BALB/c mice is shown in FIG. 7B.

EXAMPLES

Example 1: Adenovirus Isolation and Characterization

Figure 4:
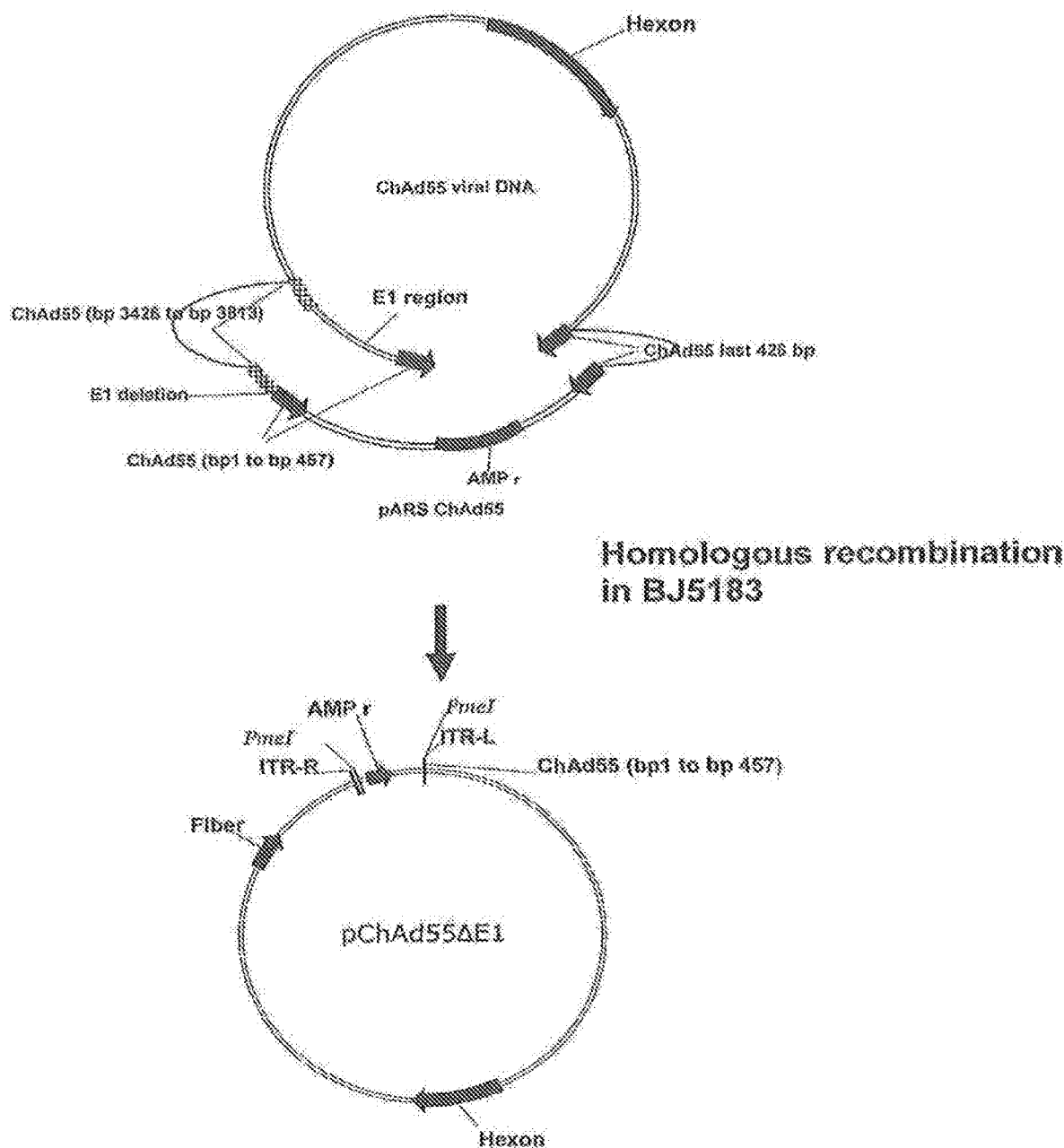
FIG. 4 Diagram of construction of a replication-defective adenovirus vector by homologous recombination with wild type viral genome and the corresponding shuttle plasmid. See also example 2.

ChAd55, ChAd73, ChAd83, ChAd146, ChAd147 are a group of chimpanzee adenoviruses obtained from healthy animals housed in different European and US facilities. ChAd55, ChAd73, ChAd83, ChAd146, ChAd147 have the property of no detectable reactivity with human sera. PanAd1, PanAd2 and PanAd3 are new adenovirus isolated from healthy bonobos (*Pan Paniscus*) housed in different European and US facilities. PanAd1, PanAd2 and PanAd3 have the property: of no detectable reactivity with human sera.

The common chimpanzee and bonobo adenovirus stocks were cloned by infecting 293 cells seeded in 96-well plates, after the first passage of amplification. The virus cloning was performed by limiting dilution of the cell lysate obtained at the first passage of the virus amplification. 5 isolated clones were picked up and serially propagated. After 3-4 serial passages of amplification, a large-scale preparation of adenovirus was performed on cells planted on 5 two-layer cell-factories (NUNC) (200 millions of cells/cell factory). Purified viral particles were obtained from cell lysate by two ultra-centrifugation steps on cesium chloride density gradients.

Genomic DNA was isolated from $3\times10^{12}$ pp of purified virus preparation by digestion with Proteinase K (0.5 mg/ml) in 1% SDS-TEN (2 hrs at 55° C.). After a Phenol-Chloroform extraction and Ethanol precipitation, the genomic DNA was resuspended in water and submitted for genomic sequencing.

An initial classification of the new isolates was obtained by sequence analysis of the hypervariable region 7 (HVR7) of the hexon gene. To this end two primers were designed on the highly conserved regions flanking HVR7: TGTCCTAC-CARCTCTTGCTTGA (SEQ NO. 3) and GTG-GAARGGCACGTAGCG (SEQ ID NO. 4). The HVR7 was amplified by PCR using purified viral DNA or crude 293 lysate as template and then sequenced. More detailed information about the isolate was obtained by sequencing the hypervariable regions 1 to 6. The DNA region containing HVR1-6 was amplified by PCR using oligonucleotides HVR1-6fd, CAYGATGTGACCACCGACCG (SEQ ID NO. 5) and HVR1-6rev, GTGTTYCTGTCYTGCAAGTC (SEQ ID NO. 6). Based on HVRs sequence analysis the new isolated viruses were classified into subgroup E (ChAd55, ChAd73, ChAd83, ChAd146, ChAd147) and subgroup C (PanAd1, PanAd2 and PanAd3) of human Ad virus classification (Horowitz, M S (1990), Adenoviridae and their replication. In Virology B. N. Fields and D. M. Knipe, eds (raven Press, New York) pp. 1679-1740).

A phylogenetic tree was obtained by alignment of human and chimp adenovirus hexon amino acid sequences. The results are consistent with the initial classification based on nucleotide sequence alignment limited to hexon HVR1-6 and 7 by using Align X program (Informax, Inc) demonstrating a close phylogenetic relationship of ChAd55, ChAd73, ChAd83, ChAd146, ChAd147 isolates with human Ad4 (subgroup E) while bonobo adenovirus isolate PanAd1, PanAd2 and PanAd3 are related to human Ad1, 2, 5, 6 (subgroup C).

Example 2: Vector Construction

The PanAd1, PanAd2 and PanAd3 and ChAd55, ChAd73, ChAd83, ChAd146, ChAd147 virus genomes were cloned in a plasmid vector following the strategy detailed below. All manipulations of the vector genome were performed in *E. coli* following standard techniques. Vector systems were developed by deleting E1 and E3 regions from ChAd and PanAd backbones. The E1 region was substituted with expression cassettes based on human CMV IE promoter and BGHpA signal containing HCV non structural region (HCV NS) and HIV gag (SEQ ID NO: 1) genes for the evaluation of the immunological potency in animal models. In addition, ChAd and PanAd vectors expressing the secreted alkaline phosphatase gene (SEAP) were constructed for the neutralization assay. The vectors were propagated in 293 cells and purified by CsCl gradients following standard protocols.

The construction of PanAd1, PanAd2 and PanAd3 ΔE1 vectors proceeded through the steps provided below.

I. Construction of PanAd Shuttle Vector

PanAd1 genome was used to construct a shuttle vector for cloning by homologous recombination the entire genome of PanAd1, PanAd2 and PanAd3. Briefly, the shuttle vector used to clone bonobo adenovirus 1 referred to herein as pBAd1RLD_EGFP was constructed as follows:

PanAd1 left end (nt 1-450) was amplified by PCR with oligonucleotides 5'-ATCTGGAATTCGTTTAAACCAT-CATCAATAATATACCTTATTTTG-3' (SEQ ID NO: 7) and 5'-TCAGGAACTAGTTCCGTATACC-TATAATAATAAAACGGAGACTTTG-3' (SEQ ID NO: 8) digested with SpeI and EcoRI then ligated into a plasmid vector already containing HCMV-EGFP-bgh polyA cassette by generating pBAd1-L. PanAd1 right end (nt 37362-37772) was then amplified by PCR with oligonucleotides 5'-TCCAGCGGCGCGCCAGACCCGAGTCT-TACCAGGA-3' (SEQ ID NO: 9) and 5'-ATTVAG-GATCCGAATTCGTTTAAACCATCAT-CAATAATATACCTTATTTTG-3' (SEQ ID NO: 10), and cloned in pBAd1-L thus generating plasmid pBAd1-RL.

A PanAd1 DNA fragment (nt 3498-4039) containing pIX coding region was subsequently amplified by PCR with the oligonucleotides 5'-TATTCTGCGATCGCTGAGGTGGGT-GAGTGGGCG-3' (SEQ ID NO: 11) and 5'-TTACTGGCGCGCCTGCCTCGACiTAAACGGCAT-TTGCAGGAGAAG-3' (SEQ ID NO: 12) then cloned into pBAd1-RL obtaining the plasmid pBAd1RLD EGFP shuttle. Shuttle plasmids containing the expression cassettes for secreted alkaline phosphatase (SEAP), HIV gag, HCV non structural region (NS) genes were also constructed by substituting the EGFP gene in pBAd1RLD EGFP shuttle.

The HIV gag HCV NS region SEAP and EGFP expression cassette based on human cytomegalovirus (HCMV) promoter and bovine growth hormone polyadenylation signal (Bgh polyA) were constructed as described in Emini et al., International Publication Number WO 03/031588. The viral DNA cassette was designed to contain restriction enzyme sites (PmeI) that are present only at the end of both ITRs to allow the release of viral DNA from plasmid DNA.

II. Construction of ΔE1 PanAd1, PanAd2 and PanAd3 Vector

PanAd1, PanAd2 and PanAd3 vectors were constructed by homologous recombination in *E. coli* strain BJ5183.

BJ5183 cells were co-transformed with PanAd1, 2 and 3 purified viral DNAs and pBAd1RLD-EGFP or pBAd1RLD-Gag. Homologous recombination between pIX genes, right ITR DNA sequences present at the ends of linearized pBAd1RLD-EGFP or pBAd1RLD-Gag and viral genomic DNAs allowed its insertion in the plasmid vector, by deleting at the same time the E1 region that was substituted by the expression cassette. This strategy allowed for the construction of the preadeno plasmids pPanAd1, pPanAd2 and pPanAd3 expressing EGFP or HIV gag transgenes. SEAP or HCV-NS expression cassettes were then cloned into pPanAd 1, 2, and 3 vectors by replacing either EGFP or Gag expression cassettes.

III. E3 Region Deletion

A deletion of the E3 region was introduced in PanAd1, PanAd2 and PanAd3 vector backbones by using a strategy involving several steps of cloning and homologous recombination in *E. coli*. PanAd1 E3 deletion spans from nucleotide 28636 to nucleotide 32596 of genomic PanAd1 sequence (SEQ ID NO.: 13); PanAd2 E3 deletion spans from nucleotide 28653 to nucleotide 32599 of genomic PanAd2 sequence (SEQ ID NO.: 62); PanAd3 E3 deletion spans from nucleotide 28684 to nucleotide 32640 of genomic PanAd3 sequence (SEQ ID NO.: 63).

IV. E4 Region Deletion

The native E4 region of PanAd1, PanAd2 and PanAd3 was deleted and replaced with Ad5 E4 ORF6 coding sequence (SEQ ID NO.: 64). The coordinates of the E4 deletion introduced in the PanAd 1, 2 and 3 backbones are the following:

PanAd1 E4 deletion spans from nucleotide 34690 to 37369 (SEQ ID NO.: 13);
PanAd2 E4 deletion spans from nucleotide 34696 to 37400. (SEQ ID NO.: 62);
PanAd3 E4 deletion spans from nucleotide 34690-37369 (SEQ ID NO.: 63).

The deleted region contains all PanAd E4 orfs while the E4 native promoter and polyadenylation signal were not deleted The HIV gag and HCV NS region expression cassette based on human cytomegalovirus (HCMV) promoter and bovine growth hormone polyadenylation signal (Bgh polyA) was constructed as described in Emini et al., International Publication Number WO 03/031588 and inserted into PanAd1, 2 and 3 ΔE1 EGFP vector by homologous recombination in *E. coli* strain BJ5183 exploiting the homologies between HCMV and Bgh polyA DNA sequences.

V. ChAd55 DE1 Expression Vector Construction and Rescue Construction of Shuttle Vector for ChAd55 Cloning ChAd55 shuttle was constructed by following the same strategy described above for PanAd vectors then used for the cloning of the ChAd55 viral genomes. To this end, the shuttle vector pARS ChAd55 containing the right end as well as the left end of viral genome (left end from the ITR to the pIX gene with the E1 region deleted and substituted with the expression cassette) was linearized with Asci restriction enzyme and co-transformed into *E. coli* strain BJ5183 with ChAd55 purified viral DNA. Homologous recombination between DNA sequences from pIX genes and right ITR present at the ends of linearized pARS ChAd55 and ChAd55, ChAd73, ChAd83, ChAd146 and ChAd147 purified viral genomic DNAs allowed their insertion into the plasmid vector by deleting at the same time the E1 region. A diagram of the chimp adenovirus 55 (ChAd55) genome cloning strategy is provided in FIG. 4.

Expression cassettes based on human cytomegalovirus (HCMV) promoter and bovine growth hormone poly-adenylation signal (Bgh polyA) were constructed to express secreted alkaline phosphatase (SEAP), EGFP, HIV gag HCV NS genes. All expression cassettes were inserted into the single SnaBI site of pARS ChAd55 vector to be transferred by homologous recombination into the ΔE1 adenovirus pre-plasmids.

Example 3: Immunization Experiments

Figure 5A:
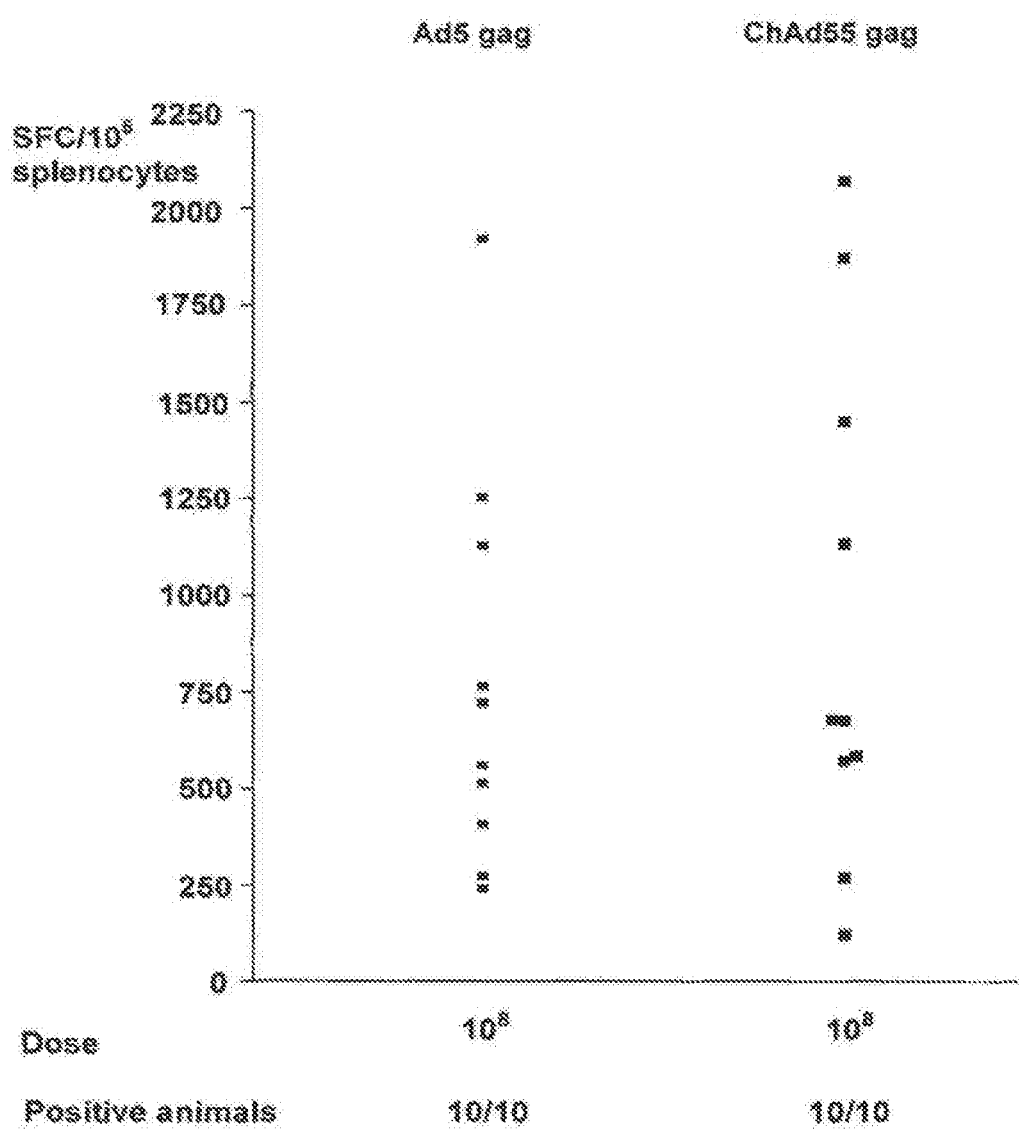
FIGS. 5A-5C Cell-mediated immune response in mice vaccinated with recombinant adenoviruses comprising an expression cassette for the expression of HIV gag protein (SEQ ID NO:1). The vaccination potency of recombinant human Ad5 and chimpanzee ChAd55 (FIG. 5A), of recombinant human Ad5 and bonobo PanAd1, PanAd2 and PanAd3 adenovirus (FIG. 5B) and of recombinant ChAd55, ChAd73, ChAd83, ChAd146 and ChAd147 was compared (FIG. 5C). The immune response was measured by Interferon-γ ELIspot assay by incubating the cells with a CD8 HIV gag epitope mapped in Balb/C mice. The results are reported as spot forming cells per $10^6$ splenocytes.
Figure 5B:
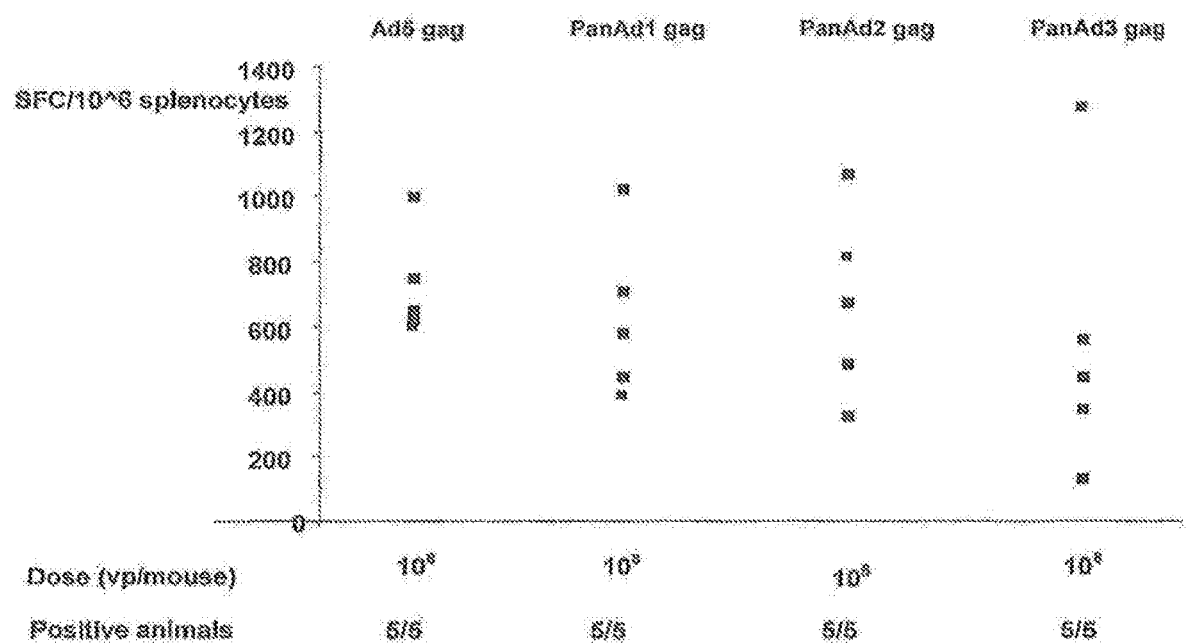
Figure 5C:
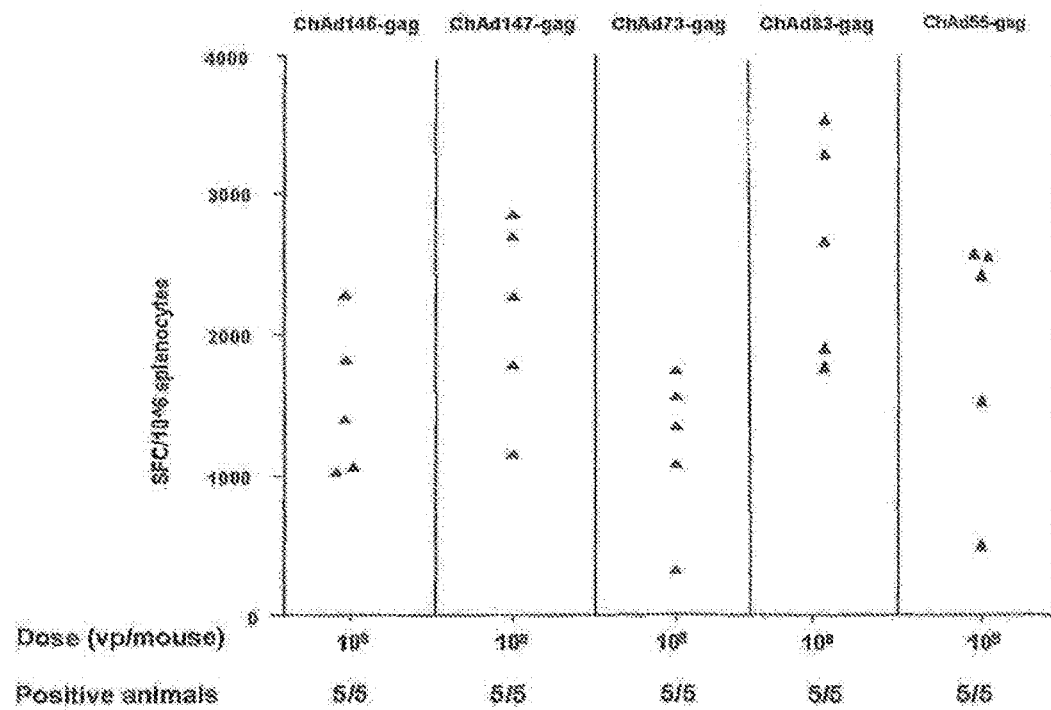

The efficiency of ChAd55, ChAd73, ChAd83, ChAd146, ChAd147, PanAd1, PanAd2 and PanAd3 vectors as potential recombinant vaccine was evaluated in mice with vectors expressing HIV gag transgene. The vector potency of ChAd55 gag was compared with human Ad5 gag in immunization experiments performed in parallel. Groups of 10 animals were injected in the quadriceps with a dose of the vector of $10^8$ vp/mouse for Ad5gag or ChAd55gag (FIG. 5A). In a separate experiment a group of 5 animals were injected with a dose of the vector of $10^8$ vp/mouse for Ad5gag or PanAd1gag, PanAd2gag and PanAd3gag (FIG. 5B). The potency of ChAd73 gag, ChAd83 gag, ChAd146 gag and Chad147gag was also determined by immunizing groups of 5 mice with a dose of vector of $10^8$ vp/mouse in parallel with ChAd55 gag (FIG. 5C). The immune response elicited against HIV gag was measured by Interferon-γ Elispot assay on splenocytes. The results of immunization experiments with ChAd55, ChAd73, ChAd83, ChAd146, ChAd147 and PanAd1, PanAd2 and PanAd3 in comparison with human Ad5 gag vector show that the novel adenoviruses of the invention are at least as effective in eliciting a specific immune response as the prior art recombinant adenovirus Ad5.

Example 4: Neutralization Studies

Figure 6:
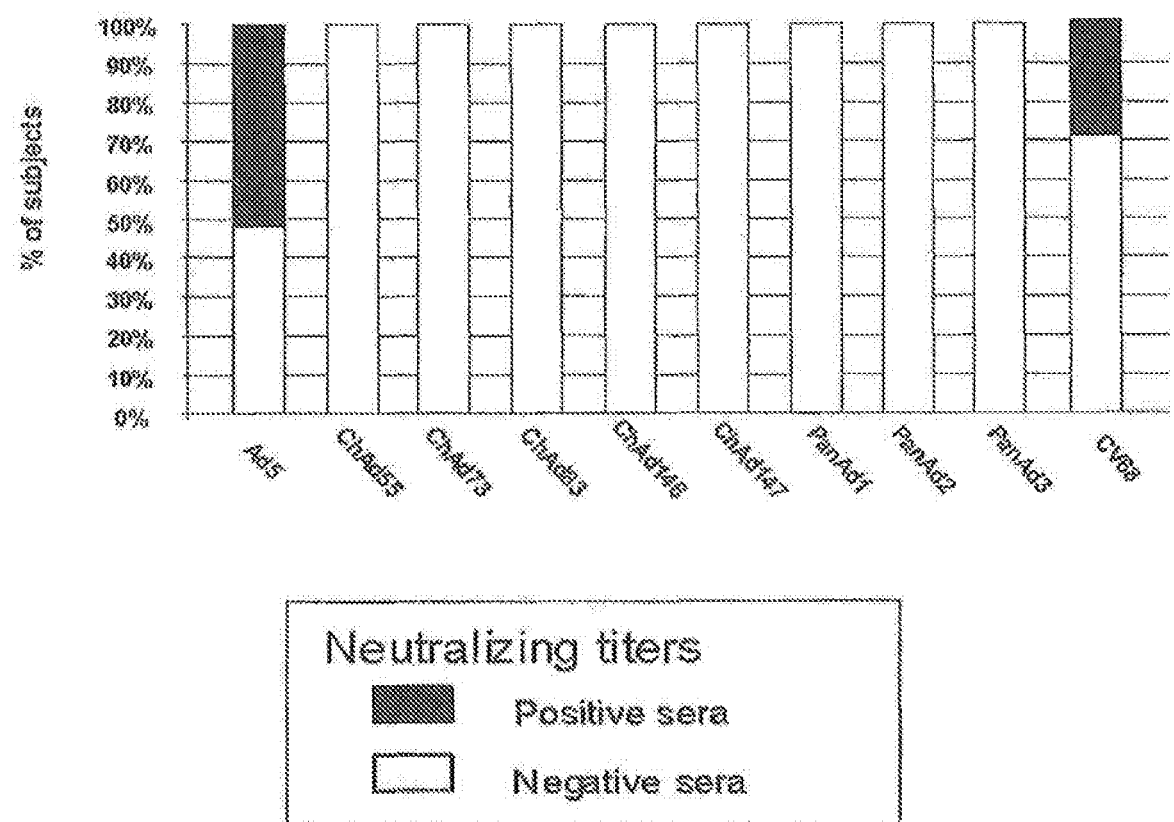
FIG. 6 The seroprevalence of novel adenovirus vectors was evaluated on a panel of human sera of European origin. The seroprevalence of human adenovirus type 5 (Ad5) and of chimpanzee adenoviruses ChAd55, ChAd73, ChAd83, ChAd146, ChAd147, PanAd1, PanAd2, PanAd3 and CV-68 were evaluated in parallel on the same panel. The data are expressed as % of subjects showing an immunoprevalence. Neutralizing antibodies were only detected against Ad5 and CV-68 adenoviruses but not for any of the novel adenoviruses of the present invention.

Neutralization assays were carried out in order to evaluate the prevalence in human sera of neutralizing antibodies against the common chimpanzee adenovirus 55, 73, 83, 146, 147 and the Bonobo adenovirus type 1, 2 and 3. The assay evaluated the effects of serum preincubation on the ability of ChAd55, ChAd73, ChAd83, ChAd146, ChAd147, PanAd1, PanAd2 and PanAd3 carrying the gene for secreted alkaline phosphatase (SEAP) to transduce human 293 cells. The neutralization titer is defined as the dilution of serum giving a 50% reduction of the SEAP activity observed in the positive control with the virus in absence of serum. Each serum sample was tested at various dilutions (five 4-fold increments starting from 1/18 dilution through 1:4608). Samples were pre-incubated for one hour at 37° C. and then added to 293 cells seeded into 96-well plates ($3\times10^4$ cells/well). A panel of human sera was tested for neutralization activity. In parallel the same panel was tested on Ads and on chimp and bonobo Ad SEAP vectors. The results are provided in FIG. 6. The results indicate that the seroprevalence on chimpanzee adenoviruses is lower than human adenovirus Ad5. However, in general the presence of neutralizing antibodies against already described ChAds (CV-68) can be detected in a subset of subjects. On the contrary, all human sera tested so far failed to neutralize ChAd55 and PanAd1, PanAd2 and PanAd3 even at very low titer. The same was observed for ChAd73, ChAd83, ChAd146 and ChAd147. Therefore, the novel adenovirus isolates ChAd55, ChAd73, ChAd83, ChAd146, ChAd147 and PanAd1, PanAd2, and PanAd3 represent the ideal solution to the problem of the pre-existing anti-human Ad immunity that limits the administration of viral vectors based on common human Ad serotypes such as Ads.

Example 5: Immunization Efficiency of PanAd1 and 3 Vectors in Comparison with Ad5 Vectors The efficiency of PanAd1 and PanAd3 vectors as potential recombinant vaccines was evaluated in BALB/c mice with vectors expressing herpes simplex virus (HSV) antigen and with vectors expressing a cancer antigen. The vector potency of PanAd1 and 3 expressing HSV Ag and the cancer Ag was compared with the corresponding vectors based on human Ads.

To evaluate the antiviral potency, 9 groups of BALB/c mice were injected in the quadriceps with increasing doses of the vectors starting from $10^7$ vp/mouse up to $10^9$ vp/mouse in parallel with PanAd1-HSV, PanAd34HSV and Ad5-HSV (see FIG. 7A). The immune response elicited against the HSV antigen was measured by Interferon-γ Elispot assay on mouse splenocytes incubated with a peptide pool covering the entire amino acid sequence of the antigen. The results of immunization experiments with PanAd1, PanAd2 and PanAd3 in comparison with human Ads vector reported in FIG. 7 showed that the novel adenoviruses of the invention are more effective in eliciting a specific immune response than the prior art recombinant adenovirus Ad5 at each concentration tested. This is clearly demonstrated by the higher frequency of antigen-specific T-cell observed in mice immunized with PanAd1 and PanAd3 vectors.

The efficiency in eliciting anti-tumoral T-cell response by PanAd vectors was evaluated by immunizing groups of BALB/c mice by injecting in the quadriceps increasing doses of the vectors starting from $10^7$ vp/mouse up to $10^9$ vp/mouse. Two groups of BALB/C mice were injected with Ads vector expressing the tumor antigen at $10^7$ vp/mouse and $10^9$ vp/mouse. In parallel 3 groups of BALB/c mice were immunized with $10^7$, $10^8$, $10^9$ vp of PanAd1 or PanAd3 vectors carrying the same tumor antigen. The T cell response was measured by Interferon-γ Elispot assay on splenocytes using a single peptide representing a mapped CD8 epitope. The results shown in FIG. 7B demonstrated a higher frequency of responding animals at the lowest dose of the vaccine as well as a higher frequency of antigen-specific T-cell in the groups of animals immunized with the PanAd vectors in comparison with those immunized with Ad5 vector.

Example 6: Immunization of *Macaca fascicularis* with PanAd Vectors

Two groups of 3 macaques were immunized by intramuscular injection of CsCl-purified PanAd1 and PanAd3 in a heterologous prime/boost regimen. Each animal in the group 1 received a dose of $10^8$ vp while the animals in the group 2 received a dose of $10^{10}$ vp of PanAd3 Gag vector in the deltoid muscle at week 0. All animals in both groups were than boosted with a single dose of PanAd1 Gag of $10^{10}$ vp at week 13.

CMI was measured at different time points by IFN-γ ELISPOT assay. This assays measure HIV antigen-specific CD8+ and CD4+ T lymphocyte responses. Peptides based on the amino acid sequence of HIV Gag protein were prepared for use in these assays to measure immune responses in adenovirus vector vaccinated monkeys. The individual peptides are overlapping 20-mers, offset by 10 amino acids.

The IFNγ-ELISPOT assay provides a quantitative determination of antigen-specific T lymphocyte responses. PBMC are serially diluted and placed in microplate wells coated with anti-rhesus IFN-γ antibody (MD-1 U-Cytech). They are cultured with a HPV Gag peptide pool for 20 hours, resulting in the restimulation of the precursor cells and secretion of IFN-γ. The cells are washed away, leaving the secreted IFN bound to the antibody-coated wells in concentrated areas where the cells were sitting. The captured IFN is detected with biotinylated anti-rhesus IFN antibody (detector Ab U-Cytech) followed by alkaline phosphatase-conjugated streptavidin (Pharmingen 13043E). The addition of insoluble alkaline phosphatase substrate results in dark spots in the wells at the sites where the cells were located, leaving one spot for each T cell that secreted IFN-γ.

Figure 8:
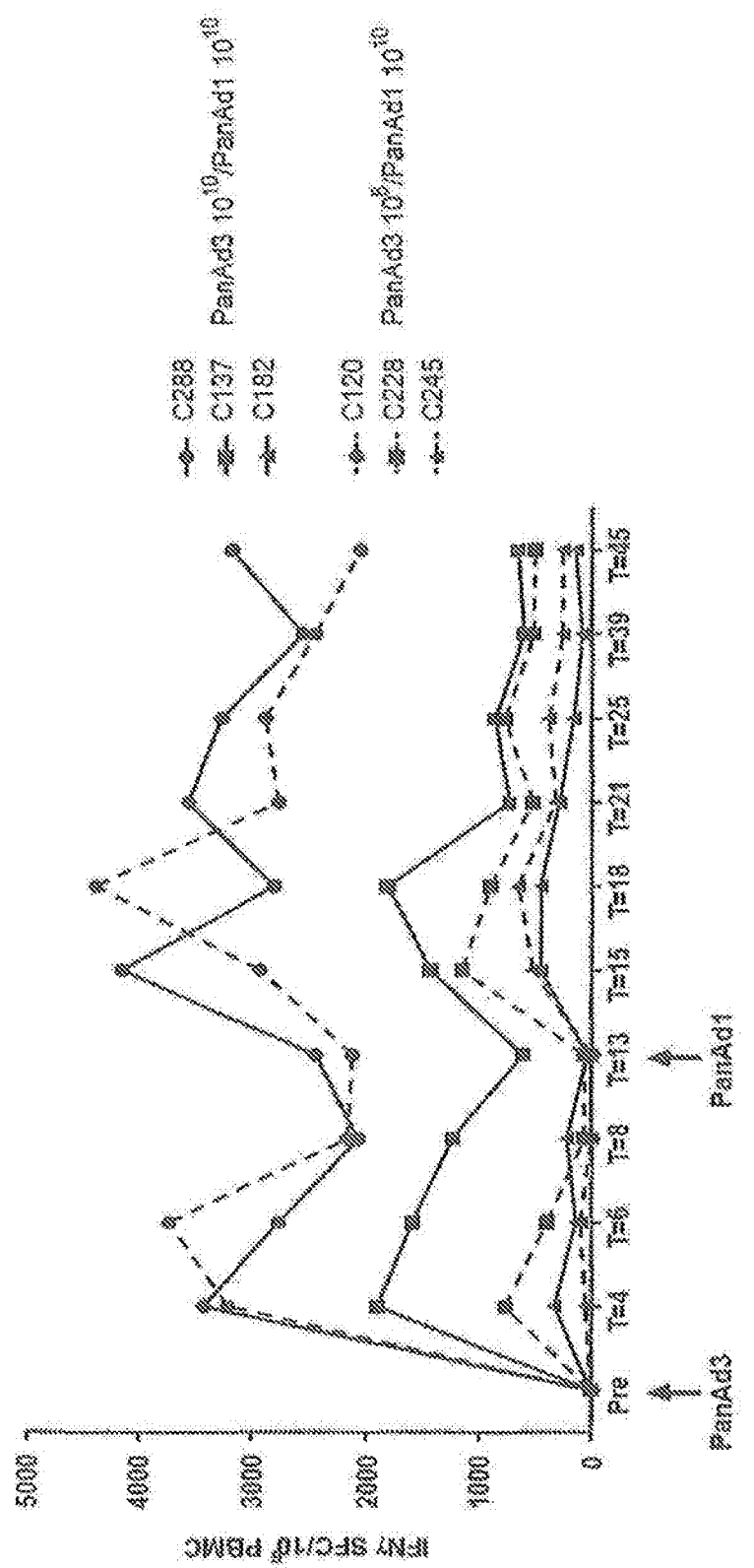
FIG. 8 PanAd HIV gag immunization of *Macaca fascicularis* is shown in a priming/boosting vaccination experiment.

The number of spots per well is directly related to the precursor frequency of antigen-specific T cells. Gamma interferon was selected as the cytokine visualized in this assay (using specific anti-gamma interferon monoclonal antibodies) because it is the most common, and one of the most abundant cytokines synthesized and secreted by activated T lymphocytes. For this assay, the number of spot forming cells (SFC) per million PBMCs is determined for samples in the presence and absence (media control) of peptide antigens. Data from macaques on PBMC obtained at different time points post dose 1 and post dose 2 are shown in FIG. 8. All animals primed with PanAd3 at both doses showed a T cell response against HIV Gag, efficiently boosted by the second injection of PanAd1 demonstrating that, as already suggested by the hexon, penton and fiber sequence alignment, PanAd1 and PanAd3 are distinct serotypes that can be combined in a heterologous prime-boost immunization regimen. Thus, in another aspect the invention provides the use of two recombinant adenoviruses of the invention for a heterologous prime-boost immunization wherein the two recombinant adenoviruses of the invention are of distinct adenoviral serotypes, most preferably of PanAd1 and PanAd3 as described herein.

The invention claimed is:

1. A recombinant adenoviral vector comprising a polynucleotide that encodes an adenoviral hexon protein, a heterologous adenoviral fiber protein and an adenoviral penton protein, wherein the heterologous adenoviral fiber protein is selected from the group consisting of:
(a) a polypeptide having the amino acid sequence of SEQ ID NO: 16;
(b) a polypeptide having the amino acid sequence of SEQ ID NO: 16, wherein the polypeptide comprises a deletion, insertion or substitution of not more than 35 amino acid residues; and
(c) a polypeptide having an amino acid sequence which is at least 90% identical over its entire length to the amino acid sequence of SEQ ID NO: 16;
and wherein the adenoviral hexon protein is a polypeptide having the amino acid sequence of SEQ ID NO: 22 and the adenoviral penton protein is a polypeptide having the amino acid sequence of SEQ ID NO: 28.

2. The recombinant adenoviral vector of claim 1, wherein the E4 region of the vector comprises ORF6 from a human adenovirus.

3. The recombinant adenoviral vector of claim 2, wherein the E4 region of the vector comprises ORF6 from human adenovirus 5 (Ad5 E4ORF6).

4. The recombinant adenoviral vector of claim 1 further comprising at least one of the following:
(a) an adenoviral 5'-end or an adenoviral 5' inverted terminal repeat;
(b) an adenoviral E1a region or a fragment thereof selected from the group consisting of 13S region, 12S region, and 9S region;
(c) an adenoviral E1b region or a fragment thereof selected from the group consisting of small T region, large T region, and IX region;
(d) an adenoviral E2b region or a fragment thereof selected from the group consisting of small pTP region, Polymerase region, and 1Va2 region;
(e) an adenoviral L1 region or a fragment thereof encoding an adenoviral protein selected from the group consisting of 28.1 kD protein, polymerase, agnoprotein, 52/55 kDa protein, and IIIa protein;
(f) an adenoviral L2 region or a fragment thereof encoding an adenoviral protein selected from the group consisting of:
a VII protein,
a V protein, and
a Mu protein;
(g) an adenoviral L3 region or a fragment thereof encoding an adenoviral protein selected from the group consisting of:
a VI protein, and
an endoprotease;
(h) an adenoviral E2a region;
(i) an adenoviral L4 region or a fragment thereof encoding an adenoviral protein selected from the group consisting of 100 kD protein, 33 kD homolog, and protein VIII;
(j) an adenoviral E3 region or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region or a fragment thereof encoding a fiber protein having the amino acid sequence of SEQ ID NO: 16;
(l) an adenoviral E4 region or a fragment thereof selected from the group consisting of E4 ORF7, E4 ORF6, E4 ORF5, E4 ORF4, E4 ORF3, E4 ORF2, and E4 ORF1; and
(m) an adenoviral 3'-end or an adenoviral 3' inverted terminal repeat.

5. The recombinant adenoviral vector according to claim 1, wherein the polynucleotide comprises a polynucleotide which is at least 90% identical over its entire length to a polynucleotide selected from the group consisting of SEQ ID NO: 65 and SEQ ID NO: 65 lacking one or more of genomic regions E1A, E1B, E2A, E2B, E3 or E4.

6. The recombinant adenoviral vector according to claim 1, wherein the vector
(i) does not comprise a gene in a genomic region selected from the group of genomic regions consisting of E1A, E1B, E2A, E2B, E3 and E4, or
(ii) comprises at least one gene of a genomic region selected from the group consisting of E1A, E1B, E2A, E2B, E3 and E4, wherein the at least one gene comprises a deletion or a mutation which renders the at least one gene non-functional.

7. The recombinant adenoviral vector according to claim 1, wherein the adenoviral vector is capable of infecting a mammalian cell.

8. The recombinant adenoviral vector according to claim 1, wherein the recombinant adenoviral vector comprises a molecule for delivery into a target cell.

9. The recombinant adenoviral vector according to claim 8, wherein the molecule for delivery into a target cell is a polynucleotide encoding an antigenic protein or a fragment thereof.

10. A composition comprising:
(i) an adjuvant;
(ii) the recombinant adenoviral vector of claim 1; and
(iii) a pharmaceutically acceptable excipient.

11. An isolated cell comprising the recombinant adenoviral vector of claim 1.

12. The isolated cell according to claim 11, wherein the cell is a host cell that expresses at least one adenoviral gene selected from the group consisting of E1a, E1b, E2a, E2b, E4, L1, L2, L3, L4, and L5.

13. The recombinant adenoviral vector of claim 1, wherein the vector comprises a polynucleotide encoding a polypeptide having the amino acid sequence of SEQ ID NO: 16, a polynucleotide encoding a polypeptide having the amino acid sequence of SEQ ID NO: 22, and a polynucleotide encoding a polypeptide having the amino acid sequence of SEQ ID NO: 28.

14. The recombinant adenoviral vector of claim 1, wherein the recombinant adenoviral vector is a recombinant simian adenoviral vector.

15. The recombinant adenoviral vector of claim 14, wherein the recombinant adenoviral vector is capable of infecting a mammalian cell.

16. The recombinant adenoviral vector of claim 14, wherein the recombinant adenoviral vector comprises a molecule for delivery into a target cell.

17. An isolated cell comprising the recombinant adenoviral vector of claim 14.

* * * * *